United States Patent
Kemper et al.

(10) Patent No.: US 12,410,258 B2
(45) Date of Patent: Sep. 9, 2025

(54) ANTIBODIES CAPABLE OF BINDING TO OX40, VARIANTS THEREOF AND USES THEREOF

(71) Applicants: Genmab A/S, Valby (DK); BioNTech SE, Mainz (DE)

(72) Inventors: Kristel Kemper, Utrecht (NL); Maarten van der Kroef, Utrecht (NL); Dennis Verzijl, Utrecht (NL); Andrea Gorlani, Utrecht (NL); Pauline Linda de Goeje, Utrecht (NL); Lars Guelen, Utrecht (NL); David Satijn, Utrecht (NL); Esther C. W. Breij, Utrecht (NL); Ugur Sahin, Mainz (DE); Sina Fellermeier-Kopf, Mainz (DE); Maren Köhne, Mainz (DE)

(73) Assignees: Ganmab A/S, Valby (DK); BioNTech SE, Mainz (DE)

( * ) Notice: Subject to any disclaimer, the term of this patent is extended or adjusted under 35 U.S.C. 154(b) by 0 days.

(21) Appl. No.: 18/660,672

(22) Filed: May 10, 2024

(65) Prior Publication Data
US 2024/0376221 A1 Nov. 14, 2024

(30) Foreign Application Priority Data

May 12, 2023 (EP) .................................... 23173143
Nov. 30, 2023 (EP) .................................... 23213531

(51) Int. Cl.
| | | |
|---|---|---|
| C07K 16/00 | (2006.01) | |
| A61K 39/00 | (2006.01) | |
| A61P 35/00 | (2006.01) | |
| C07K 16/28 | (2006.01) | |
| C07K 16/42 | (2006.01) | |

(52) U.S. Cl.
CPC .......... *C07K 16/2878* (2013.01); *A61P 35/00* (2018.01); *C07K 16/4241* (2013.01); *A61K 2039/505* (2013.01); *C07K 2317/24* (2013.01); *C07K 2317/31* (2013.01); *C07K 2317/35* (2013.01); *C07K 2317/52* (2013.01); *C07K 2317/565* (2013.01); *C07K 2317/75* (2013.01); *C07K 2317/92* (2013.01)

(58) Field of Classification Search
CPC ............ C07K 16/2878; C07K 16/4241; C07K 2317/24; C07K 2317/31; C07K 2317/35; C07K 2317/52; C07K 2317/565; C07K 2317/75; C07K 2317/92; C07K 2317/33; C07K 2317/71; C07K 2317/73; C07K 16/28; A61P 35/00; A61K 2039/505; A61K 39/00

See application file for complete search history.

(56) References Cited

U.S. PATENT DOCUMENTS

| | | |
|---|---|---|
| 5,589,466 A | 12/1996 | Felgner et al. |
| 5,973,972 A | 10/1999 | Kwon et al. |
| 6,077,835 A | 6/2000 | Hanson et al. |
| 6,602,684 B1 | 8/2003 | Umana et al. |
| 6,808,710 B1 | 10/2004 | Wood et al. |
| 7,262,028 B2 | 8/2007 | Van Berkel et al. |
| 7,488,802 B2 | 2/2009 | Collins et al. |
| 7,612,181 B2 | 11/2009 | Wu et al. |
| 7,951,918 B2 | 5/2011 | Glaser et al. |
| 8,008,449 B2 | 8/2011 | Korman et al. |
| 8,168,757 B2 | 5/2012 | Finnefrock et al. |
| 8,354,509 B2 | 1/2013 | Carven et al. |
| 8,735,553 B1 | 5/2014 | Li et al. |
| 8,779,105 B2 | 7/2014 | Korman et al. |
| 9,006,399 B2 | 4/2015 | Liu et al. |
| 9,221,891 B2 | 12/2015 | Bancel et al. |
| 9,254,311 B2 | 2/2016 | Bancel et al. |
| 9,834,606 B2 | 12/2017 | Li et al. |
| 10,195,156 B2 | 2/2019 | Benenato et al. |
| 10,259,882 B2 | 4/2019 | Van Dijk et al. |
| 10,449,233 B2 | 10/2019 | Schreiber et al. |
| 2003/0115614 A1 | 6/2003 | Kanda et al. |
| 2010/0155133 A1 | 6/2010 | Makwinski et al. |
| 2010/0226923 A1 | 9/2010 | Rao et al. |
| 2014/0348839 A1 | 11/2014 | Chowdhury et al. |
| 2014/0377284 A1 | 12/2014 | Simons et al. |

(Continued)

FOREIGN PATENT DOCUMENTS

| | | |
|---|---|---|
| CN | 102250246 A | 11/2011 |
| CN | 107840887 A | 3/2018 |

(Continued)

OTHER PUBLICATIONS

Abdiche et al., "Antibodies Targeting Closely Adjacent or Minimally Overlapping Epitopes Can Displace One Another", PLoS One, Jan. 6, 2017, 12(1): e0169535.

(Continued)

*Primary Examiner* — Janet L Epps-Smith
*Assistant Examiner* — Estella M. Gustilo
(74) *Attorney, Agent, or Firm* — LATHROP GPM LLP; James H. Velema, Esq.

(57) ABSTRACT

The present invention relates to antibodies capable of binding to human OX40 and to variants thereof comprising a modified Fc region comprising at least one mutation that enhances the Fc-Fc interaction of the antibody and at least one mutation that reduces the Fc effector functions of the antibody. The invention further provides pharmaceutical compositions comprising the antibodies and use of the antibodies for therapeutic and diagnostic procedures, in particular in cancer therapy.

23 Claims, 64 Drawing Sheets

Figure 1:
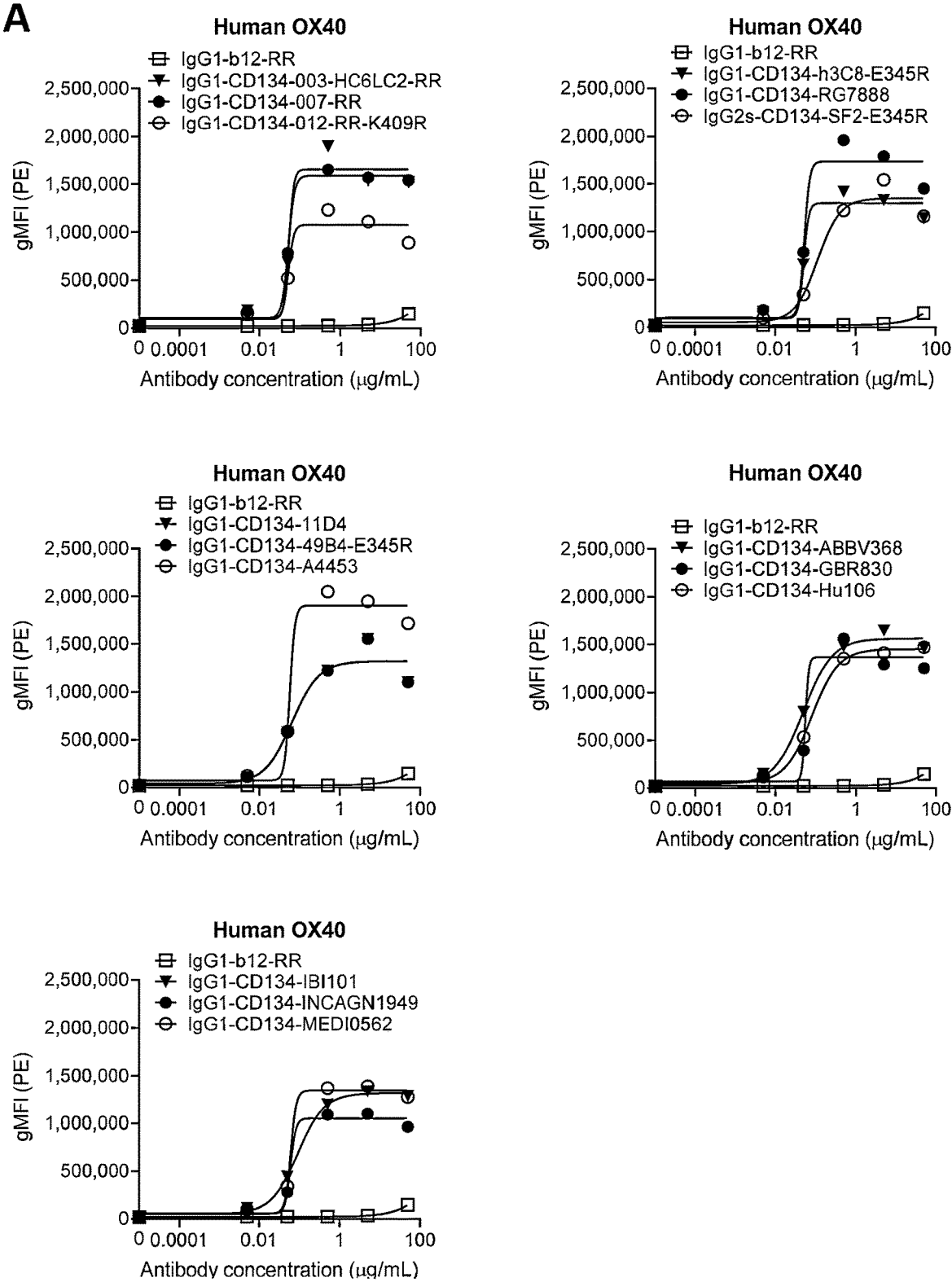

Specification includes a Sequence Listing.

(56) References Cited

U.S. PATENT DOCUMENTS

| | | | |
|---|---|---|---|
| 2015/0079109 A1 | 3/2015 | Li et al. | |
| 2015/0203579 A1 | 7/2015 | Papadopoulos et al. | |
| 2016/0185840 A1 | 6/2016 | Hoerr et al. | |
| 2016/0272708 A1 | 9/2016 | Chen | |
| 2016/0376367 A1 | 12/2016 | Yuan et al. | |
| 2017/0210806 A1 | 7/2017 | Liu | |
| 2017/0334995 A1 | 11/2017 | Zettl et al. | |
| 2018/0170866 A1 | 6/2018 | Payne et al. | |
| 2018/0185482 A1 | 7/2018 | Sheng et al. | |
| 2018/0222989 A1 | 8/2018 | Hoos et al. | |
| 2019/0022247 A1 | 1/2019 | Ansell et al. | |
| 2019/0276549 A1 | 9/2019 | De Jong et al. | |
| 2021/0253725 A1* | 8/2021 | Sahin | A61P 35/00 |
| 2023/0109496 A1* | 4/2023 | Ioan | C07K 16/4208 |
| | | | 424/133.1 |
| 2023/0212291 A1 | 7/2023 | Jiang et al. | |
| 2024/0400703 A1* | 12/2024 | Kemper | C07K 16/4241 |

FOREIGN PATENT DOCUMENTS

| | | | | |
|---|---|---|---|---|
| EP | 0629240 | A1 | 12/1994 | |
| EP | 1176195 | A1 | 1/2002 | |
| EP | 1870459 | A1 | 12/2007 | |
| EP | 2391343 | A2 | 12/2011 | |
| EP | 2972360 | A1 | 1/2016 | |
| EP | 3118224 | A1 | 1/2017 | |
| EP | 3174998 | A1 | 6/2017 | |
| WO | WO 1992/022653 | A1 | 12/1992 | |
| WO | WO 1998/050431 | A2 | 11/1998 | |
| WO | WO 1999/054342 | A1 | 10/1999 | |
| WO | WO 2000/046147 | A2 | 8/2000 | |
| WO | WO 2000/061739 | A1 | 10/2000 | |
| WO | WO 2000/070087 | A1 | 11/2000 | |
| WO | WO 2001/029246 | A1 | 4/2001 | |
| WO | WO 2002/020039 | A2 | 3/2002 | |
| WO | WO 2002/030954 | A1 | 4/2002 | |
| WO | WO 2002/031140 | A1 | 4/2002 | |
| WO | WO 2003/035835 | A2 | 5/2003 | |
| WO | WO 2003/042402 | A2 | 5/2003 | |
| WO | WO 2003/099196 | A2 | 12/2003 | |
| WO | WO 2006/121168 | A1 | 11/2006 | |
| WO | WO 2006/132670 | A2 | 12/2006 | |
| WO | WO 2007/059782 | A1 | 5/2007 | |
| WO | WO 2007/110205 | A2 | 10/2007 | |
| WO | WO 2008/003116 | A2 | 1/2008 | |
| WO | WO 2008/156712 | A1 | 12/2008 | |
| WO | WO 2008/157379 | A2 | 12/2008 | |
| WO | WO 2009/014708 | A2 | 1/2009 | |
| WO | WO 2009/079335 | A1 | 6/2009 | |
| WO | WO 2009/089004 | A1 | 7/2009 | |
| WO | WO 2009/101611 | A1 | 8/2009 | |
| WO | WO 2009/114335 | A2 | 9/2009 | |
| WO | WO 2010/026923 | A1 | 3/2010 | |
| WO | WO 2010/027827 | A2 | 3/2010 | |
| WO | WO 2010/036959 | A2 | 4/2010 | |
| WO | WO 2010/080538 | A1 | 7/2010 | |
| WO | WO 2010/089411 | A2 | 8/2010 | |
| WO | WO 2010/129304 | A2 | 11/2010 | |
| WO | WO 2010/151792 | A1 | 12/2010 | |
| WO | WO 2011/028952 | A1 | 3/2011 | |
| WO | WO 2011/066342 | A2 | 6/2011 | |
| WO | WO 2011/069104 | A2 | 6/2011 | |
| WO | WO 2011/082400 | A2 | 7/2011 | |
| WO | WO 2011/117329 | A1 | 9/2011 | |
| WO | WO 2011/131746 | A2 | 10/2011 | |
| WO | WO 2011/143545 | A1 | 11/2011 | |
| WO | WO 2011/159877 | A2 | 12/2011 | |
| WO | WO 2011/161699 | A2 | 12/2011 | |
| WO | WO 2012/023053 | A1 | 2/2012 | |
| WO | WO 2012/025525 | A1 | 3/2012 | |
| WO | WO 2012/025530 | A1 | 3/2012 | |
| WO | WO 2012/058768 | A1 | 5/2012 | |
| WO | WO-2012075340 | A2 * | 6/2012 | A61K 31/485 |
| WO | WO 2012/145493 | A1 | 10/2012 | |
| WO | WO 2013/004842 | A2 | 1/2013 | |
| WO | WO 2013/157953 | A1 | 10/2013 | |
| WO | WO 2013/173223 | A1 | 11/2013 | |
| WO | WO-2013184218 | A1 * | 12/2013 | C07K 16/28 |
| WO | WO 2014/031646 | A2 | 2/2014 | |
| WO | WO 2014/055648 | A1 | 4/2014 | |
| WO | WO 2014/108198 | A1 | 7/2014 | |
| WO | WO 2014/152774 | A1 | 9/2014 | |
| WO | WO 2014/179664 | A2 | 11/2014 | |
| WO | WO 2014/194302 | A2 | 12/2014 | |
| WO | WO 2015/035606 | A1 | 3/2015 | |
| WO | WO 2015/112800 | A1 | 7/2015 | |
| WO | WO 2015/112900 | A1 | 7/2015 | |
| WO | WO 2016/110584 | A1 | 7/2015 | |
| WO | WO 2015/158867 | A1 | 10/2015 | |
| WO | WO 2016/164480 | A1 | 10/2016 | |
| WO | WO 2016/200835 | A1 | 12/2016 | |
| WO | WO 2017/019805 | A1 | 2/2017 | |
| WO | WO 2017/019846 | A1 | 2/2017 | |
| WO | WO 2017/024465 | A1 | 2/2017 | |
| WO | WO 2017/025016 | A1 | 2/2017 | |
| WO | WO 2017/025051 | A1 | 2/2017 | |
| WO | WO 2017/040790 | A1 | 3/2017 | |
| WO | WO 2017/055547 | A1 | 4/2017 | |
| WO | WO 2017/071625 | A1 | 5/2017 | |
| WO | WO 2017/106656 | A1 | 6/2017 | |
| WO | WO-2017093447 | A1 * | 6/2017 | A61P 35/00 |
| WO | WO 2017/132825 | A1 | 8/2017 | |
| WO | WO 2017/133540 | A1 | 8/2017 | |
| WO | WO 2017/166804 | A1 | 10/2017 | |
| WO | WO 2018/006052 | A1 | 1/2018 | |
| WO | WO 2018/022831 | A1 | 2/2018 | |
| WO | WO 2018/031258 | A1 | 2/2018 | |
| WO | WO 2018/036472 | A1 | 3/2018 | |
| WO | WO 2018/083126 | A1 | 5/2018 | |
| WO | WO-2018/103017 | A1 | 6/2018 | |
| WO | WO 2018/103501 | A1 | 6/2018 | |
| WO | WO 2018/114877 | A1 | 6/2018 | |
| WO | WO 2018/114878 | A1 | 6/2018 | |
| WO | WO 2018/114879 | A1 | 6/2018 | |
| WO | WO 2018/146317 | A1 | 8/2018 | |
| WO | WO 2018/222711 | A2 | 12/2018 | |
| WO | WO 2019/000146 | A1 | 1/2019 | |
| WO | WO 2019/086497 | A2 | 5/2019 | |
| WO | WO 2019/223733 | A1 | 11/2019 | |
| WO | WO 2020/030570 | A1 | 2/2020 | |
| WO | WO 2023/031473 | A1 | 3/2023 | |
| WO | WO 2023/217987 | A1 | 11/2023 | |

OTHER PUBLICATIONS

Barbas et al., "Molecular profile of an antibody response to HIV-1 as probed by combinatorial libraries", J. Mol. Biol., Apr. 5, 1993, 230(3): 812-823.

Bebbington et al., "High-level expression of a recombinant antibody from myeloma cells using a glutamine synthetase gene as an amplifiable selectable marker", Biotechnology, Feb. 1992, 10(2): 169-175.

Benvenisty et al., "Direct introduction of genes into rats and expression of the genes.", PNAS USA, Dec. 1986, 83(24): 9551-9555.

Beurskens et al., "Exhaustion of cytotoxic effector systems may limit monoclonal antibody-based immunotherapy in cancer patients", J. Immunol., Apr. 1, 2012, 188(7): 3532-3541. Epub Feb. 24, 2012.

Bitter et al., "Expression and secretion vectors for yeast", Methods in Enzymol., 1987, 153: 516-544.

Bleeker et al., "Accelerated autoantibody clearance by intravenous immunoglobulin therapy: studies in experimental models to determine the magnitude and time course of the effect", Blood, Nov. 15, 2001, 98(10): 3136-3142.

Brochet et al., "IMGT/V-QUEST: the highly customized and integrated system for IG and TR standardized V-J and V-D-J sequence analysis", Nucl. Acids Res., Jul. 1, 2008, 36: W503-508.

Choi et al., "T-cell agonists in cancer immunotherapy", J. Immunother. Cancer, Oct. 5, 2020, 8(2): e000966.

(56) References Cited

OTHER PUBLICATIONS

Corsaro et al., "Enhancing the efficiency of DNA-mediated gene transfer in mammalian cells", Somatic Cell Genetics, Sep. 1981, 7(5): 603-616.
Croft et al., "The significance of OX40 and OX40L to T-cell biology and immune disease", Immunol. Rev., May 2009, 229(1): 173-191.
Davies et al., "Expression of GnTIII in a recombinant anti-CD20 CHO production cell line: Expression of antibodies with altered glycoforms leads to an increase in ADCC through higher affinity for FC gamma RIII", Biotechnol. Bioeng., Aug. 2001, 74(4): 288-294.
De Jong et al., "A Novel Platform for the Potentiation of Therapeutic Antibodies Based on Antigen-Dependent Formation of IgG Hexamers at the Cell Surface", PLoS Biol. Jan. 6, 2016, 14(1): e1002344.
Dick et al., "C-terminal lysine variants in fully human monoclonal antibodies: investigation of test methods and possible causes", Biotechnol. Bioeng., Aug. 15, 2008, 100(6): 1132-1143.
Dimasi et al., "The design and characterization of oligospecific antibodies for simultaneous targeting of multiple disease mediators", J. Mol. Biol., Oct. 30, 2009, 393(3): 672-692. Epub Aug. 20, 2009.
Gutierrez et al., "OX40 Agonist BMS-986178 Alone or in Combination With Nivolumab and/or Ipilimumab in Patients With Advanced Solid Tumors", Clin. Cancer Res., Jan. 15, 2021, 27(2): 460-472. Epub Nov. 4, 2020.
Hamers-Casterman et al., "Naturally occurring antibodies devoid of light chains", Nature, Jun. 3, 1993, 363(6428): 446-448.
He et al., "The emerging role of co-stimulatory molecules and their agonistic mAb-based combination therapies in melanoma", Int. Immunopharmacol., Dec. 2020, 89(Pt B): 107097. Epub Oct. 19, 2020.
Laustsen et al., "Soluble OX40L is associated with presence of autoantibodies in early rheumatoid arthritis", Arthritis Res Ther., Oct. 30, 2014, 16(5): 474.
Lefranc et al., "IMGT, the international ImMunoGeneTics database", Nucleic Acids Research, Jan. 1, 1999, 27(1): 209-212.
Lindhofer et al., "Preferential species-restricted heavy/light chain pairing in rat/mouse quadromas. Implications for a single-step purification of bispecific antibodies", J. Immunol., Jul. 1, 1995, 155(1): 219-225.
Liu et al., "Heterogeneity of monoclonal antibodies", J. Pharm. Sci., Jul. 2008, 97(7): 2426-2447.
Okazaki et al., "Fucose depletion from human IgG1 oligosaccharide enhances binding enthalpy and association rate between IgG1 and FcgammaRIIIa", Mar. 5, 2004, J. Mol. Biol., 336(5): 1239-1249.
Patel et al., "In vivo delivery of synthetic human DNA-encoded monoclonal antibodies protect against ebolavirus infection in a mouse model", Cell Reports, Nov. 13, 2018, 25(7): 1982-1993.e4.
Rice et al., "EMBOSS: The European Molecular Biology Open Software Suite", Trends Genet., Jun. 2000, 16(6): 276-277.
Ruby et al., "OX40 Agonists can drive Treg expansion if the cytokine milieu is right", J. Immunol., Sep. 28, 2009, 183(8): 4853-4857.
Schakowski et al., "A novel minimal-size vector (MIDGE) improves transgene expression in colon carcinoma cells and avoids transfection of undesired DNA", Mol. Ther., May 2001, 3(5 Pt. 1): 793-800.
Schlake et al., "mRNA: A Novel Avenue to Antibody Therapy?", Mol Ther., Mar. 6, 2019, 27(4): 773-784.
Shen et al., "Single variable domain antibody as a versatile building block for the construction of IgG-like bispecific antibodies", J. Immunol. Methods, Jan. 10, 2007, 318(1-2): 65-74. Epub Oct. 26, 2006.
Shields et al., "Lack of fucose on human IgG1 N-linked oligosaccharide improves binding to human Fcgamma RIII and antibody-dependent cellular toxicity", J. Biol. Chem., Jul. 26, 2002, 277: 26733-26740.
Shinkawa et al., "The absence of fucose but not the presence of galactose or bisecting N-acetylglucosamine of human IgG1 complex-type oligosaccharides shows the critical role of enhancing antibody-dependent cellular cytotoxicity", J. Biol. Chem., Jan. 31, 2003, 278(5): 3466-3473.
Sykes et al., "Linear expression elements: a rapid, in vivo, method to screen for gene functions", Nat. Biotech., Apr. 1999, 17(4): 355-359.
Umana et al., "Engineered glycoforms of an antineuroblastoma IgG1 with optimized antibody-dependent cellular cytotoxic activity", Nat. Biotech., Feb. 1999, 17(2): 176-180.
Van Heeke et al., "Expression of human asparagine synthetase in *Escherichia coli*", J. Biol. Chem., Apr. 5, 1989, 264(10): 5503-5509.
Wigler et al., "Biochemical transfer of single-copy eucaryotic genes using total cellular DNA as donor", Cell, Jul. 1978, 14(3): 725-731.
Willoughby et al., "OX40: Structure and function—What questions remain?", Mol. Immunol., Mar. 2017, 83: 13-22. Epub Jan. 13, 2017.
Zhang et al., "Ligand-Blocking and Membrane-Proximal Domain Targeting Anti-OX40 Antibodies Mediate Potent T Cell-Stimulatory and Anti-Tumor Activity", Cell Rep., Jun. 11, 2019, 27(11): 3117-3123.e5.
Zhang et al., "Fc Engineering Approaches to Enhance the Agonism and Effector Functions of an Anti-OX40 Antibody", J. Biol. Chem., Dec. 30, 2016, 291(53): 27134-27146. Epub Nov. 17, 2016.
Ruby et al., "Cutting Edge: OX40 Agonists Can Drive Regulatory T Cell Expansion if the Cytokine Milieu Is Right", J. Immunol., Oct. 15, 2009, 183(8): 4853-4857, Epublished Sep. 29, 2009.
U.S. Appl. No. 18/660,847, filed May 10, 2024, Kristel Kemper, Antibodies Capable of Binding to OX40, Variants Thereof and Uses Thereof.
U.S. Appl. No. 18/660,672 2024/0376221, filed May 10, 2024 Nov. 14, 2024, Kristel Kemper, Antibodies Capable of Binding to OX40, Variants Thereof and Uses Thereof.
U.S. Appl. No. 18/660,847 2024/0400703, filed May 10, 2024 Dec. 5, 2024, Kristel Kemper, Antibodies Capable of Binding to OX40, Variants Thereof and Uses Thereof.
Guo et al., PD-1 Blockade and OX40 triggering synergistically protects against tumor growth in a Murine Model of ovarian cancer, PLOS One, Feb. 2014, 9(2): e89350.
Calvo et al., Interim results of a phase 1/2 study of JNJ-63723283, an anti-PD-1 monoclonal antibody, in patients with advanced cancers., Journal of Clinical Oncology, 2018, 36 (Suppl. 5): Abstract 58.
Fu et al., Therapeutic strategies for the costimulatory molecule OX40 in T-cell-mediated immunity, Acta Pharmaceutica Sinica B, 2020, 10(3): 414-433.
Garber et al., Immune agonist antibodies face critical test, Nat. Rev. Drug Discov., Jan. 2020, 19(1): 3-5.
Hardy et al., A Monoclonal Antibody against a Human B Lymphoblastoid Cell Line Induces Tumor Regression in Mice, Cancer Research, Nov. 15, 1994, 54(22): 5793-5796.
Huang et al., Safety, Activity, and Biomarkers of SHR-1210, an Anti-PD-1 Antibody, for Patients with Advanced Esophageal Carcinoma, Clinical Cancer Research, Mar. 15, 2018, 24(6): 1296-1304.
Ishida et al., Induced expression of PD-1, a novel member of the immunoglobulin gene superfamily, upon programmed cell death, The EMBO Journal, 1992, 11(11): 3887-3895.
Johnson et al., Phase I trial of the programmed death receptor 1 (PD-1) inhibitor, BI 754091, in patients (pts) with advanced solid tumors, Journal of Clinical Oncology, 2018, 36(5): Abstract 212.
Labrijn et al., Efficient generation of stable bispecific IgG1 by controlled Fab-arm exchange, PNAS, 2013, 110(13): 5145-5150.
Lao et al., OX40 enhances T cell immune response to PD-1 blockade therapy in non-small cell lung cancer, Int Immunopharmacology, Jul. 2022, 108: 108813.
Li et al., A Mini-Review for Cancer Immunotherapy: Molecular Understanding of Pd-1/PD-L1 Pathway & Translational Blockade of Immune Checkpoints, Int J of Molecular Sciences, Jul. 18, 2016, 17: 1151.
Ma et al., Combination of PD-1 Inhibitor and OX40 Agonist Induces Tumor Rejection and Immune Memory in Mouse Models of Pancreatic Cancer, Gastroenterology, 2020, 159: 306-319.

(56) References Cited

OTHER PUBLICATIONS

Naing et al., A first-in-human phase I study of the anti-PD-1 antibody PDR001 in patients with advanced solid tumors, Journal of Clinical Oncology, 2016, 34 (Suppl 15): 3060 (Abstract 3060).

Needleman et al., A general method applicable to the search for similarities in the amino acid sequence of two proteins, J Mol Biol, Mar. 1970, 48(3): 443-453.

Sasikumar et al., Small-Molecule Immune Checkpoint Inhibitors Targeting PD1/PDL1 and Other Emerging Checkpoint Pathways, Bio Drugs, 2018, 32: 481-497.

Shaabani et al., A patent review on PD-1/PD-L1 antagonists: small molecules, peptides, and macrocycles (2015-2018), Taylor & Francis, Sep. 2, 2018, 28(9): 665-678.

Taylor et al., Identification of a soluble OX40 isoform: development of a specific and quantitative immunoassay, Elsevier, Sep. 2001, 255(1-2): 67-72.

Youssef et al., Abstract 2667: In vitro properties and pre-clinical activity of PF-06801591, a high-affinity engineered anti-human PD-1, Cancer research, 2017, 33 (Suppl 13): 2667.

U.S. Appl. No. 19/062,470, filed Feb. 25, 2025, Kristel Kemper, Antibodies Capable of Binding to OX40, Variants Thereof and Uses Thereof.

U.S. Appl. No. 19/062,474, filed Feb. 25, 2025, Kristel Kemper, Antibodies Capable of Binding to OX40, Variants Thereof and Uses Thereof.

\* cited by examiner

*Figure 1 – continued*
B
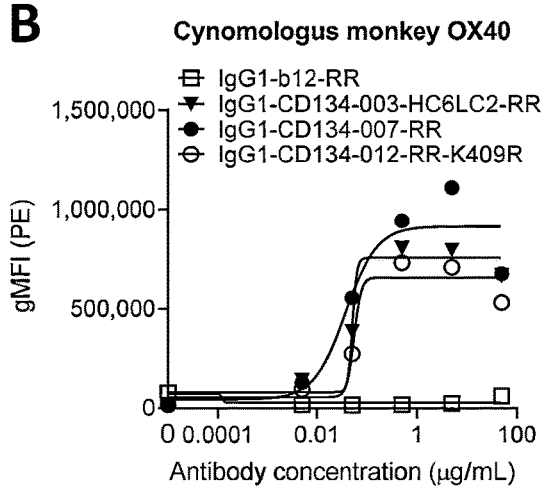
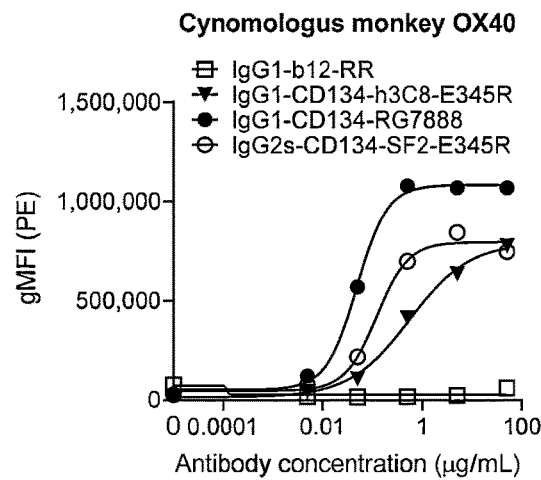
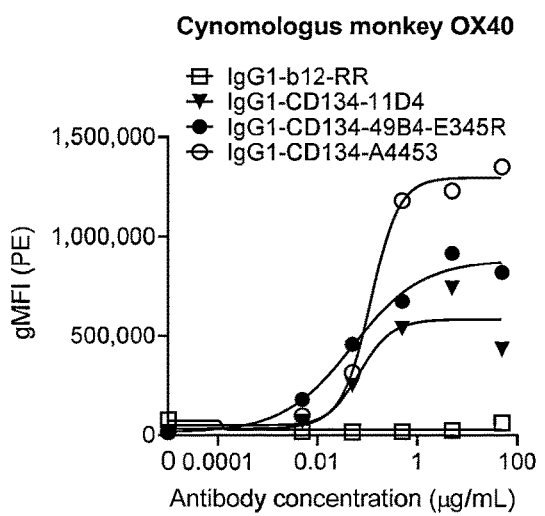
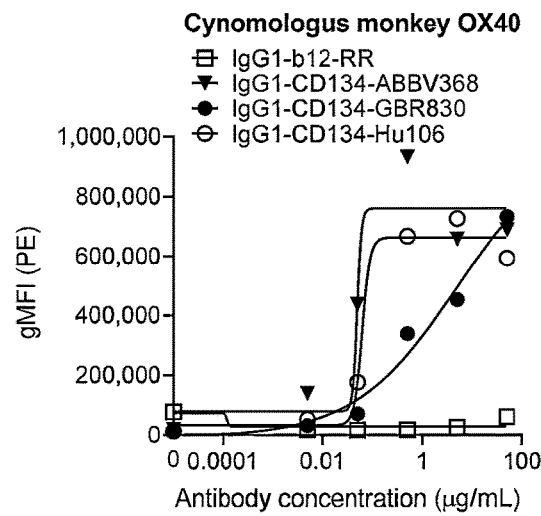
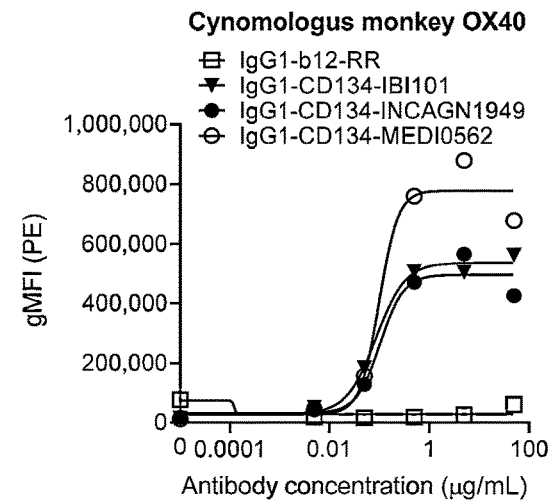

Figure 3

```
                              10        20        30        40        50
TNR4_HUMAN           MCVGARRLGRGPCAALLL-LGLGLSTVTGLHCVGDTYPSNDRCCHECRPG
TNR4_HUMAN Shuffle 1 MCVGARRLGRGPCAALLL-LGLGLSTVTGLNCVKHTYPSGHKCCRECQPG
                                                         Shuffle 1
TNR4_HUMAN Shuffle 2 MCVGARRLGRGPCAALLL-LGLGLSTVTGLHCVGDTYPSNDRCCHECRPG
TNR4_HUMAN Shuffle 3 MCVGARRLGRGPCAALLL-LGLGLSTVTGLHCVGDTYPSNDRCCHECRPG
TNR4_HUMAN Shuffle 4 MCVGARRLGRGPCAALLL-LGLGLSTVTGLHCVGDTYPSNDRCCHECRPG
TNR4_MOUSE           ----MYVWVQQPTALLLALTLGV-TARRLNCVKHTYPSGHKCCRECQPG 60        70        80        90       100
TNR4_HUMAN           NGMVSRCSRSQNTVCRPCGPGFYNDVVSSKPCKPCTWCNLRSGSERKQLC
TNR4_HUMAN Shuffle 1 HGMVSRCDHTRDTLCHPCGPGFYNDVVSSKPCKPCTWCNLRSGSERKQLC
                            Shuffle 1
TNR4_HUMAN Shuffle 2 NGMVSRCSRSQNTVCRPCETGFYNEAVNYDTCKQCTQCNHRSGSELKQNC
                                         Shuffle 2
TNR4_HUMAN Shuffle 3 NGMVSRCSRSQNTVCRPCGPGFYNDVVSSKPCKPCTWCNLRSGSERKQLC
TNR4_HUMAN Shuffle 4 NGMVSRCSRSQNTVCRPCGPGFYNDVVSSKPCKPCTWCNLRSGSERKQLC
TNR4_MOUSE           HGMVSRCDHTRDTLCHPCETGFYNEAVNYDTCKQCTQCNHRSGSELKQNC 110       120       130       140       150
TNR4_HUMAN           TATQDTVCRCRAGTQP-LDS-YKPGVDCAPCPPGHFSPGDNQACKPWTNC
TNR4_HUMAN Shuffle 1 TATQDTVCRCRAGTQP-LDS-YKPGVDCAPCPPGHFSPGDNQACKPWTNC
TNR4_HUMAN Shuffle 2 TPTQDTVCRCRAGTQP-LDS-YKPGVDCAPCPPGHFSPGDNQACKPWTNC
TNR4_HUMAN Shuffle 3 TATQDTVCRCRPGTQPRQDSGYKLGVDCVPCPPGHFSPGDNQACKPWTNC
                                Shuffle 3
TNR4_HUMAN Shuffle 4 TATQDTVCRCRAGTQP-LDS-YKPGVDCAPCPPGHFSPGNNQACKPWTNC
                                                           Shuffle 4
TNR4_MOUSE           TPTQDTVCRCRPGTQPRQDSGYKLGVDCVPCPPGHFSPGNNQACKPWTNC 160       170       180       190       200
TNR4_HUMAN           TLAGKHTLQPASNSSDAICEDRDPPATQPQETQGPPARPITVQPTEAWPR
TNR4_HUMAN Shuffle 1 TLAGKHTLQPASNSSDAICEDRDPPATQPQETQGPPARPITVQPTEAWPR
TNR4_HUMAN Shuffle 2 TLAGKHTLQPASNSSDAICEDRDPPATQPQETQGPPARPITVQPTEAWPR
TNR4_HUMAN Shuffle 3 TLAGKHTLQPASNSSDAICEDRDPPATQPQETQGPPARPITVQPTEAWPR
TNR4_HUMAN Shuffle 4 TLSGKQTRHPASDSLDAVCEDRDPPATQPQETQGPPARPITVQPTEAWPR
TNR4_MOUSE           TLSGKQTRHPASDSLDAVCEDRSLLATLLWETQRPTERPTTVQSTTVWPR 210       220       230       240       250
TNR4_HUMAN           TSQGPSTRPVEVPGGRAVAAILGLGLVLGLLGPLAILLALYLLRRDQRLP
TNR4_HUMAN Shuffle 1 TSQGPSTRPVEVPGGRAVAAILGLGLVLGLLGPLAILLALYLLRRDQRLP
TNR4_HUMAN Shuffle 2 TSQGPSTRPVEVPGGRAVAAILGLGLVLGLLGPLAILLALYLLRRDQRLP
TNR4_HUMAN Shuffle 3 TSQGPSTRPVEVPGGRAVAAILGLGLVLGLLGPLAILLALYLLRRDQRLP
TNR4_HUMAN Shuffle 4 TSQGPSTRPVEVPGGRAVAAILGLGLVLGLLGPLAILLALYLLRRDQRLP
TNR4_MOUSE           TSELPSPPTLVTPEGPAFAVLGLG--LGLLAPLTVLLALYLLRKAWRLP 260       270       280
TNR4_HUMAN           PDAHKPPGGGSFRTPIQEEQADAHSTLAKI
TNR4_HUMAN Shuffle 1 PDAHKPPGGGSFRTPIQEEQADAHSTLAKI
TNR4_HUMAN Shuffle 2 PDAHKPPGGGSFRTPIQEEQADAHSTLAKI
TNR4_HUMAN Shuffle 3 PDAHKPPGGGSFRTPIQEEQADAHSTLAKI
TNR4_HUMAN Shuffle 4 PDAHKPPGGGSFRTPIQEEQADAHSTLAKI
TNR4_MOUSE           -NTPKPCWGNSFRTPIQEEHTDAHFTLAKI
```

*Figure 4*

```
                         10         20         30         40         50
Human (TNR4_HUMAN)  MCVGARRLGRGPCAALLLLGLGLS-TVTGLHCVGDTYPSNDRCCHECRPG
Mouse (TNR4_MOUSE)  ------MYVWVQQPTALLLLALTLGVTARRLNCVKHTYPSGHKCCRECQPG 60         70         80         90        100
Human (TNR4_HUMAN)  NGMVSRCSRSQNTVCRPCGPGFYNDVVSSKPCKPCTWCNLRSGSERKQLC
Mouse (TNR4_MOUSE)  HGMVSRCDHTRDTLCHPCETGFYNEAVNYDTCKQCTQCNHRSGSELKQNC 110        120        130        140        150
Human (TNR4_HUMAN)  TATQDTVCRCRAGTQP-LDS-YKPGVDCAPCPPGHFSPGDNQACKPWTNC
Mouse (TNR4_MOUSE)  TPTQDTVCRCRPGTQPRQDSGYKLGVDCVPCPPGHFSPGNNQACKPWTNC 160        170        180        190        200
Human (TNR4_HUMAN)  TLAGKHTLQPASNSSDAICEDRDPPATQPQETQGPPARPITVQPTEAWPR
Mouse (TNR4_MOUSE)  TLSGKQTRHPASDSLDAVCEDRSLLATLLWETQRPTERPTTVQSTTVWPR 210        220        230        240        250
Human (TNR4_HUMAN)  TSQGPSTRPVEVPGGRAVAAILGLGLVLGLLGPLAILLALYLLRRDQRLP
Mouse (TNR4_MOUSE)  TSELPSPPTLVTPEGEAFAVLGLG--LGLLAPLTVLLALYLLRKAWRLP 260        270        280
Human (TNR4_HUMAN)  PDAHKPPGGSFRTPIQEEQADAHSTLAKI
Mouse (TNR4_MOUSE)  -NTPKPCWGNSFRTPIQEEHTDAHETLAKI
```

Figure 10
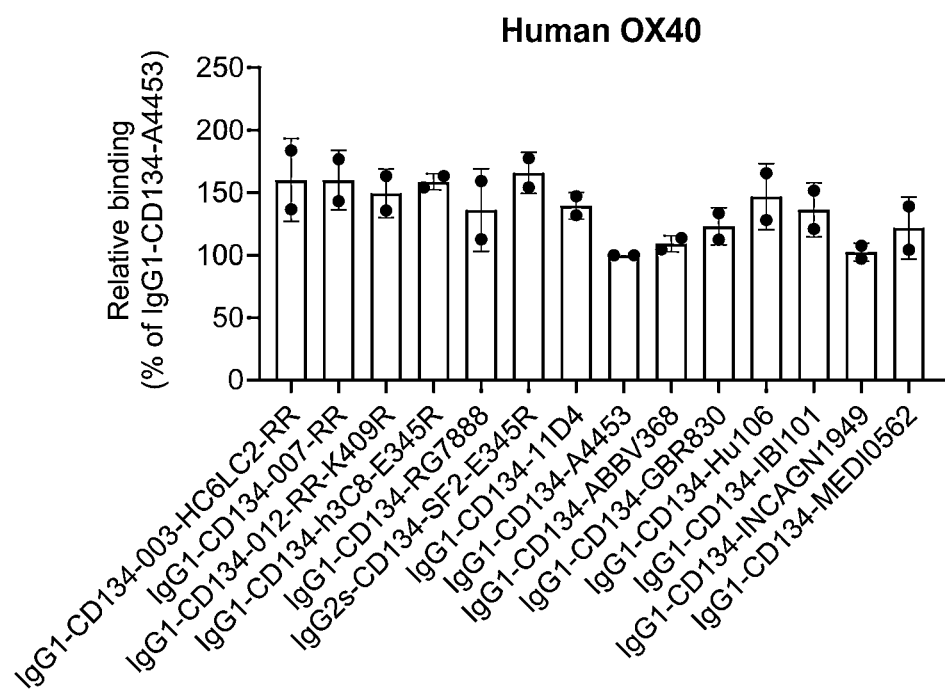
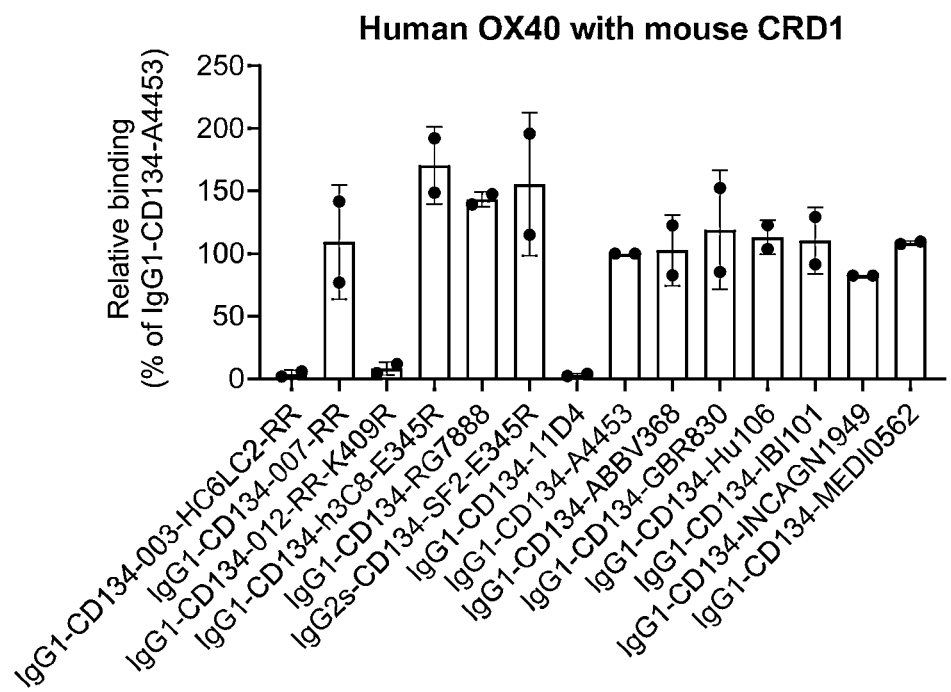

*Figure 10 – continued*
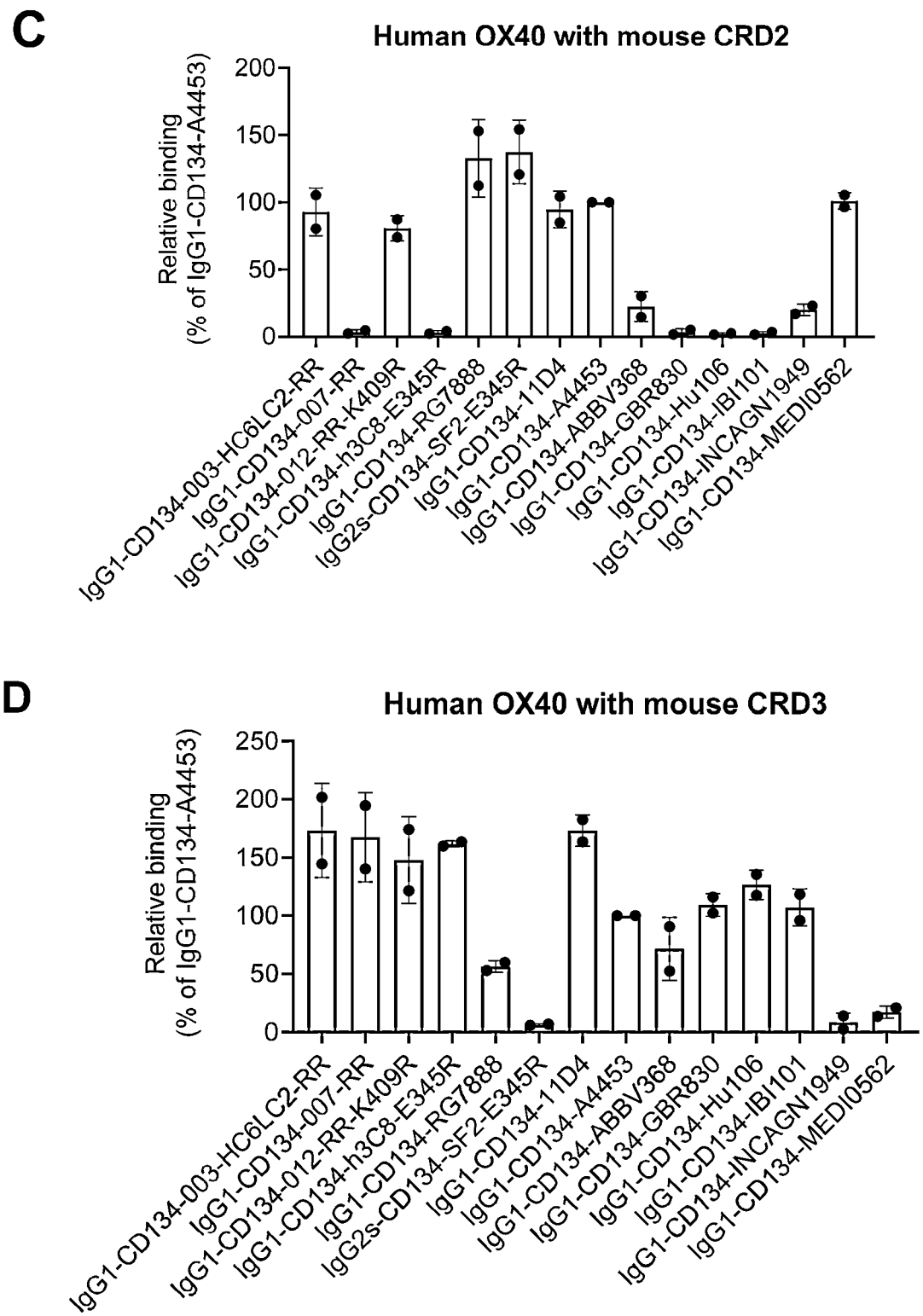

*Figure 10 – continued*
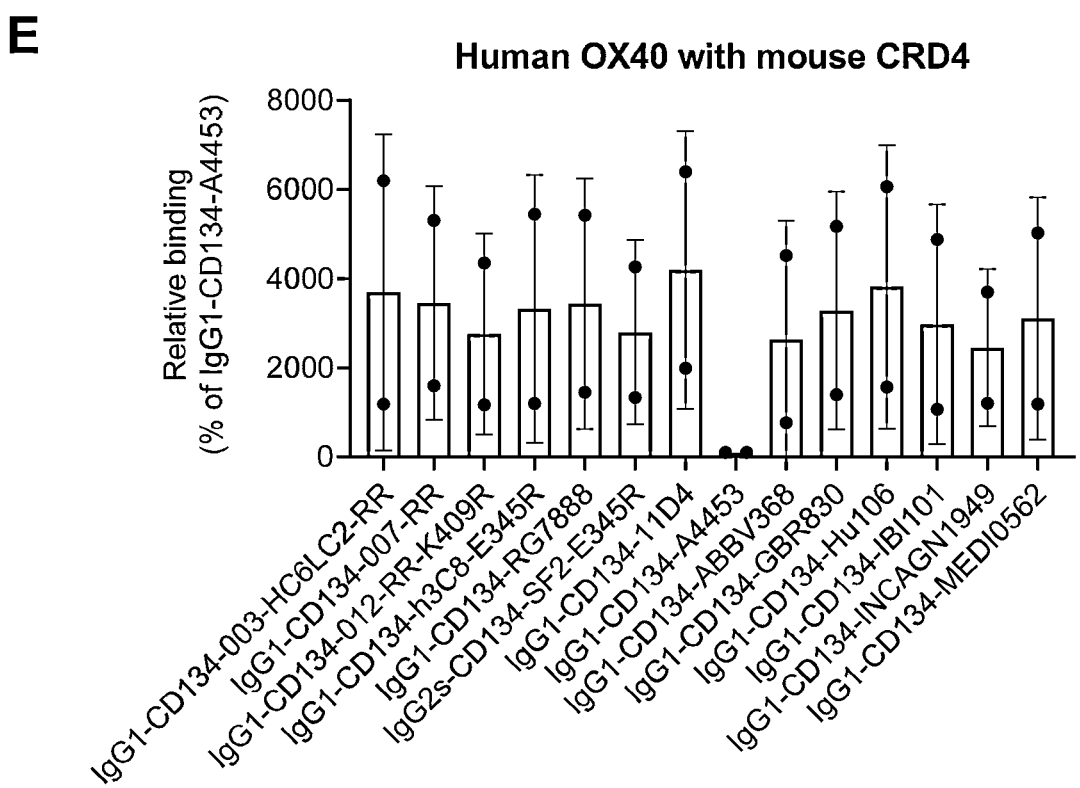

Figure 11:
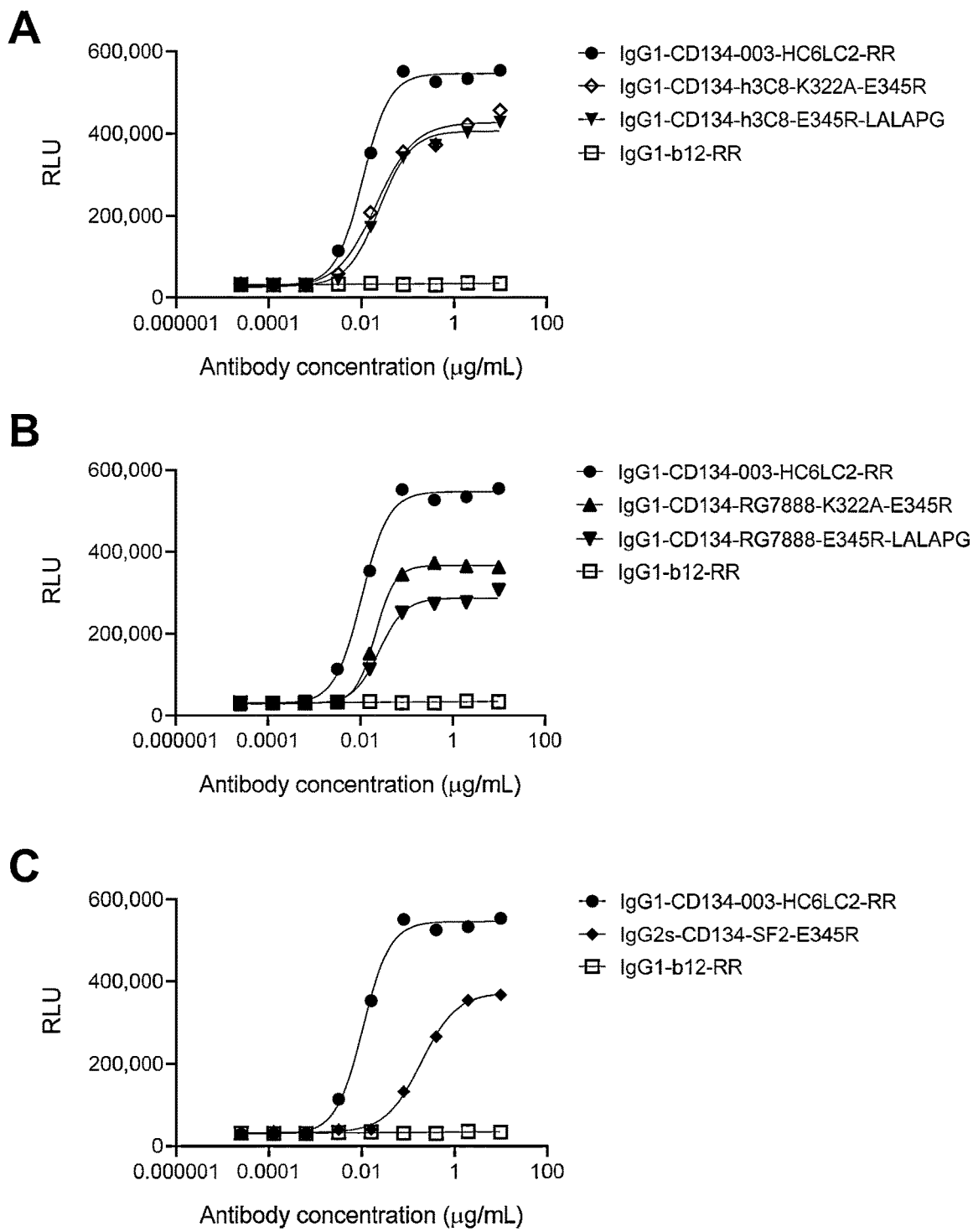

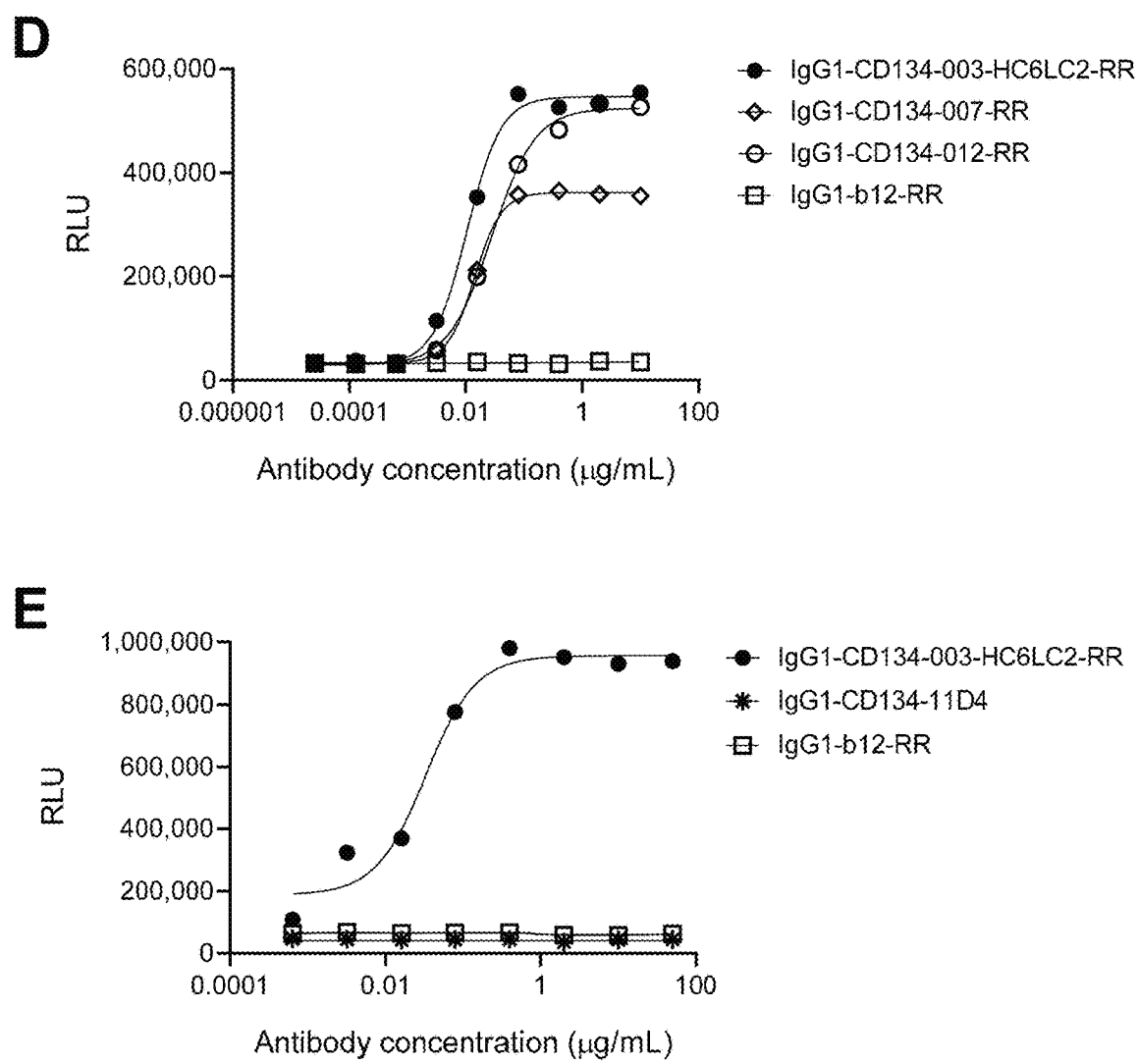
Figure 11 - continued

Figure 13:
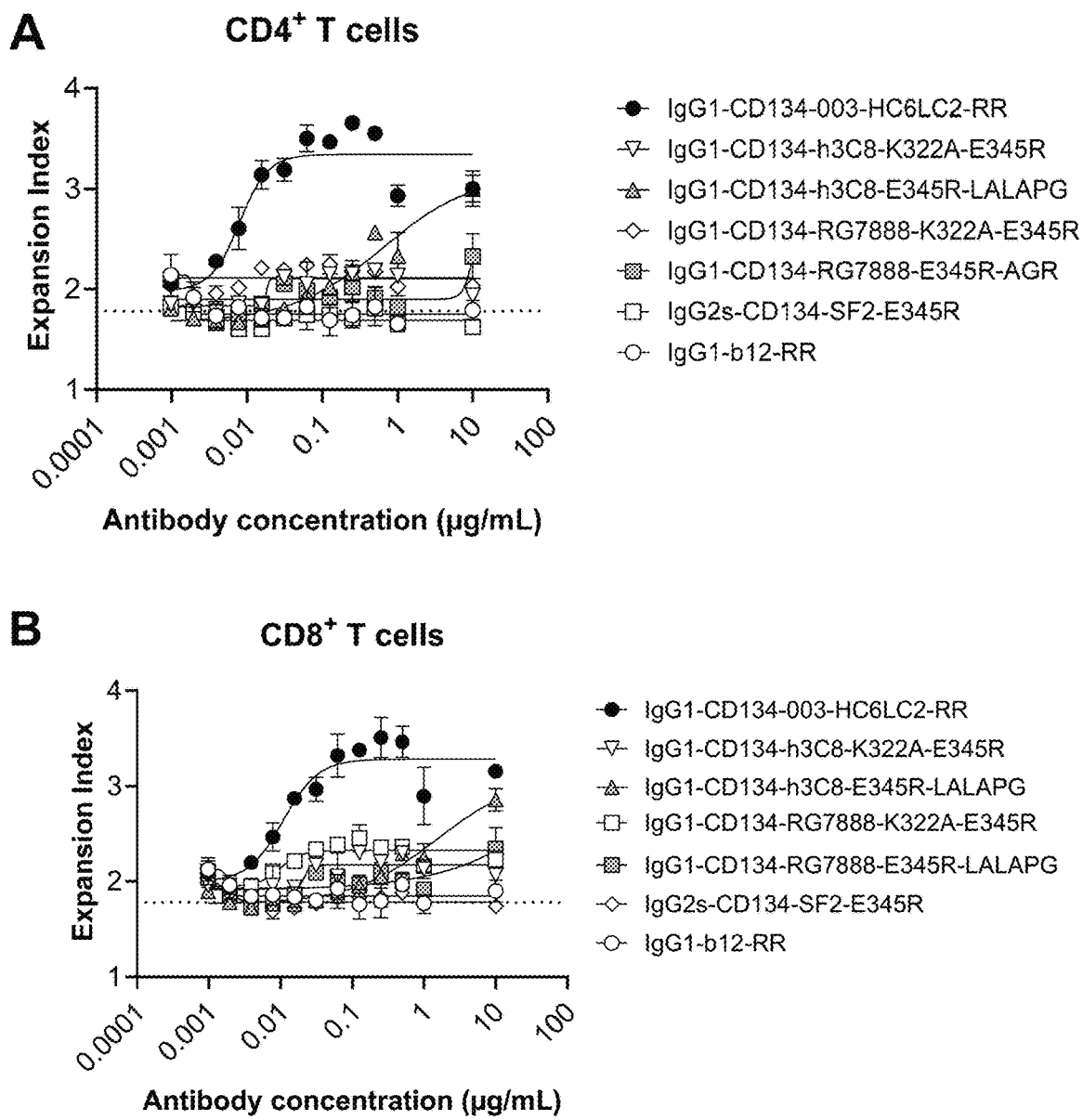

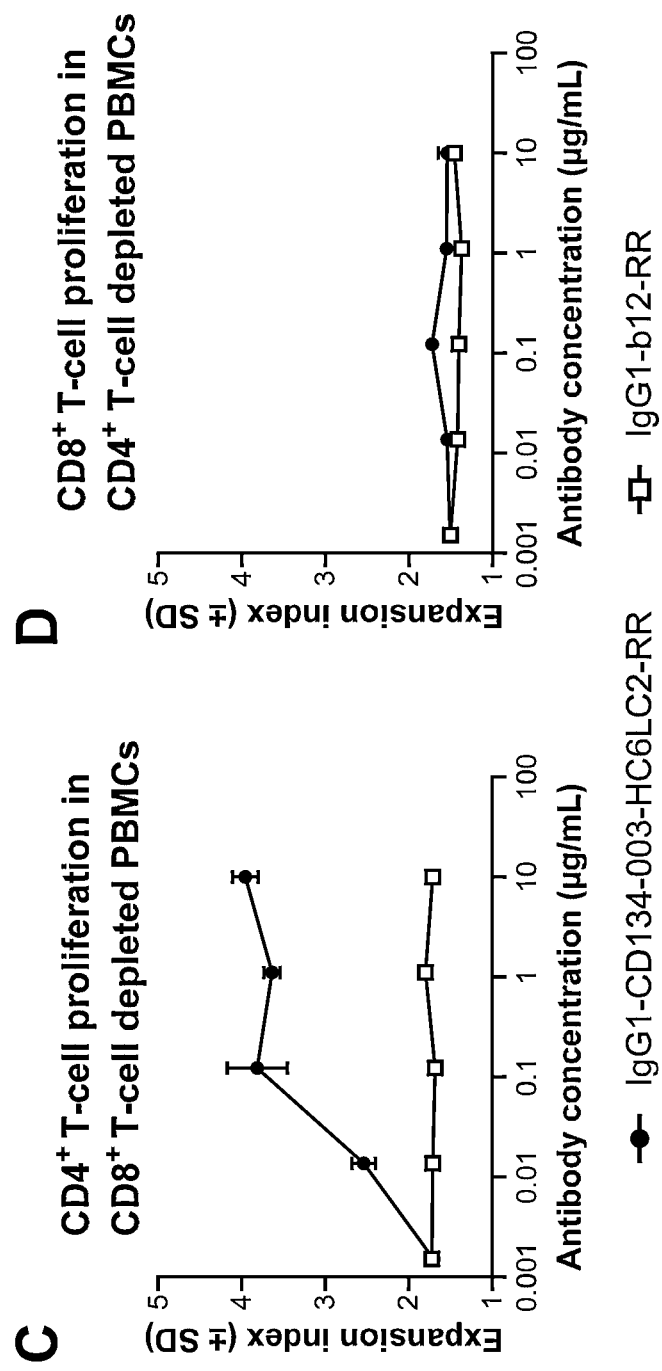
Figure 13 – continued

*Figure 14*
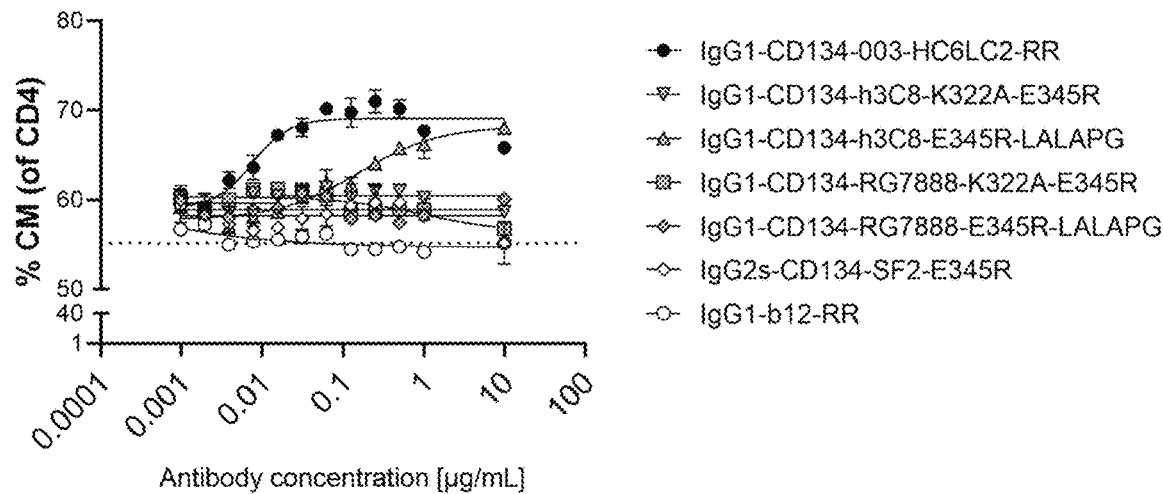
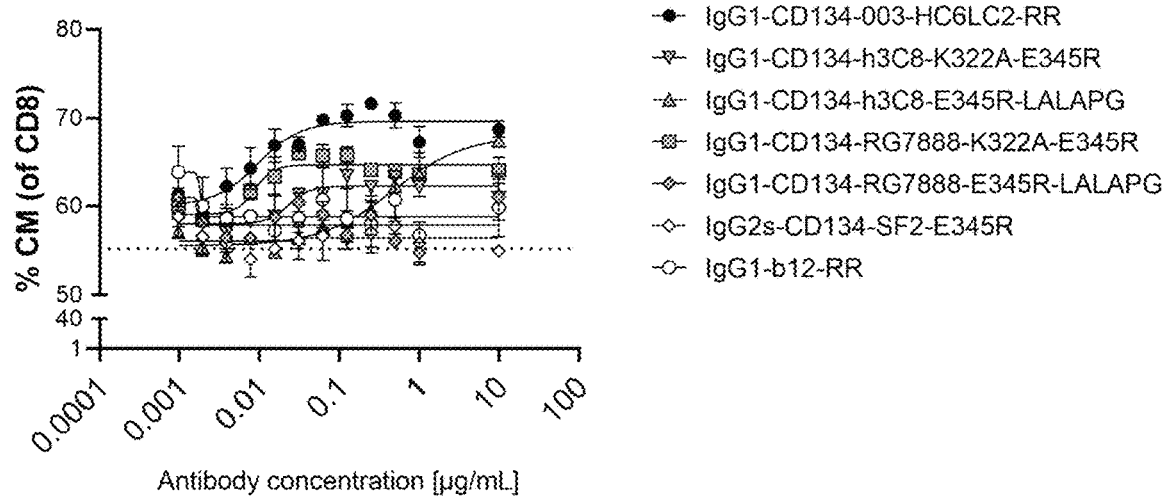

Figure 17:
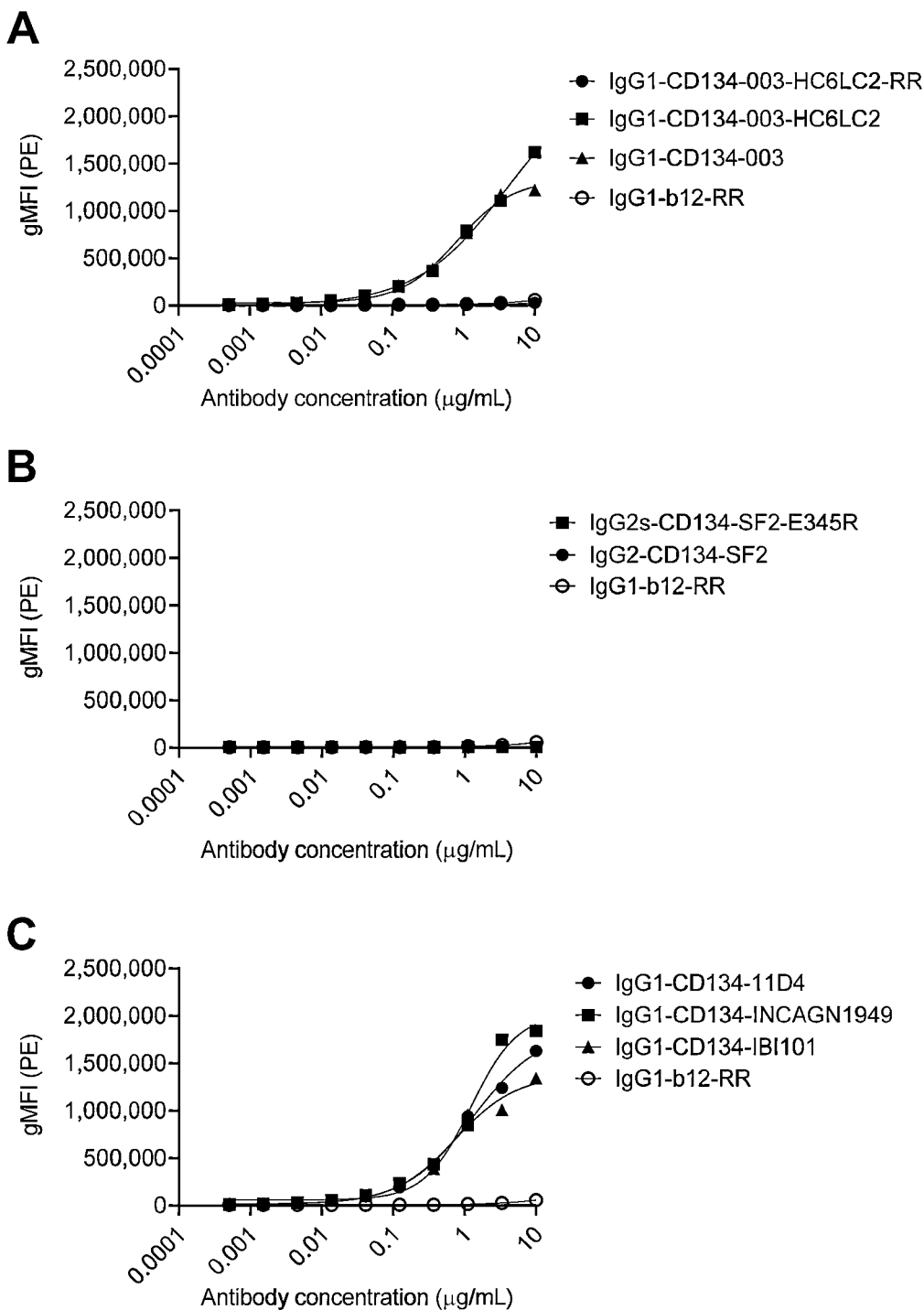

*Figure 17 - continued*
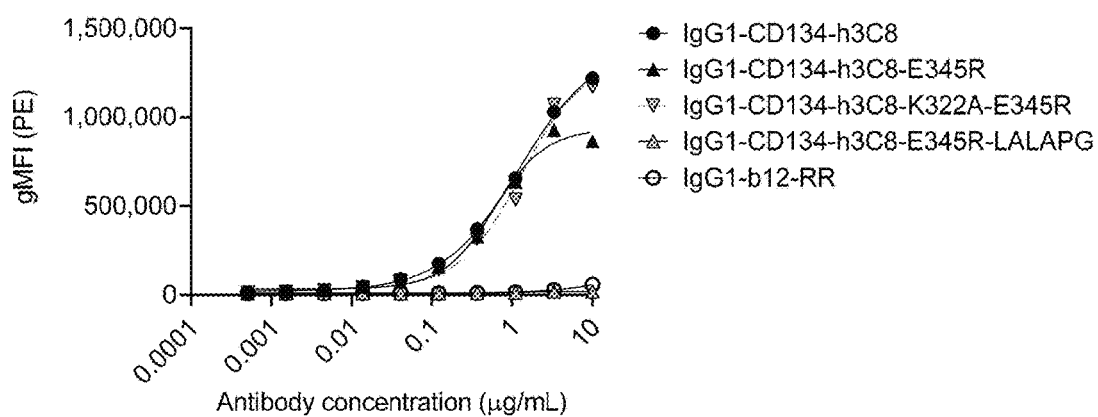
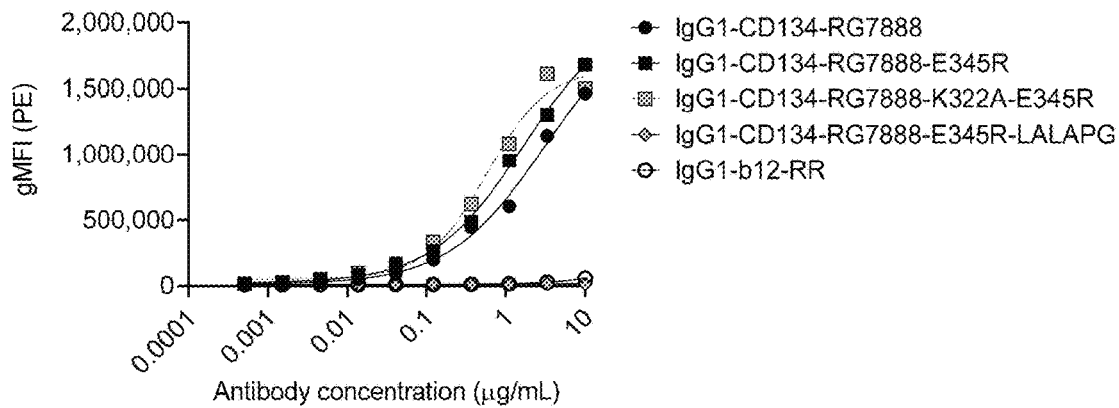

Figure 21:
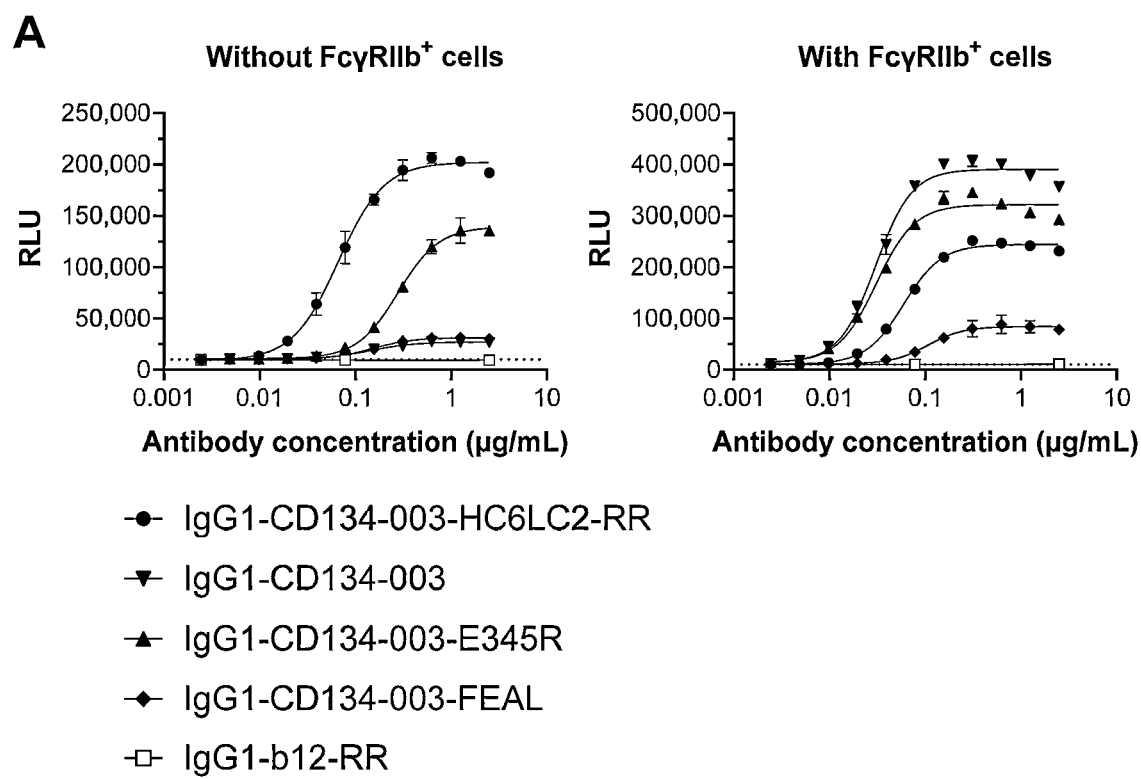

Figure 21 - continued
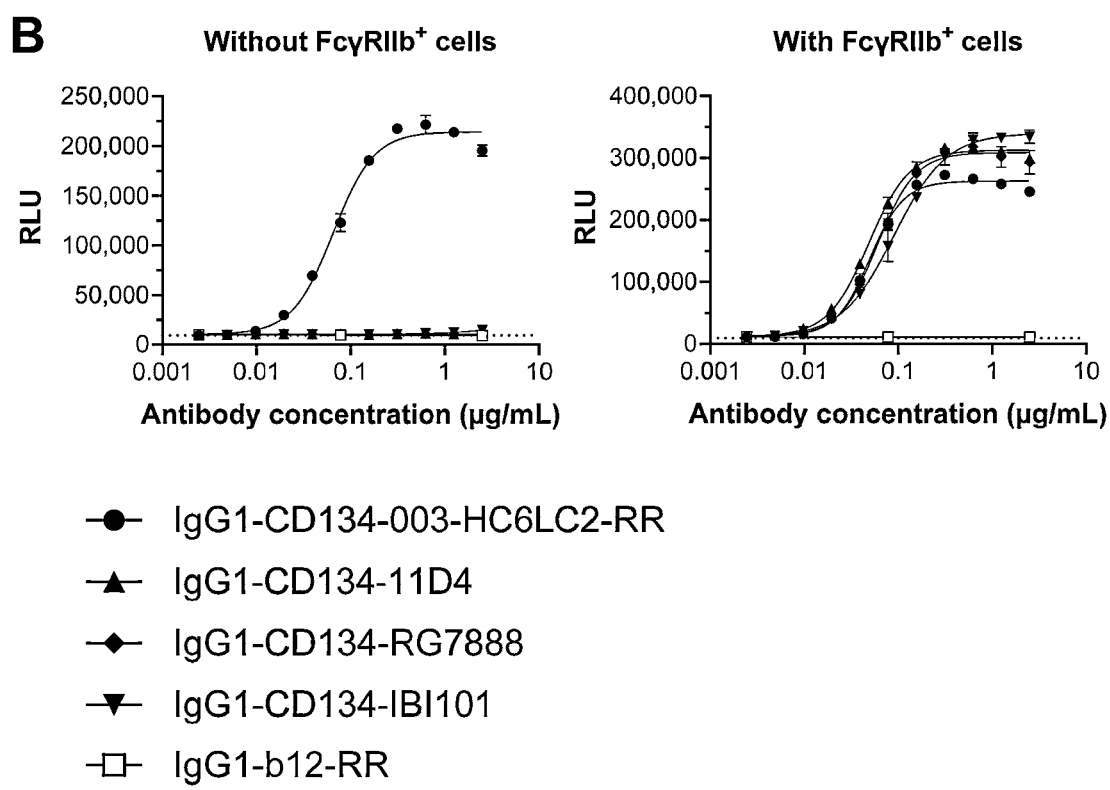

Figure 22:
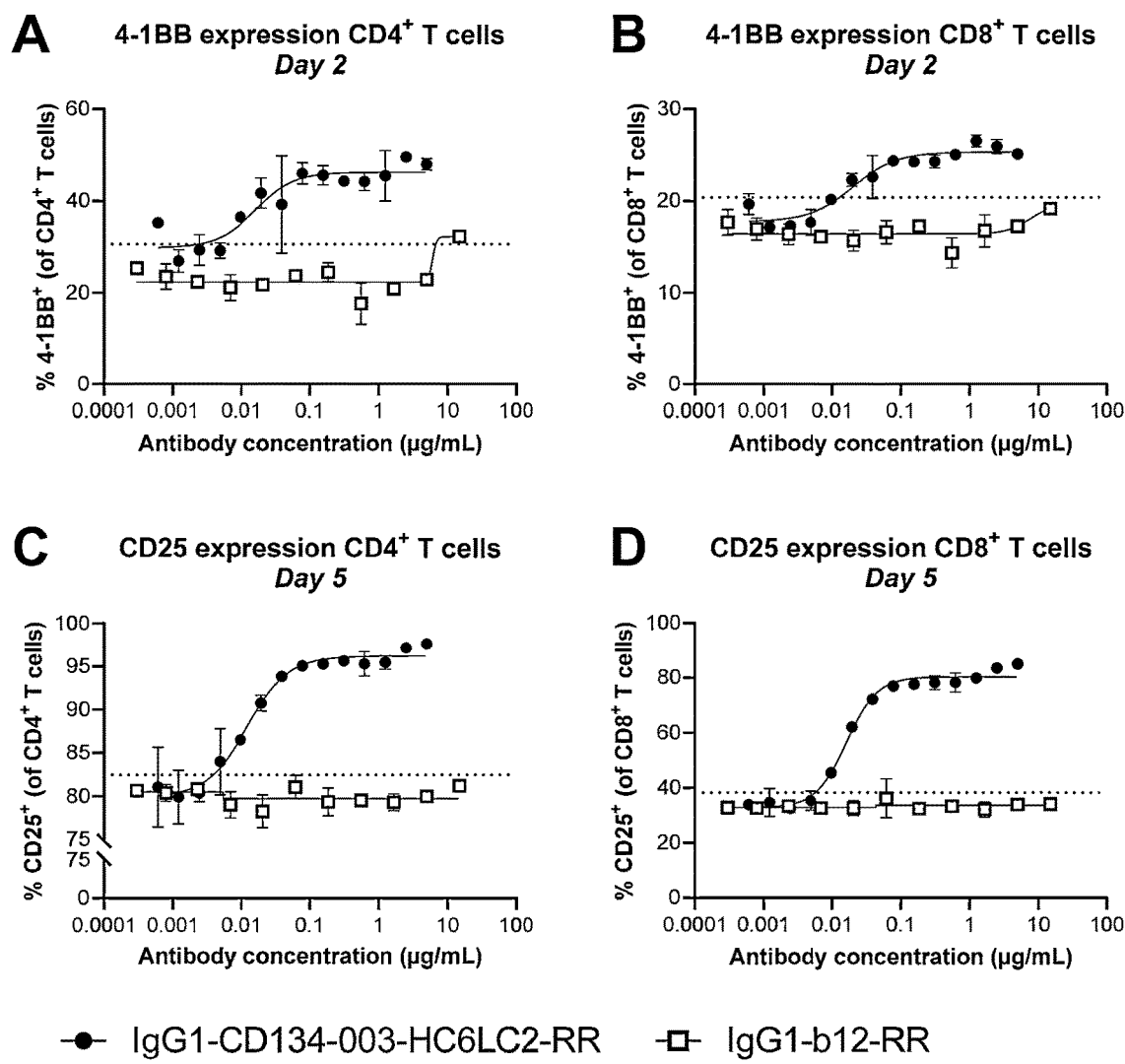

Figure 22 – *continued*
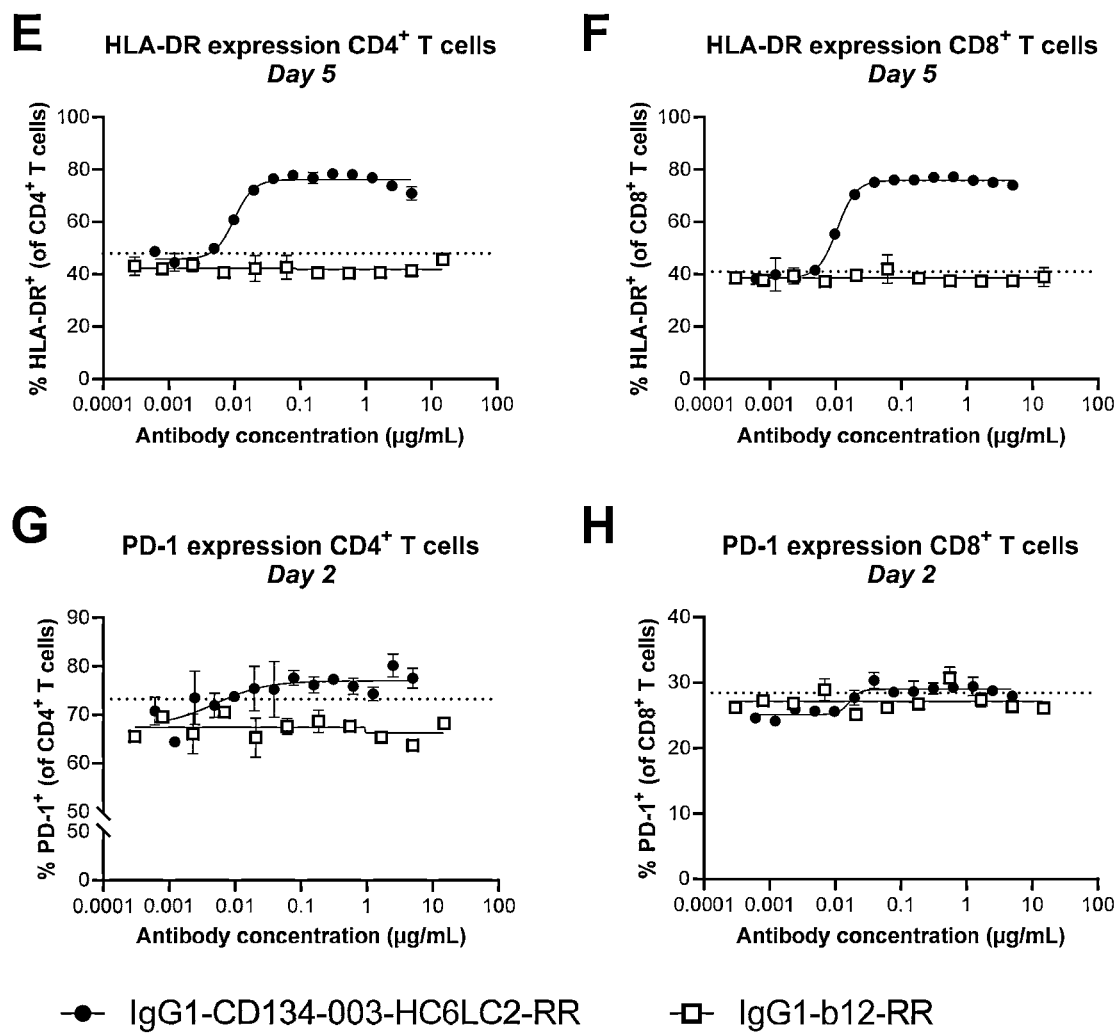

Figure 22 – *continued*
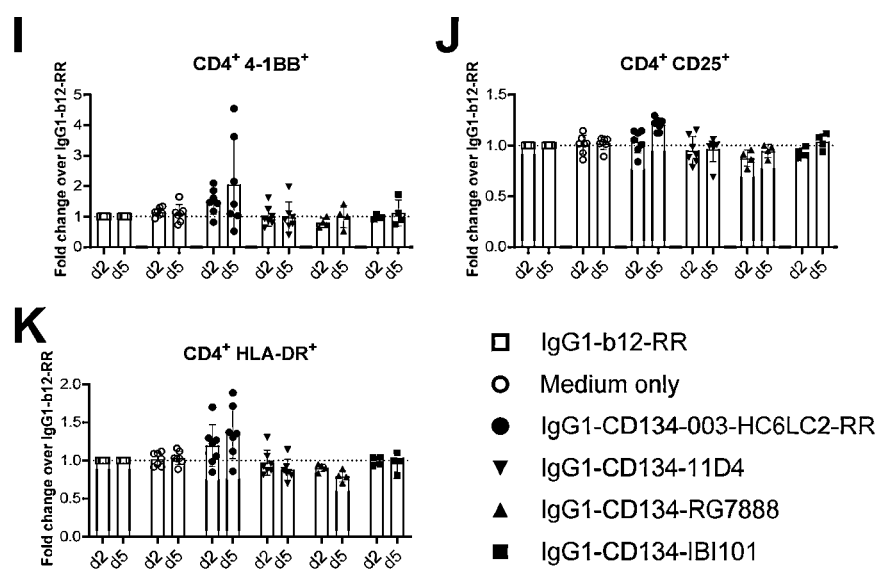

Figure 22 – *continued*
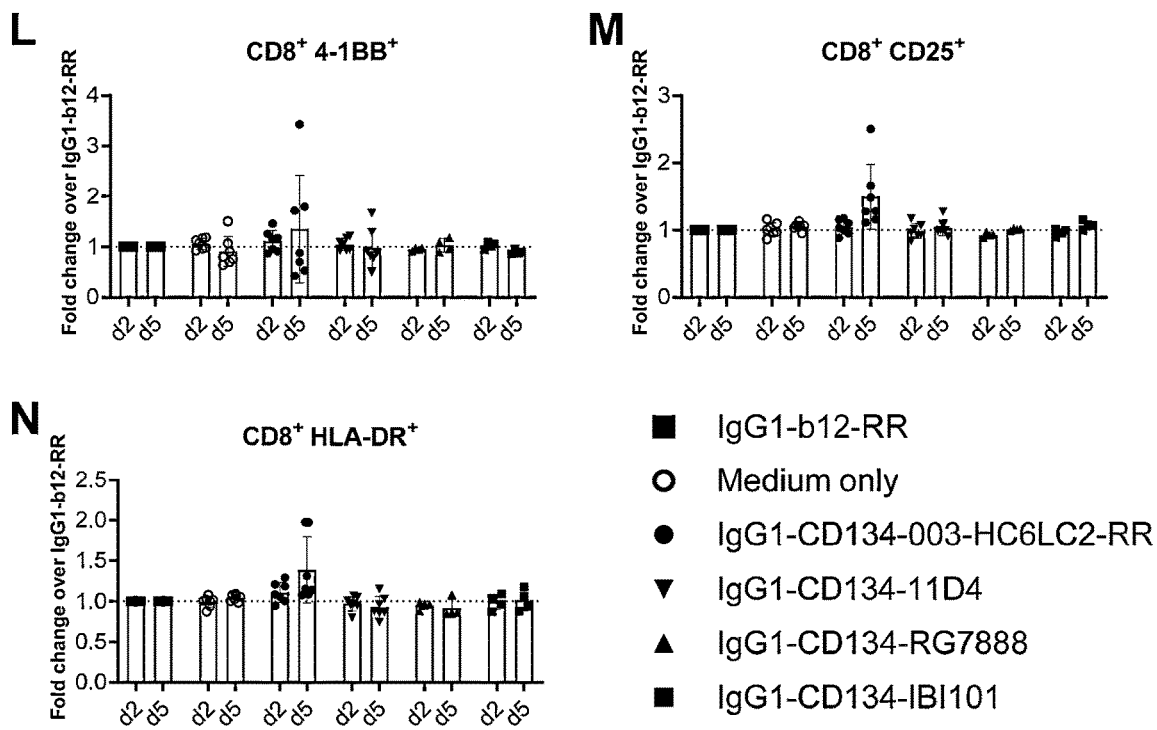

Figure 31
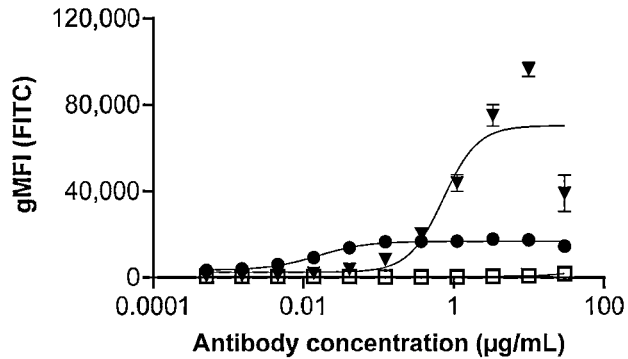
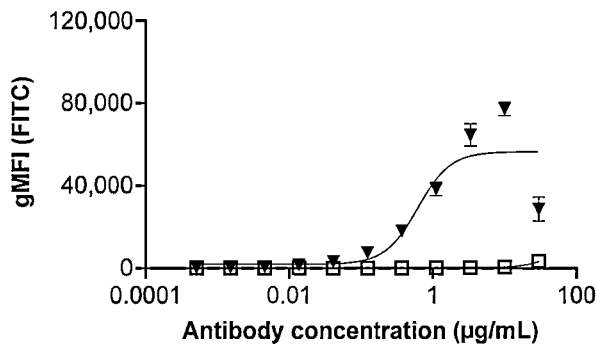
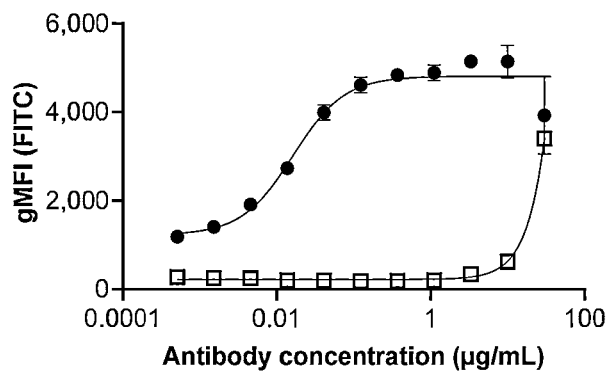

Figure 31 *continued*
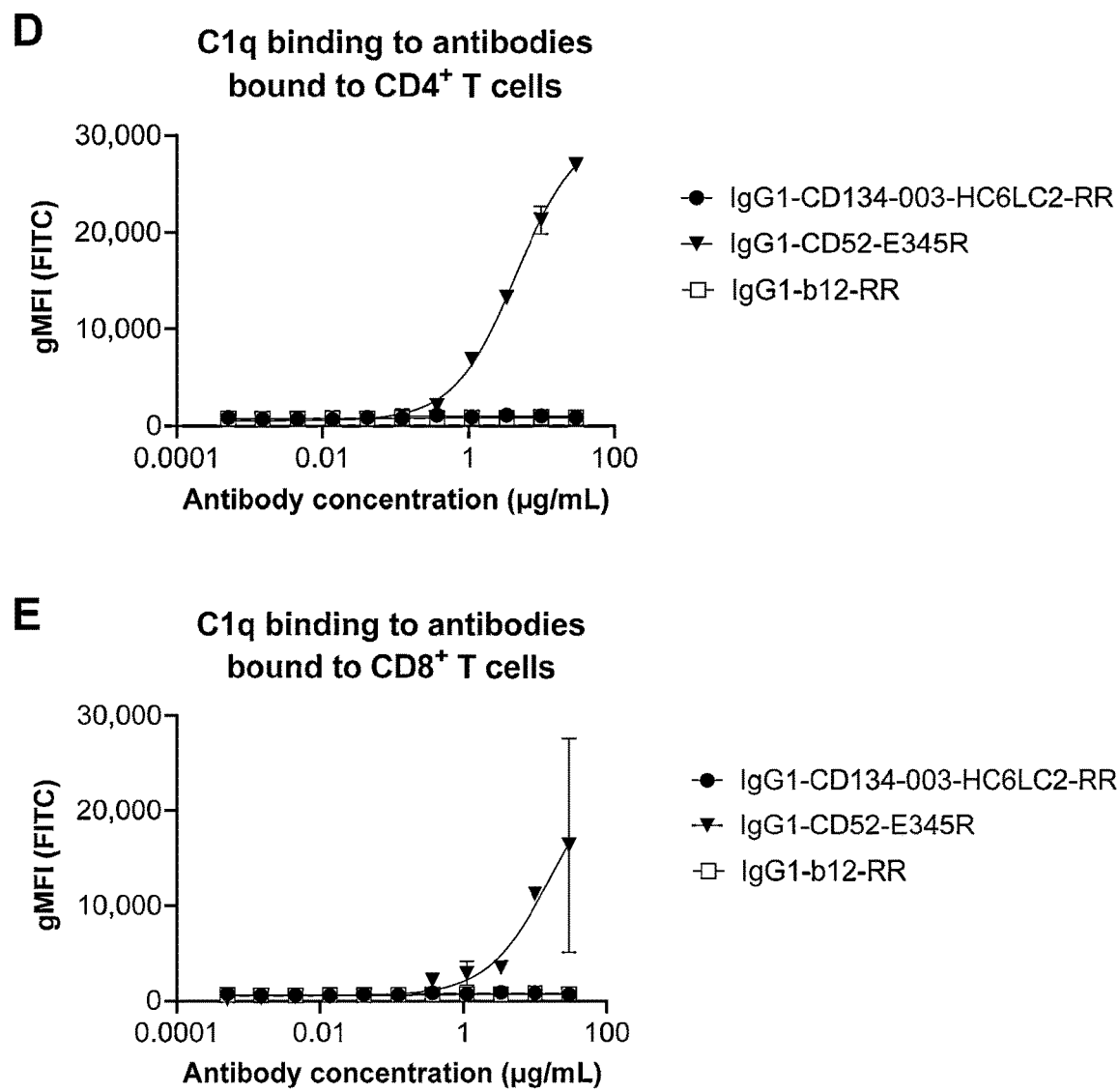

Figure 39:
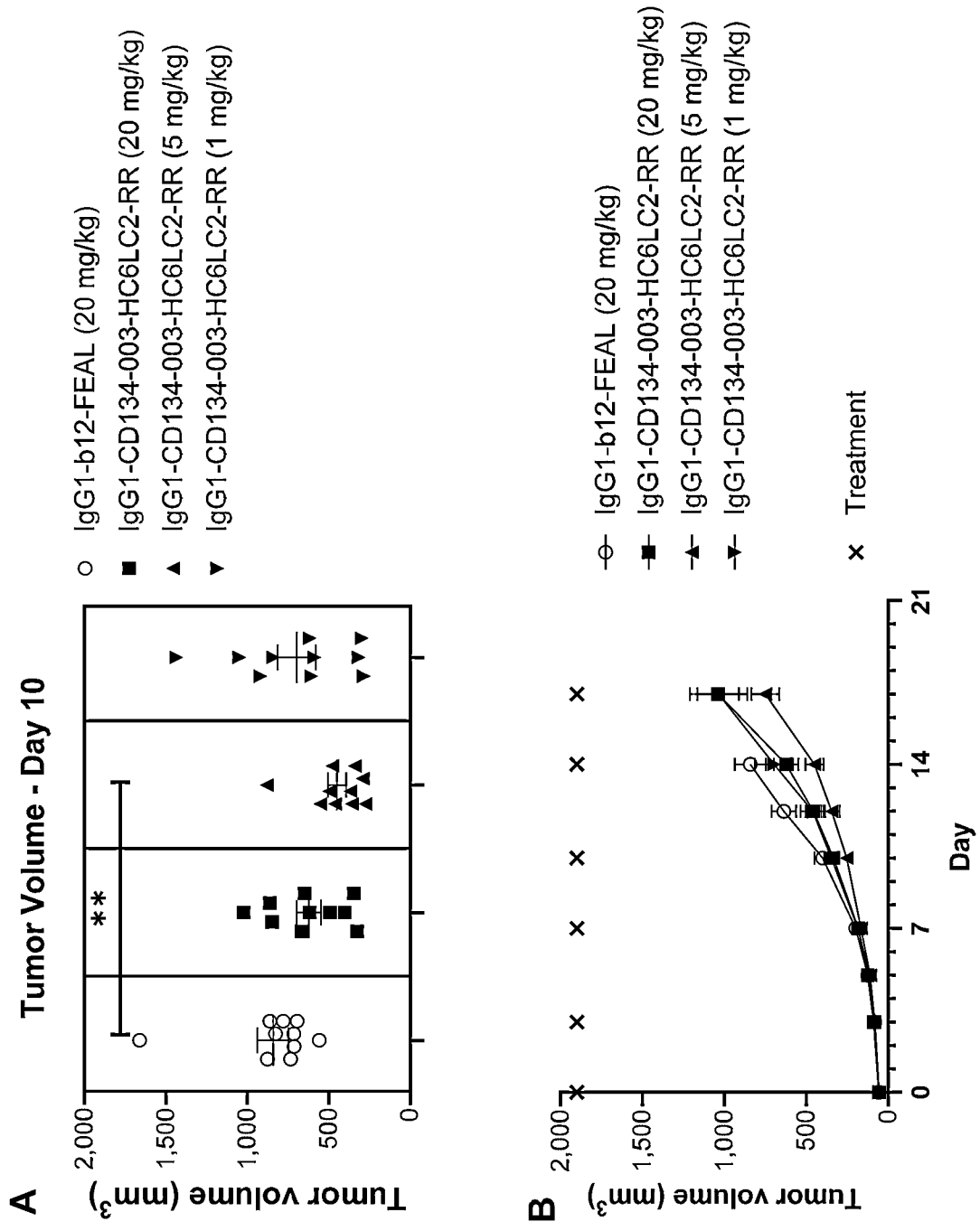

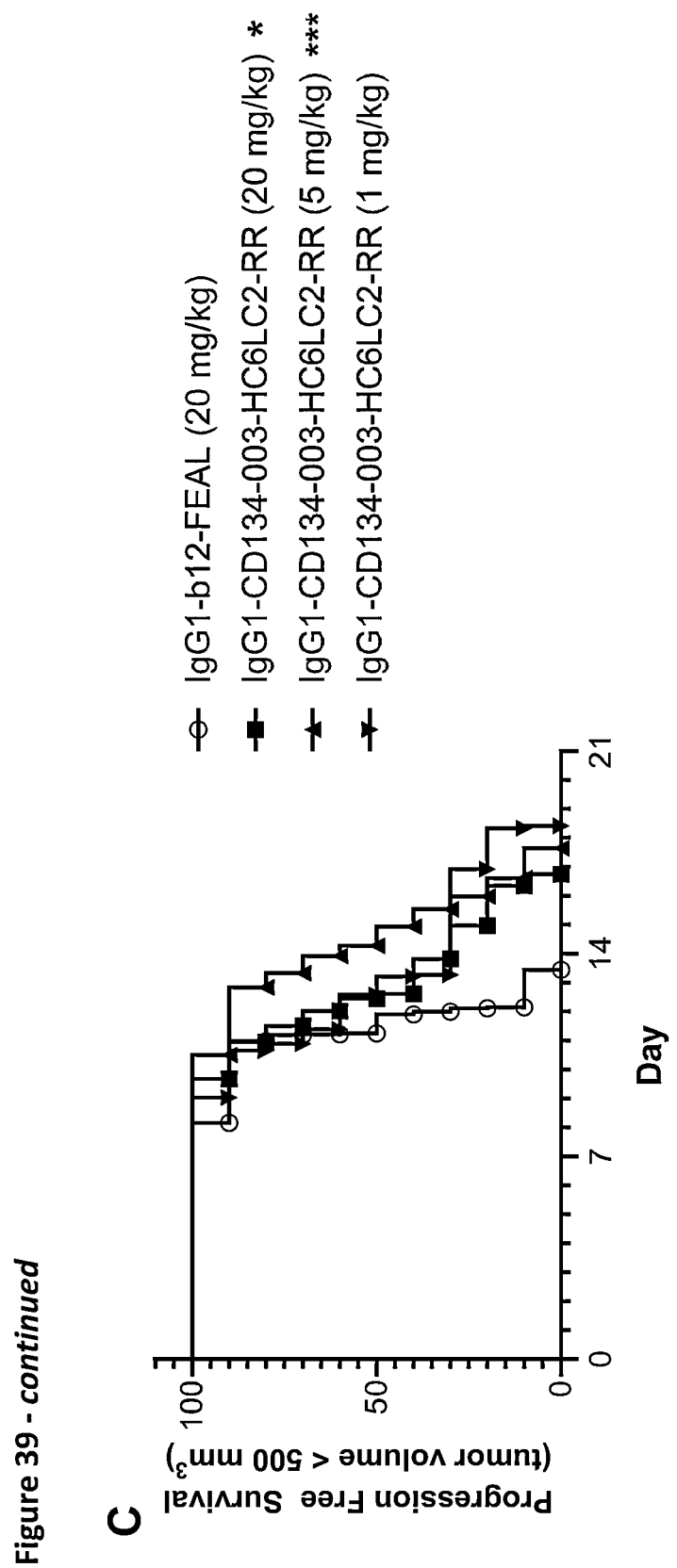
Figure 39 - continued

Figure 44:
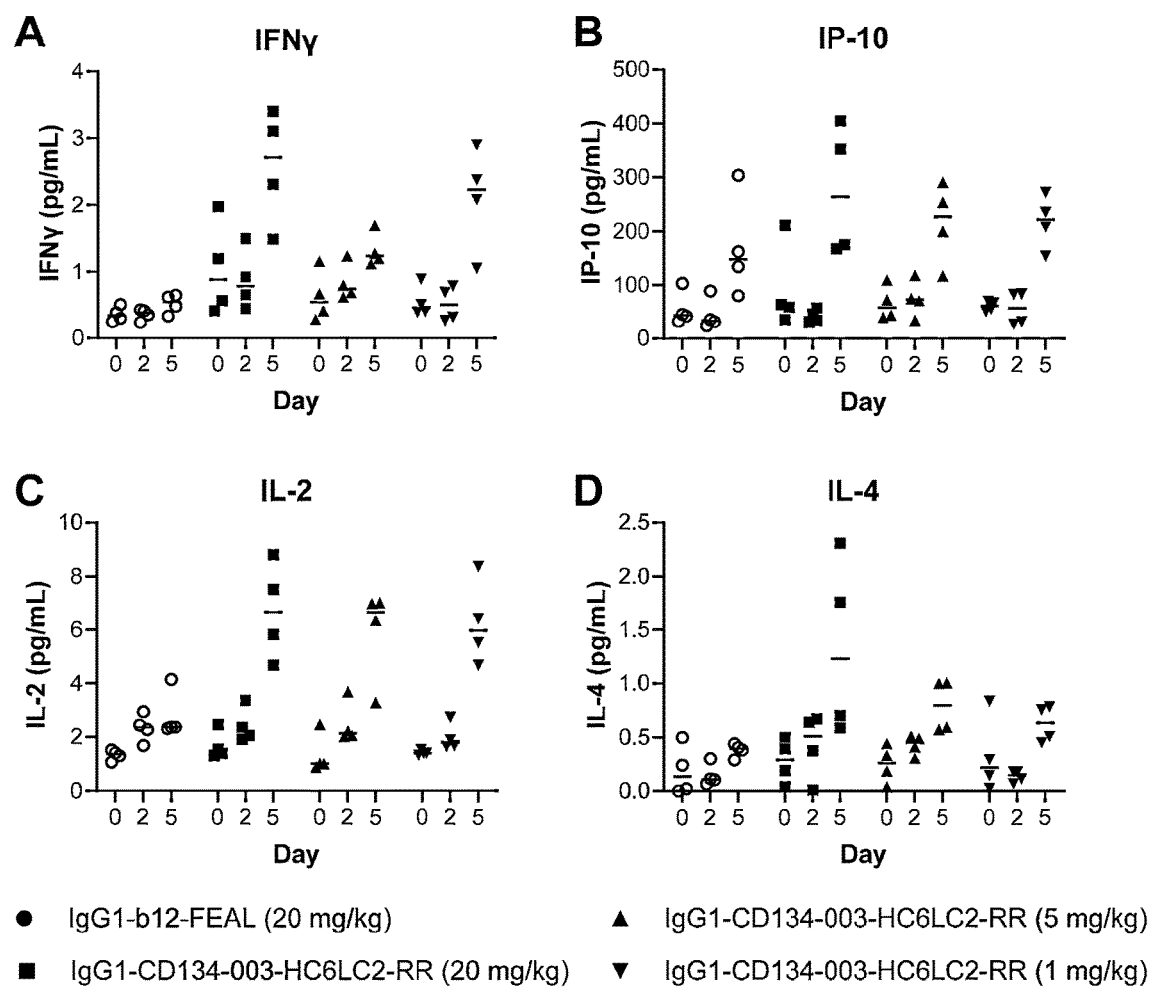

Figure 44 – *continued*
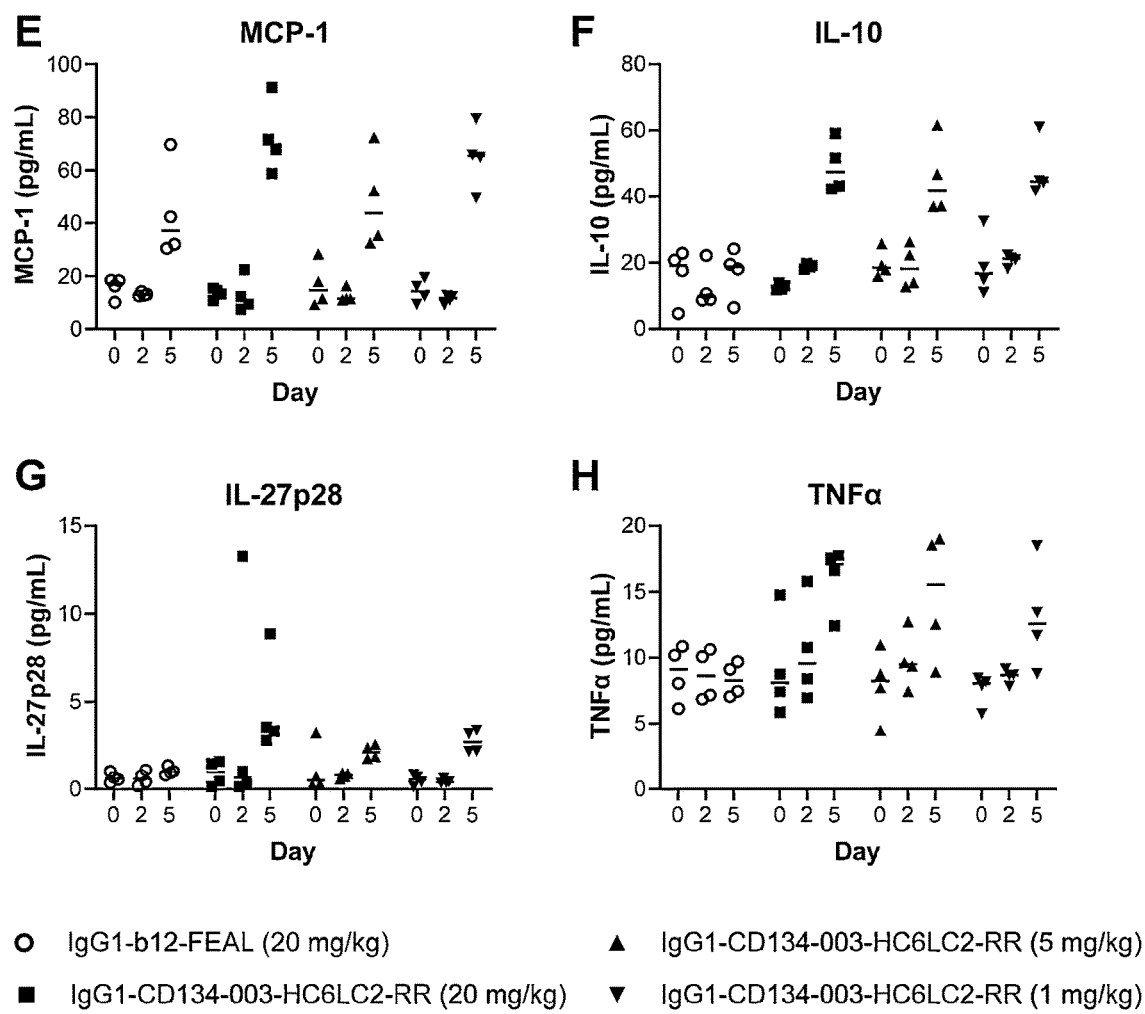

Figure 45:
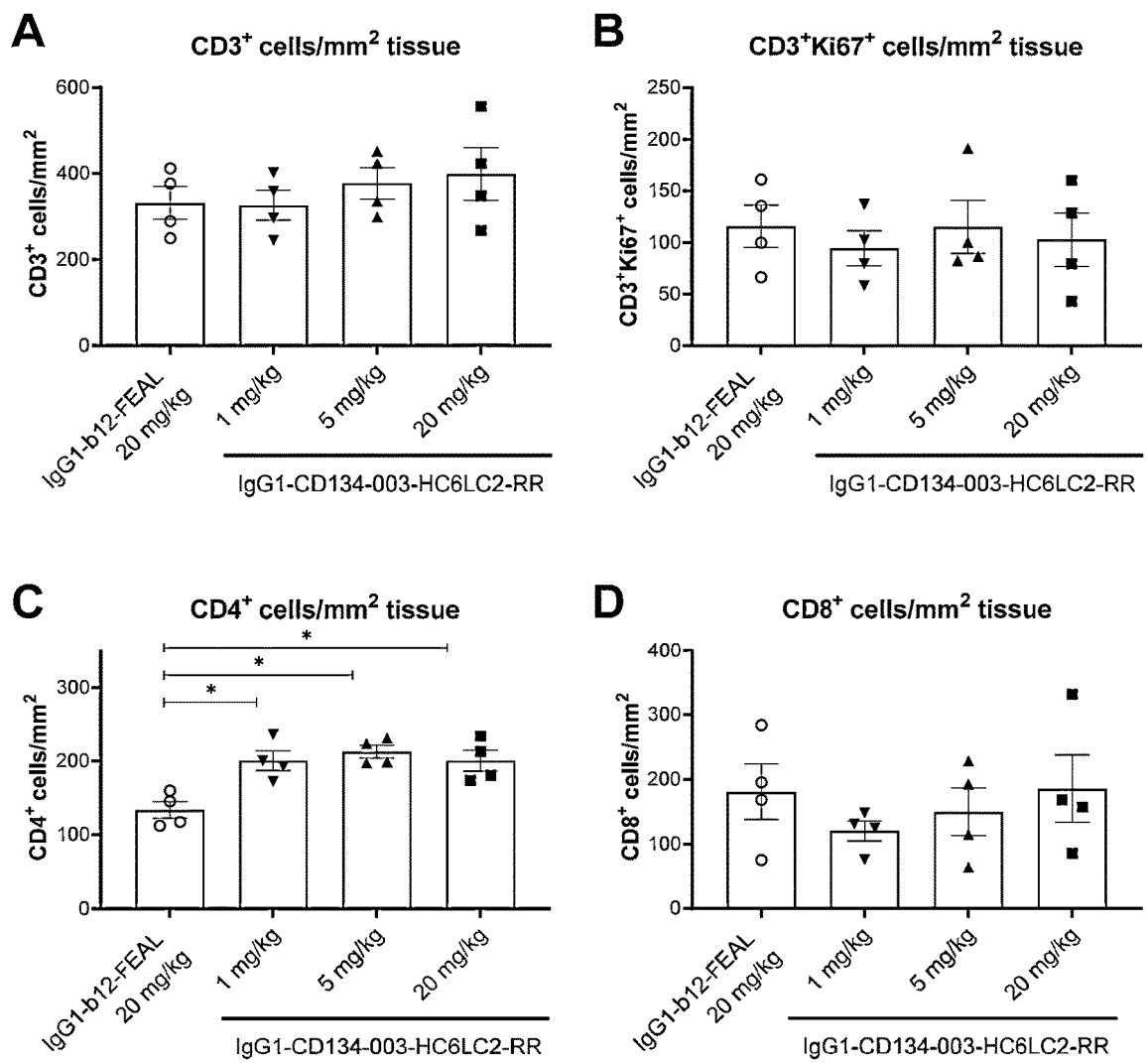

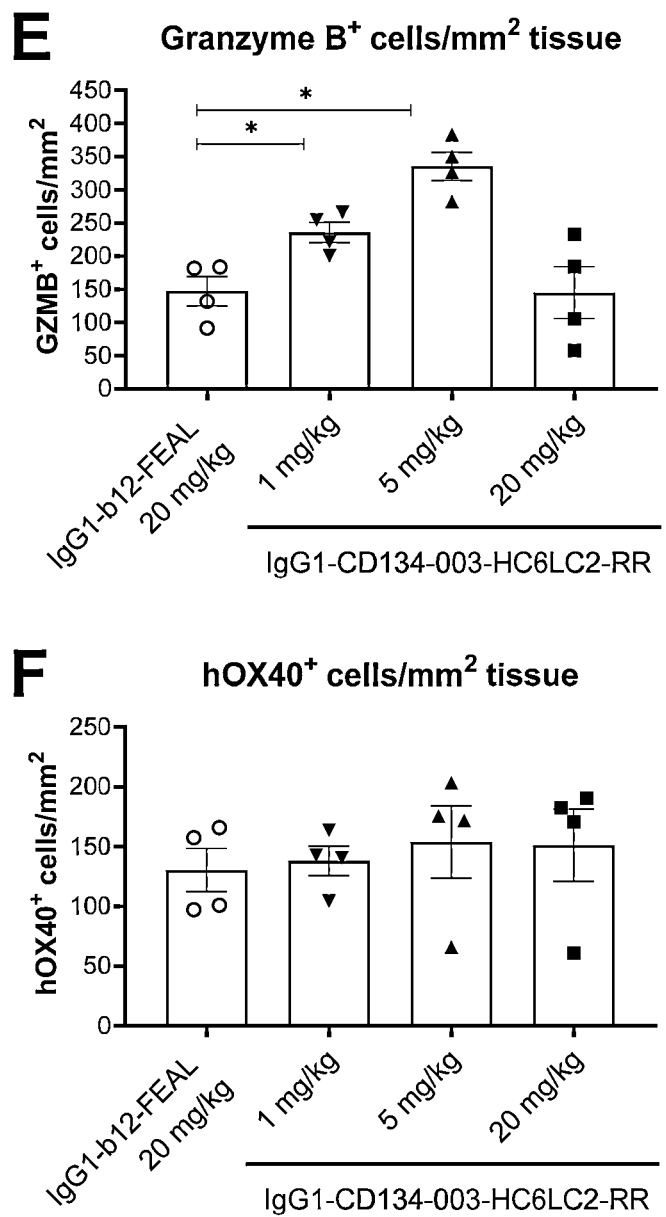
Figure 45 - *continued*

Figure 46:
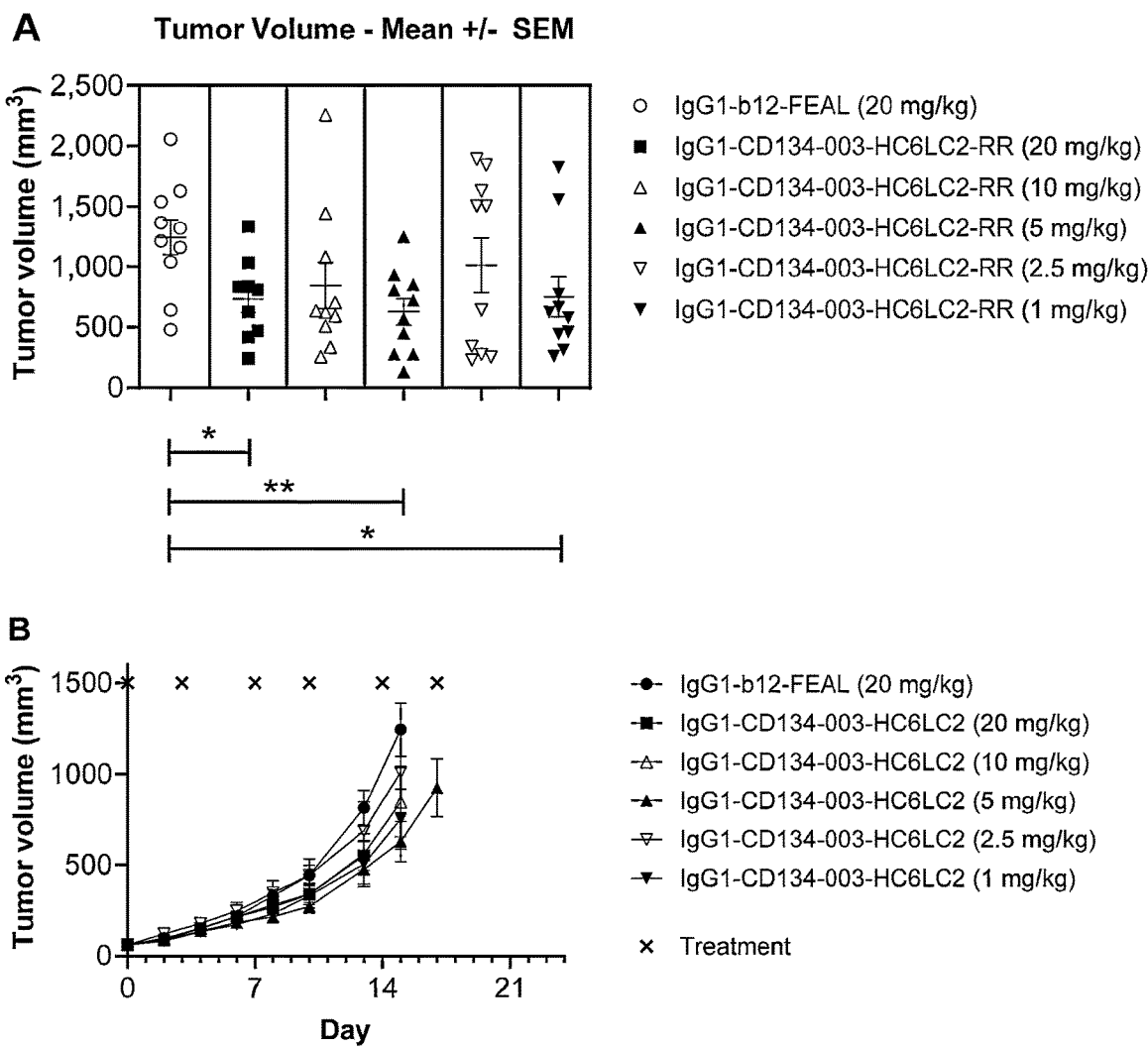

Figure 46 - continued
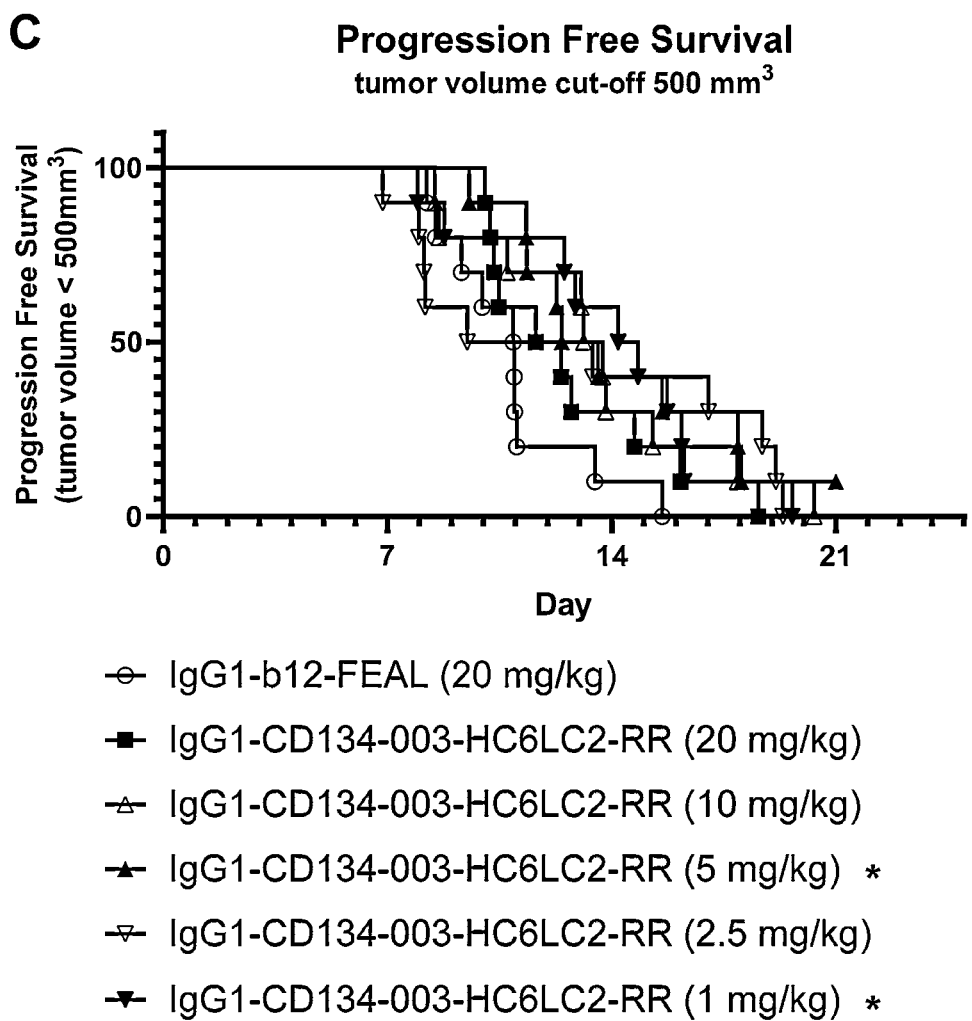

Figure 47:
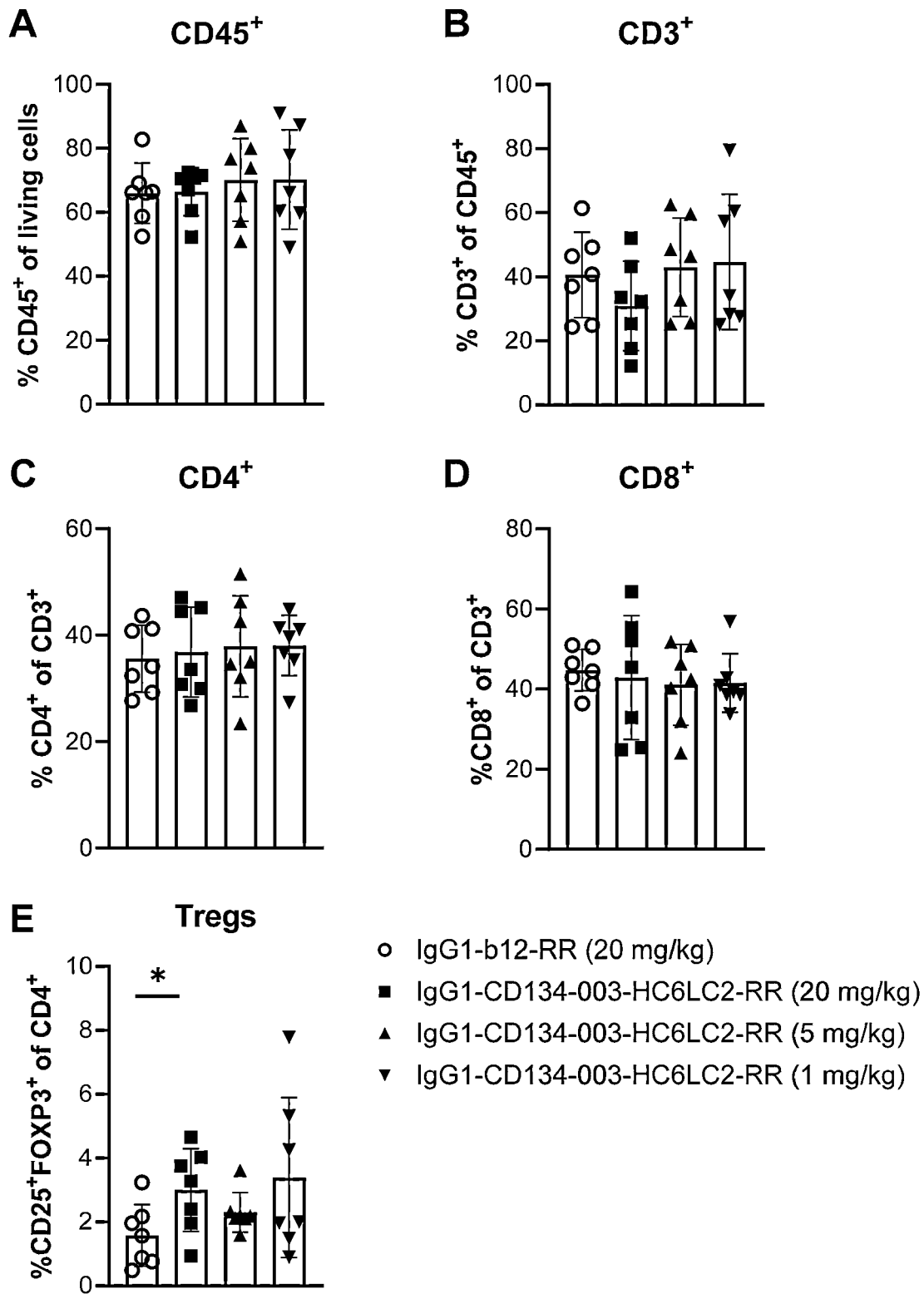

Figure 47 - *continued*
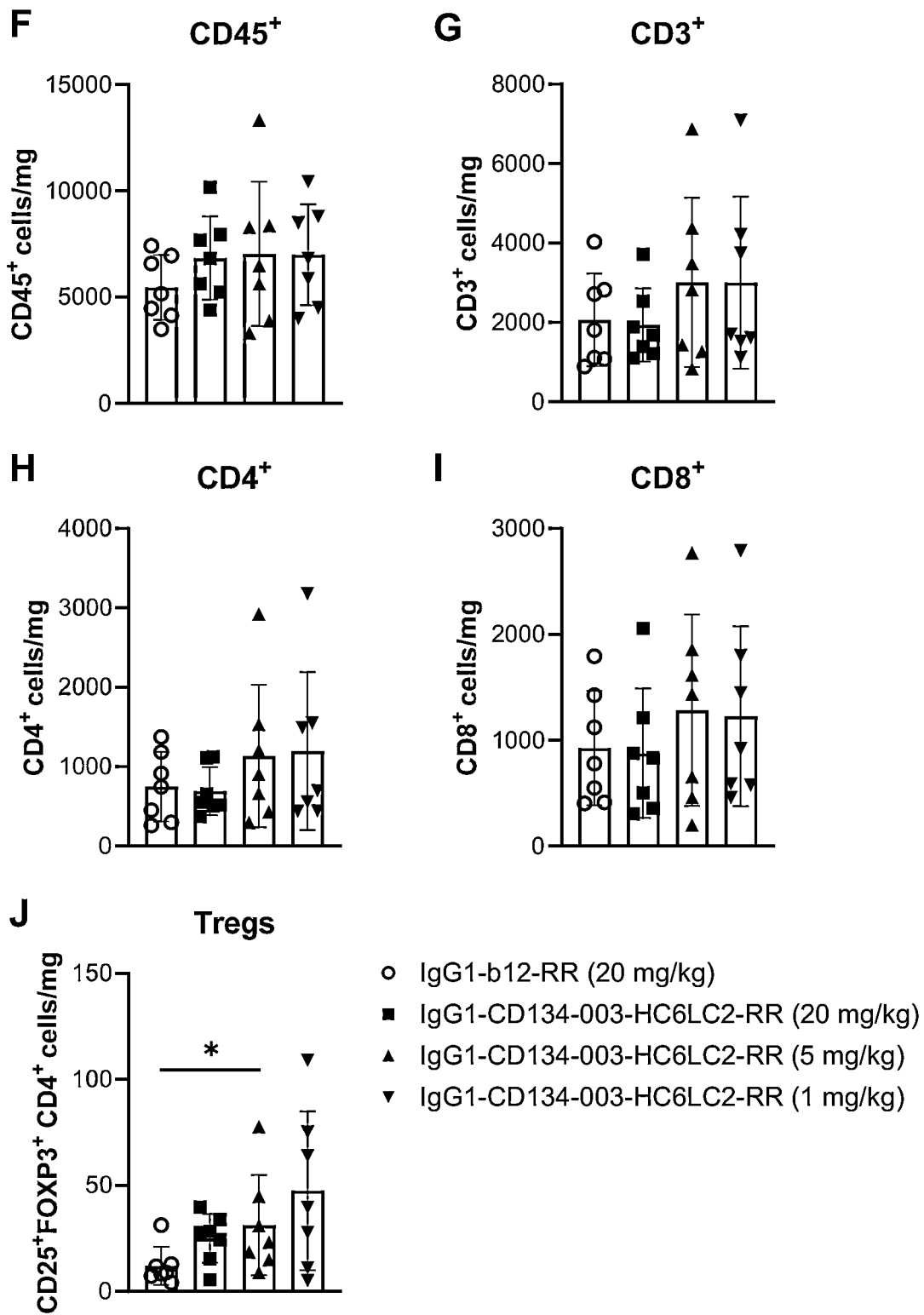

SEQUENCE LISTING

```
Sequence total quantity: 78
SEQ ID NO: 1            moltype = AA  length = 329
FEATURE                 Location/Qualifiers
source                  1..329
                        mol_type = protein
                        organism = unidentified
SEQUENCE: 1
ASTKGPSVFP LAPSSKSTSG GTAALGCLVK DYFPEPVTVS WNSGALTSGV HTFPAVLQSS  60
GLYSLSSVVT VPSSSLGTQT YICNVNHKPS NTKVDKRVEP KSCDKTHTCP PCPAPELLGG 120
PSVFLFPPKP KDTLMISRTP EVTCVVVDVS HEDPEVKFNW YVDGVEVHNA KTKPREEQYN 180
STYRVVSVLT VLHQDWLNGK EYKCKVSNKA LPAPIEKTIS KAKGQPREPQ VYTLPPSREE 240
MTKNQVSLTC LVKGFYPSDI AVEWESNGQP ENNYKTTPPV LDSDGSFFLY SKLTVDKSRW 300
QQGNVFSCSV MHEALHNHYT QKSLSLSPG                                  329

SEQ ID NO: 2            moltype = AA  length = 329
FEATURE                 Location/Qualifiers
source                  1..329
                        mol_type = protein
                        organism = unidentified
SEQUENCE: 2
ASTKGPSVFP LAPSSKSTSG GTAALGCLVK DYFPEPVTVS WNSGALTSGV HTFPAVLQSS  60
GLYSLSSVVT VPSSSLGTQT YICNVNHKPS NTKVDKRVEP KSCDKTHTCP PCPAPELLGG 120
PSVFLFPPKP KDTLMISRTP EVTCVVVDVS HEDPEVKFNW YVDGVEVHNA KTKPREEQYN 180
STYRVVSVLT VLHQDWLNGK EYKCKVSNKA LPAPIEKTIS KAKGQPRRPQ VYTLPPSREE 240
MTKNQVSLTC LVKGFYPSDI AVEWESNGQP ENNYKTTPPV LDSDGSFFLY SKLTVDKSRW 300
QQGNVFSCSV MHEALHNHYT QKSLSLSPG                                  329

SEQ ID NO: 3            moltype = AA  length = 329
FEATURE                 Location/Qualifiers
source                  1..329
                        mol_type = protein
                        organism = unidentified
SEQUENCE: 3
ASTKGPSVFP LAPSSKSTSG GTAALGCLVK DYFPEPVTVS WNSGALTSGV HTFPAVLQSS  60
GLYSLSSVVT VPSSSLGTQT YICNVNHKPS NTKVDKRVEP KSCDKTHTCP PCPAPELLGG 120
PSVFLFPPKP KDTLMISRTP EVTCVVVDVS HEDPEVKFNW YVDGVEVHNA KTKPREEQYN 180
STYRVVSVLT VLHQDWLNGK EYKCKVSNKA LRAPIEKTIS KAKGQPRRPQ VYTLPPSREE 240
MTKNQVSLTC LVKGFYPSDI AVEWESNGQP ENNYKTTPPV LDSDGSFFLY SKLTVDKSRW 300
QQGNVFSCSV MHEALHNHYT QKSLSLSPG                                  329

SEQ ID NO: 4            moltype = AA  length = 329
FEATURE                 Location/Qualifiers
source                  1..329
                        mol_type = protein
                        organism = unidentified
SEQUENCE: 4
ASTKGPSVFP LAPSSKSTSG GTAALGCLVK DYFPEPVTVS WNSGALTSGV HTFPAVLQSS  60
GLYSLSSVVT VPSSSLGTQT YICNVNHKPS NTKVDKRVEP KSCDKTHTCP PCPAPELLGG 120
PSVFLFPPKP KDTLMISRTP EVTCVVVDVS HEDPEVKFNW YVDGVEVHNA KTKPREEQYN 180
STYRVVSVLT VLHQDWLNGK EYKCAVSNKA LPAPIEKTIS KAKGQPRRPQ VYTLPPSREE 240
MTKNQVSLTC LVKGFYPSDI AVEWESNGQP ENNYKTTPPV LDSDGSFFLY SKLTVDKSRW 300
QQGNVFSCSV MHEALHNHYT QKSLSLSPG                                  329

SEQ ID NO: 5            moltype = AA  length = 329
FEATURE                 Location/Qualifiers
source                  1..329
                        mol_type = protein
                        organism = unidentified
SEQUENCE: 5
ASTKGPSVFP LAPSSKSTSG GTAALGCLVK DYFPEPVTVS WNSGALTSGV HTFPAVLQSS  60
```

```
GLYSLSSVVT VPSSSLGTQT YICNVNHKPS NTKVDKRVEP KSCDKTHTCP PCPAPEAAGG    120
PSVFLFPPKP KDTLMISRTP EVTCVVVDVS HEDPEVKFNW YVDGVEVHNA KTKPREEQYN    180
STYRVVSVLT VLHQDWLNGK EYKCKVSNKA LGAPIEKTIS KAKGQPRRPQ VYTLPPSREE    240
MTKNQVSLTC LVKGFYPSDI AVEWESNGQP ENNYKTTPPV LDSDGSFFLY SKLTVDKSRW    300
QQGNVFSCSV MHEALHNHYT QKSLSLSPG                                     329

SEQ ID NO: 6            moltype = AA   length = 329
FEATURE                 Location/Qualifiers
source                  1..329
                        mol_type = protein
                        organism = unidentified
SEQUENCE: 6
ASTKGPSVFP LAPSSKSTSG GTAALGCLVK DYFPEPVTVS WNSGALTSGV HTFPAVLQSS    60
GLYSLSSVVT VPSSSLGTQT YICNVNHKPS NTKVDKRVEP KSCDKTHTCP PCPAPELLRG    120
PSVFLFPPKP KDTLMISRTP EVTCVVVDVS HEDPEVKFNW YVDGVEVHNA KTKPREEQYN    180
STYRVVSVLT VLHQDWLNGK EYKCKVSNKA LPAPIEKTIS KAKGQPRRPQ VYTLPPSREE    240
MTKNQVSLTC LVKGFYPSDI AVEWESNGQP ENNYKTTPPV LDSDGSFFLY SKLTVDKSRW    300
QQGNVFSCSV MHEALHNHYT QESLSLSPG                                     329

SEQ ID NO: 7            moltype = AA   length = 107
FEATURE                 Location/Qualifiers
source                  1..107
                        mol_type = protein
                        organism = unidentified
SEQUENCE: 7
RTVAAPSVFI FPPSDEQLKS GTASVVCLLN NFYPREAKVQ WKVDNALQSG NSQESVTEQD    60
SKDSTYSLSS TLTLSKADYE KHKVYACEVT HQGLSSPVTK SFNRGEC                 107

SEQ ID NO: 8            moltype = AA   length = 106
FEATURE                 Location/Qualifiers
source                  1..106
                        mol_type = protein
                        organism = unidentified
SEQUENCE: 8
GQPKAAPSVT LFPPSSEELQ ANKATLVCLI SDFYPGAVTV AWKADSSPVK AGVETTTPSK    60
QSNNKYAASS YLSLTPEQWK SHRSYSCQVT HEGSTVEKTV APTECS                  106

SEQ ID NO: 9            moltype = AA   length = 451
FEATURE                 Location/Qualifiers
source                  1..451
                        mol_type = protein
                        organism = unidentified
SEQUENCE: 9
EQLKETGGGL VQPGGSLTLS CKASGFDFSS GYMSWVRQAP GKGLEWIGYI DPVFGSTYYA    60
SWVNGRFAIS SHNAQNTLYL QLNSLTAADT ATYFCARDLR AFYSGWGGIN LWGPGTLVTV    120
SSASTKGPSV FPLAPSSKST SGGTAALGCL VKDYFPEPVT VSWNSGALTS GVHTFPAVLQ    180
SSGLYSLSSV VTVPSSSLGT QTYICNVNHK PSNTKVDKRV EPKSCDKTHT CPPCPAPELL    240
GGPSVFLFPP KPKDTLMISR TPEVTCVVVD VSHEDPEVKF NWYVDGVEVH NAKTKPREEQ    300
YNSTYRVVSV LTVLHQDWLN GKEYKCKVSN KALPAPIEKT ISKAKGQPRE PQVYTLPPSR    360
EEMTKNQVSL TCLVKGFYPS DIAVEWESNG QPENNYKTTP PVLDSDGSFF LYSKLTVDKS    420
RWQQGNVFSC SVMHEALHNH YTQKSLSLSP G                                  451

SEQ ID NO: 10           moltype = AA   length = 218
FEATURE                 Location/Qualifiers
source                  1..218
                        mol_type = protein
                        organism = unidentified
SEQUENCE: 10
AAVLTQTPSP VSAAVGGTVT IKCQSSQIVV NNNFLSWYQQ KPGQPPKLLI YDASNLASGV    60
PDRFSGSGSG TQFTLTISGV QSDDAATYYC LGGYDDDAEN AFGGGTEVVV QRTVAAPSVF    120
IFPPSDEQLK SGTASVVCLL NNFYPREAKV QWKVDNALQS GNSQESVTEQ DSKDSTYSLS    180
STLTLSKADY EKHKVYACEV THQGLSSPVT KSFNRGEC                           218

SEQ ID NO: 11           moltype = AA   length = 122
FEATURE                 Location/Qualifiers
source                  1..122
                        mol_type = protein
                        organism = unidentified
SEQUENCE: 11
EQLKETGGGL VQPGGSLTLS CKASGFDFSS GYMSWVRQAP GKGLEWIGYI DPVFGSTYYA    60
SWVNGRFAIS SHNAQNTLYL QLNSLTAADT ATYFCARDLR AFYSGWGGIN LWGPGTLVTV    120
SS                                                                  122

SEQ ID NO: 12           moltype = AA   length = 8
FEATURE                 Location/Qualifiers
source                  1..8
                        mol_type = protein
                        organism = unidentified
SEQUENCE: 12
```

```
GFDFSSGY                                                                       8

SEQ ID NO: 13           moltype = AA  length = 8
FEATURE                 Location/Qualifiers
source                  1..8
                        mol_type = protein
                        organism = unidentified
SEQUENCE: 13
IDPVFGST                                                                       8

SEQ ID NO: 14           moltype = AA  length = 16
FEATURE                 Location/Qualifiers
source                  1..16
                        mol_type = protein
                        organism = unidentified
SEQUENCE: 14
ARDLRAFYSG WGGINL                                                             16

SEQ ID NO: 15           moltype = AA  length = 111
FEATURE                 Location/Qualifiers
source                  1..111
                        mol_type = protein
                        organism = unidentified
SEQUENCE: 15
AAVLTQTPSP VSAAVGGTVT IKCQSSQIVV NNNFLSWYQQ KPGQPPKLLI YDASNLASGV             60
PDRFSGSGSG TQFTLTISGV QSDDAATYYC LGGYDDDAEN AFGGGTEVVV Q                     111

SEQ ID NO: 16           moltype = AA  length = 8
FEATURE                 Location/Qualifiers
source                  1..8
                        mol_type = protein
                        organism = unidentified
SEQUENCE: 16
QIVVNNNF                                                                       8

SEQ ID NO: 17           moltype = AA  length = 11
FEATURE                 Location/Qualifiers
source                  1..11
                        mol_type = protein
                        organism = unidentified
SEQUENCE: 17
LGGYDDDAEN A                                                                  11

SEQ ID NO: 18           moltype = AA  length = 452
FEATURE                 Location/Qualifiers
source                  1..452
                        mol_type = protein
                        organism = unidentified
SEQUENCE: 18
EVQLLESGGG LVQPGGSLRL SCKASGFDFS SGYMSWVRQA PGKGLEWIGY IDPVFGSTYY             60
ASWVNGRFTI SRDNSKNTLY LQMNSLRAED TATYYCARDL RAFYSGWGGI NLWGQGTLVT            120
VSSASTKGPS VFPLAPSSKS TSGGTAALGC LVKDYFPEPV TVSWNSGALT SGVHTFPAVL            180
QSSGLYSLSS VVTVPSSSLG TQTYICNVNH KPSNTKVDKR VEPKSCDKTH TCPPCPAPEL            240
LGGPSVFLFP PKPKDTLMIS RTPEVTCVVV DVSHEDPEVK FNWYVDGVEV HNAKTKPREE            300
QYNSTYRVVS VLTVLHQDWL NGKEYKCKVS NKALRAPIEK TISKAKGQPR EPQVYTLPPS            360
REEMTKNQVS LTCLVKGFYP SDIAVEWESN GQPENNYKTT PPVLDSDGSF FLYSKLTVDK            420
SRWQQGNVFS CSVMHEALHN HYTQKSLSLS PG                                          452

SEQ ID NO: 19           moltype = AA  length = 218
FEATURE                 Location/Qualifiers
source                  1..218
                        mol_type = protein
                        organism = unidentified
SEQUENCE: 19
AAVLTQSPSS LSASVGDRVT ITCQSSQIVV NNNFLSWYQQ KPGKAPKLLI YDASNLASGV             60
PDRFSGSGSG TDFTFTISSL QPEDIATYYC LGGYDDDAEN AFGGGTKVEI KRTVAAPSVF            120
IFPPSDEQLK SGTASVVCLL NNFYPREAKV QWKVDNALQS GNSQESVTEQ DSKDSTYSLS            180
STLTLSKADY EKHKVYACEV THQGLSSPVT KSFNRGEC                                    218

SEQ ID NO: 20           moltype = AA  length = 123
FEATURE                 Location/Qualifiers
source                  1..123
                        mol_type = protein
                        organism = unidentified
SEQUENCE: 20
EVQLLESGGG LVQPGGSLRL SCKASGFDFS SGYMSWVRQA PGKGLEWIGY IDPVFGSTYY             60
ASWVNGRFTI SRDNSKNTLY LQMNSLRAED TATYYCARDL RAFYSGWGGI NLWGQGTLVT            120
VSS                                                                          123
```

-continued

```
SEQ ID NO: 21            moltype = AA   length = 111
FEATURE                  Location/Qualifiers
source                   1..111
                         mol_type = protein
                         organism = unidentified
SEQUENCE: 21
AAVLTQSPSS LSASVGDRVT ITCQSSQIVV NNNFLSWYQQ KPGKAPKLLI YDASNLASGV   60
PDRFSGSGSG TDFTFTISSL QPEDIATYYC LGGYDDDAEN AFGGGTKVEI K           111

SEQ ID NO: 22            moltype = AA   length = 446
FEATURE                  Location/Qualifiers
source                   1..446
                         mol_type = protein
                         organism = unidentified
SEQUENCE: 22
QSVEESGGRL VTPGTFLTLT CTVSGFSLSS YAMNWVRQSP GKGLEWIGII YSDDIAYYAS   60
WAKGRFTISK TSTTVTLKMT SLTVADTATY FCARGDGDRS IWSFDLWGPG TLVTVSSAST  120
KGPSVFPLAP SSKSTSGGTA ALGCLVKDYF PEPVTVSWNS GALTSGVHTF PAVLQSSGLY  180
SLSSVVTVPS SSLGTQTYIC NVNHKPSNTK VDKRVEPKSC DKTHTCPPCP APELLGGPSV  240
FLFPPKPKDT LMISRTPEVT CVVVDVSHED PEVKFNWYVD GVEVHNAKTK PREEQYNSTY  300
RVVSVLTVLH QDWLNGKEYK CKVSNKALPA PIEKTISKAK GQPREPQVYT LPPSREEMTK  360
NQVSLTCLVK GFYPSDIAVE WESNGQPENN YKTTPPVLDS DGSFFLYSKL TVDKSRWQQG  420
NVFSCSVMHE ALHNHYTQKS LSLSPG                                     446

SEQ ID NO: 23            moltype = AA   length = 219
FEATURE                  Location/Qualifiers
source                   1..219
                         mol_type = protein
                         organism = unidentified
SEQUENCE: 23
AQVLTQTPSP VSAAVGGTVT ISCQSSESVW NNNWLAWYQQ KPGQPPNLLI YEASTLASGV   60
SSRFKGSGSG TQFTLTVSEV QSDDAATYYC QGGYYDSSPI WTFGGGTEVV VKRTVAAPSV  120
FIFPPSDEQL KSGTASVVCL LNNFYPREAK VQWKVDNALQ SGNSQESVTE QDSKDSTYSL  180
SSTLTLSKAD YEKHKVYACE VTHQGLSSPV TKSFNRGEC                        219

SEQ ID NO: 24            moltype = AA   length = 117
FEATURE                  Location/Qualifiers
source                   1..117
                         mol_type = protein
                         organism = unidentified
SEQUENCE: 24
QSVEESGGRL VTPGTFLTLT CTVSGFSLSS YAMNWVRQSP GKGLEWIGII YSDDIAYYAS   60
WAKGRFTISK TSTTVTLKMT SLTVADTATY FCARGDGDRS IWSFDLWGPG TLVTVSS    117

SEQ ID NO: 25            moltype = AA   length = 8
FEATURE                  Location/Qualifiers
source                   1..8
                         mol_type = protein
                         organism = unidentified
SEQUENCE: 25
GFSLSSYA                                                           8

SEQ ID NO: 26            moltype = AA   length = 7
FEATURE                  Location/Qualifiers
source                   1..7
                         mol_type = protein
                         organism = unidentified
SEQUENCE: 26
IYSDDIA                                                            7

SEQ ID NO: 27            moltype = AA   length = 14
FEATURE                  Location/Qualifiers
source                   1..14
                         mol_type = protein
                         organism = unidentified
SEQUENCE: 27
ARGDGDRSIW SFDL                                                   14

SEQ ID NO: 28            moltype = AA   length = 112
FEATURE                  Location/Qualifiers
source                   1..112
                         mol_type = protein
                         organism = unidentified
SEQUENCE: 28
AQVLTQTPSP VSAAVGGTVT ISCQSSESVW NNNWLAWYQQ KPGQPPNLLI YEASTLASGV   60
SSRFKGSGSG TQFTLTVSEV QSDDAATYYC QGGYYDSSPI WTFGGGTEVV VK         112

SEQ ID NO: 29            moltype = AA   length = 8
FEATURE                  Location/Qualifiers
```

```
source                        1..8
                              mol_type = protein
                              organism = unidentified
SEQUENCE: 29
ESVWNNNW                                                                       8

SEQ ID NO: 30                 moltype = AA  length = 12
FEATURE                       Location/Qualifiers
source                        1..12
                              mol_type = protein
                              organism = unidentified
SEQUENCE: 30
QGGYYDSSPI WT                                                                 12

SEQ ID NO: 31                 moltype = AA  length = 447
FEATURE                       Location/Qualifiers
source                        1..447
                              mol_type = protein
                              organism = unidentified
SEQUENCE: 31
QSLEESGGRL VTPGTPLTLI CTVSGIDLSS GAMGWVRQAP GKGLEYIGYI YTGSGTTSYA             60
SWVNGRFTIS MTSTTVDLKI TSPTTEDTAT YFCARDAASS YWGHFTLWGQ GTLVTVSSAS            120
TKGPSVFPLA PSSKSTSGGT AALGCLVKDY FPEPVTVSWN SGALTSGVHT FPAVLQSSGL            180
YSLSSVVTVP SSSLGTQTYI CNVNHKPSNT KVDKRVEPKS CDKTHTCPPC PAPELLGGPS            240
VFLFPPKPKD TLMISRTPEV TCVVVDVSHE DPEVKFNWYV DGVEVHNAKT KPREEQYNST            300
YRVVSVLTVL HQDWLNGKEY KCKVSNKALP APIEKTISKA KGQPREPQVY TLPPSREEMT            360
KNQVSLTCLV KGFYPSDIAV EWESNGQPEN NYKTTPPVLD SDGSFFLYSK LTVDKSRWQQ            420
GNVFSCSVMH EALHNHYTQK SLSLSPG                                                447

SEQ ID NO: 32                 moltype = AA  length = 219
FEATURE                       Location/Qualifiers
source                        1..219
                              mol_type = protein
                              organism = unidentified
SEQUENCE: 32
DIVMTQTPAS VEAAVGGTVT IKCQASENIY SSLAWYQQKP GQPPKLLIYR TSTLASGVPS             60
RFKGSGSGTQ FTLTISDLES DDAATYYCQS YYHNSGGGYD YGFGGGTEVV AKRTVAAPSV            120
FIFPPSDEQL KSGTASVVCL LNNFYPREAK VQWKVDNALQ SGNSQESVTE QDSKDSTYSL            180
SSTLTLSKAD YEKHKVYACE VTHQGLSSPV TKSFNRGEC                                   219

SEQ ID NO: 33                 moltype = AA  length = 118
FEATURE                       Location/Qualifiers
source                        1..118
                              mol_type = protein
                              organism = unidentified
SEQUENCE: 33
QSLEESGGRL VTPGTPLTLI CTVSGIDLSS GAMGWVRQAP GKGLEYIGYI YTGSGTTSYA             60
SWVNGRFTIS MTSTTVDLKI TSPTTEDTAT YFCARDAASS YWGHFTLWGQ GTLVTVSS              118

SEQ ID NO: 34                 moltype = AA  length = 8
FEATURE                       Location/Qualifiers
source                        1..8
                              mol_type = protein
                              organism = unidentified
SEQUENCE: 34
GIDLSSGA                                                                       8

SEQ ID NO: 35                 moltype = AA  length = 7
FEATURE                       Location/Qualifiers
source                        1..7
                              mol_type = protein
                              organism = unidentified
SEQUENCE: 35
YTGSGTT                                                                        7

SEQ ID NO: 36                 moltype = AA  length = 14
FEATURE                       Location/Qualifiers
source                        1..14
                              mol_type = protein
                              organism = unidentified
SEQUENCE: 36
ARDAASSYWG HFTL                                                               14

SEQ ID NO: 37                 moltype = AA  length = 112
FEATURE                       Location/Qualifiers
source                        1..112
                              mol_type = protein
                              organism = unidentified
SEQUENCE: 37
```

-continued

```
DIVMTQTPAS VEAAVGGTVT IKCQASENIY SSLAWYQQKP GQPPKLLIYR TSTLASGVPS   60
RFKGSGSGTQ FTLTISDLES DDAATYYCQS YYHNSGGGYD YGFGGGTEVV AK          112

SEQ ID NO: 38           moltype = AA  length = 6
FEATURE                 Location/Qualifiers
source                  1..6
                        mol_type = protein
                        organism = unidentified
SEQUENCE: 38
ENIYSS                                                               6

SEQ ID NO: 39           moltype = AA  length = 14
FEATURE                 Location/Qualifiers
source                  1..14
                        mol_type = protein
                        organism = unidentified
SEQUENCE: 39
QSYYHNSGGG YDYG                                                     14

SEQ ID NO: 40           moltype = AA  length = 447
FEATURE                 Location/Qualifiers
source                  1..447
                        mol_type = protein
                        organism = unidentified
SEQUENCE: 40
EVQLVESGGG LVQPGGSLRL SCAASGFTFS SYSMNWVRQA PGKGLEWVSY ISSSSSTIDY   60
ADSVKGRFTI SRDNAKNSLY LQMNSLRDED TAVYYCARES GWYLFDYWGQ GTLVTVSSAS  120
TKGPSVFPLA PSSKSTSGGT AALGCLVKDY FPEPVTVSWN SGALTSGVHT FPAVLQSSGL  180
YSLSSVVTVP SSSLGTQTYI CNVNHKPSNT KVDKRVEPKS CDKTHTCPPC PAPELLGGPS  240
VFLFPPKPKD TLMISRTPEV TCVVVDVSHE DPEVKFNWYV DGVEVHNAKT KPREEQYNST  300
YRVVSVLTVL HQDWLNGKEY KCKVSNKALP APIEKTISKA KGQPREPQVY TLPPSREEMT  360
KNQVSLTCLV KGFYPSDIAV EWESNGQPEN NYKTTPPVLD SDGSFFLYSK LTVDKSRWQQ  420
GNVFSCSVMH EALHNHYTQK SLSLSPG                                      447

SEQ ID NO: 41           moltype = AA  length = 214
FEATURE                 Location/Qualifiers
source                  1..214
                        mol_type = protein
                        organism = unidentified
SEQUENCE: 41
DIQMTQSPSS LSASVGDRVT ITCRASQGIS SWLAWYQQKP EKAPKSLIYA ASSLQSGVPS   60
RFSGSGSGTD FTLTISSLQP EDFATYYCQQ YNSYPPTFGG GTKVEIKRTV AAPSVFIFPP  120
SDEQLKSGTA SVVCLLNNFY PREAKVQWKV DNALQSGNSQ ESVTEQDSKD STYSLSSTLT  180
LSKADYEKHK VYACEVTHQG LSSPVTKSFN RGEC                              214

SEQ ID NO: 42           moltype = AA  length = 118
FEATURE                 Location/Qualifiers
source                  1..118
                        mol_type = protein
                        organism = unidentified
SEQUENCE: 42
EVQLVESGGG LVQPGGSLRL SCAASGFTFS SYSMNWVRQA PGKGLEWVSY ISSSSSTIDY   60
ADSVKGRFTI SRDNAKNSLY LQMNSLRDED TAVYYCARES GWYLFDYWGQ GTLVTVSS    118

SEQ ID NO: 43           moltype = AA  length = 8
FEATURE                 Location/Qualifiers
source                  1..8
                        mol_type = protein
                        organism = unidentified
SEQUENCE: 43
GFTFSSYS                                                             8

SEQ ID NO: 44           moltype = AA  length = 8
FEATURE                 Location/Qualifiers
source                  1..8
                        mol_type = protein
                        organism = unidentified
SEQUENCE: 44
ISSSSSTI                                                             8

SEQ ID NO: 45           moltype = AA  length = 11
FEATURE                 Location/Qualifiers
source                  1..11
                        mol_type = protein
                        organism = unidentified
SEQUENCE: 45
ARESGWYLFD Y                                                        11

SEQ ID NO: 46           moltype = AA  length = 107
```

```
FEATURE                 Location/Qualifiers
source                  1..107
                        mol_type = protein
                        organism = unidentified
SEQUENCE: 46
DIQMTQSPSS LSASVGDRVT ITCRASQGIS SWLAWYQQKP EKAPKSLIYA ASSLQSGVPS    60
RFSGSGSGTD FTLTISSLQP EDFATYYCQQ YNSYPPTFGG GTKVEIK                 107

SEQ ID NO: 47           moltype = AA  length = 6
FEATURE                 Location/Qualifiers
source                  1..6
                        mol_type = protein
                        organism = unidentified
SEQUENCE: 47
QGISSW                                                                6

SEQ ID NO: 48           moltype = AA  length = 9
FEATURE                 Location/Qualifiers
source                  1..9
                        mol_type = protein
                        organism = unidentified
SEQUENCE: 48
QQYNSYPPT                                                             9

SEQ ID NO: 49           moltype = AA  length = 325
FEATURE                 Location/Qualifiers
source                  1..325
                        mol_type = protein
                        organism = unidentified
SEQUENCE: 49
ASTKGPSVFP LAPCSRSTSE STAALGCLVK DYFPEPVTVS WNSGALTSGV HTFPAVLQSS    60
GLYSLSSVVT VPSSNFGTQT YTCNVDHKPS NTKVDKTVER KCCVECPPCP APPVAGPSVF   120
LFPPKPKDTL MISRTPEVTC VVVDVSHEDP EVQFNWYVDG VEVHNAKTKP REEQFNSTFR   180
VVSVLTVVHQ DWLNGKEYKC KVSNKGLPAP IEKTISKTKG QPREPQVYTL PPSREEMTKN   240
QVSLTCLVKG FYPSDIAVEW ESNGQPENNY KTTPPMLDSD GSFFLYSKLT VDKSRWQQGN   300
VFSCSVMHEA LHNHYTQKSL SLSPG                                        325

SEQ ID NO: 50           moltype = AA  length = 325
FEATURE                 Location/Qualifiers
source                  1..325
                        mol_type = protein
                        organism = unidentified
SEQUENCE: 50
ASTKGPSVFP LAPCSRSTSE STAALGCLVK DYFPEPVTVS WNSGALTSGV HTFPAVLQSS    60
GLYSLSSVVT VPSSNFGTQT YTCNVDHKPS NTKVDKTVER KCCVECPPCP APPAAASSVF   120
LFPPKPKDTL MISRTPEVTC VVVDVSAEDP EVQFNWYVDG VEVHNAKTKP REEQFNSTFR   180
VVSVLTVVHQ DWLNGKEYKC KVSNKGLPSS IEKTISKTKG QPRRPQVYTL PPSREEMTKN   240
QVSLTCLVKG FYPSDIAVEW ESNGQPENNY KTTPPMLDSD GSFFLYSKLT VDKSRWQQGN   300
VFSCSVMHEA LHNHYTQKSL SLSPG                                        325

SEQ ID NO: 51           moltype = AA  length = 277
FEATURE                 Location/Qualifiers
source                  1..277
                        mol_type = protein
                        organism = Macaca fascicularis
SEQUENCE: 51
MCVGARRLGR GPCAALLLLG LGLSTTAKLH CVGDTYPSND RCCQECRPGN GMVSRCNRSQ    60
NTVCRPCGPG FYNDVVSAKP CKACTWCNLR SGSERKQPCT ATQDTVCRCR AGTQPLDSYK   120
PGVDCAPCPP GHFSPGDNQA CKPWTNCTLA GKHTLQPASN SSDAICEDRD PPPTQPQETQ   180
GPPARPTTVQ PTEAWPRTSQ RPSTRPVEVP RGPAVAAILG LGLALGLLGP LAMLLALLLL   240
RRDQRLPPDA PKAPGGGSFR TPIQEEQADA HSALAKI                           277

SEQ ID NO: 52           moltype = AA  length = 277
FEATURE                 Location/Qualifiers
source                  1..277
                        mol_type = protein
                        organism = Homo sapiens
SEQUENCE: 52
MCVGARRLGR GPCAALLLLG LGLSTVTGLH CVGDTYPSND RCCHECRPGN GMVSRCSRSQ    60
NTVCRPCGPG FYNDVVSSKP CKPCTWCNLR SGSERKQLCT ATQDTVCRCR AGTQPLDSYK   120
PGVDCAPCPP GHFSPGDNQA CKPWTNCTLA GKHTLQPASN SSDAICEDRD PPATQPQETQ   180
GPPARPITVQ PTEAWPRTSQ GPSTRPVEVP GGRAVAAILG LGLVLGLLGP LAILLALYLL   240
RRDQRLPPDA HKPPGGGSFR TPIQEEQADA HSTLAKI                           277

SEQ ID NO: 53           moltype = AA  length = 272
FEATURE                 Location/Qualifiers
source                  1..272
                        mol_type = protein
                        organism = Mus musculus
```

```
SEQUENCE: 53
MYVWVQQPTA LLLLALTLGV TARRLNCVKH TYPSGHKCCR ECQPGHGMVS RCDHTRDTLC     60
HPCETGFYNE AVNYDTCKQC TQCNHRSGSE LKQNCTPTQD TVCRCRPGTQ PRQDSGYKLG    120
VDCVPCPPGH FSPGNNQACK PWTNCTLSGK QTRHPASDSL DAVCEDRSLL ATLLWETQRP    180
TFRPTTVQST TVWPRTSELP SPPTLVTPEG PAFAVLLGLG LGLLAPLTVL LALYLLRKAW    240
RLPNTPKPCW GNSFRTPIQE EHTDAHFTLA KI                                 272

SEQ ID NO: 54           moltype = AA  length = 277
FEATURE                 Location/Qualifiers
source                  1..277
                        mol_type = protein
                        organism = unidentified
SEQUENCE: 54
MCVGARRLGR GPCAALLLLG LGLSTVTGLN CVKHTYPSGH KCCRECQPGH GMVSRCDHTR     60
DTLCHPCGPG FYNDVVSSKP CKPCTWCNLR SGSERKQLCT ATQDTVCRCR AGTQPLDSYK    120
PGVDCAPCPP GHFSPGDNQA CKPWTNCTLA GKHTLQPASN SSDAICEDRD PPATQPQETQ    180
GPPARPITVQ PTEAWPRTSQ GPSTRPVEVP GGRAVAAILG LGLVLGLLGP LAILLALYLL    240
RRDQRLPPDA HKPPGGGSFR TPIQEEQADA HSTLAKI                            277

SEQ ID NO: 55           moltype = AA  length = 277
FEATURE                 Location/Qualifiers
source                  1..277
                        mol_type = protein
                        organism = unidentified
SEQUENCE: 55
MCVGARRLGR GPCAALLLLG LGLSTVTGLH CVGDTYPSND RCCHECRPGN GMVSRCSRSQ     60
NTVCRPCETG FYNEAVNYDT CKQCTQCNHR SGSELKQNCT PTQDTVCRCR AGTQPLDSYK    120
PGVDCAPCPP GHFSPGDNQA CKPWTNCTLA GKHTLQPASN SSDAICEDRD PPATQPQETQ    180
GPPARPITVQ PTEAWPRTSQ GPSTRPVEVP GGRAVAAILG LGLVLGLLGP LAILLALYLL    240
RRDQRLPPDA HKPPGGGSFR TPIQEEQADA HSTLAKI                            277

SEQ ID NO: 56           moltype = AA  length = 279
FEATURE                 Location/Qualifiers
source                  1..279
                        mol_type = protein
                        organism = unidentified
SEQUENCE: 56
MCVGARRLGR GPCAALLLLG LGLSTVTGLH CVGDTYPSND RCCHECRPGN GMVSRCSRSQ     60
NTVCRPCGPG FYNDVVSSKP CKPCTWCNLR SGSERKQLCT ATQDTVCRCR PGTQPRQDSG    120
YKLGVDCVPC PPGHFSPGDN QACKPWTNCT LAGKHTLQPA SNSSDAICED RDPPATQPQE    180
TQGPPARPIT VQPTEAWPRT SQGPSTRPVE VPGGRAVAAI LGLGLVLGLL GPLAILLALY    240
LLRRDQRLPP DAHKPPGGGS FRTPIQEEQA DAHSTLAKI                          279

SEQ ID NO: 57           moltype = AA  length = 277
FEATURE                 Location/Qualifiers
source                  1..277
                        mol_type = protein
                        organism = unidentified
SEQUENCE: 57
MCVGARRLGR GPCAALLLLG LGLSTVTGLH CVGDTYPSND RCCHECRPGN GMVSRCSRSQ     60
NTVCRPCGPG FYNDVVSSKP CKPCTWCNLR SGSERKQLCT ATQDTVCRCR AGTQPLDSYK    120
PGVDCAPCPP GHFSPGNNQA CKPWTNCTLS GKQTRHPASD SLDAVCEDRD PPATQPQETQ    180
GPPARPITVQ PTEAWPRTSQ GPSTRPVEVP GGRAVAAILG LGLVLGLLGP LAILLALYLL    240
RRDQRLPPDA HKPPGGGSFR TPIQEEQADA HSTLAKI                            277

SEQ ID NO: 58           moltype = AA  length = 231
FEATURE                 Location/Qualifiers
source                  1..231
                        mol_type = protein
                        organism = unidentified
SEQUENCE: 58
EPKSCDKTHT CPPCPAPELL GGPSVFLFPP KPKDTLMISR TPEVTCVVVD VSHEDPEVKF     60
NWYVDGVEVH NAKTKPREEQ YNSTYRVVSV LTVLHQDWLN GKEYKCKVSN KALRAPIEKT    120
ISKAKGQPRR PQVYTLPPSR EEMTKNQVSL TCLVKGFYPS DIAVEWESNG QPENNYKTTP    180
PVLDSDGSFF LYSKLTVDKS RWQQGNVFSC SVMHEALHNH YTQKSLSLSP G            231

SEQ ID NO: 59           moltype = AA  length = 231
FEATURE                 Location/Qualifiers
source                  1..231
                        mol_type = protein
                        organism = unidentified
SEQUENCE: 59
EPKSCDKTHT CPPCPAPELL GGPSVFLFPP KPKDTLMISR TPEVTCVVVD VSHEDPEVKF     60
NWYVDGVEVH NAKTKPREEQ YNSTYRVVSV LTVLHQDWLN GKEYKCKVSN KALRAPIEKT    120
ISKAKGQPRR PQVYTLPPSR DELTKNQVSL TCLVKGFYPS DIAVEWESNG QPENNYKTTP    180
PVLDSDGSFF LYSKLTVDKS RWQQGNVFSC SVMHEALHNH YTQKSLSLSP G            231

SEQ ID NO: 60           moltype = AA  length = 231
FEATURE                 Location/Qualifiers
```

```
source                  1..231
                        mol_type = protein
                        organism = unidentified
SEQUENCE: 60
EPKSCDKTHT CPPCPAPELL GGPSVFLFPP KPKDTLMISR TPEVTCVVVD VSHEDPEVKF      60
NWYVDGVEVH NAKTKPREEQ YNSTYRVVSV LTVLHQDWLN GKEYKCKVSN KALRAPIEKT     120
ISKAKGQPRR PQVYTLPPSR EEMTKNQVSL TCLVKGFYPS DIAVEWESNG QPENNYKTTP     180
PVLDSDGSFF LYSKLTVDKS RWQQGNVFSC SVMHEGLHNH YTQKSLSLSP G              231

SEQ ID NO: 61           moltype = AA   length = 231
FEATURE                 Location/Qualifiers
source                  1..231
                        mol_type = protein
                        organism = unidentified
SEQUENCE: 61
EPKSCDKTHT CPPCPAPELL GGPSVFLFPP KPKDTLMISR TPEVTCVVVD VSHEDPEVKF      60
NWYVDGVEVH NAKTKPREEQ YNSTYRVVSV LTVLHQDWLN GKEYKCKVSN KALRAPIEKT     120
ISKAKGQPRR PQVYTLPPSR EEMTKNQVSL TCLVKGFYPS DIAVEWESNG QPENNYKTTP     180
PVLDSDGSFF LYSKLTVDKS RWQQGNVFSC SVMHEALHNH YTQKSLSLSP G              231

SEQ ID NO: 62           moltype = AA   length = 329
FEATURE                 Location/Qualifiers
source                  1..329
                        mol_type = protein
                        organism = unidentified
SEQUENCE: 62
ASTKGPSVFP LAPSSKSTSG GTAALGCLVK DYFPEPVTVS WNSGALTSGV HTFPAVLQSS      60
GLYSLSSVVT VPSSSLGTQT YICNVNHKPS NTKVDKRVEP KSCDKTHTCP PCPAPEFEGG     120
PSVFLFPPKP KDTLMISRTP EVTCVVVAVS HEDPEVKFNW YVDGVEVHNA KTKPREEQYN     180
STYRVVSVLT VLHQDWLNGK EYKCKVSNKA LPAPIEKTIS KAKGQPREPQ VYTLPPSREE     240
MTKNQVSLTC LVKGFYPSDI AVEWESNGQP ENNYKTTPPV LDSDGSFLLY SKLTVDKSRW     300
QQGNVFSCSV MHEALHNHYT QKSLSLSPG                                      329

SEQ ID NO: 63           moltype = AA   length = 329
FEATURE                 Location/Qualifiers
source                  1..329
                        mol_type = protein
                        organism = unidentified
SEQUENCE: 63
ASTKGPSVFP LAPSSKSTSG GTAALGCLVK DYFPEPVTVS WNSGALTSGV HTFPAVLQSS      60
GLYSLSSVVT VPSSSLGTQT YICNVNHKPS NTKVDKRVEP KSCDKTHTCP PCPAPELLGG     120
PSVFLFPPKP KDTLMISRTP EVTCVVVDVS HEDPEVKFNW YVDGVEVHNA KTKPREEQYN     180
STYRVVSVLT VLHQDWLNGK EYKCKVSNKA LRAPIEKTIS KAKGQPRRPQ VYTLPPSREE     240
MTKNQVSLTC LVKGFYPSDI AVEWESNGQP ENNYKTTPPV LDSDGSFFLY SRLTVDKSRW     300
QQGNVFSCSV MHEALHNHYT QKSLSLSPG                                      329

SEQ ID NO: 64           moltype = AA   length = 121
FEATURE                 Location/Qualifiers
source                  1..121
                        mol_type = protein
                        organism = unidentified
SEQUENCE: 64
QVQLQESGPG LVRPSQTLSL TCTVSGFTFT DFYMNWVRQP PGRGLEWIGF IRDKAKGYTT      60
EYNPSVKGRV TMLVDTSKNQ FSLRLSSVTA ADTAVYYCAR EGHTAAPFDY WGQGSLVTVS     120
S                                                                    121

SEQ ID NO: 65           moltype = AA   length = 8
FEATURE                 Location/Qualifiers
source                  1..8
                        mol_type = protein
                        organism = unidentified
SEQUENCE: 65
GFTFTDFY                                                               8

SEQ ID NO: 66           moltype = AA   length = 10
FEATURE                 Location/Qualifiers
source                  1..10
                        mol_type = protein
                        organism = unidentified
SEQUENCE: 66
IRDKAKGYTT                                                            10

SEQ ID NO: 67           moltype = AA   length = 12
FEATURE                 Location/Qualifiers
source                  1..12
                        mol_type = protein
                        organism = unidentified
SEQUENCE: 67
AREGHTAAPF DY                                                         12
```

```
SEQ ID NO: 68          moltype = AA   length = 107
FEATURE                Location/Qualifiers
source                 1..107
                       mol_type = protein
                       organism = unidentified
SEQUENCE: 68
DIQMTQSPSS LSASVGDRVT ITCKASQNID KYLNWYQQKP GKAPKLLIYN TNNLQTGVPS    60
RFSGSGSGTD FTFTISSLQP EDIATYYCLQ HISRPRTFGQ GTKVEIK                 107

SEQ ID NO: 69          moltype = AA   length = 6
FEATURE                Location/Qualifiers
source                 1..6
                       mol_type = protein
                       organism = unidentified
SEQUENCE: 69
QNIDKY                                                                6

SEQ ID NO: 70          moltype = AA   length = 9
FEATURE                Location/Qualifiers
source                 1..9
                       mol_type = protein
                       organism = unidentified
SEQUENCE: 70
LQHISRPRT                                                             9

SEQ ID NO: 71          moltype = AA   length = 127
FEATURE                Location/Qualifiers
source                 1..127
                       mol_type = protein
                       organism = unidentified
SEQUENCE: 71
QVQLVQSGAE VKKPGASVKV SCQASGYRFS NFVIHWVRQA PGQRFEWMGW INPYNGNKEF    60
SAKFQDRVTF TADTSANTAY MELRSLRSAD TAVYYCARVG PYSWDDSPQD NYYMDVWGKG   120
TTVIVSS                                                             127

SEQ ID NO: 72          moltype = AA   length = 8
FEATURE                Location/Qualifiers
source                 1..8
                       mol_type = protein
                       organism = unidentified
SEQUENCE: 72
GYRFSNFV                                                              8

SEQ ID NO: 73          moltype = AA   length = 8
FEATURE                Location/Qualifiers
source                 1..8
                       mol_type = protein
                       organism = unidentified
SEQUENCE: 73
INPYNGNK                                                              8

SEQ ID NO: 74          moltype = AA   length = 20
FEATURE                Location/Qualifiers
source                 1..20
                       mol_type = protein
                       organism = unidentified
SEQUENCE: 74
ARVGPYSWDD SPQDNYYMDV                                                20

SEQ ID NO: 75          moltype = AA   length = 108
FEATURE                Location/Qualifiers
source                 1..108
                       mol_type = protein
                       organism = unidentified
SEQUENCE: 75
EIVLTQSPGT LSLSPGERAT FSCRSSHSIR SRRVAWYQHK PGQAPRLVIH GVSNRASGIS    60
DRFSGSGSGT DFTLTITRVE PEDFALYYCQ VYGASSYTFG QGTKLERK                108

SEQ ID NO: 76          moltype = AA   length = 7
FEATURE                Location/Qualifiers
source                 1..7
                       mol_type = protein
                       organism = unidentified
SEQUENCE: 76
HSIRSRR                                                               7

SEQ ID NO: 77          moltype = AA   length = 9
FEATURE                Location/Qualifiers
```

```
source                  1..9
                        mol_type = protein
                        organism = unidentified
SEQUENCE: 77
QVYGASSYT                                                                           9

SEQ ID NO: 78           moltype = AA  length = 329
FEATURE                 Location/Qualifiers
source                  1..329
                        mol_type = protein
                        organism = unidentified
SEQUENCE: 78
ASTKGPSVFP LAPSSKSTSG GTAALGCLVK DYFPEPVTVS WNSGALTSGV HTFPAVLQSS    60
GLYSLSSVVT VPSSSLGTQT YICNVNHKPS NTKVDKRVEP KSCDKTHTCP PCPAPELLGG   120
PSVFLFPPKP KDTLMISRTP EVTCVVVDVS HEDPEVKFNW YVDGVEVHNA KTKPREEQYN   180
STYRVVSVLT VLHQDWLNGK EYKCKVSNKA LRAPIEKTIS KAKGQPRRPQ VYTLPPSREE   240
MTKNQVSLTC LVKGFYPSDI AVEWESNGQP ENNYKTTPPV LDSDGSFLLY SKLTVDKSRW   300
QQGNVFSCSV MHEALHNHYT QKSLSLSPG                                    329
```

ANTIBODIES CAPABLE OF BINDING TO OX40, VARIANTS THEREOF AND USES THEREOF

RELATED APPLICATIONS

This application claims priority to European Patent Application Nos. 23213531.9, filed Nov. 30, 2023, and 23173143.1, filed May 12, 2023, the entire disclosures of which are hereby incorporated herein by reference.

SEQUENCE LISTING

The instant application contains a Sequence Listing which has been submitted electronically in XML format and is hereby incorporated by reference in its entirety. Said XML file, created on May 7, 2024, is named 754_GMB9-028_ST26.xml and is 79,166 bytes in size.

FIELD OF THE INVENTION

The present invention relates to antibodies capable of binding to OX40 and to antibody variants thereof comprising one or more mutations in the Fc region and to the use of such antibodies and Fc variants.

BACKGROUND OF THE INVENTION

OX40 (CD134, TNFRSF4), a 277 amino acid long type I transmembrane protein, is a member of the tumor necrosis factor (TNF) receptor superfamily (TNFRSF) which co-stimulates T-cell activation after binding to its ligand OX40 ligand (OX40L). OX40 is expressed in humans on the cell membrane of activated CD4+ and CD8+ T cells and on regulatory T cells (Tregs), but not on resting naïve T cells.

The only known ligand for OX40 is the type II transmembrane glycoprotein OX40L (TNFSF4; CD252). OX40L is not constitutively expressed but its expression can be induced on antigen-presenting cells (APCs), including dendritic cells (DCs), macrophages and B cells. Apart from APCs, OX40L is also expressed on other hematopoietic cells such as activated natural killer (NK) cells or mast cells, and non-hematopoietic cells such as endothelial cells and smooth muscle cells (Croft et al. Immunol Rev. 2009 May; 229 (1): 173-91).

In humans, binding of OX40L to OX40 leads to downstream signaling, and ultimately to effector T-cell expansion and survival. In addition, OX40 signaling promotes the generation of memory T cells and inhibits the function of Tregs (Croft et al. Immunol Rev. 2009 May; 229 (1): 173-91). Moreover, agonistic OX40 antibodies help deplete tumor-infiltrating OX40-expressing Tregs via antibody-dependent cellular cytotoxicity (ADCC) induced by myeloid and NK cells after interacting with Tregs (Choi et al. J Immunother Cancer. 2020 Oct.; 8 (2): e000966). However, in certain conditions, such as when IFN-γ and IL-4 are absent, it was reported that OX40 signaling may induce Treg proliferation (Ruby et al. J Immunol. 2009 Oct. 15; 183 (8): 4853-7).

A small retrospective study using melanoma cell lines and samples from patients suggests that lower levels of OX40 in the tumor micro-environment (TME) are associated with worse prognosis following anti-PD-1 treatment, especially in patients with low numbers of tumor-infiltrating lymphocytes (TILs). The activation of OX40 signaling by treatment with an anti-OX40 agonistic monoclonal antibody (mAb), in combination with adoptive T-cell therapy, helps to restore or boost the T cell-mediated antitumor response, resulting in a survival benefit of prostate tumor-bearing mice. The antitumor activity of OX40 mAbs is associated with the infiltration of T cells into the tumor and intratumoral proliferation of effector T cells (He et al. Int Immunopharmacol. 2020 Dec.; 89 (Pt B): 107097).

Despite numerous efforts, however, there is still a need for agonistic OX40 therapeutic antibodies exhibiting potent agonistic activities that enhance antitumor immune responses.

SUMMARY OF THE INVENTION

The present invention concerns OX40 binding antibodies and Fc variants thereof.

So, in one aspect, the invention relates to an antibody capable of binding to human OX40, said antibody comprises an antigen-binding region comprising a heavy chain variable (VH) region wherein the CDR1, CDR2, and CDR3 comprising the sequences as set forth in SEQ ID NOs: 12, 13, and 14, respectively, and a light chain variable (VL) region wherein the CDR1, CDR2, and CDR3 comprising the sequences as set forth in SEQ ID NO: 16, DAS and 17, respectively, and a human IgG1 Fc region comprising a P329R mutation and an E345R mutation, wherein the amino acid positions are numbered according to Eu numbering.

In one aspect the invention relates to an antibody comprising a VH region having the sequence as set forth in SEQ ID NO: 20 and a VL region having the sequence set forth in SEQ ID NO: 21.

In one aspect the invention relates to an antibody comprising a VH region having the sequence as set forth in SEQ ID NO: 20 and a VL region having the sequence set forth in SEQ ID NO: 21, and further comprising a light chain constant region (CL) and a heavy chain constant region (CH).

In one aspect the invention relates to an antibody comprising the VH and VL regions comprising the sequences as set forth in SEQ ID NO: 20 and SEQ ID NO: 21, respectively, and further comprising a light chain constant region (CL) and a heavy chain constant region (CH) wherein the antibody is of the human IgG1 isotype.

In one aspect the invention relates to an antibody wherein the antibody has a binding affinity KD for human OX40 of $3,4 \times 10^{-9}$ M.

In one aspect the invention relates to a humanized antibody.

In one aspect the invention relates to an antibody wherein the Fc region comprises the sequence set forth in SEQ ID NO: 3.

In one aspect the invention relates to an antibody wherein the antibody has a heavy chain constant region comprising the sequence set forth in SEQ ID NO: 58.

In one aspect the invention relates to an antibody wherein the antibody comprises a heavy chain (HC) as set forth in SEQ ID NO: 18 and a light chain (LC) as set forth in SEQ ID NO: 19.

In one aspect the invention relates a composition comprising an antibody according to any aspect or embodiment herein.

In one aspect the invention relates a composition comprising an antibody according to any aspect or embodiment herein and a pharmaceutically acceptable carrier.

In one aspect the invention relates to an antibody according to any aspect or embodiment herein for use as a medicament.

In one aspect the invention relates to an antibody according to any aspect or embodiment herein for use as a medicament, wherein the disease is cancer.

In one aspect the invention relates to a method of treating a disease, the method comprising administering an antibody according to any aspect or embodiment herein to a subject in need thereof.

In one aspect the invention relates to a method of treating a disease, the method comprising administering composition or pharmaceutical composition as defined herein to a subject in need thereof.

In one aspect, the invention relates to an isolated nucleic acid encoding the antibody according to any aspect or embodiment herein.

In one aspect, the invention relates to an expression vector comprising such a nucleic acid.

In one aspect, the invention relates to a recombinant host cell which produces an antibody according to any aspect or embodiment herein.

In one aspect the invention relates to a kit-of-parts, such as a kit for use as a companion diagnostic/for identifying within a population of patients those patients which have a propensity to respond to treatment with an antibody according to any aspect or embodiment herein.

In one aspect the invention relates to an anti-idiotypic antibody, which binds to the antigen-binding region capable of binding to OX40 as defined in any one aspect or embodiment herein.

LEGENDS TO THE FIGURES

FIG. 1 shows binding of anti-human OX40 antibodies to (A) human and (B) cynomolgus monkey OX40 expressed on OX40-transfected HEK293F cells, as determined by flow cytometry. Non-binding antibody IgG1-b12-RR was included as negative control. Data shown are the geometric mean of the fluorescence intensity (gMFI) from one representative experiment out of two experiments performed.

Figure 2:
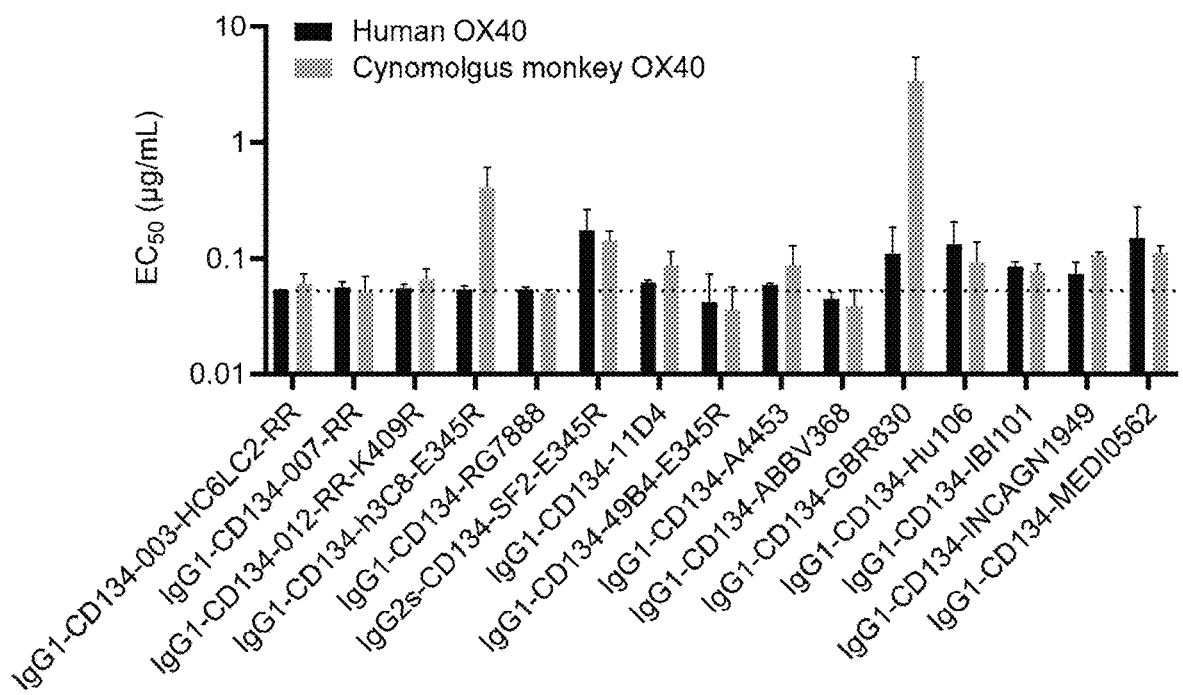

FIG. 2 shows the half-maximal effective concentration (EC50) of anti-human OX40 antibodies for binding to human and cynomolgus monkey OX40 expressed on OX40-transfected HEK293F cells, as determined by flow cytometry. Data shown are the mean EC50+SD from two experiments performed. The dotted black line indicates the mean EC50 of IgG1-CD134-003-HC6LC2-RR for binding to human OX40.

FIG. 3 shows sequence alignments of OX40 shuffle constructs with wild-type human and mouse OX40 (TNR4). Amino acids in shuffle constructs that differ from those in the human OX40 sequence are highlighted in black. Shuffle 1=human OX40 with mouse CRD1; Shuffle 2=human OX40 with mouse CRD2; Shuffle 3=human OX40 with mouse CRD3; Shuffle 4=human OX40 with mouse CRD4.

FIG. 4 shows sequence alignments for human and mouse OX40 (TNR4). Amino acids in mouse OX40 that differ from those in the human OX40 sequence are highlighted in black.

Figure 5:
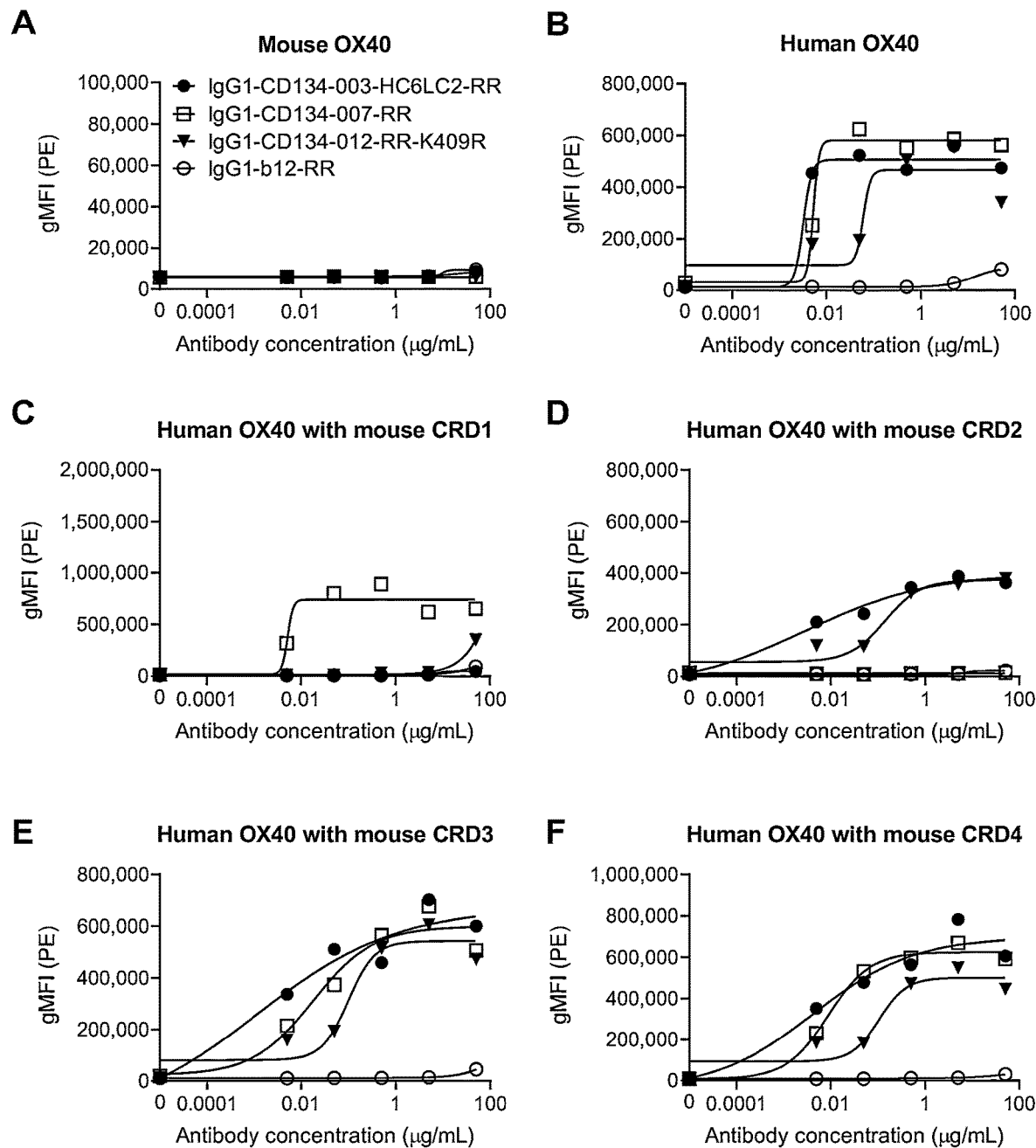

FIG. 5 shows binding of anti-human OX40 antibodies IgG1-CD134-003-HC6LC2-RR, IgG1-CD134-007-RR, and IgG1-CD134-012-RR-K409R to ExpiCHO-S cells transiently transfected to express mouse OX40 (A), human OX40 (B), or one of four shuffle constructs in which an individual CRD of human OX40 is replaced by the mouse analogue (C-F), as determined by flow cytometry. Non-binding antibody IgG1-b12-RR was included as negative control. Data shown are the geometric mean of the fluorescence intensity (gMFI) from one representative experiment out of two experiments performed.

Figure 6:
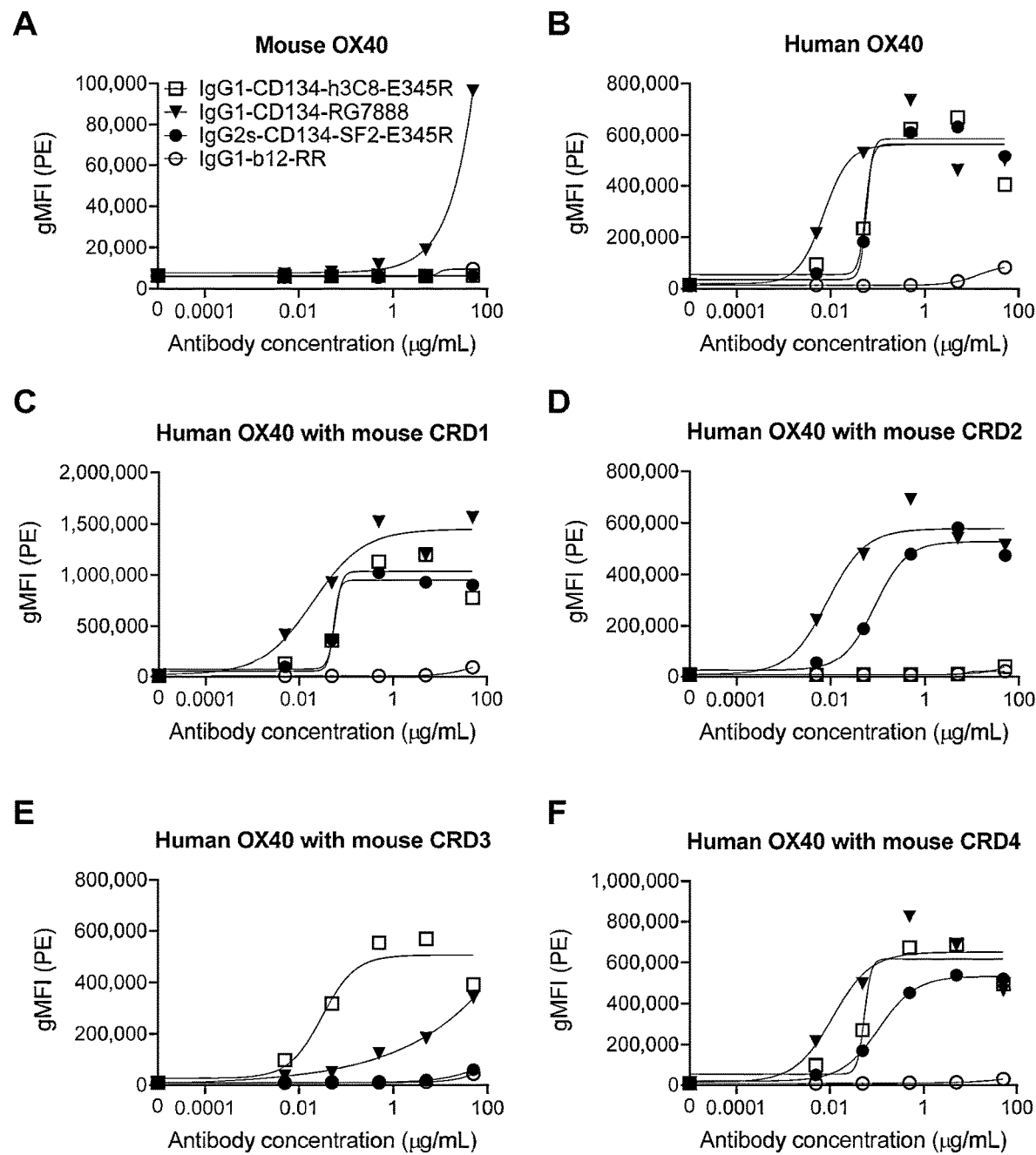

FIG. 6 shows binding of anti-human OX40 antibodies IgG1-CD134-h3C8-E345R, IgG1-CD134-RG7888, and IgG2s-CD134-SF2-E345R to ExpiCHO-S cells transiently transfected to express mouse OX40 (A), human OX40 (B), or one of four shuffle constructs in which an individual CRD of human OX40 is replaced by the mouse analogue (C-F), as determined by flow cytometry. Non-binding antibody IgG1-b12-RR was included as negative control. Data shown are the geometric mean of the fluorescence intensity (gMFI) from one representative experiment out of two experiments performed.

Figure 7:
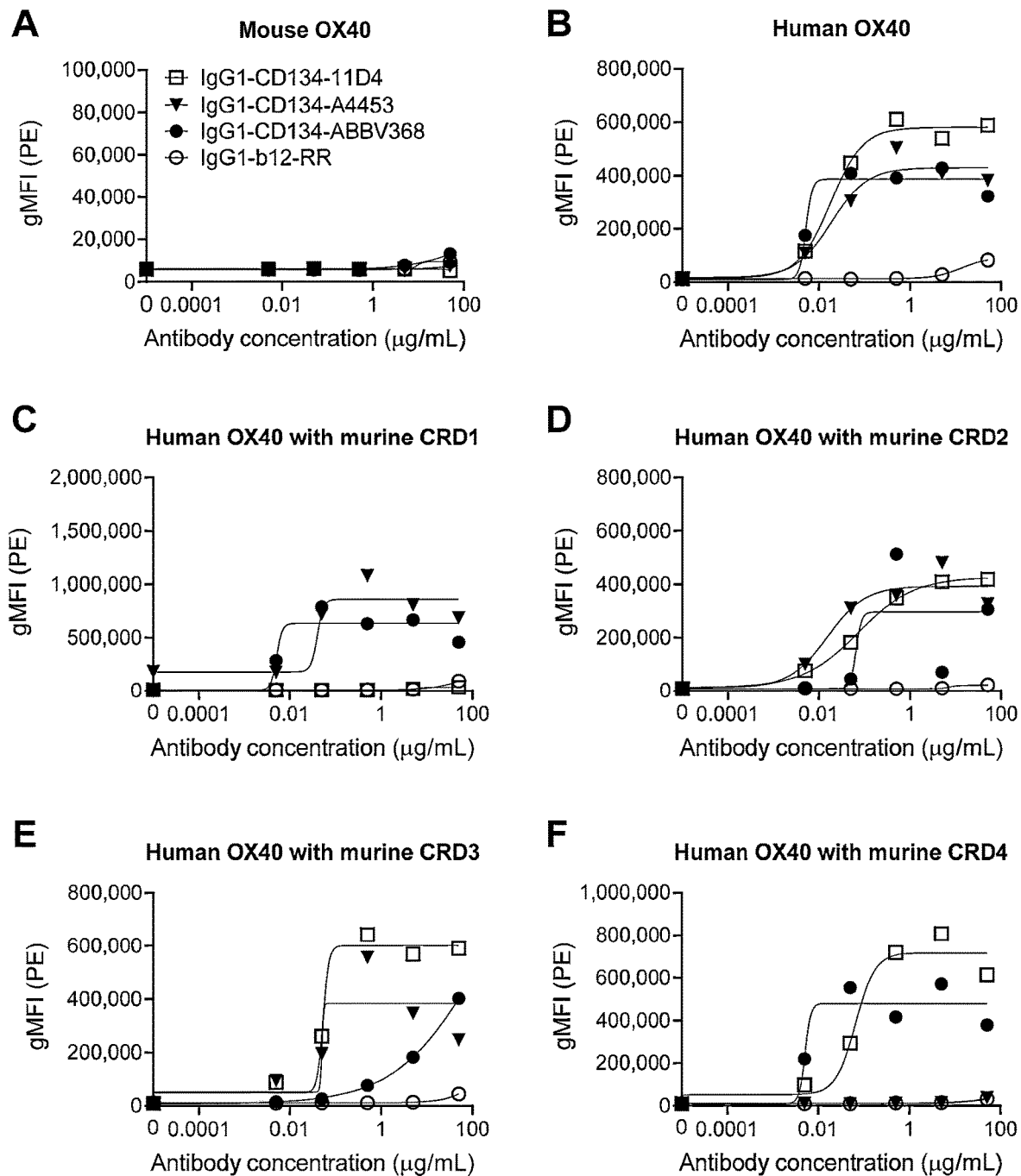

FIG. 7 shows binding of anti-human OX40 antibodies IgG1-CD134-11D4, IgG1-CD134-A4453, and IgG1-CD134-ABBV368 to ExpiCHO-S cells transiently transfected to express mouse OX40 (A), human OX40 (B), or one of four shuffle constructs in which an individual CRD of human OX40 is replaced by the mouse analogue (C-F), as determined by flow cytometry. Non-binding antibody IgG1-b12-RR was included as negative control. Data shown are the geometric mean of the fluorescence intensity (gMFI) from one representative experiment out of two experiments performed.

Figure 8:
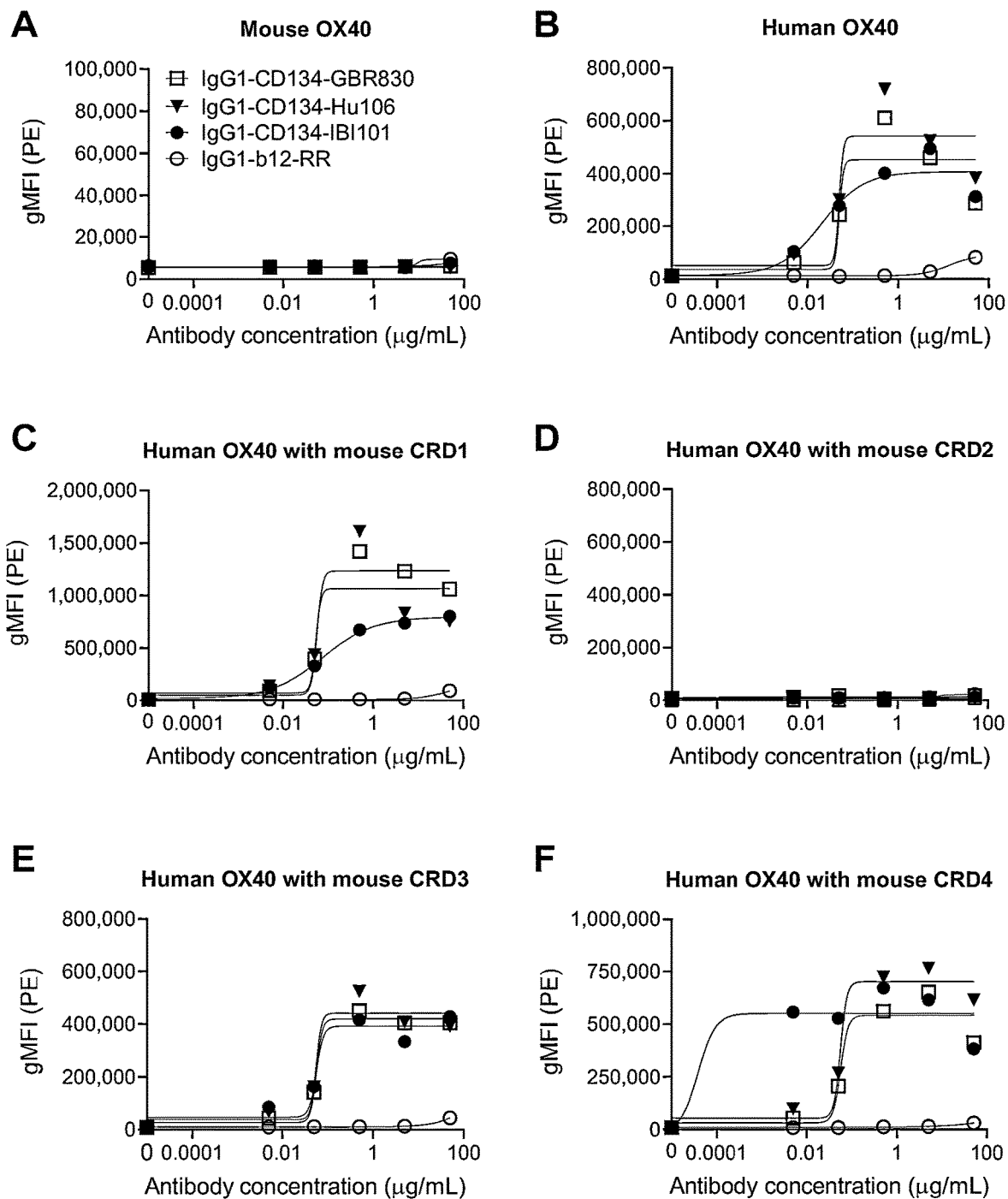

FIG. 8 shows binding of anti-human OX40 antibodies IgG1-CD134-GBR830, IgG1-CD134-Hu106, and IgG1-CD134-IBI101 to ExpiCHO-S cells transiently transfected to mouse OX40 (A), human OX40 (B), or one of four shuffle constructs in which an individual CRD of human OX40 is replaced by the mouse analogue (C-F), as determined by flow cytometry. Non-binding antibody IgG1-b12-RR was included as negative control. Data shown are the geometric mean of the fluorescence intensity (gMFI) from one representative experiment out of two experiments performed.

Figure 9:
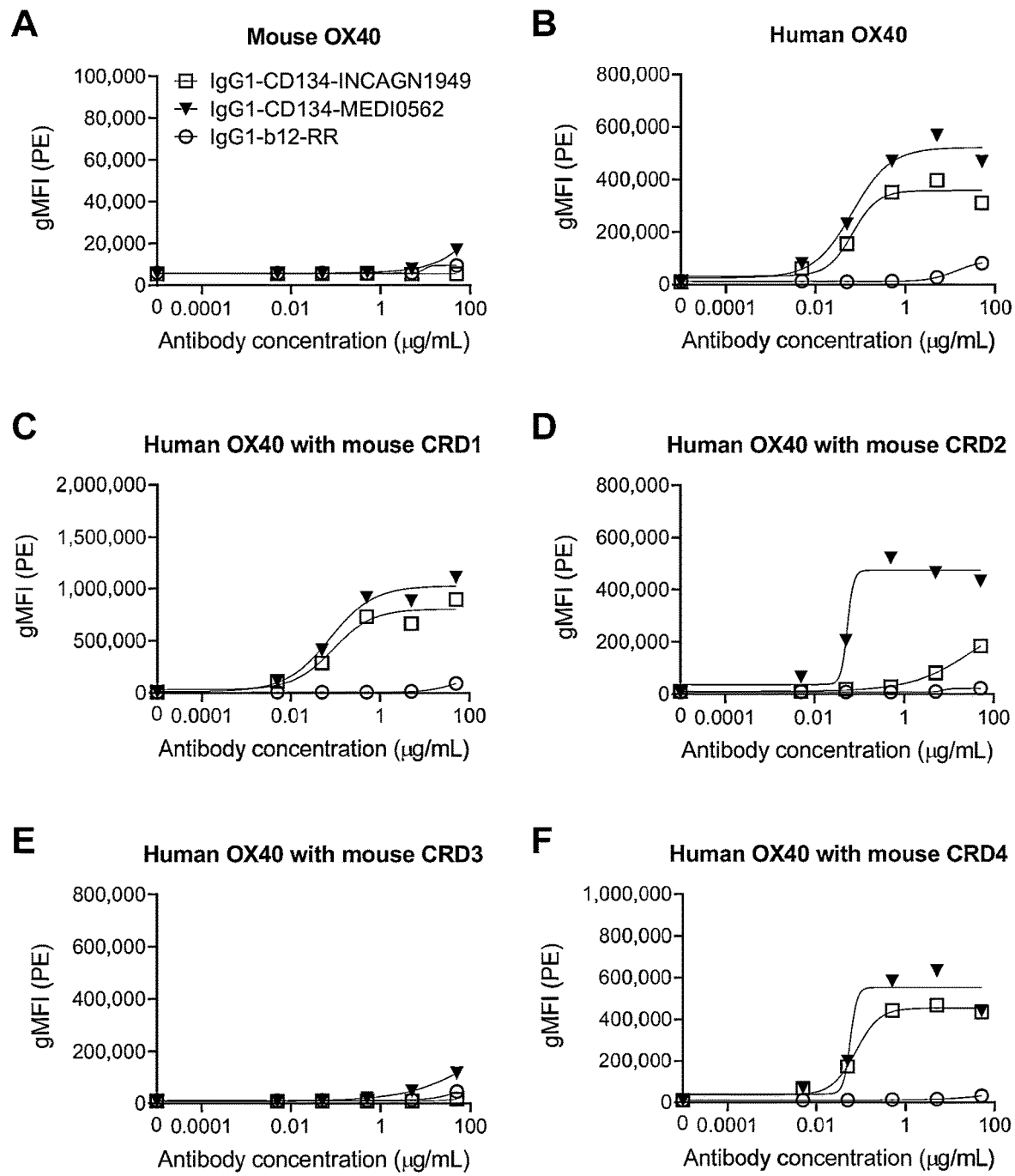

FIG. 9 shows binding of anti-human OX40 antibodies IgG1-CD134-INCAGN1949 and IgG1-CD134-MEDI0562 to ExpiCHO-S cells transiently transfected to express mouse OX40 (A), human OX40 (B), or one of four shuffle constructs in which an individual CRD of human OX40 is replaced by the mouse analogue (C-F), as determined by flow cytometry. Non-binding antibody IgG1-b12-RR was included as negative control. Data shown are the geometric mean of the fluorescence intensity (gMFI) from one representative experiment out of two experiments performed.

FIG. 10 shows relative binding of anti-human OX40 antibodies to ExpiCHO-S cells transiently transfected to express human OX40 (A), human OX40 with mouse CRD1 (B), human OX40 with mouse CRD2 (C), human OX40 with mouse CRD3 (D), or human OX40 with mouse CRD4 (E), as measured by flow cytometry. Data shown are the mean fluorescence intensity (MFI) measured at an antibody concentration of 5 µg/ml normalized to the MFI of antibody IgG1-CD134-A4453. Black dots indicate individual measurements and horizontal bars indicate the mean and SD of two experiments performed.

FIG. 11 shows activation of OX40-expressing reporter cells by IgG1-CD134-003-HC6LC2-RR and by variants of antibody IgG1-CD134-h3C8 (A), variants of antibody IgG1-CD134-RG7888 (B), IgG2s-CD134-SF2-E345R (C), IgG1-CD134-007-RR and IgG1-CD134-012-RR (D), and IgG1-CD134-11D4 (E). Non-binding antibody IgG1-b12-RR was included as negative control. Data shown are relative luminescence units (RLU) from singlicate measurements, or the mean RLU of duplicate (for IgG1-CD134-003-HC6LC2-RR in figures A-D) or quintuplicate (for IgG1-CD134-003-HC6LC2-RR in Figure E) measurements in one experiment performed.

Figure 12:
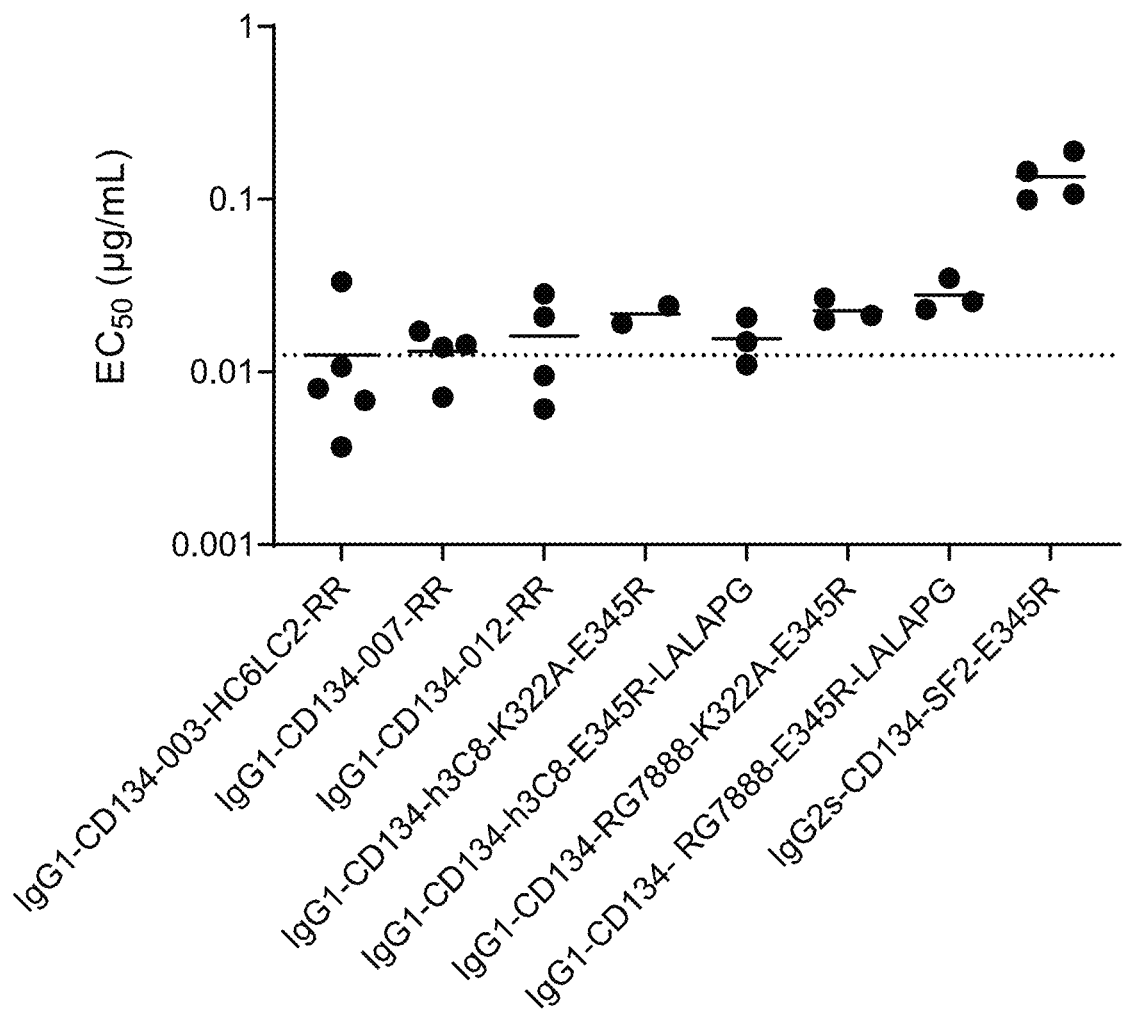

FIG. 12 shows the half-maximal effective concentration (EC50) of anti-human OX40 antibodies for activation of reporter cells overexpressing human OX40. Shown are individual EC50 values derived from two to five independent experiments, with horizontal lines indicating the mean EC50 of all experiments combined. The dotted black line represents the mean EC50 of IgG1-CD134-003-HC6LC2-RR.

FIG. 13 shows the effect of IgG1-CD134-003-HC6LC2-RR and of variants of antibodies IgG1-CD134-h3C8, IgG1-CD134-RG7888, and IgG2s-CD134-SF2 on the proliferation of activated primary human CD4+ (A) and CD8+ (B) T cells, as analyzed by flow cytometry. Non-binding antibody IgG1-b12-RR was included as negative control. Data shown is the mean expansion index of (A) CD4+ and (B) CD8+ T cells±SD from duplicate measurements of one representative donor out of four to eight donors tested. The dotted black lines represent the expansion indices of CD4+ or CD8+ T cells cultured in absence of anti-human OX40 antibodies. (C) Expansion index of CD4+ T cells within polyclonally activated healthy human donor CD8-PBMCs, and (D) expansion index of CD8+ T cells within polyclonally activated healthy human donor CD4. PBMCs as analyzed on day four. Data are derived from one representative donor out of four donors tested in three experiments performed.

FIG. 14 shows the effect of IgG1-CD134-003-HC6LC2-RR and of variants of antibodies IgG1-CD134-h3C8 and IgG1-CD134-RG7888 on the percentage of CD4+ central memory T cells within the CD4+ T-cell population, as analyzed by flow cytometry. Non-binding antibody IgG1-b12-RR was included as negative control. Data shown is the mean percentage of CCR7+CD45RA− cells among (A) CD4+ T cells and (B) CD8+ T cells±SD from duplicate measurements of one representative donor out of six donors tested. The dotted black line represents the percentage of CCR7+CD45RA− cells among CD4+ T cells cultured in absence of anti-human OX40 antibodies.

Figure 15:
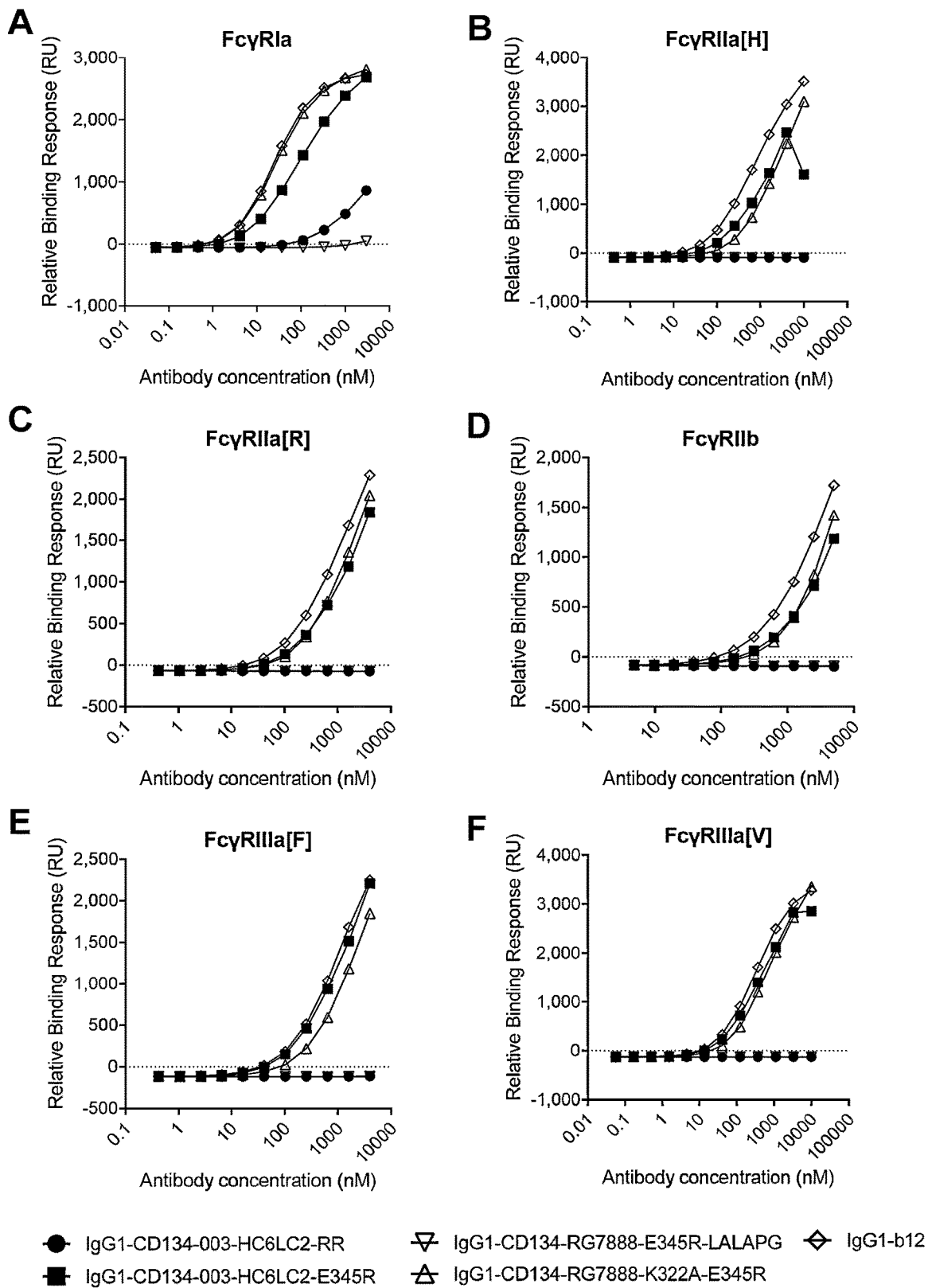

FIG. 15 shows the binding of IgG1-CD134-003-HC6LC2-RR, its variant without Fc-inertness mutation (i.e., IgG1-CD134-003-HC6LC2-E345R), and two variants of antibody IgG1-CD134-RG7888 to immobilized human recombinant FcγRIa (A), FcγRIIa[H] (B), FcγRIIa[R] (C), FcγRIIb (D), FcγRIIIa[F] (E), and FcγRIIIa[V] (F) constructs, as analyzed by SPR. Anti-HIV gp120 antibody IgG1-b12 with a wild-type Fc domain was included as positive control. Data shown are the relative binding response, measured in singlicate in one experiment performed.

Figure 16:
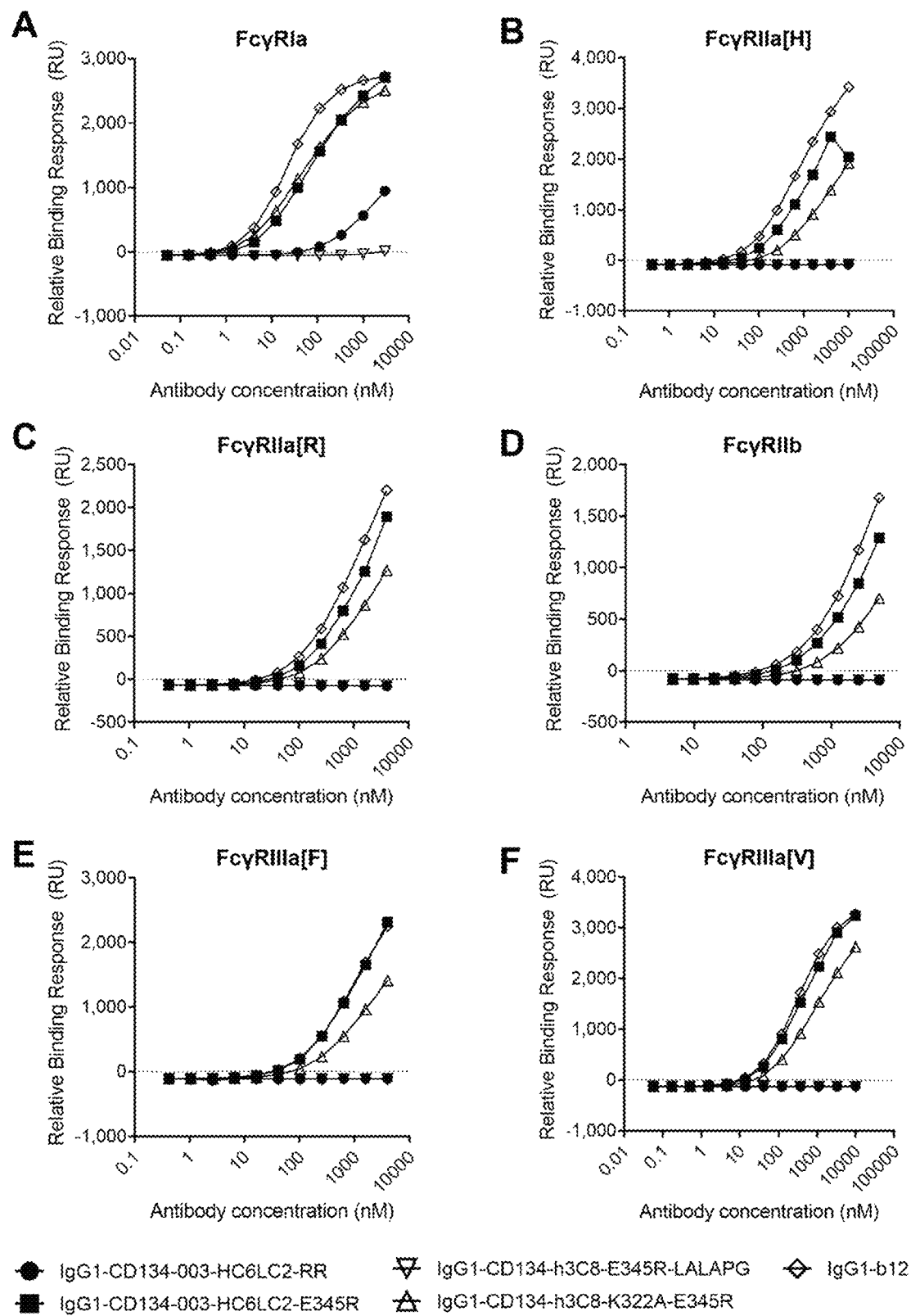

FIG. 16 shows the binding of IgG1-CD134-003-HC6LC2-RR, its variant without Fc-inertness mutation (i.e., IgG1-CD134-003-HC6LC2-E345R), and two variants of antibody IgG1-CD134-h3C8 to immobilized human recombinant FcγRIa (A), FcγRIIa[H] (B), FcγRIIa[R] (C), FcγRIIb (D), FcγRIIIa[F] (E), and FcγRIIIa[V] (F) constructs, as analyzed by SPR. Anti-HIV gp120 antibody IgG1-b12 with a wild-type Fc domain was included as positive control. Data shown are the relative binding response, measured in singlicate in one experiment performed.

FIG. 17 shows binding of anti-human OX40 antibodies to ExpiCHO-S cells transiently transfected to express FcγRIa. Binding is shown for IgG1-CD134-003-HC6LC2-RR, its variant without Fc mutations (i.e., IgG1-CD134-003-HC6LC2), and its parental chimeric antibody (i.e., IgG1-CD134-003) (A), and for (variants of) antibodies IgG2-CD134-SF2 (B), IgG1-CD134-11D4, IgG1-CD134-INCAGN1949, and IgG1-CD134-IBI101 (C), IgG1-CD134-h3C8 (D), and IgG1-CD134-RG7888 (E), as analyzed by flow cytometry. Non-binding antibody IgG1-b12-RR was included as negative control. Data shown are the geometric mean of the fluorescence intensity (gMFI) from one representative experiment out of two experiments performed.

Figure 18:
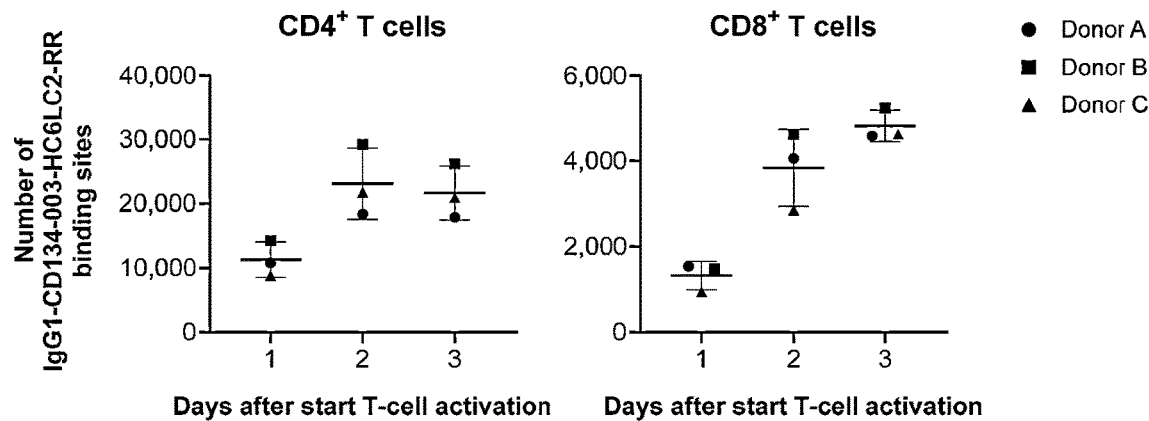

FIG. 18 shows the binding capacity of IgG1-CD134-003-HC6LC2-RR on anti-CD3/CD28 beads-activated primary human CD4+ and CD8+ T cells as analyzed by quantitative flow cytometry, after 1, 2, or 3 days of T-cell activation, using a saturating concentration of IgG1-CD134-003-HC6LC2-RR. Data presented are mean number of antibody binding sites±SD from three donors, with symbols representing numbers from individual donors.

Figure 19:
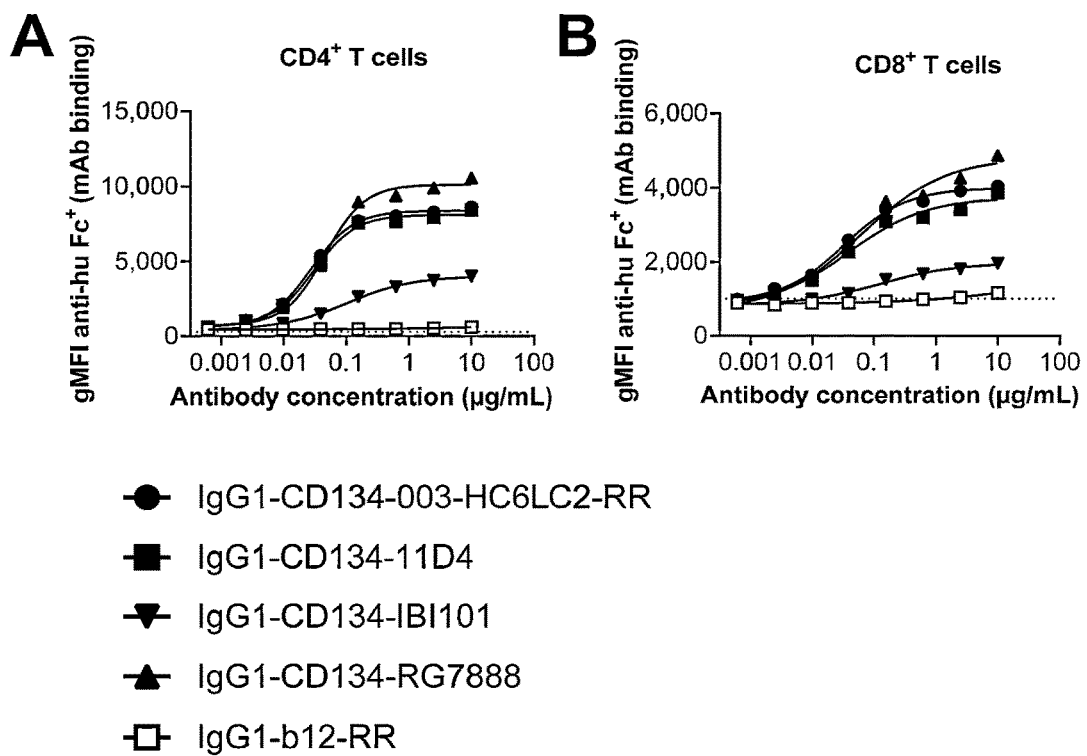

FIG. 19 shows dose-dependent binding of IgG1-CD134-003-HC6LC2-RR to activated human CD4+ and CD8+ T cells. Human PBMCs were cultured in the presence of anti-CD3/CD28 antibodies for 2 days and subsequently incubated with IgG1-CD134-003-HC6LC2-RR, IgG1-CD134-IBI101, IgG1-CD134-11D4, IgG1-CD134-RG7888, or nonbinding control antibody IgG1-b12-RR. Binding of anti-human OX40 antibodies to T cells was evaluated by flow cytometric detection of an anti-human Fcγ antibody. Data shown are the mean±SD of duplicate wells from one representative donor out of three donors tested.

Figure 20:
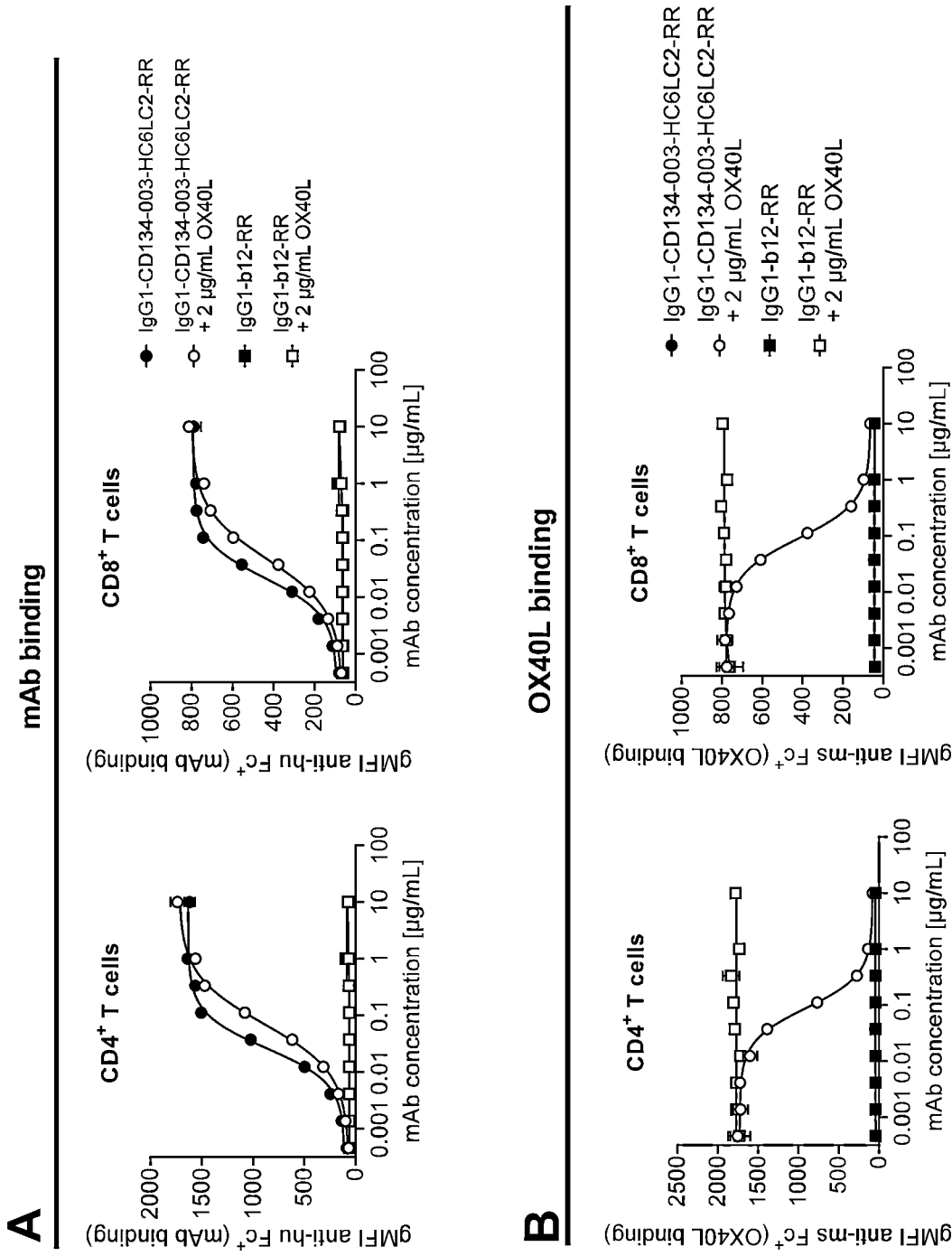

FIG. 20 shows binding of IgG1-CD134-003-HC6LC2-RR or soluble OX40L (sOX40L) to activated human CD4+ and CD8+ T cells. Human CD4+ and CD8+ T cells, activated for two days by anti-CD3/CD28 beads, were incubated with IgG1-CD134-003-HC6LC2-RR or control antibody IgG1-b12-RR in the presence and absence of a saturating concentration (2 μg/mL) of sOX40L. Binding was analyzed by flow cytometry. (A) Antibody binding to CD4+ and CD8+ T cells. (B) sOX40L binding to CD4+ and CD8+ T cells. Data shown are mean geometric mean fluorescence intensities (mean gMFI) from duplicate wells±SD of one representative donor out of three.

FIG. 21 shows activation of OX40-expressing reporter cells by anti-human OX40 antibodies. (A) Mean±SD bioluminescence, as a surrogate for OX40 agonist activity, presented as RLU±SD in OX40+ Jurkat reporter T cells incubated with IgG1-CD134-003-HC6LC2-RR, IgG1-CD134-003-E345R, IgG1-CD134-003, IgG1-CD134-003-FEAL or nonbinding control antibody IgG1-b12-RR in the absence or presence of FcγRIIb-CHO-K1 cells. Data shown are from one experiment. (B) Mean±SD bioluminescence in OX40+ Jurkat reporter T cells incubated with IgG1-CD134-003-HC6LC2-RR, IgG1-CD134-11D4, IgG1-CD134-RG7888, IgG1-CD134-IBI101, or non-binding control antibody IgG1-b12-RR, in the absence or presence of FcγRIIb-CHO-K1 cells. Dotted lines represent mean RLU values of wells without antibody treatment. Data shown are from one representative experiment out of two experiments.

FIG. 22 shows expression of cell surface-expressed markers associated with human T-cell activation after incubation of polyclonally activated healthy donor PBMC samples with IgG1-CD134-003-HC6LC2-RR or non-binding control antibody IgG1-b12-RR for two or five days. Percentages±SD of CD4+ (A, C, E, G) and CD8+ T cells (B, D, F, H) expressing 4-1BB, CD25, HLA-DR, or PD-1 were determined using flow cytometry. Data shown were selected from either day two or five, depending on which day the maximal effect of IgG1-CD134-003-HC6LC2-RR was observed for each marker. Dotted lines represent percentages of marker expressing T cells incubated with CD3 antibody only. All data shown are derived from one representative donor out of seven donors tested in three experiments. Percentages±SD of CD4+ (I-K) and CD8+ T cells (L-N) expressing 4-1BB, CD25, or HLA-DR after stimulation with 5 μg/mL IgG1-CD134-003-HC6LC2-RR, IgG1-b12-RR, or OX40 agonistic reference antibody analogs IgG1-CD134-RG7888, IgG1-CD134-11D4 and IgG1-CD134-IBI101, as analyzed by flow cytometry after two and five days of stimulation. Data shown are mean normalized data±SD of pooled data from 4 to 7 donors evaluated in 2 to 3 independent experiments.

Figure 23:
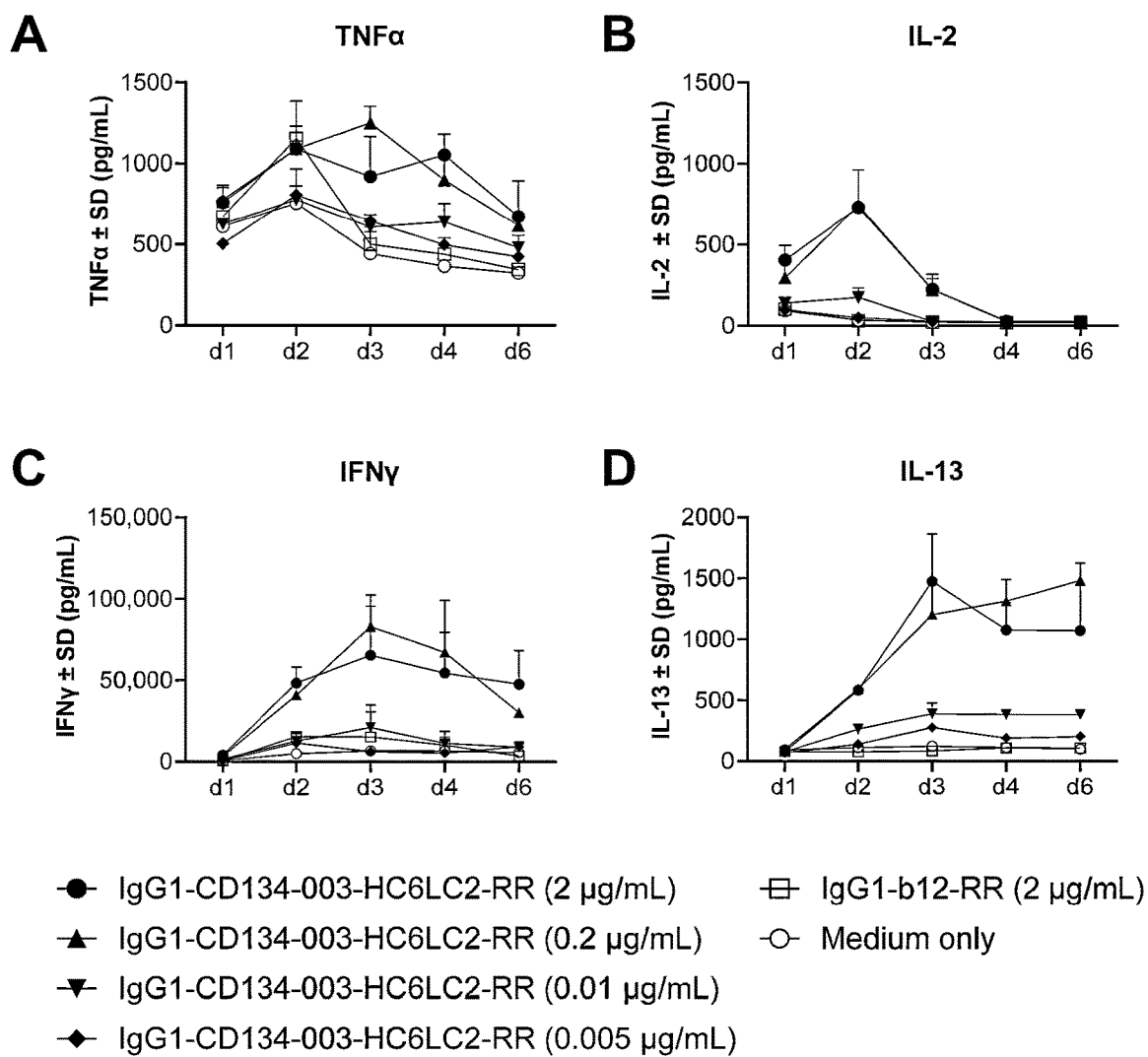

FIG. 23 shows the kinetics of cytokine concentrations in supernatants of polyclonally activated healthy human donor PBMC samples incubated with IgG1-CD134-003-HC6LC2-RR or nonbinding control antibody IgG1-b12-RR for 1, 2, 3, 4, or 6 days. Mean±SD calculated concentrations of (A) TNFα, (B) IL-2, (C) IFNγ, and (D) IL-13, as determined by multiplexed ECLIA. Data shown are derived from one representative donor out of three donors tested in total.

Figure 24:
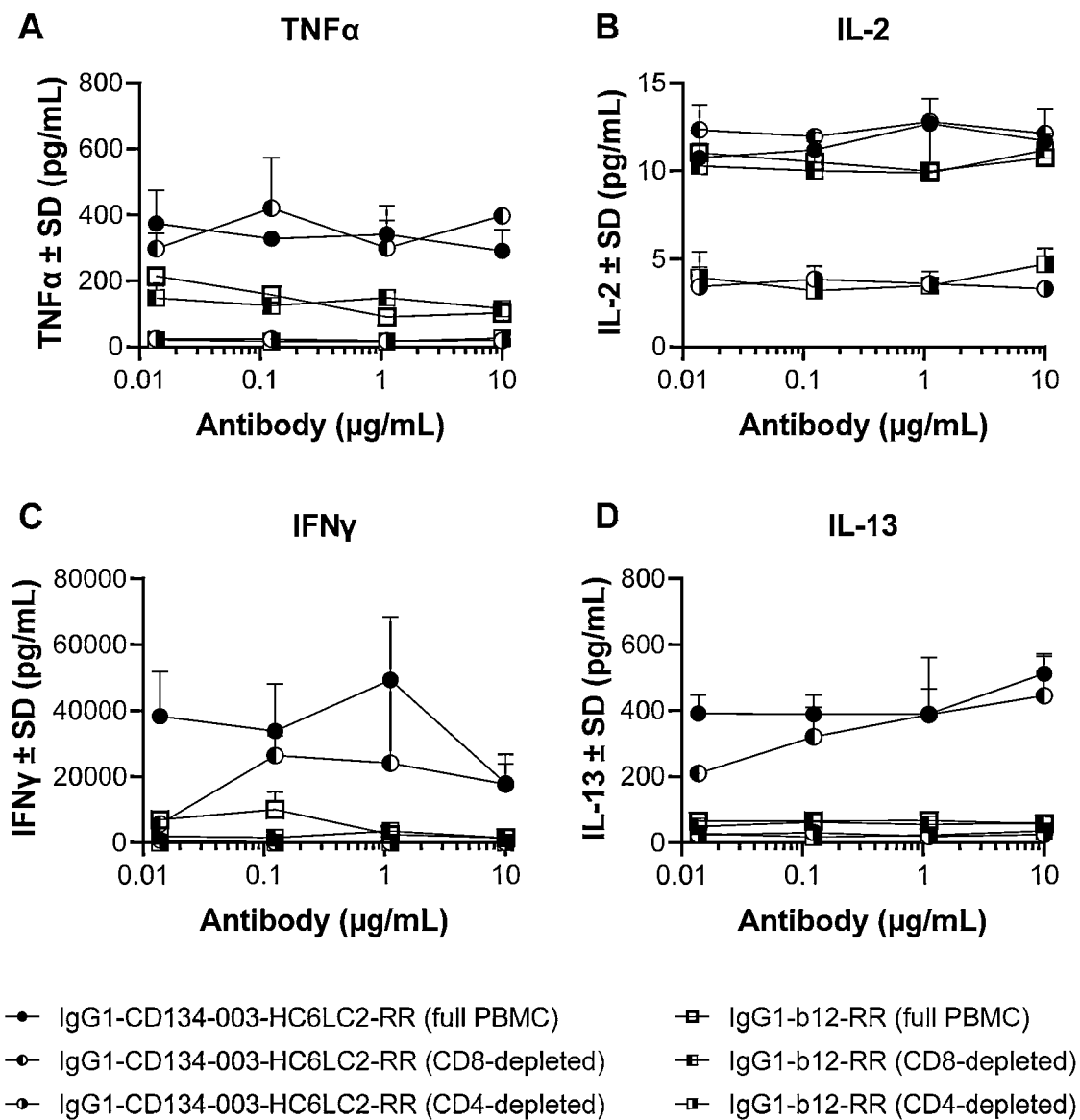

FIG. 24 shows cytokine concentrations in supernatants of polyclonally activated healthy human donor PBMC samples incubated with IgG1-CD134-003-HC6LC2-RR or nonbinding control antibody IgG1-b12-RR for four days. PBMC samples were non-depleted or either depleted of CD4+ or CD8+ T cells before incubation. Mean±SD calculated concentrations of (A) TNFα, (B) IL-2, (C) IFNγ, and (D) IL-13, as determined by multiplexed ECLIA. Data shown are derived from one representative donor out of three donors tested in total.

Figure 25:
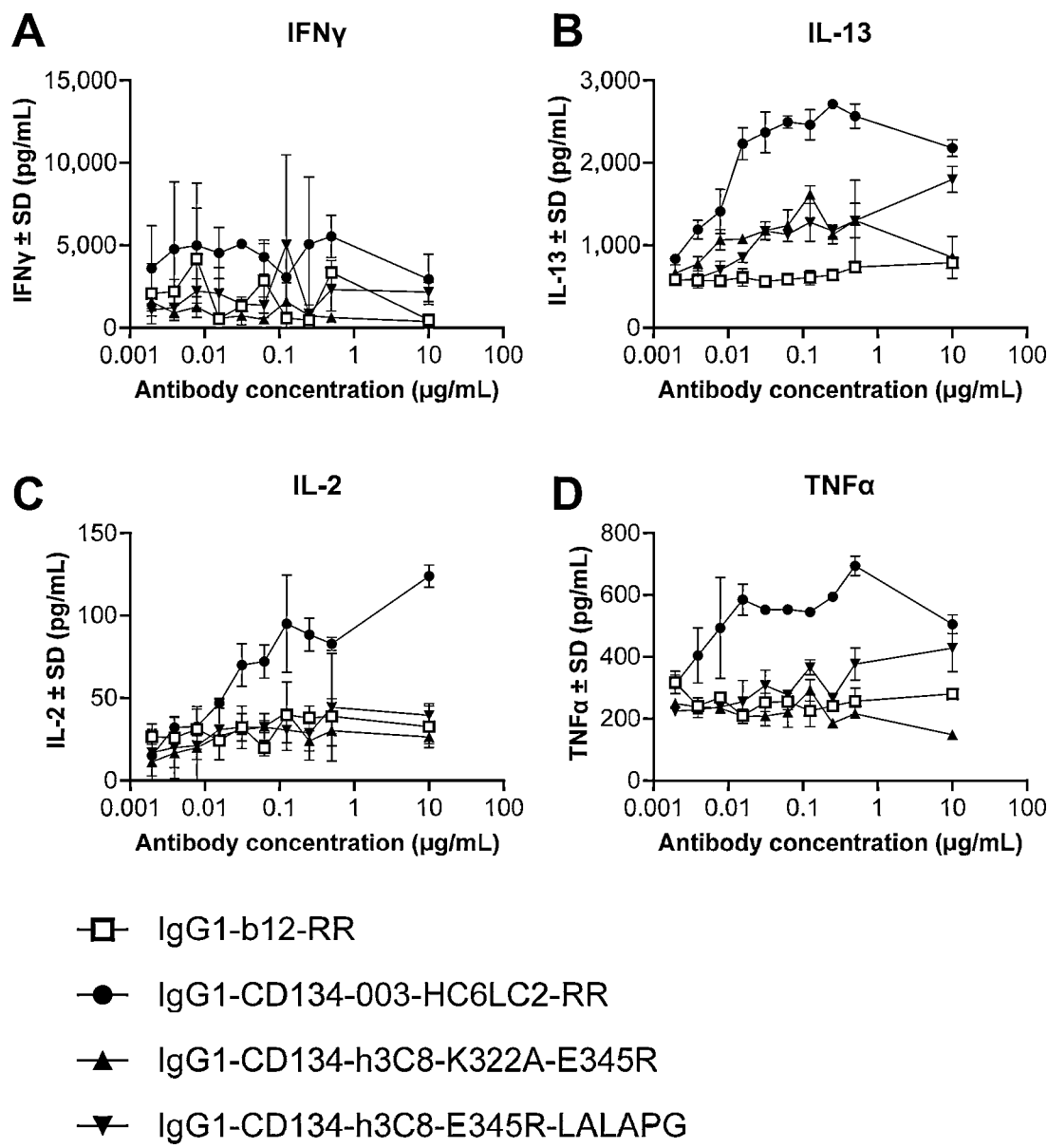

FIG. 25 shows cytokine concentrations in supernatants of polyclonally activated healthy human donor PBMC samples incubated with IgG1-CD134-003-HC6LC2-RR, IgG1-CD134-h3C8-K322A-E345R, IgG1-CD134-h3C8-E345R-LALAPG, or nonbinding control antibody IgG1-b12-RR for four days. Mean±SD calculated concentrations of (A) IFNγ, (B) IL-13, (C) IL-2, and (D) TNFα, as determined by multiplexed ECLIA. Data shown are derived from one donor out of two donors tested in total.

Figure 26:
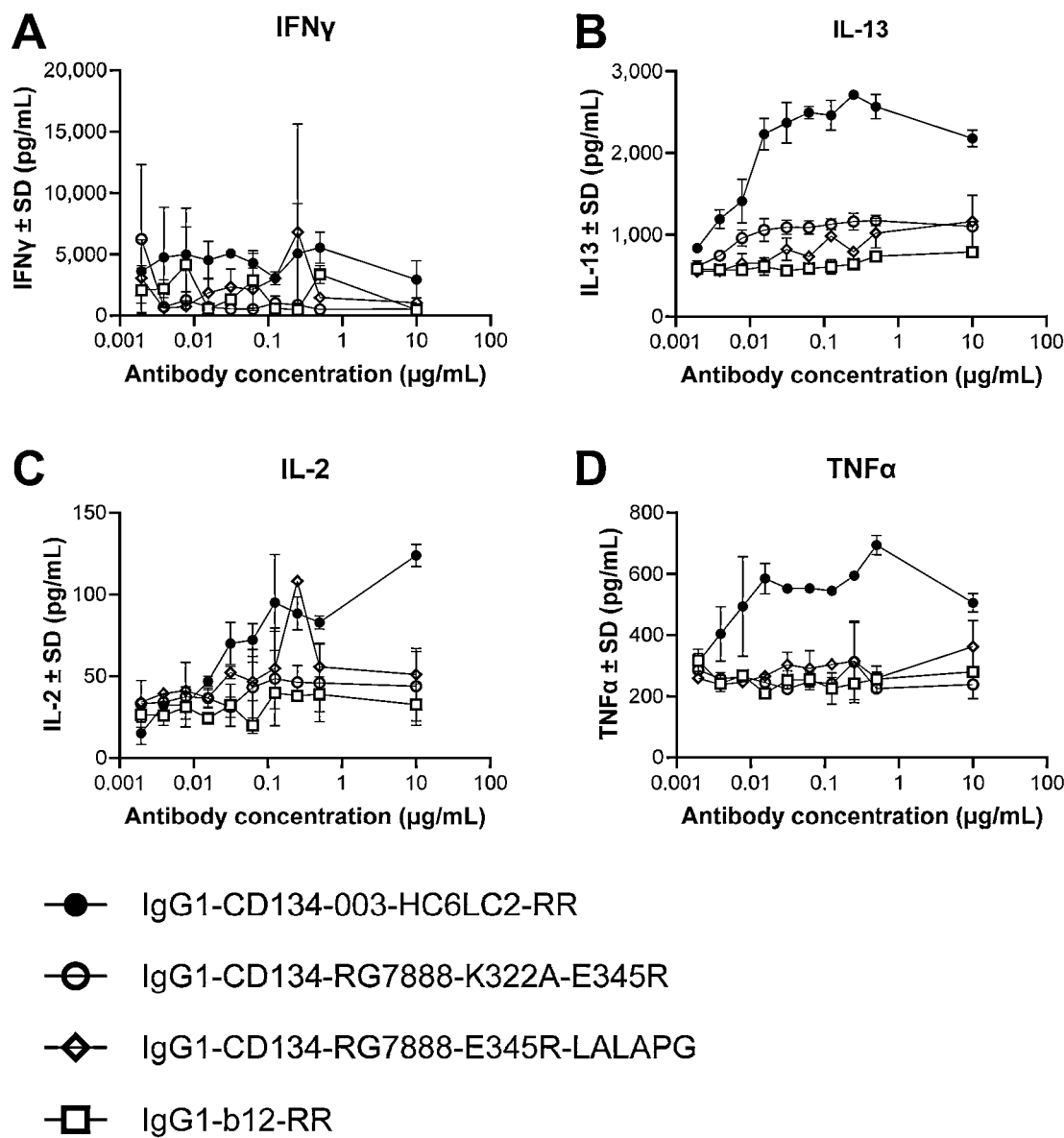

FIG. 26 shows cytokine concentrations in supernatants of polyclonally activated healthy human donor PBMC samples incubated with IgG1-CD134-003-HC6LC2-RR, IgG1-CD134-RG7888-K322A-E345R, IgG1-CD134-RG7888-E345R-LALAPG, or nonbinding control antibody IgG1-b12-RR for four days. Mean±SD calculated concentrations of (A) IFNγ, (B) IL-13, (C) IL-2, and (D) TNFα, as determined by multiplexed ECLIA. Data shown are derived from one donor out of two donors tested in total.

Figure 27:
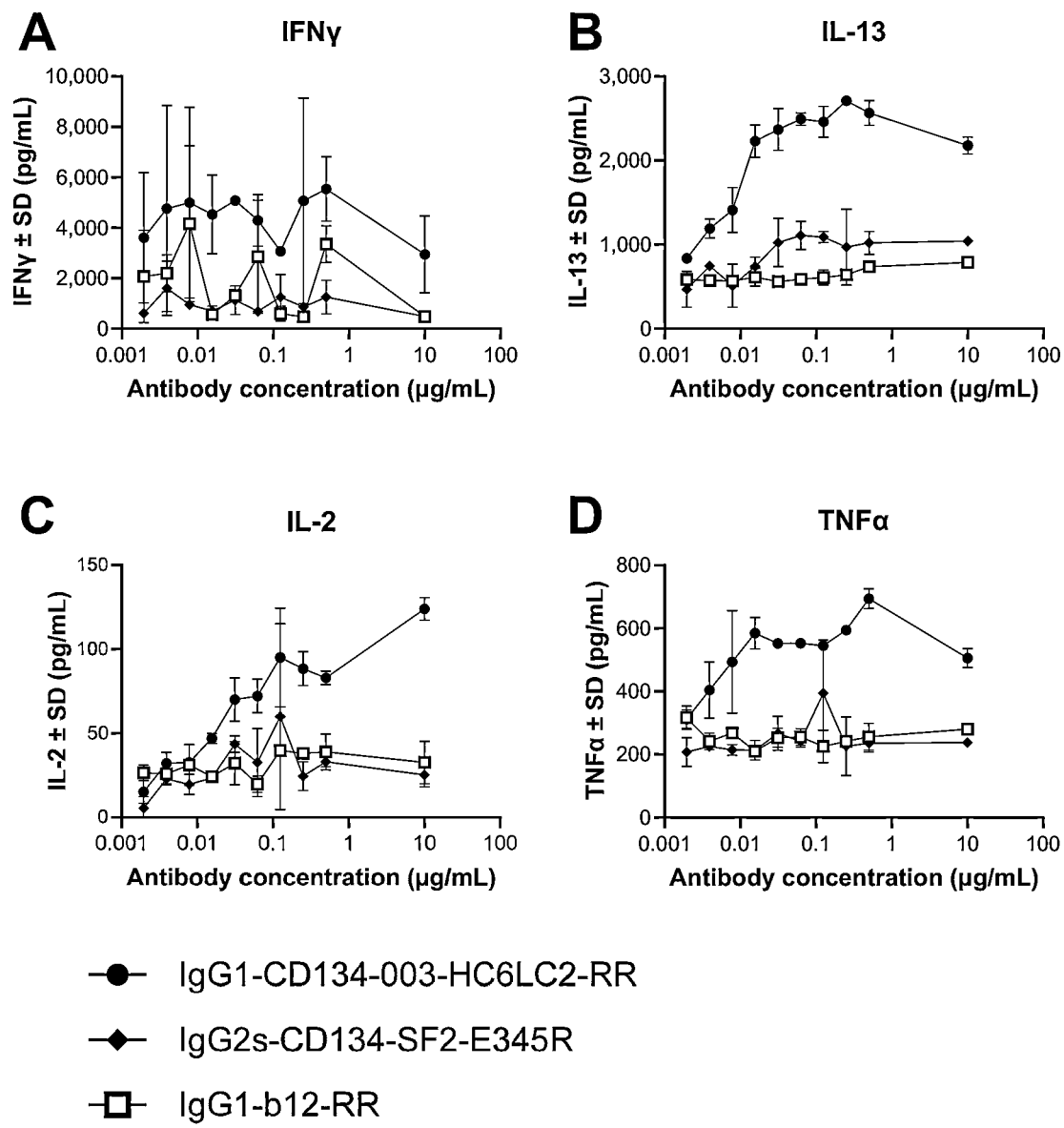

FIG. 27 shows cytokine concentrations in supernatants of polyclonally activated healthy human donor PBMC samples incubated with IgG1-CD134-003-HC6LC2-RR, IgG2sCD134-SF2-E345R, or nonbinding control antibody IgG1-b12-RR. Mean±SD calculated concentrations of (A) IFNγ, (B) IL-13, (C) IL-2, and (D) TNFα, as determined by multiplexed ECLIA. Data shown are derived from one donor out of two donors tested in total.

Figure 28:
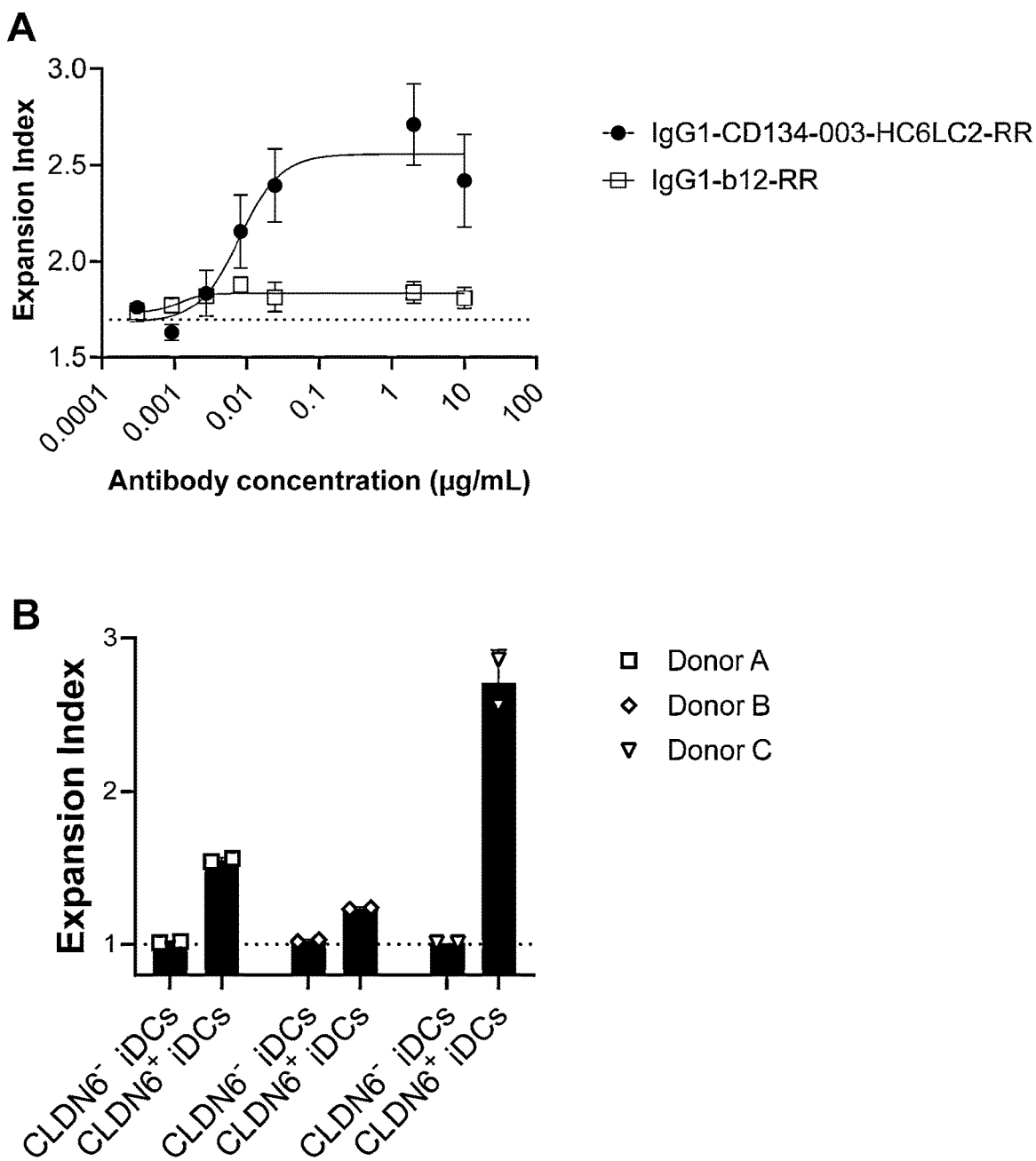

FIG. 28 shows CD8+ T-cell proliferation on day four in an antigen-specific human T-cell proliferation assay upon treatment with IgG1-CD134-003-HC6LC2-RR or nonbinding control antibody IgG1-b12-RR, as assessed by flow cytometry. (A) Mean±SD expansion indices for OX40-expressing CLDN6-specific CD8+ T cells incubated with IgG1-CD134-003-HC6LC2-RR or IgG1-b12-RR of duplicate wells from one representative donor out of three donors tested in two experiments. Dotted black line indicates baseline values as determined from iDC: CD8+ T-cell cocultures incubated without antibody (medium only). (B) Mean±SD expansion indices of duplicate wells of OX40-expressing CLDN6-specific CD8+ T cells incubated with autologous CLDN6-expressing (CLDN6+) or mock transfected (CLDN6−) iDCs in the presence of 2 µg/ml IgG1-CD134-003-HC6LC2-RR. Data shown for all three donors tested.

Figure 29:
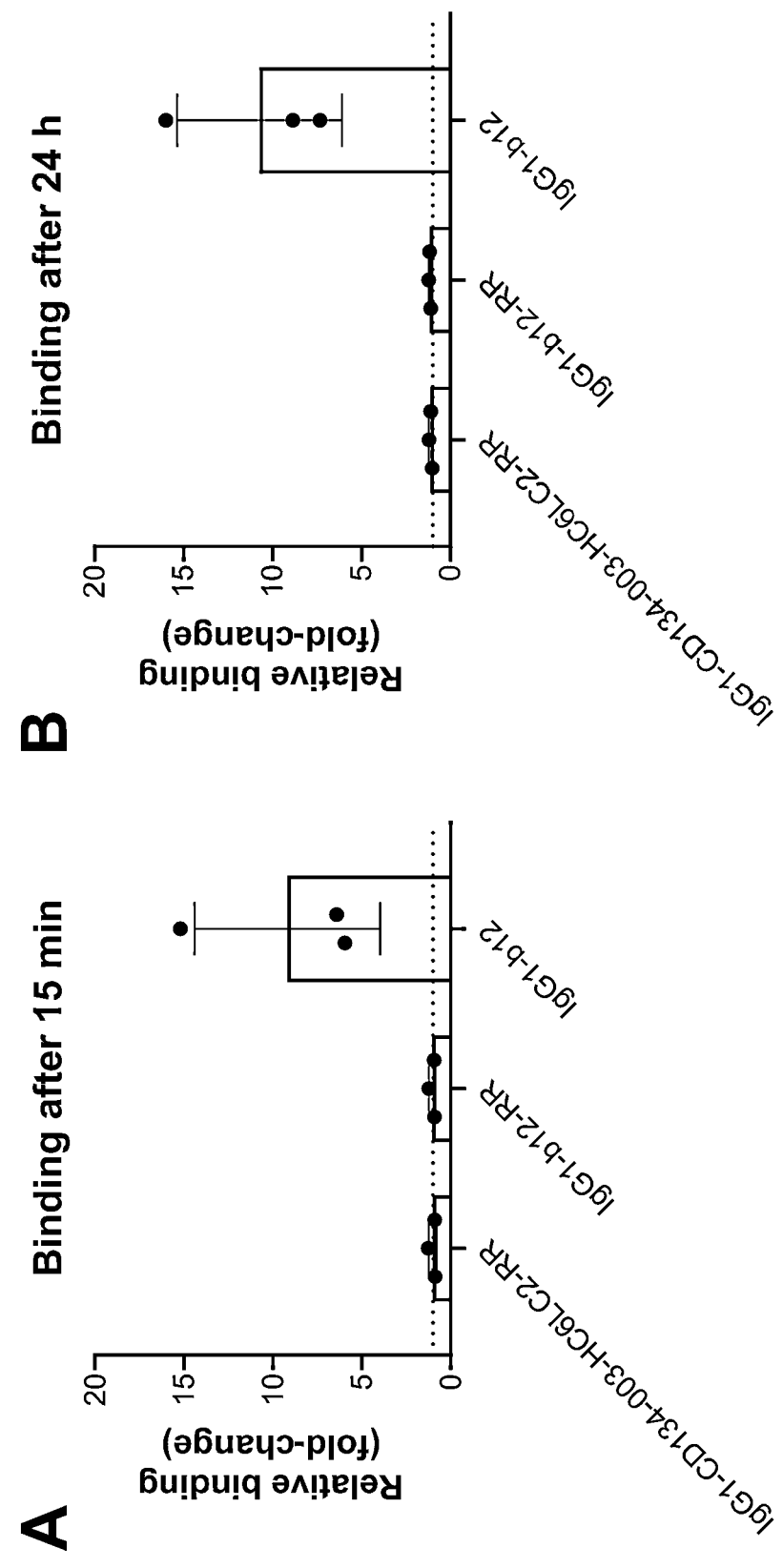

FIG. 29 shows lack of binding of IgG1-CD134-003-HC6LC2-RR to FcγRIa-expressing human monocyte-derived M2c-like macrophages as analyzed by flow cytometry. Binding of IgG1-CD134-003-HC6LC2-RR, or nonbinding control antibodies IgG1-b12-RR or IgG1-b12 to FcγRIa-expressing human monocyte-derived M2c-like macrophages after 15 min (A) and 24 h (B) of incubation. Binding is shown relative to that of the background control (binding with secondary antibody only, indicated by the dotted black line). Dots represent three individual donors measured in two independent experiments, and bar graphs and error bars represent the mean fold-change and SD of the three donors, respectively.

Figure 30:
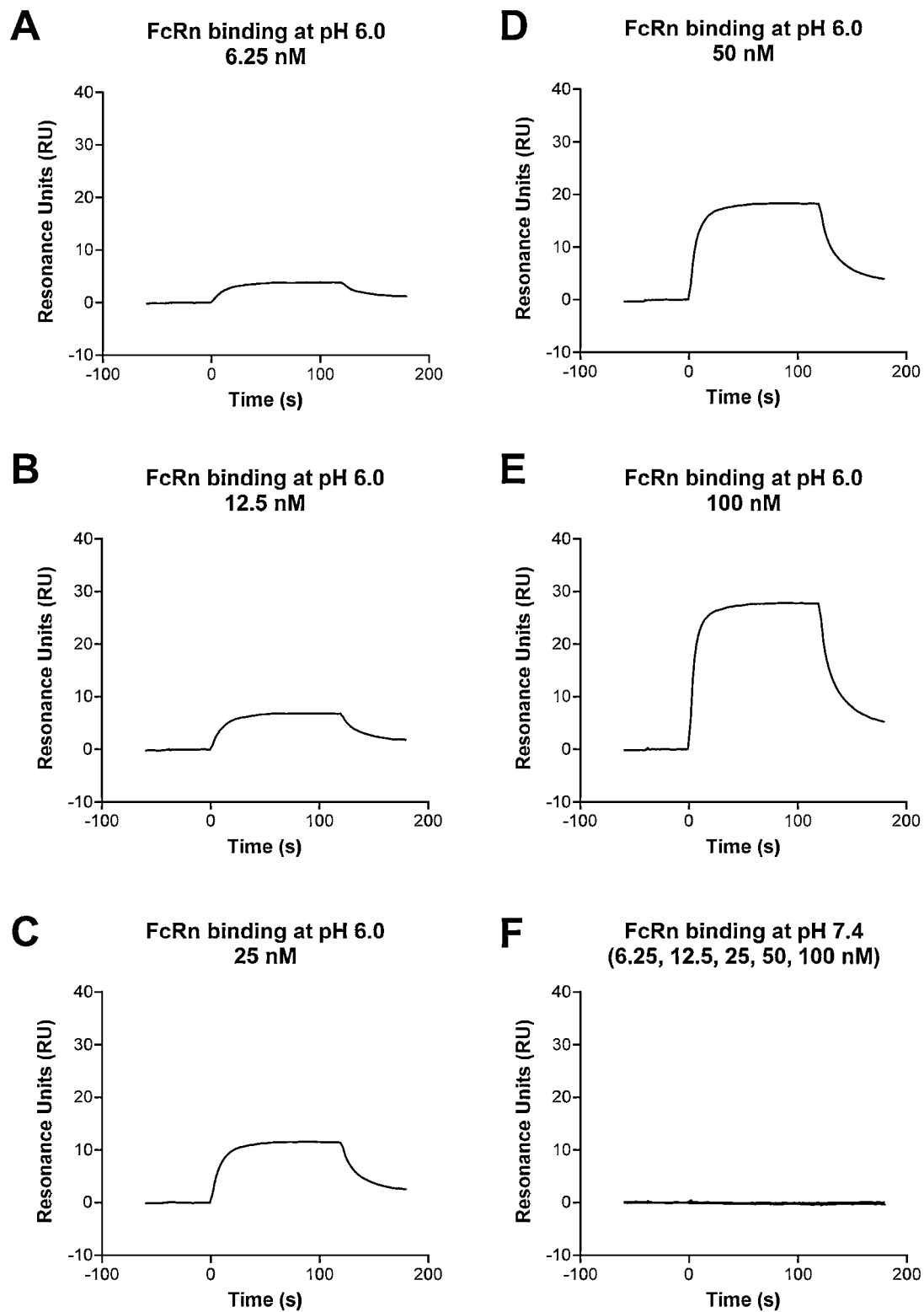

FIG. 30 shows binding of IgG1-CD134-003-HC6LC2-RR to human neonatal receptor FcRn, as analyzed by SPR. Data shown are sensorgrams for the interaction between FcRn and IgG1-CD134-003-HC6LC2-RR at pH 6.0 (A-E) and pH 7.4 (F), with IgG1-CD134-003-HC6LC2-RR tested in different concentrations as indicated in each subpanel. Data shown are from one representative experiment out of three experiments for binding at pH 6.0 and out of two experiments for binding at pH 7.4.

FIG. 31 shows binding of IgG1-CD134-003-HC6LC2-RR and IgG1-CD52-E345R to activated CD4+ and CD8+ T cells, and C1q binding thereto. (A-C) Primary human T cells were stimulated with anti-CD3/CD28 beads and subsequently incubated with IgG1-CD134-003-HC6LC2-RR, IgG1-CD52-E345R, or IgG1-b12-RR to evaluate antibody binding to the cells by flow cytometry. Shown is binding of antibodies to CD4+ (A) and CD8+ (B and C) T cells. FIG. C displays the same data for IgG1-b12-RR as Figure B, but with a different Y-axis range. Data are expressed as mean gMFI±SD of duplicate wells from one representative donor out of three donors tested in three experiments. Binding of C1q to IgG1-CD134-003-HC6LC2-RR, IgG1-CD52-E345R, or IgG1-b12-RR to OX40 on the cell membrane of activated CD4+ (D) and CD8+ (E) T cells, as analyzed by flow cytometry. All data shown are mean gMFI±SD of duplicate wells from one representative donor, out of three donors tested in three experiments.

Figure 32:
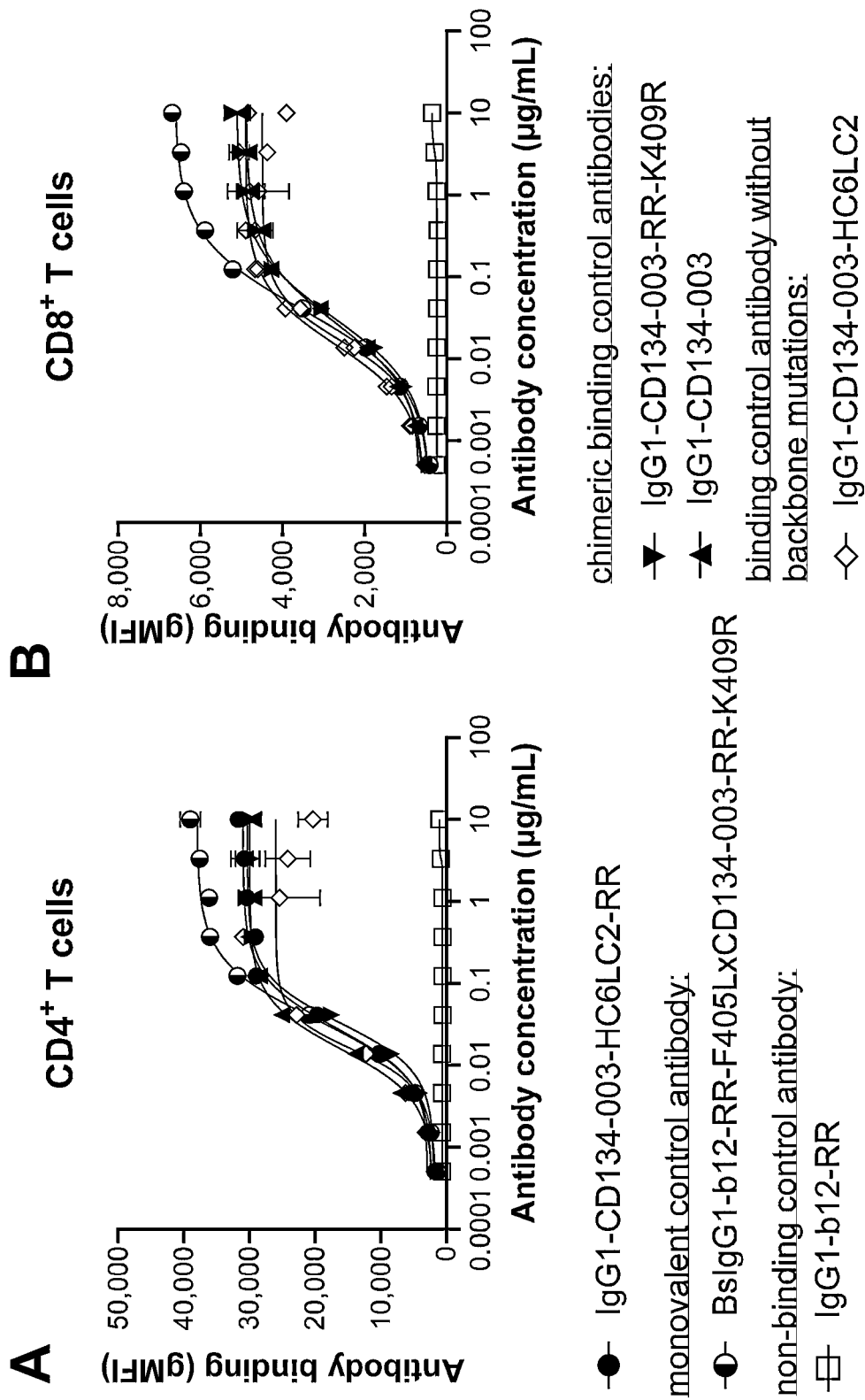

FIG. 32 shows binding of monovalent and bivalent anti-human OX40 antibodies to activated human T cells. Human CD4+ (A) and CD8+ (B) T cells, activated for three days using anti-CD3/CD28 beads, were incubated with IgG1-CD134-003-HC6LC2-RR, monovalent OX40 antibody BsIgG1-b12-RR-F405LxCD134-003-RR-K409R, IgG1-CD134-003-RR-K409R, IgG1-CD134-003, IgG1-CD134-003-HC6LC2, or nonbinding control antibody IgG1-b12-RR and binding was evaluated by flow cytometry. Data shown are mean gMFI±SD from duplicate wells of one representative donor out of four donors tested.

Figure 33:
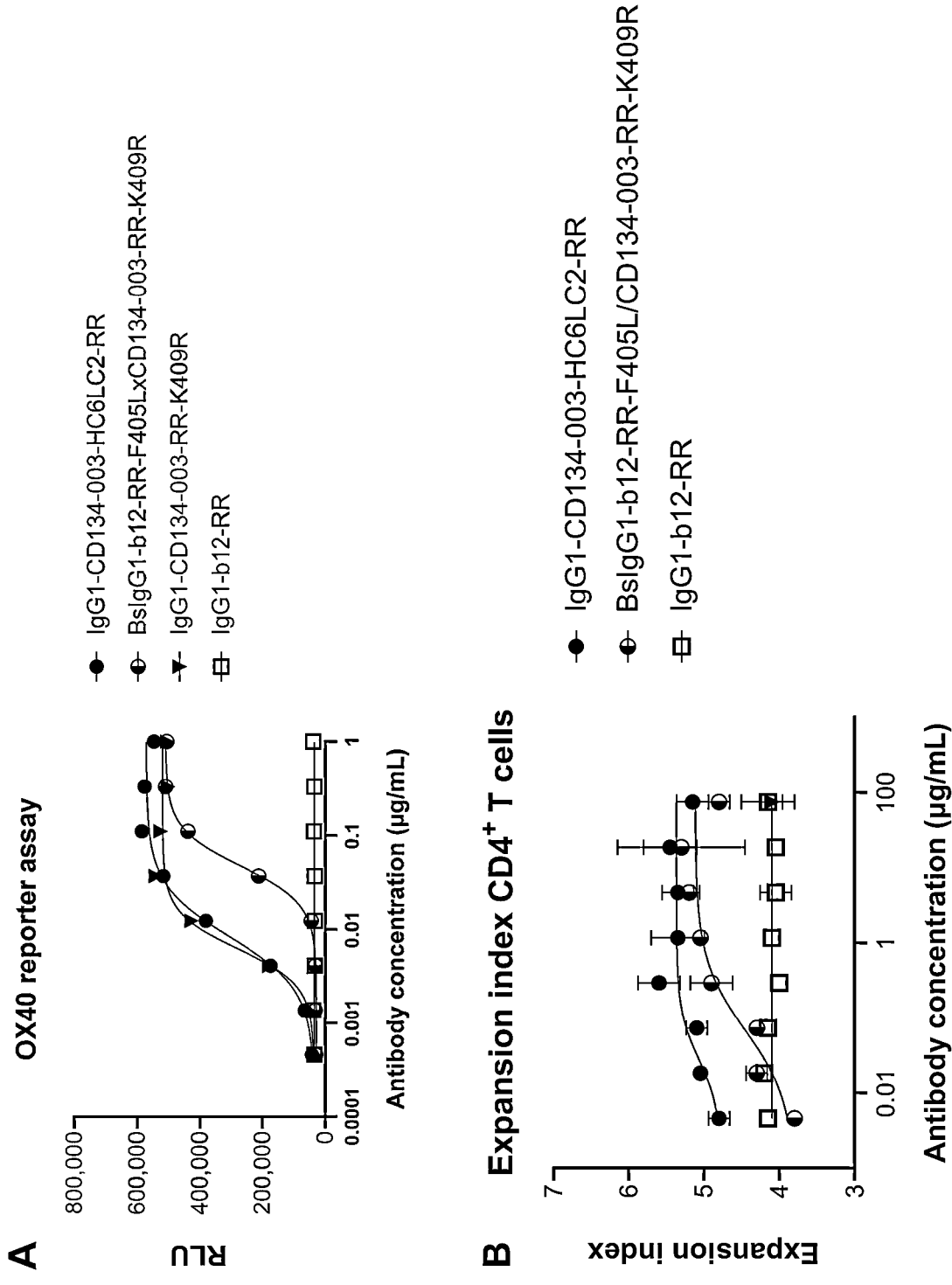

FIG. 33 shows the functional activity of BsIgG1-b12-RR-F405LxCD134-003-RR-K409R, IgG1-CD134-003-HC6LC2-RR, and IgG1-CD134-003-RR-K409R in an OX40+ T-cell reporter assay and polyclonal T-cell proliferation assay. (A) Bioluminescence, as a surrogate for OX40 agonist activity was as RLU, in OX40+Jurkat reporter T cells incubated with BsIgG1-b12-RR-F405LxCD134-003-RR-K409R, IgG1-CD134-003-HC6LC2-RR, IgG1-CD134-003-RR-K409R, or IgG1-b12-RR. Data shown are from one representative experiment out of four experiments in total. (B) Enhancement of CD4+ T-cell proliferation in a polyclonal T-cell proliferation assay, after incubation with concentration ranges of BsIgG1-b12-RR-F405LxCD134-003-RR-K409R, IgG1-CD134-003-HC6LC2-RR, or IgG1-b12-RR, as analyzed by flow cytometry and presented as mean±SD of duplicate wells. Data shown are CD4+ T-cell expansion indices from one donor out of three donors tested in one experiment.

Figure 34:
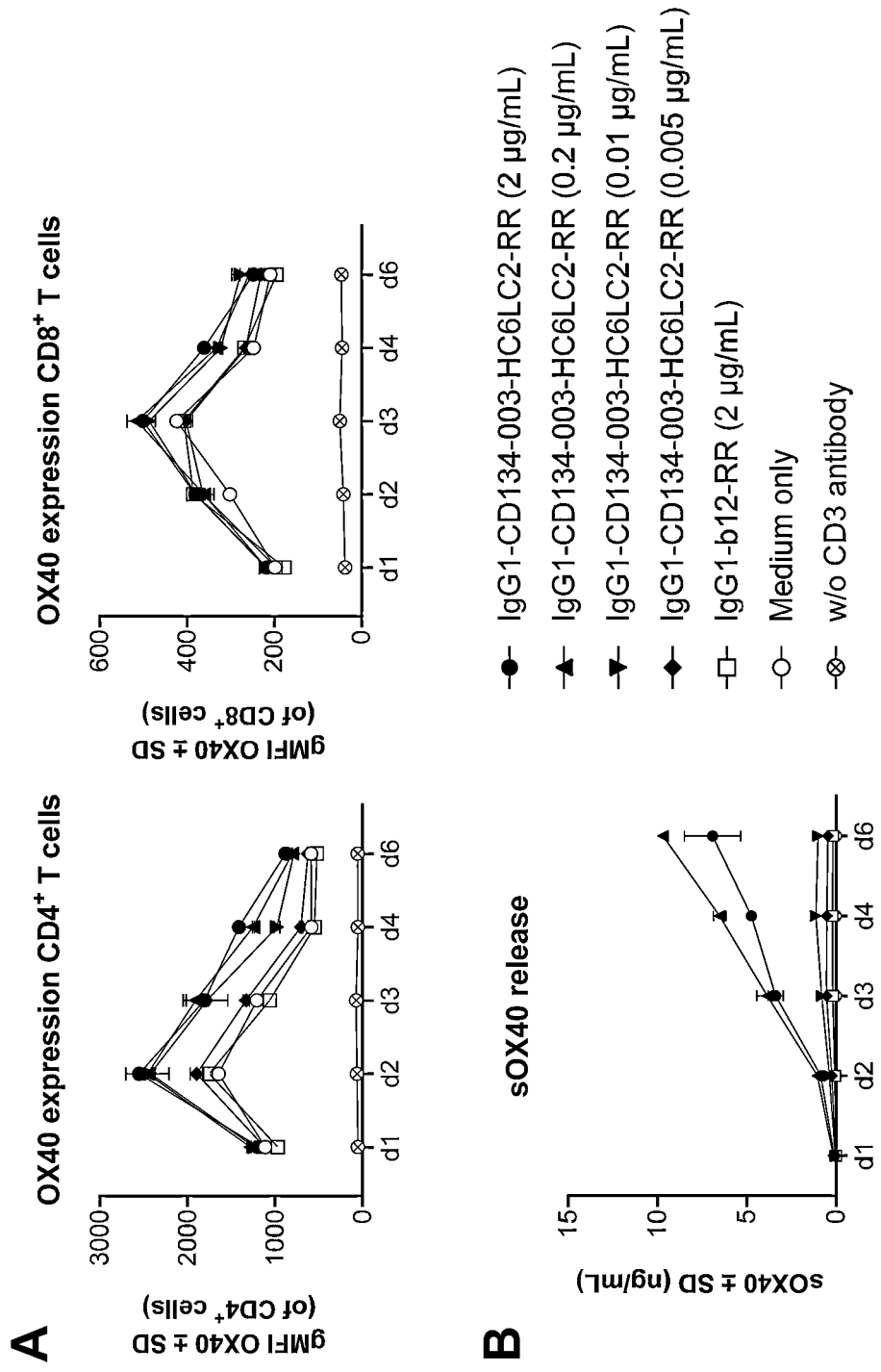

FIG. 34 shows membrane OX40 expression and soluble OX40 (sOX40) levels in polyclonally activated healthy human donor PBMC cultures upon treatment with IgG1-CD134-003-HC6LC2-RR or nonbinding control antibody IgG1-b12-RR. (A) Mean±SD of duplicate wells of cell surface-expression of OX40 on CD4+ and CD8+ T cells, as assessed by flow cytometry. (B) Mean concentrations±SD of duplicate wells of sOX40 in the supernatants, as measured by ECLIA. Data shown are from one representative donor out of three donors tested in a similar experimental setup.

Figure 35:
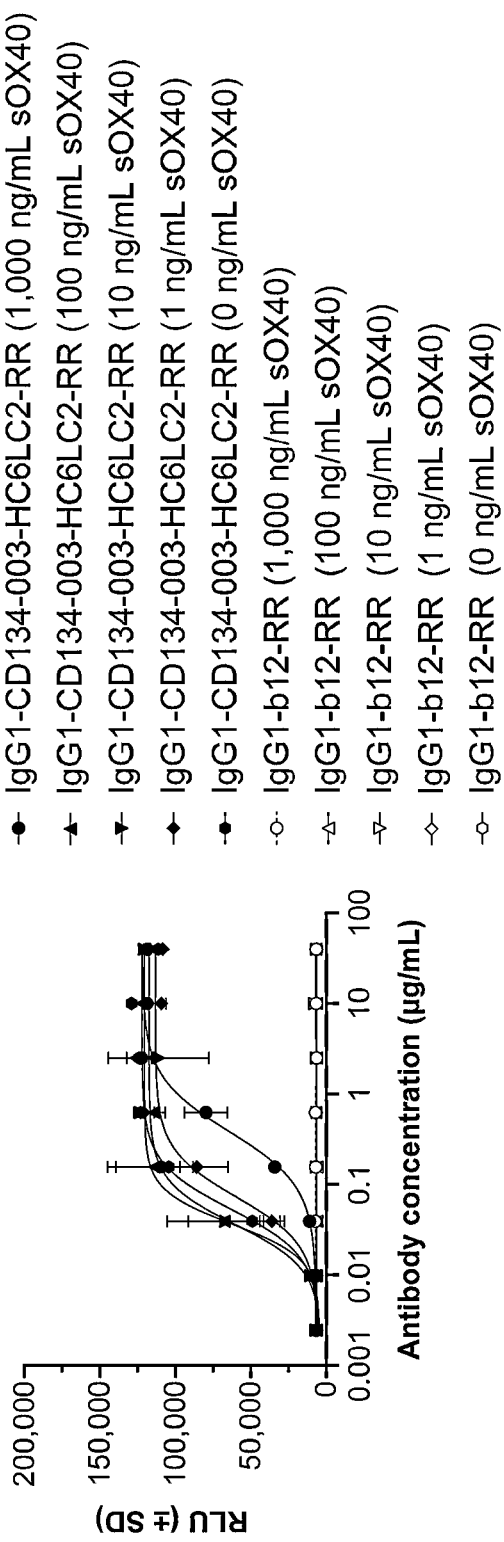

FIG. 35 shows activation of OX40-expressing reporter cells by IgG1-CD134-003-HC6LC2-RR in the presence of soluble OX40 (sOX40). OX40+Jurkat reporter cells were cultured for 5 h in the presence of different concentrations of IgG1-CD134-003-HC6LC2-RR or nonbinding control antibody IgG1-b12-RR, and sOX40. Bioluminescence, as a surrogate for OX40 agonist activity, was measured as mean RLU±SD of duplicate wells. Data shown are derived from one experiment out of two experiments.

Figure 36:
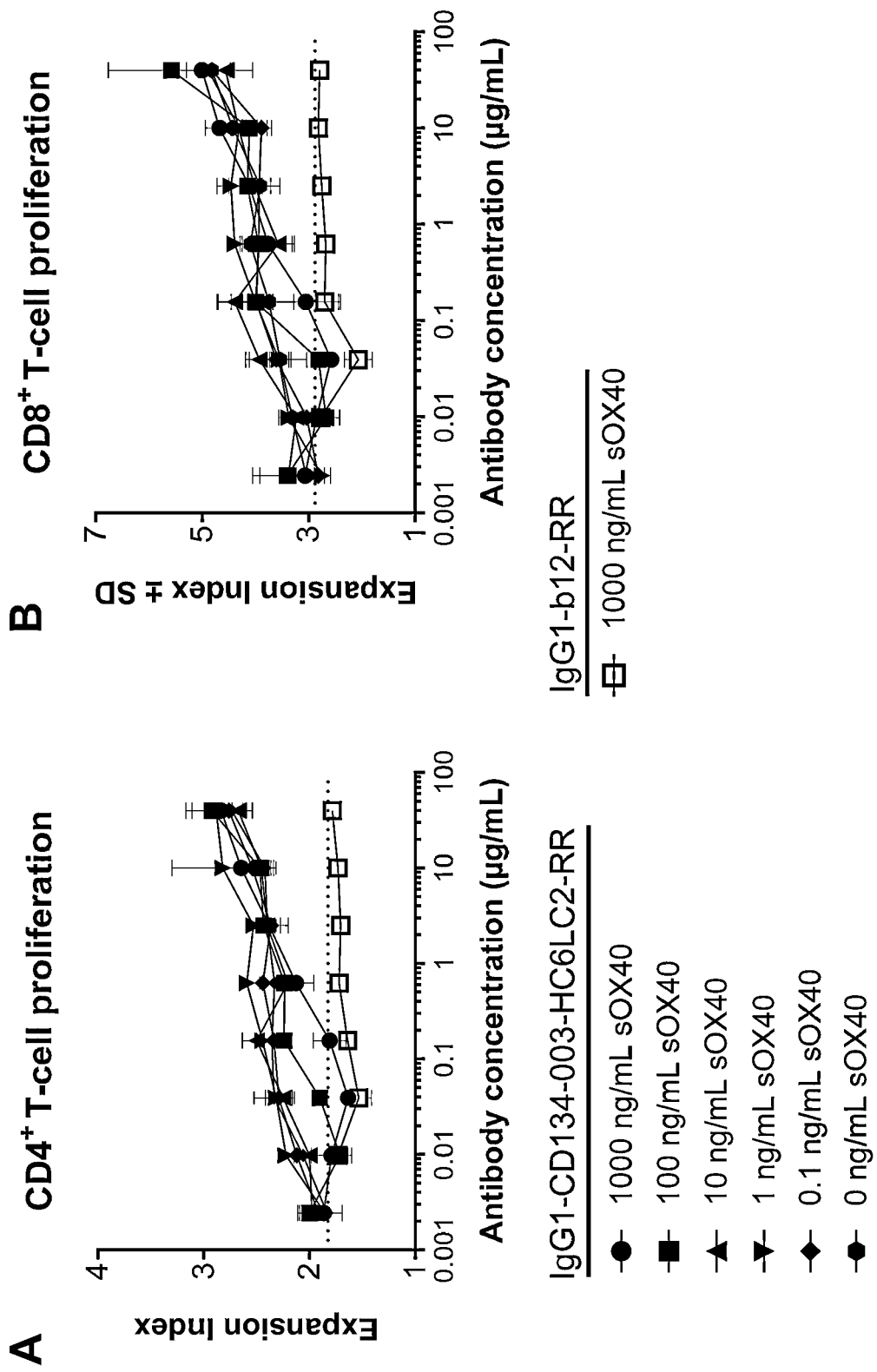

FIG. 36 shows proliferation of polyclonally activated CD4+ and CD8+ T cells upon treatment with IgG1-CD134-003-HC6LC2-RR or nonbinding control antibody IgG1-b12-RR in presence or absence of sOX40, in a polyclonal T-cell proliferation assay. Data shown are mean±SD of duplicate wells of (A) CD4+ T-cell expansion indices, and (B) CD8+ T-cell expansion indices, as determined by flow cytometry on day four. Data are derived from one representative donor out of four donors tested in one experiment performed.

Figure 37:
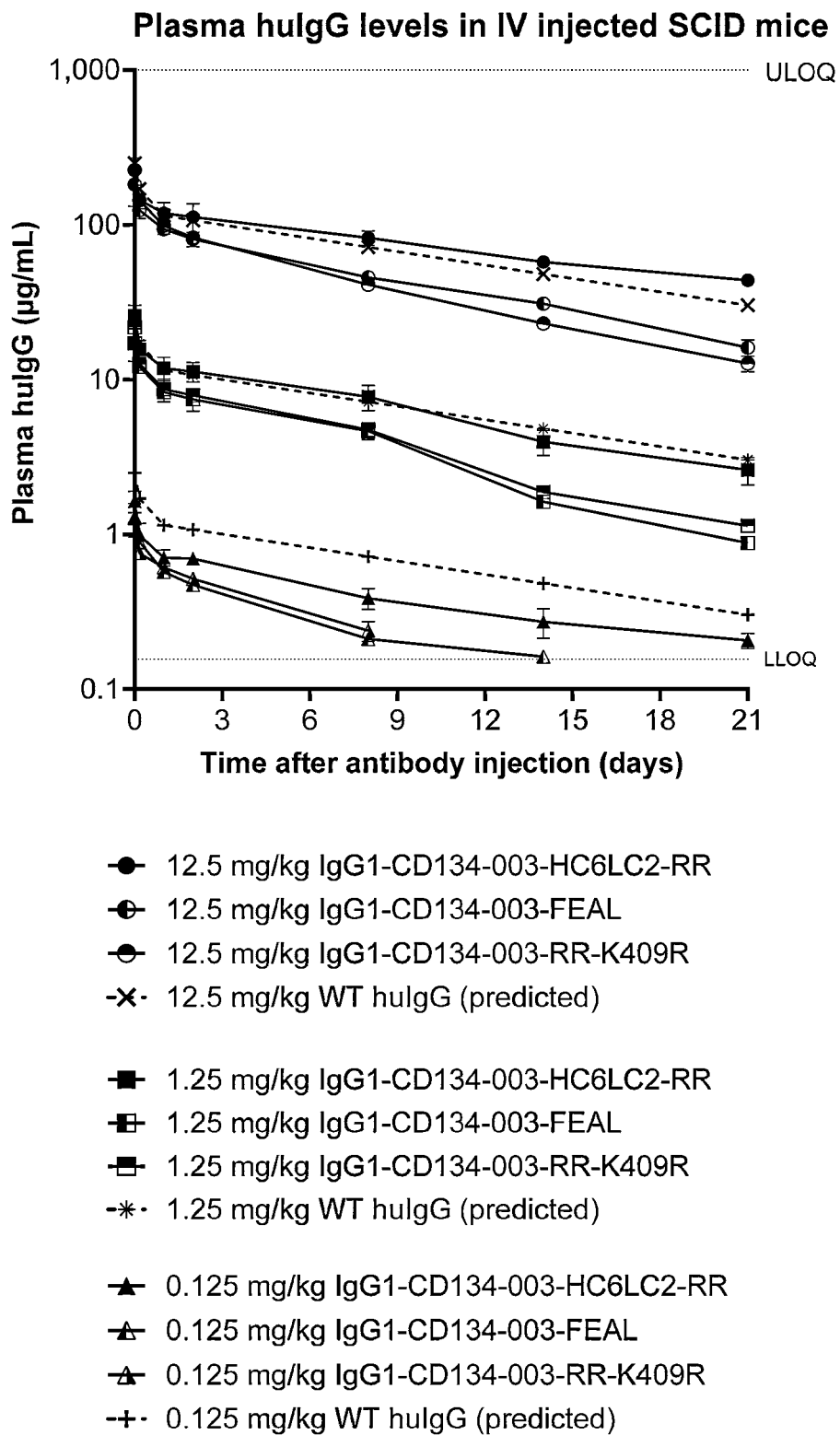

FIG. 37 shows total huIgG levels in SCID mouse plasma after intravenous anti-human OX40 antibody administration as determined by ECLIA in serially obtained plasma samples. Data are represented as mean huIgG concentration±SD of three mice per treatment group, except for groups of mice that received IgG1-CD134-003-RR-K409R at 0.125 mg/kg or 1.25 mg/kg (N=2), IgG1-CD134-003-FEAL at 0.125 mg/kg (N=1), or IgG1-CD134-003-HC6LC2-RR at 12.5 mg/kg (N=2). Values below the lower level of quantification (LLOQ) are not shown (N=3 for mice receiving 0.125 mg/kg IgG1-CD134-003-RR-K409R after day 8, N=1 for mice receiving 0.125 mg/kg IgG1-CD134-003-FEAL after day 14). Dashed lines indicate the predicted plasma concentrations of a WT huIgG according to a two-compartment model. Horizontal dotted lines indicate the LLOQ and upper limit of quantification (ULOQ) of the ECLIA assay. Data shown are from one experiment.

Figure 38:
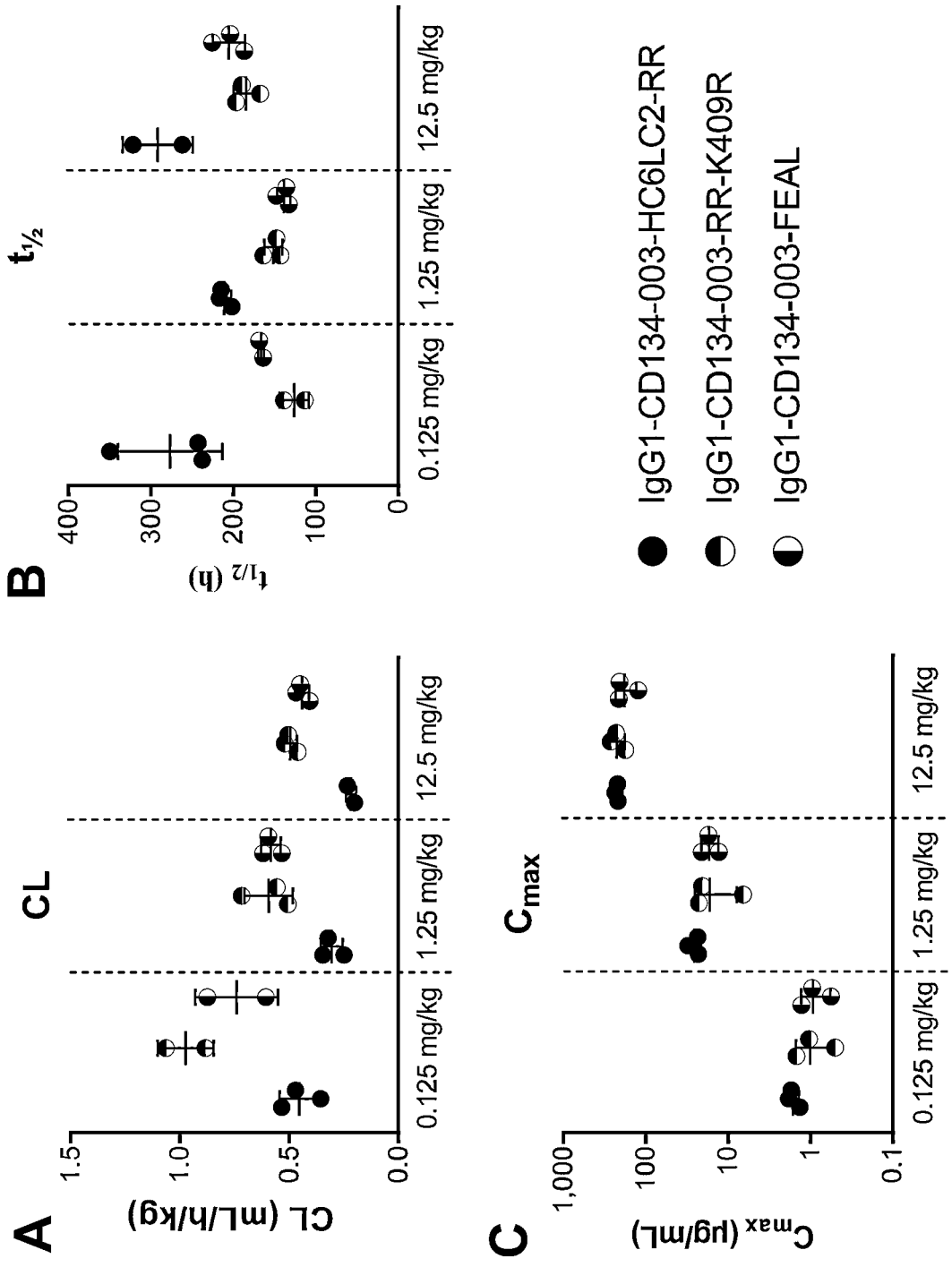

FIG. 38 shows antibody pharmacokinetic parameters in individual mice. SCID mice received a single intravenous injection of IgG1-CD134-003-HC6LC2-RR, IgG1-CD134-003-RR-K409R, or IgG1-CD134-003-FEAL at t=0 and total huIgG levels were determined by ECLIA in serially obtained plasma samples to calculate the CL (A), t½ (B) and Cmax (C). Values for individual mice are plotted with horizontal bars indicating mean±SD per treatment group.

FIG. 39 shows tumor volumes measured in human OX40 knock-in (hOX40 KI) mice bearing MC38 tumors. Mice were treated intraperitoneally on Day 0 with different concentrations of IgG1-CD134-003-HC6LC2-RR or 20 mg/kg IgG1-b12-FEAL. (A) Tumor volumes measured on Day 10 after starting treatment. Values for individual mice are plotted with horizontal bars indicating mean±SEM per treatment group. Statistically significant differences between treatment groups assessed using Mann-Whitney analysis (** P<0.01). (B) Mean tumor volumes (±SEM) measured over time in hOX40 KI mice bearing MC38 tumors treated as indicated in the figure. (C) Kaplan-Meier curve showing progression-free survival proportions (defined as tumor volumes <500 mm3) of MC38-tumor bearing mice treated as indicated. Significance calculated using Mantel-Cox analysis (*P<0.05 and *** P<0.001 compared to the IgG1-b12-FEAL control group).

Figure 40:
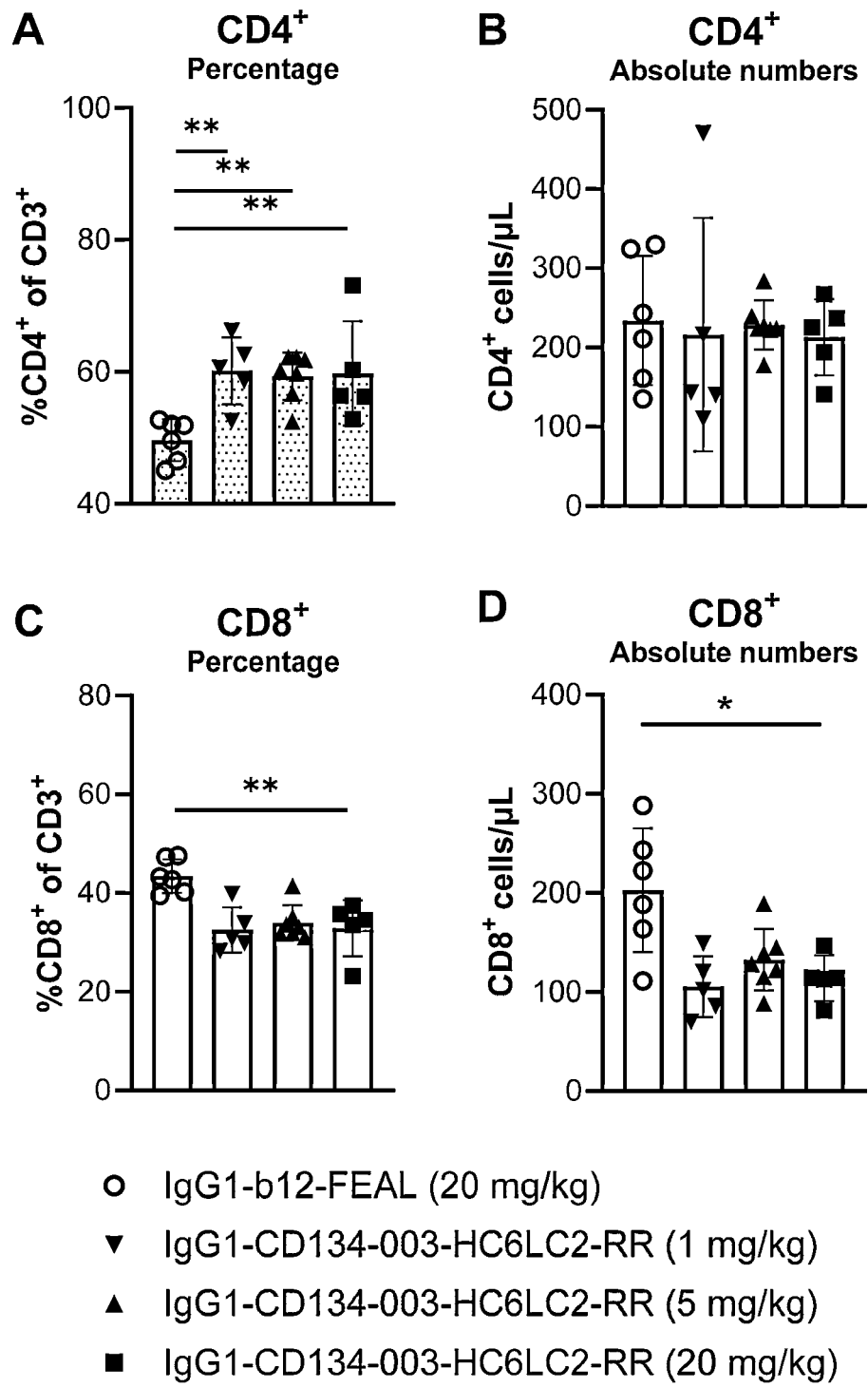

FIG. 40 shows T-cell percentages and absolute numbers in peripheral blood samples from MC38 tumor-bearing hOX40 KI mice treated with IgG1-CD134-003-HC6LC2-RR or IgG1-b12-FEAL as analyzed by flow cytometry. Percentage within the CD3+ T-cell population (A, C) and absolute numbers (B, D) of CD4+ (A, B) and CD8+ T cells (C, D) are shown. Dots in the graphs represent individual mice, and the columns and error bars represent the mean±SD of all animals included from one experiment. Statistically significant differences between treatment groups assessed using Mann-Whitney analysis (* P<0.05; ** P<0.01).

Figure 41:
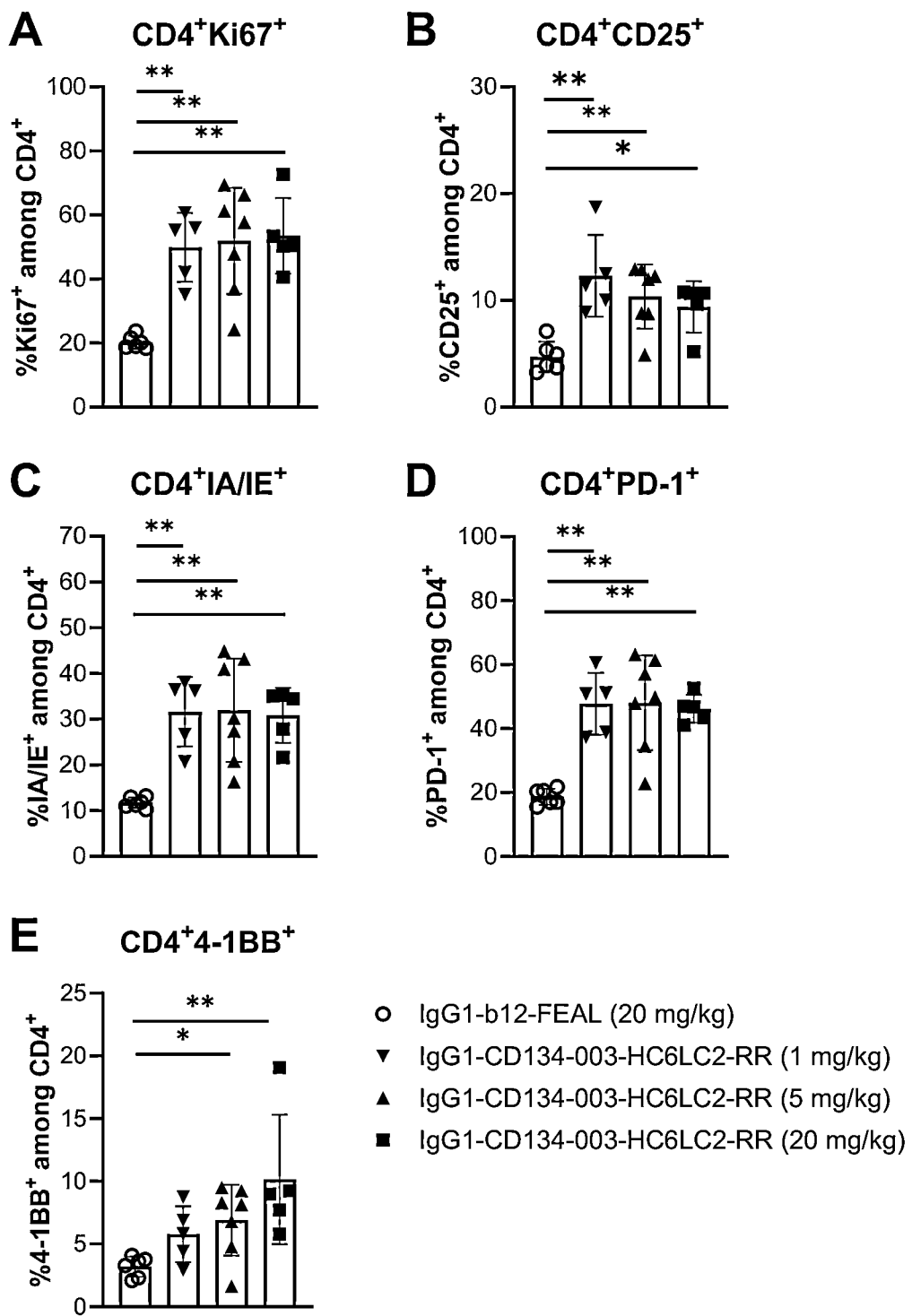

FIG. 41 shows percentages of CD4+ T cells expressing proliferation marker Ki67 (A), CD25 (B), IA/IE (C), PD-1 (D), and 4-1BB (E), as analyzed by flow cytometry in peripheral blood samples taken on Day 5 (after two treatments) from MC38 tumor-bearing hOX40 KI mice treated with IgG1-CD134-003-HC6LC2-RR or IgG1-b12-FEAL. Dots in the graphs represent individual mice, and the columns and error bars represent the mean±SD of all animals included from one experiment. Statistically significant differences between treatment groups assessed using Mann-Whitney analysis (* P<0.05; ** P<0.01).

Figure 42:
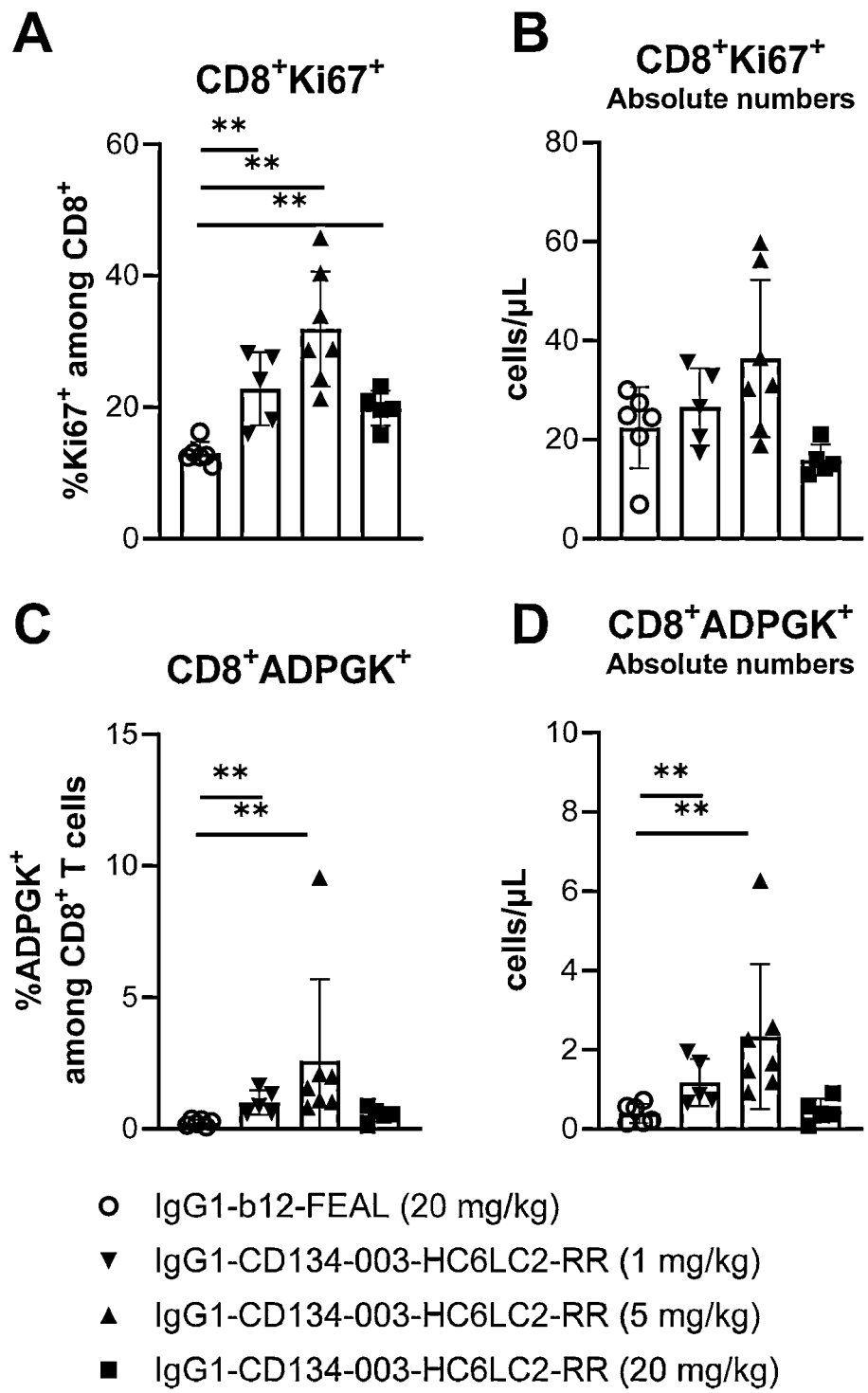

FIG. 42 shows percentages and absolute numbers of proliferating and tumor-specific (ADPGK-tetramer specific) CD8+ T cells. Data shown are (A) percentage of CD8+ T cells expressing proliferation marker Ki67, (B) absolute numbers of CD8+Ki67+ cells, (C) percentage of tumor-specific CD8+ T cells, and (D) absolute numbers of tumor-specific CD8+ T cells, as analyzed by flow cytometry in peripheral blood samples taken on Day 5 (after two treatments) from MC38 tumor-bearing hOX40 KI mice treated with IgG1-CD134-003-HC6LC2-RR or IgG1-b12-FEAL. Dots in the graphs represent individual mice, and the columns and error bars represent the mean±SD of all animals included from one experiment. Statistically significant differences between treatment groups assessed using Mann-Whitney analysis (** P<0.01).

Figure 43:
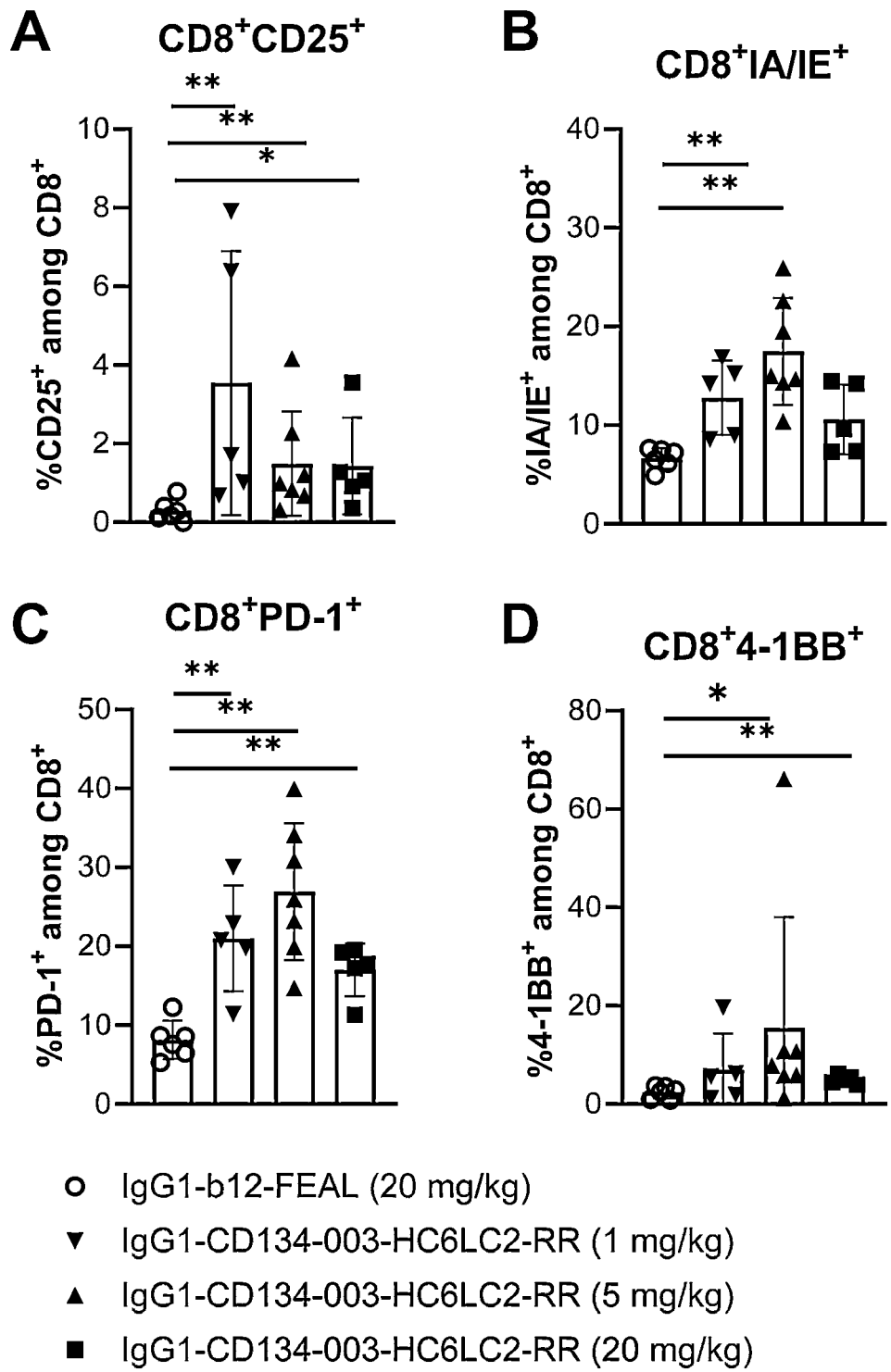

FIG. 43 shows percentages of CD8+ T cells expressing proliferation marker CD25 (A), IA/IE (B), PD-1 (C), and 4-1BB (D), as analyzed by flow cytometry in peripheral blood samples taken on Day 5 (after two treatments) from MC38 tumor-bearing hOX40 KI mice treated with IgG1-CD134-003-HC6LC2-RR or IgG1-b12-FEAL. Dots in the graphs represent individual mice, and the columns and error bars represent the mean±SD of all animals included from one experiment. Statistically significant differences between treatment groups assessed using Mann-Whitney analysis (* P<0.05; ** P<0.01).

FIG. 44 shows plasma cytokine concentrations in IgG1-CD134-003-HC6LC2-RR-treated MC38 tumor-bearing hOX40 KI mice. Plasma samples were collected on Day 0 (pretreatment) and Days 2 and 5 after one or two treatments with IgG1-CD134-003-HC6LC2-RR or IgG1-b12-FEAL, respectively. Cytokine analysis in plasma samples was performed by ECLIA. Data shown are concentrations of four individual mice and mean concentrations of (A) IFNγ, (B) IP-10, (C) IL-2, (D) IL-4, (E) MCP-1, (F) IL-10, (G) IL-27p28, and (H) TNFα. Data shown are derived from one experiment.

FIG. 45 shows the numbers of intratumoral immune cells per mm2 tumor tissue collected from MC38-bearing hOX40 KI mice treated with IgG1-CD134-003-HC6LC2-RR or IgG1-b12-FEAL. Number per mm2 tumor tissue of (A)

CD3+ cells, (B) CD3+Ki67+ cells, (C) CD4+ cells, (D) CD8+ cells, (E) Granzyme B+ cells, and (F) human OX40+ cells, as determined by quantitative immunohistochemistry analysis on tumor tissues. Dots in the graphs represent individual mice, and the columns and error bars represent the mean±SD. * p<0.05 as determined by Mann-Whitney test.

FIG. 46 shows tumor volumes measured in hOX40 KI mice bearing MC38 tumors. Mice were treated intraperitoneally on Day 0 with different concentrations of IgG1-CD134-003-HC6LC2-RR or 20 mg/kg IgG1-b12-FEAL. (A) Tumor volumes measured on Day 15 after starting treatment. Values for individual mice are plotted with horizontal bars indicating mean±SEM per treatment group included from one experiment. Statistically significant differences between treatment groups assessed using Mann-Whitney analysis (* P<0.05; ** P<0.01). (B) Mean tumor volumes (±SEM) measured over time in hOX40 KI mice bearing MC38 tumors treated as indicated in the figure. (C) Kaplan-Meier curve showing progression-free survival proportions (defined as tumor volumes <500 mm3) of MC38-tumor bearing mice treated as indicated. Significance calculated using Mantel-Cox analysis (*P<0.05 compared to the IgG1-b12-FEAL control group).

FIG. 47 shows percentages of (A) CD45+ cells, (B) CD3+ cells, (C) CD4+ T cells, (D) CD8+ T cells, and (D) Tregs detected in tumor samples collected from MC38 tumor-bearing hOX40 KI on Day 5 (after 2 treatments) after starting treatment with IgG1-CD134-003-HC6LC2-RR or IgG1-b12-RR, using flow cytometry. Also shown are the absolute numbers of (F) CD45+ cells, (G) CD3+ cells, (H) CD4+ T cells, (I) CD8+ T cells, and (J) Tregs, as detected using flow cytometry. Dots in the graphs represent individual mice, and the columns and error bars represent the mean±SD of all animals included from one experiment. Significance calculated using Mann-Whitney analysis (* P<0.05).

Figure 48:
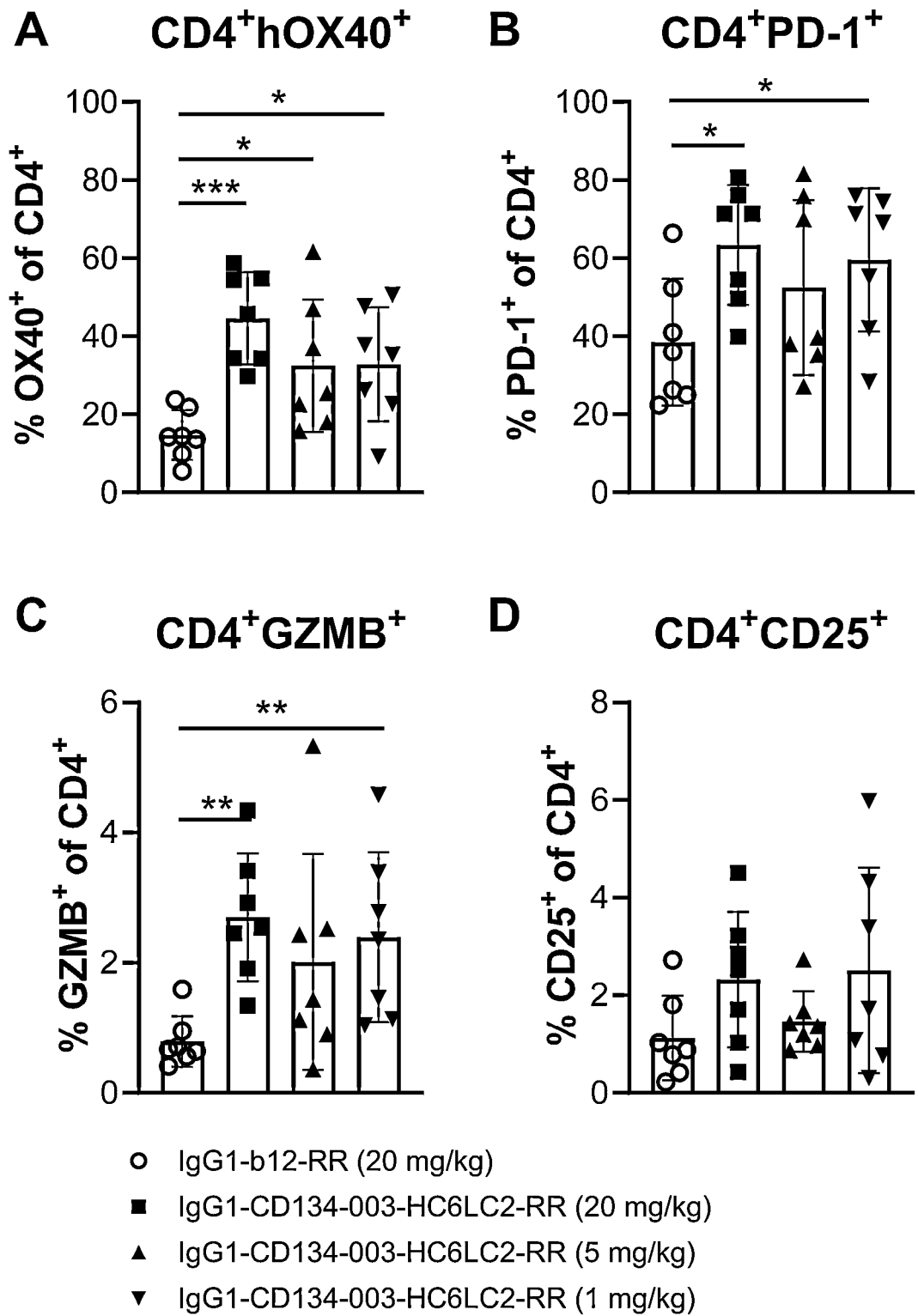

FIG. 48 shows the percentages of conventional CD4+ T cells expressing (A) CD25, (B) Granzyme B (GZMB), (C) human OX40, and (D) PD-1, as analyzed by flow cytometry in tumor samples taken on Day 5 (after two treatments) from MC38 tumor-bearing hOX40 KI mice treated with IgG1-CD134-003-HC6LC2-RR or IgG1-b12-RR. Dots in the graphs represent individual mice, and the columns and error bars represent the mean±SD of all animals included from one experiment. Statistically significant differences between treatment groups assessed using Mann-Whitney analysis (* P<0.05;  P<0.01; * P<0.001).

Figure 49:
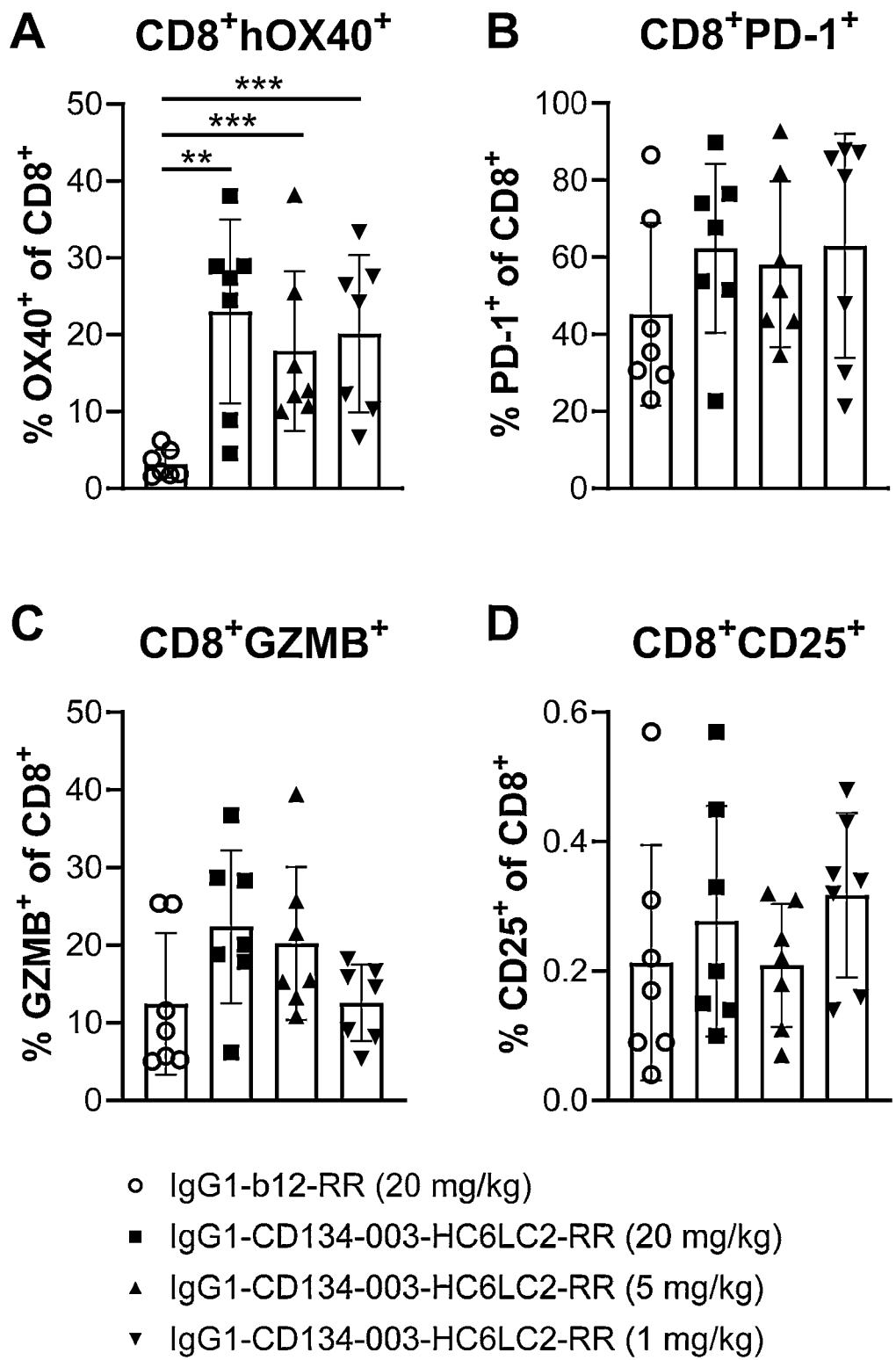

FIG. 49 shows the percentages of CD8+ T cells expressing (A) CD25, (B) Granzyme B (GZMB), (C) human OX40, and (D) PD-1, as analyzed by flow cytometry in tumor samples taken on Day 5 (after two treatments) from MC38 tumor-bearing hOX40 KI mice treated with IgG1-CD134-003-HC6LC2-RR or IgG1-b12-RR. Dots in the graphs represent individual mice, and the columns and error bars represent the mean±SD of all animals included from one experiment. Statistically significant differences between treatment groups assessed using Mann-Whitney analysis ( P<0.01; * P<0.001).

DETAILED DESCRIPTION OF THE INVENTION

Definitions

The term "antibody" (Ab) in the context of the present invention refers to an immunoglobulin molecule, a fragment of an immunoglobulin molecule, or a derivative of either thereof, which has the ability to specifically bind to an antigen. The antibody of the present invention comprises an Fc domain of an immunoglobulin and an antigen-binding region. An antibody generally contains two CH2-CH3 regions and a connecting region, e.g., a hinge region, e.g. at least an Fc domain. Thus, the antibody of the present invention may comprise an Fc region and an antigen-binding region. The variable regions of the heavy and light chains of the immunoglobulin molecule contain a binding domain that interacts with an antigen. The constant or "Fc" regions of the antibodies may mediate the binding of the immunoglobulin to host tissues or factors, including various cells of the immune system (such as effector cells) and components of the complement system such as C1q, the first component in the classical pathway of complement activation. As used herein, unless contradicted by context, the Fc region of an immunoglobulin typically contains at least a CH2 domain and a CH3 domain of an immunoglobulin CH, and may comprise a connecting region, e.g., a hinge region. An Fc-region is typically in dimerized form via, e.g., disulfide bridges connecting the two hinge regions and/or non-covalent interactions between the two CH3 regions. The dimer may be a homodimer (where the two Fc region monomer amino acid sequences are identical) or a heterodimer (where the two Fc region monomer amino acid sequences differ in one or more amino acids). An Fc region-fragment of a full-length antibody can, for example, be generated by digestion of the full-length antibody with papain, as is well known in the art. An antibody as defined herein may, in addition to an Fc region and an antigen-binding region, further comprise one or both of an immunoglobulin CH1 region and a CL region. An antibody may also be a multi-specific antibody, such as a bispecific antibody or similar molecule. The term "bispecific antibody" refers to an antibody having specificities for at least two different, typically non-overlapping, epitopes. Such epitopes may be on the same or different targets. If the epitopes are on different targets, such targets may be on the same cell or different cells or cell types. As indicated above, unless otherwise stated or clearly contradicted by the context, the term antibody herein includes fragments of an antibody which comprise at least a portion of an Fc-region and which retain the ability to specifically bind to the antigen. Such fragments may be provided by any known technique, such as enzymatic cleavage, peptide synthesis and recombinant expression techniques. It has been shown that the antigen-binding function of an antibody may be performed by fragments of a full-length antibody. Examples of binding fragments encompassed within the term "Ab" or "antibody" include, without limitation, monovalent antibodies (described in WO2007059782 by Genmab); heavy-chain antibodies, consisting only of two heavy chains and naturally occurring in e.g. camelids (e.g., Hamers-Casterman (1993) Nature 363: 446); ThioMabs, Roche, WO2011069104); strand-exchange engineered domain (SEED or Seed-body) which are asymmetric and bispecific antibody-like molecules (Merck, WO2007110205); Triomab (Pharma/Fresenius Biotech, Lindhofer et al. 1995 J Immunol 155:219; WO2002020039); FcΔAdp (Regeneron, WO2010151792); Azymetric Scaffold (Zymeworks/Merck, WO2012/058768); mAb-Fv (Xencor, WO2011/028952); Xmab (Xencor); Dual variable domain immunoglobulin (Abbott, DVD-Ig,U.S. Pat. No. 7,612,181); Dual domain double head antibodies (Unilever; Sanofi Aventis, WO20100226923); Di-diabody (ImClone/Eli Lilly); Knobs-into-holes antibody formats (Genentech, WO9850431); DuoBody (Genmab, WO 2011/131746); Bispecific IgG1 and IgG2 (Pfizer/Rinat, WO11143545); Duet- Mab (Medimmune, US2014/0348839); Electrostatic steering antibody formats (Amgen, EP1870459 and WO 2009089004; Chugai, US201000155133; Oncomed, WO2010129304A2); bispecific IgG1 and IgG2 (Rinat neurosciences Corporation, WO11143545); CrossMAbs (Roche, WO2011117329); LUZ-Y (Genentech); Biclonic (Merus, WO2013157953); Dual Targeting domain antibodies (GSK/Domantis); Two-in-one Antibodies or Dual action Fabs recognizing two targets (Genentech, Novimmune, Adimab); Cross-linked Mabs (Karmanos Cancer Center); covalently fused mAbs (AIMM); CovX-body (CovX/Pfizer); FynomAbs (Covagen/Janssen ilag); DutaMab (Dutalys/Roche); iMab (MedImmune); IgG-like Bispecific (ImClone/Eli Lilly, Shen, J., et al. J Immunol Methods, 2007. 318 (1-2): p. 65-74); TIG-body, DIG-body and PIG-body (Pharmabcine); Dual-affinity retargeting molecules (Fc-DART or Ig-DART, Macrogenics, WO/2008/157379, WO/2010/080538); BEAT (Glenmark); Zybodies (Zyngenia); approaches with common light chain (Crucell/Merus, U.S. Pat. No. 7,262,028) or common heavy chains (K) Bodies by NovImmune, WO2012023053), as well as fusion proteins comprising a polypeptide sequence fused to an antibody fragment containing an Fc-region like scFv fusions, like BsAb by ZymoGenetics/BMS, HERCULES by Biogen Idec (US007951918); SCORPIONS (Emergent BioSolutions/Trubion and Zymogenetics/BMS); Ts2Ab (MedImmune/AZ (Dimasi, N., et al. J Mol Biol, 2009. 393 (3): p. 672-92); scFv fusion (Genentech/Roche); scFv fusion (Novartis); scFv fusion (Immunomedics); scFv fusion (Changzhou Adam Biotech Inc, CN 102250246); TvAb (Roche,WO 2012025525, WO 2012025530); mAb2 (f-Star, WO2008/003116); and dual scFv fusion. It should be understood that the term antibody, unless otherwise specified, includes monoclonal antibodies (such as human monoclonal antibodies), polyclonal antibodies, chimeric antibodies, humanized antibodies, monospecific antibodies (such as bivalent monospecific antibodies), bispecific antibodies, antibodies of any isotype and/or allotype; antibody mixtures (recombinant polyclonals) for instance generated by technologies exploited by Symphogen and Merus (Oligoclonics), multimeric Fc proteins as described in WO2015/158867, and fusion proteins as described in WO2014/031646. While these different antibody fragments and formats are generally included within the meaning of antibody, they collectively and each independently are unique features of the present invention, exhibiting different biological properties and utility.

An "agonistic antibody" for a natural receptor is a compound which binds the receptor to form a receptor-antibody complex and which activates said receptor, thereby initiating a pathway signaling and further biological process.

The term "agonism" and "agonistic" are used interchangeably herein and refer to or describe an antibody which is capable of, directly or indirectly, substantially inducing, promoting, or enhancing OX40 biological activity or activation. Optionally, an "agonistic OX40 antibody" is an antibody which is capable of activating OX40 receptor by a similar mechanism as the ligand for OX40, known as OX40L (CD134L, OX-40L, TNLG2B, OX4OL, GP34, CD252 Antigen, CD134 Ligand, TAX transcriptionally-activated glycoprotein 1,, CD252, OX40 ligand, OX40L, TNFSF4, Tumor necrosis factor ligand superfamily member 4, Glycoprotein Gp34, TNF Superfamily Member 4, TXGP1,Tax-Transcriptionally Activated Glycoprotein 1 (34 kD), Tumor Necrosis Factor (Ligand) Superfamily, Member 4, Tumor Necrosis Factor (Ligand) Superfamily Member 4, Tumor Necrosis Factor Superfamily Member 4), which results in an activation of one or more intracellular signaling pathway which may include activation of NF-KB and MAPK8/INK pathways.

A "OX40 antibody" or "anti-OX40 antibody" as described herein is an antibody which binds specifically to the protein OX40, in particular to human OX40.

A "variant" as used herein refers to a protein or polypeptide sequence which differs in one or more amino acid residues from a parent or reference sequence. A variant may, for example, have a sequence identity of at least 80%, such as 90%, or 95%, or 97%, or 98%, or 99%, to a parent or reference sequence. Also, or alternatively, a variant may differ from the parent or reference sequence by 12 or less, such as 11, 10, 9, 8, 7, 6, 5, 4, 3, 2 or 1 mutation(s) such as substitutions, insertions, or deletions of amino acid residues. Accordingly, a "variant antibody" or an "antibody variant", used interchangeably herein, refers to an antibody that differs in one or more amino acid residues as compared to a parent or reference antibody, e.g., in the antigen-binding region, Fc-region or both. Likewise, a "variant Fc region" or "Fc region variant" refers to an Fc region that differs in one or more amino acid residues as compared to a parent or reference Fc region, optionally differing from the parent or reference Fc region amino acid sequence by 12 or less, such as 11, 10, 9, 8, 7, 6, 5, 4, 3, 2 or 1 mutation(s) such as substitutions, insertions, or deletions of amino acid residues. The parent or reference Fc region is typically the Fc region of a human wild-type antibody which, depending on the context, may be a particular isotype. A variant Fc region may, in dimerized form, be a homodimer or heterodimer, e.g., where one of the amino acid sequences of the dimerized Fc region comprises a mutation while the other is identical to a parent or reference wild-type amino acid sequence. Examples of wild-type (typically a parent or reference sequence) IgG CH and variant IgG constant region amino acid sequences, which comprise Fc region amino acid sequences, are set out in Table 3.

The term "immunoglobulin heavy chain" or "heavy chain of an immunoglobulin" as used herein is intended to refer to one of the heavy chains of an immunoglobulin. A heavy chain is typically comprised of a heavy chain variable region (abbreviated herein as VH) and a heavy chain constant region (abbreviated herein as CH) which defines the isotype of the immunoglobulin. The heavy chain constant region typically is comprised of three domains, CH1, CH2, and CH3. The term "immunoglobulin" as used herein is intended to refer to a class of structurally related glycoproteins consisting of two pairs of polypeptide chains, one pair of light (L) low molecular weight chains and one pair of heavy (H) chains, all four potentially inter-connected by disulfide bonds. The structure of immunoglobulins has been well characterized (see for instance Fundamental Immunology Ch. 7 Paul, W., 2nd ed. Raven Press, N.Y. 1989). Within the structure of the immunoglobulin, the two heavy chains are inter-connected via disulfide bonds in the so-called "hinge region". Equally to the heavy chains, each light chain is typically comprised of several regions; a light chain variable region (abbreviated herein as VL) and a light chain constant region. The light chain constant region typically is comprised of one domain, CL. Furthermore, the VH and VL regions may be further subdivided into regions of hypervariability (or hypervariable regions which may be hypervariable in sequence and/or form of structurally defined loops), also termed complementarity-determining regions (CDRs), interspersed with regions that are more conserved, termed framework regions (FRs). Each VH and VL is typically composed of three CDRs and four FRs, arranged from amino-terminus to carboxy-terminus in the following order: FR1, CDR1, FR2, CDR2, FR3, CDR3, FR4. CDR sequences herein are defined according to IMGT (see Lefranc MP. et al., Nucleic Acids Research, 27, 209-212, 1999] and Brochet X. Nucl. Acids Res. 36, W503-508 (2008)).

When used herein, the terms "half molecule", "Fab arm" and "arm" refer to one heavy chain-light chain pair. When a bispecific antibody is described to comprise a half-molecule antibody "derived from" a first antibody, and a half-molecule antibody "derived from" a second antibody, the term "derived from" indicates that the bispecific antibody was generated by recombining, by any known method, said half-molecules from each of said first and second antibodies into the resulting bispecific antibody. In this context, "recombining" is not intended to be limited by any particular method of recombining and thus includes all of the methods for producing bispecific antibodies described herein below, including for example recombining by "half-molecule exchange" also described in the art as "Fab-arm exchange" and the DuoBody® method, as well as recombining at nucleic acid level and/or through co-expression of two half-molecules in the same cells.

The term "antigen-binding region" or "binding region" or antigen-binding domain as used herein, refers to the region of an antibody which is capable of binding to the antigen. This binding region is typically defined by the VH and VL domains of the antibody which may be further subdivided into regions of hypervariability (or hypervariable regions which may be hypervariable in sequence and/or form of structurally defined loops), also termed complementarity-determining regions (CDRs), interspersed with regions that are more conserved, termed framework regions (FRs). The antigen can be any molecule, such as a polypeptide, e.g., present on a cell, bacterium, or virion. The terms "antigen-binding region" and "antigen-binding site" and "antigen-binding domain" may, unless contradicted by the context, be used interchangeably in the context of the present invention.

The terms "antigen" and "target" may, unless contradicted by the context, be used interchangeably in the context of the present invention.

The term "binding" as used herein refers to the binding of an antibody to a predetermined antigen or target, typically with a binding affinity corresponding to a $K_D$ of $1E^6$ M or less, e.g. $5E^7$ M or less, $1E^7$ M or less, such as $5E^8$ M or less, such as $1E^8$ M or less, such as $5E^9$ M or less, or such as $1E^9$ M or less, when determined by biolayer interferometry using the antibody as the ligand and the antigen as the analyte and binds to the predetermined antigen with an affinity corresponding to a $K_D$ that is at least ten-fold lower, such as at least 100-fold lower, for instance at least 1,000-fold lower, such as at least 10,000-fold lower, for instance at least 100,000-fold lower than its affinity for binding to a non-specific antigen (e.g., BSA, casein) other than the predetermined antigen or a closely-related antigen.

The term "$K_D$" (M), as used herein, refers to the dissociation equilibrium constant of a particular antibody-antigen interaction, and is obtained by dividing $k_d$ by $k_a$.

The term "$k_d$" ($sec^{-1}$), as used herein, refers to the dissociation rate constant of a particular antibody-antigen interaction. Said value is also referred to as the $k_{off}$ value or off-rate.

The term "$k_a$" ($M^{-1} \times sec^{-1}$), as used herein, refers to the association rate constant of a particular antibody-antigen interaction. Said value is also referred to as the $k_{on}$ value or on-rate.

The term "OX40" as used herein, refers to the human protein entitled OX40, also known as tumor necrosis factor receptor superfamily member 4 (TNFRSF4). In the amino acid sequence shown in SEQ ID NO: 52, amino acid residues 1-28 are a signal peptide, and amino acid residues 29-277 are the mature polypeptide.

In cynomolgus monkey (*Macaca fascicularis*), the OX40 protein has the amino acid sequence shown in SEQ ID NO: 51.

Agonistic IgG1 antibodies against human OX40 for the treatment of cancer have been disclosed.

WO2009/079335A1 discloses human OX40-binding antibody 11D4, which showed agonistic activity in multiple murine tumor models. Antibody clone 11D4 was shown to induce T-cell activation upon incubation of anti-human CD3-preincubated primary T cells or healthy donor PBMC samples. 11D4 blocked binding of natural ligand OX40L and was shown to also bind cynomolgus monkey T cells. Gutierrez et al reported that 11D4-based clinical candidate antibody BMS-986178 did not induce dose-limiting toxicities nor objective responses in advanced cancer patients in a phase 1/2a clinical trial when administered as monotherapy treatment (Gutierrez et al. Clin Cancer Res. 2021 Jan. 15; 27 (2): 460-472).

Other OX40 antibodies that were described to induce T-cell activation via engagement of human OX40 include clones A4453 (WO2019/223733), Hu106 (WO2020/030570A1), MEDI0562 (INN 10420, tavolimab), ABBV368 (INN 11242, revdofilimab), IBI101 (INN 11200; cudarolimab), INCAGN1949 (U.S. Pat. No. 10,259,882B2), GSK-3174998 (U.S. Pat. No. 9,006,399), and 49B4 (WO2019/086497A2).

The term "antibody binding region" refers to a region of the antigen, which comprises the epitope to which the antibody binds. An antibody binding region may be determined by epitope binding using biolayer interferometry, by alanine scan, or by shuffle assays (using antigen constructs in which regions of the antigen are exchanged with that of another species and determining whether the antibody still binds to the antigen or not). The amino acids within the antibody binding region that are involved in the interaction with the antibody may be determined by hydrogen/deuterium exchange mass spectrometry and by crystallography of the antibody bound to its antigen.

The term "epitope" means an antigenic determinant which is specifically bound by an antibody. Epitopes usually consist of surface groupings of molecules such as amino acids, sugar side chains or a combination thereof and usually have specific three-dimensional structural characteristics, as well as specific charge characteristics. Conformational and non-conformational epitopes are distinguished in that the binding to the former but not the latter is lost in the presence of denaturing solvents. The epitope may comprise amino acid residues which are directly involved in the binding, and other amino acid residues, which are not directly involved in the binding, such as amino acid residues which are effectively blocked or covered by the antibody when it is bound to the antigen (in other words, the amino acid residue is within or closely adjacent to the footprint of the specific antibody).

The terms "monoclonal antibody", "monoclonal Ab", "monoclonal antibody composition", "mAb", or the like, as used herein refer to a preparation of antibody molecules of single molecular composition. A monoclonal antibody composition displays a single binding specificity and affinity for a particular epitope. Accordingly, the term "human monoclonal antibody" refers to antibodies displaying a single binding specificity which have variable and constant regions derived from human germline immunoglobulin sequences. The human monoclonal antibodies may be produced by a hybridoma which includes a B cell obtained from a transgenic or trans-chromosomal non-human animal, such as a transgenic mouse or rat, having a genome comprising a human heavy chain transgene and a light chain transgene, fused to an immortalized cell. Monoclonal antibodies may also be produced from recombinantly modified host cells, or systems that use cellular extracts supporting in vitro transcription and/or translation of nucleic acid sequences encoding the antibody.

The term "isotype" as used herein refers to the immunoglobulin class (for instance IgG, IgG1, IgG2, IgG3, IgG4, IgD, IgA, IgE, or IgM) or any allotypes thereof, such as IgG1m(za) and IgG1m(f)) that is encoded by heavy chain constant region genes. Further, each heavy chain isotype can be combined with either a kappa (κ) or lambda (λ) light chain.

The term "full-length antibody" when used herein, indicates that the antibody is not a fragment, but contains all of the domains of the particular isotype normally found for that isotype in nature, e.g., the VH, CH1, CH2, CH3, hinge, VL and CL domains for an IgG1 antibody. In a full-length variant antibody, the heavy and light chain constant and variable domains may in particular contain amino acid substitutions that improve the functional properties of the antibody when compared to the full-length parent or wild-type antibody. A full-length antibody according to the present invention may be produced by a method comprising the steps of (i) cloning the CDR sequences into a suitable vector comprising complete heavy chain sequences and complete light chain sequence, and (ii) expressing the complete heavy and light chain sequences in suitable expression systems. It is within the knowledge of the skilled person to produce a full-length antibody when starting out from either CDR sequences or full variable region sequences. Thus, the skilled person would know how to generate a full-length antibody according to the present invention.

The term "human antibody", as used herein, is intended to include antibodies comprising variable and framework regions derived from human germline immunoglobulin sequences and a human immunoglobulin constant domain. The human antibodies of the invention may include amino acid residues not encoded by human germline immunoglobulin sequences (e.g., mutations, insertions or deletions introduced by random or site-specific mutagenesis in vitro or by somatic mutation in vivo). However, the term "human antibody", as used herein, is not intended to include antibodies in which CDR sequences derived from the germline of another non-human species, such as a mouse, have been grafted onto human framework sequences.

The term "humanized antibody" as used herein, refers to a genetically engineered non-human antibody, which contains human antibody constant domains and non-human variable domains modified to contain a high level of sequence homology to human variable domains. This can be achieved by grafting of the six non-human antibody complementarity-determining regions (CDRs), which together form the antigen binding site, onto a homologous human acceptor framework region (FR) (see WO92/22653 and EP0629240). In order to fully reconstitute the binding affinity and specificity of the parental antibody, the substitution of framework residues from the parental antibody (i.e., the non-human antibody) into the human framework regions (back-mutations) may be required. Structural homology modeling may help to identify the amino acid residues in the framework regions that are important for the binding properties of the antibody. Thus, a humanized antibody may comprise non-human CDR sequences, primarily human framework regions optionally comprising one or more amino acid back-mutations to the non-human amino acid sequence, and fully human constant regions. Optionally, additional amino acid modifications, which are not necessarily back-mutations, may be applied to obtain a humanized antibody with preferred characteristics, such as affinity and biochemical properties.

The term "Fc region" or "Fc domain" as used herein may be used interchangeably and refers to a region of the heavy chain constant region comprising, in the direction from the N- to C-terminal end of the antibody, at least a hinge region, a CH2 region and a CH3 region. An Fc region of the antibody may mediate the binding of the immunoglobulin to host tissues or factors, including various cells of the immune system (such as effector cells) and components of the complement system.

The term "parent polypeptide" or "parent antibody", is to be understood as a polypeptide or antibody, which is identical to a polypeptide or antibody according to the invention, but where the parent polypeptide or parent antibody is without mutations, unless otherwise stated or clearly contradicted by the context. For example, the antibody IgG1-CD134-003 is the parent antibody of IgG1-CD134-003-P329R-E345R.

The term "hinge region" as used herein refers to the hinge region of an immunoglobulin heavy chain. Thus, for example the hinge region of a human IgG1 antibody corresponds to amino acids 216-230 according to the Eu numbering (Eu-index) as set forth in Kabat, E. A. et al., Sequences of proteins of immunological interest. 5th Edition-US Department of Health and Human Services, NIH publication No. 91-3242, pp 662680,689 (1991). However, the hinge region may also be any of the other subtypes as described herein.

The term "CH1 region" or "CH1 domain" as used herein refers to the CH1 region of an immunoglobulin heavy chain. Thus, for example the CH1 region of a human IgG1 antibody corresponds to amino acids 118-215 according to the Eu numbering as set forth in Kabat (ibid). However, the CH1 region may also be any of the other subtypes as described herein.

The term "CH2 region" or "CH2 domain" as used herein refers to the CH2 region of an immunoglobulin heavy chain. Thus, for example the CH2 region of a human IgG1 antibody corresponds to amino acids 231-340 according to the Eu numbering as set forth in Kabat (ibid). However, the CH2 region may also be any of the other subtypes as described herein.

The term "CH3 region" or "CH3 domain" as used herein refers to the CH3 region of an immunoglobulin heavy chain. Thus, for example the CH3 region of a human IgG1 antibody corresponds to amino acids 341-447 according to the Eu numbering as set forth in Kabat (ibid). However, the CH3 region may also be any of the other subtypes as described herein.

The term "Fc-mediated effector functions" or "Fc effector functions" as used herein are used interchangeably and is intended to refer to functions that are a consequence of binding a polypeptide or antibody to its target or antigen on a cell membrane wherein the Fc-mediated effector function is attributable to the Fc region of the polypeptide or antibody. Examples of Fc-mediated effector functions include (i) C1q binding, (ii) complement activation, (iii) complement-dependent cytotoxicity (CDC), (iv) antibody-dependent cell-mediated cytotoxity (ADCC), (v) Fc gamma receptor (FcγR)-binding, (vi) antibody-dependent, FcγR-mediated antigen crosslinking, (vii) antibody-dependent cellular phagocytosis (ADCP), (viii) complement-enhanced cytotoxicity, (ix) binding to complement receptor of an opsonized antibody mediated by the antibody, (x) opsonization, and (xi) a combination of any of (i) to (x).

The term "decreased Fc effector function(s)" or "Decreased Fc-mediated effector functions", as used herein are used interchangeably and is intended to refer to an Fc effector function that is decreased for an antibody when directly compared to the Fc effector function of the parent polypeptide or antibody in the same assay.

The term "inertness", "inert" or "non-activating" as used herein, refers to an Fc region which is at least not able to bind one or more FcγR, induce Fc-mediated crosslinking of FcγRs, or induce FcγR-mediated crosslinking of target antigens via two Fc regions of individual antibodies, or is not able to bind C1q. Thus, in certain embodiments of the invention the Fc region is inert. Therefore, in certain embodiments some or all of the Fc-mediated effector functions are attenuated or completely absent.

The term "oligomerization", as used herein, is intended to refer to a process that converts monomers to a finite degree of polymerization. Antibodies according to the invention can form oligomers, such as hexamers, via non-covalent association of Fc-regions after target binding, e.g., at a cell surface. Oligomerization of anti-OX40 antibodies upon cell surface binding through Fc: Fc interactions may increase OX40 clustering resulting in activation of OX40 intracellular signaling. The capacity of antibodies comprising the E345R or E430G mutation to form oligomers, such as hexamers, upon cell surface binding can be evaluated as described in: de Jong R N et al, PLOS Biol. 2016 Jan. 6; 14 (1): e1002344. Fc-Fc-mediated oligomerization of antibodies occurs after target binding on a (cell) surface through the intermolecular association of Fc-regions between neighboring antibodies and is increased by introduction of a E345R or a E430G mutation (numbering according to Eu-index).

The term "clustering", as used herein, refers to oligomerization of antibodies through non-covalent interactions.

The term "Fc-Fc enhancing", as used herein, is intended to refer to increasing the binding strength between, or stabilizing the interaction between, the Fc regions of two Fc-region containing antibodies so that the antibodies form oligomers such as hexamers on the cell surface. This enhancement can be obtained by certain amino acid mutations in the Fc regions of the antibodies, such as E345R or E430G. The term "monovalent antibody", in the context of the present invention, refers to an antibody molecule that can interact with a specific epitope on an antigen, with only one antigen binding domain (e.g. one Fab arm). In the context of a bispecific antibody, "monovalent antibody binding" refers to the binding of the bispecific antibody to one specific epitope on an antigen with only one antigen binding domain (e.g. one Fab arm).

The term "monospecific antibody" in the context of the present invention, refers to an antibody that has binding specificity to one epitope only. The antibody may be a monospecific, monovalent antibody (i.e. carrying only one antigen binding region) or a monospecifc, bivalent antibody (i.e. an antibody with two identical antigen binding regions).

The term "bispecific antibody" refers to an antibody comprising two non-identical antigen binding domains, e.g. two non-identical Fab arms or two Fab arms with non-identical CDR regions. In the context of this invention, bispecific antibodies have specificity for at least two different epitopes. Such epitopes may be on the same or different antigens or targets. If the epitopes are on different antigens, such antigens may be on the same cell or different cells, cell types or structures, such as extracellular matrix or vesicles and soluble protein. A bispecific antibody may thus be capable of crosslinking multiple antigens, e.g. two different cells. A particular bispecific antibody of the present invention is capable of binding to OX40 and a second target.

The term "bivalent antibody" refers to an antibody that has two antigen binding regions, which bind to epitopes on one or two targets or antigens or binds to one or two epitopes on the same antigen. Hence, a bivalent antibody may be a monospecific, bivalent antibody or a bispecific, bivalent antibody.

The term "amino acid" and "amino acid residue" may herein be used interchangeably and are not to be understood limiting. Amino acids are organic compounds containing amine ($-NH_2$) and carboxyl ($-COOH$) functional groups, along with a side chain (R group) specific to each amino acid. In the context of the present invention, amino acids may be classified based on structure and chemical characteristics. Thus, classes of amino acids may be reflected in one or both of the following tables:

TABLE 1

Main classification based on structure and general chemical characterization of R group

| Class | Amino acid |
|---|---|
| Acidic Residues | D and E |
| Basic Residues | K, R, and H |
| Hydrophilic Uncharged Residues | S, T, N, and Q |
| Aliphatic Uncharged Residues | G, A, V, L, and I |
| Non-polar Uncharged Residues | C, M, and P |
| Aromatic Residues | F, Y, and W |

TABLE 2

Alternative Physical and Functional Classifications of Amino Acid Residues

| Class | Amino acid |
|---|---|
| Hydroxyl group containing residues | S and T |
| Aliphatic residues | I, L, V, and M |
| Cycloalkenyl-associated residues | F, H, W, and Y |
| Hydrophobic residues | A, C, F, G, H, I, L, M, R, T, V, W, and Y |
| Negatively charged residues | D and E |
| Polar residues | C, D, E, H, K, N, Q, R, S, and T |
| Positively charged residues | H, K, and R |
| Small residues | A, C, D, G, N, P, S, T, and V |
| Very small residues | A, G, and S |
| Residues involved in turn formation | A, C, D, E, G, H, K, N, Q, R, S, P, and T |
| Flexible residues | Q, T, K, S, G, P, D, E, and R |

Substitution of one amino acid for another may be classified as a conservative or non-conservative substitution. In the context of the invention, a "conservative substitution" is a substitution of one amino acid with another amino acid having similar structural and/or chemical characteristics, such substitution of one amino acid residue for another amino acid residue of the same class as defined in any of the two tables above: for example, leucine may be substituted with isoleucine as they are both aliphatic, branched hydrophobes. Similarly, aspartic acid may be substituted with glutamic acid since they are both small, negatively charged residues.

In the context of the present invention, a substitution in an antibody is indicated as:

Original amino acid—position—substituted amino acid;

Referring to the well-recognized nomenclature for amino acids, the three-letter code, or one letter code, is used, including the codes "Xaa" or "X" to indicate any amino acid residue. Thus, Xaa or X may typically represent any of the 20 naturally occurring amino acids. The term "naturally occurring" as used herein refers to any one of the following amino acid residues; glycine, alanine, valine, leucine, isoleucine, serine, threonine, lysine, arginine, histidine, aspartic acid, asparagine, glutamic acid, glutamine, proline, tryptophan, phenylalanine, tyrosine, methionine, and cysteine. Accordingly, the notation "K409R" or "Lys409Arg" means, that the antibody comprises a substitution of lysine with arginine in amino acid position 409.

Substitution of an amino acid at a given position to any other amino acid is referred to as:

Original amino acid—position; or e.g. "K409"

For a modification where the original amino acid(s) and/or substituted amino acid(s) may comprise more than one, but not all amino acid(s), the more than one amino acid may be separated by ",", or "/". E.g. the substitution of lysine with arginine, alanine, or phenylalanine in position 409 is:

"Lys409Arg,Ala,Phe" or "Lys409Arg/Ala/Phe" or "K409R,A,F" or "K409R/A/F" or "K409 to R, A, or F".

Such designation may be used interchangeably in the context of the invention but have the same meaning and purpose.

Furthermore, the term "a substitution" embraces a substitution into any one or the other nineteen natural amino acids, or into other amino acids, such as non-natural amino acids. For example, a substitution of amino acid K in position 409 includes each of the following substitutions: 409A, 409C, 409D, 409E, 409F, 409G, 409H, 409I, 409L, 409M, 409N, 409Q, 409R, 409S, 409T, 409V, 409W, 409P, and 409Y. This is, by the way, equivalent to the designation 409X, wherein the X designates any amino acid other than the original amino acid. These substitutions may also be designated K409A, K409C, etc. or K409A,C, etc. or K409A/C/etc. The same applies by analogy to each and every position mentioned herein, to specifically include herein any one of such substitutions.

The antibody according to the invention may also comprise a deletion of an amino acid residue. Such deletion may be denoted "del", and includes, e.g., writing as K409del. Thus, in such embodiments, the lysine in position 409 has been deleted from the amino acid sequence.

The term "host cell", as used herein, is intended to refer to a cell into which an expression vector has been introduced. It should be understood that such terms are intended to refer not only to the particular subject cell, but also to the progeny of such a cell. Because certain modifications may occur in succeeding generations due to either mutation or environmental influences, such progeny may not, in fact, be identical to the parent cell, but are still included within the scope of the term "host cell" as used herein. Recombinant host cells include, for example, transfectomas, such as CHO cells, HEK293 cells, Expi293F cells, PER.C6 cells, NS0 cells, and lymphocytic cells, and prokaryotic cells such as *E. coli* and other eukaryotic hosts such as plant cells and fungi.

The term "transfectoma", as used herein, includes recombinant eukaryotic host cells expressing the antibody or a target antigen, such as CHO cells, PER.C6 cells, NS0 cells, HEK293 cells, Expi293F cells, plant cells, or fungi, including yeast cells.

For purposes of the present invention, the sequence identity between two amino acid sequences is determined using the Needleman-Wunsch algorithm (Needleman and Wunsch, 1970, J. Mol. Biol. 48:443-453) as implemented in the Needle program of the EMBOSS package (EMBOSS: The European Molecular Biology Open Software Suite, Rice et al., 2000, Trends Genet. 16:276-277), preferably version 5.0.0 or later. The parameters used are gap open penalty of 10, gap extension penalty of 0.5, and the EBLOSUM62 (EMBOSS version of BLOSUM62) substitution matrix. The output of Needle labeled "longest identity" (obtained using the-nobrief option) is used as the percent identity and is calculated as follows:

(Identical Residues×100)/(Length of Alignment −

Total Number of Gaps in Alignment).

The retention of similar residues may also or alternatively be measured by a similarity score, as determined by use of a BLAST program (e.g., BLAST 2.2.8 available through the NCBI using standard settings BLOSUM62, Open Gap=11 and Extended Gap=1). Suitable variants typically exhibit at least about 45%, such as at least about 55%, at least about 65%, at least about 75%, at least about 85%, at least about 90%, at least about 95%, or more (e.g., about 99%) similarity to the parent sequence.

As used herein, the term "effector cell" refers to an immune cell which is involved in the effector phase of an immune response. Exemplary immune cells include a cell of a myeloid or lymphoid origin, for instance lymphocytes (such as B cells and T cells including cytolytic T cells (CTLs)), killer cells, natural killer cells, macrophages, monocytes, eosinophils, polymorphonuclear cells, such as neutrophils, granulocytes, mast cells, and basophils. Some effector cells express Fc receptors (FcγRs) or complement receptors and carry out specific immune functions. In some embodiments, an effector cell such as, e.g., a natural killer cell, is capable of inducing ADCC. For example, monocytes, macrophages, neutrophils, dendritic cells and Kupffer cells which express FcγRs, are involved in specific killing of target cells and/or presenting antigens to other components of the immune system, or binding to cells that present antigens. In some embodiments the ADCC can be further enhanced by antibody driven classical complement activation resulting in the deposition of activated C3 fragments on the target cell. C3 cleavage products are ligands for complement receptors (CRs), such as CR3, expressed on myeloid cells. The recognition of complement fragments by CRs on effector cells may promote enhanced Fc receptor-mediated ADCC. In some embodiments antibody driven classical complement activation leads to C3 fragments on the target cell. These C3 cleavage products may promote direct complement-dependent cellular cytotoxicity (CDCC). In some embodiments, an effector cell may phagocytose a target antigen, target particle or target cell which may depend on antibody binding and mediated by FcγRs expressed by the effector cells. The expression of a particular FcγR or complement receptor on an effector cell may be regulated by humoral factors such as cytokines. For example, expression of FcγRI has been found to be up-regulated by interferon γ (IFN γ) and/or G-CSF. This enhanced expression increases the cytotoxic activity of FcγRI-bearing cells against targets. An effector cell can phagocytose a target antigen or phagocytose or lyse a target cell. In some embodiments antibody driven classical complement activation leads to C3 fragments on the target cell. These C3 cleavage products may promote direct phagocytosis by effector cells or indirectly by enhancing antibody mediated phagocytosis. In certain embodiments herein where the antibody has an inert Fc region the antibody does not induce an Fc-mediated effector function.

"Effector T cells" or "Teffs" or "Teff" as used herein refers to T lymphocytes that carry out a function of an immune response, such as killing tumor cells and/or activating an antitumor immune response which can result in clearance of the tumor cells from the body. Examples of Teff phenotypes include CD3+CD4+ and CD3+CD8+. Teffs may secrete, contain, or express markers such as IFNγ, granzyme B and ICOS. It is appreciated that Teffs may not be fully restricted to these phenotypes.

"Memory T cells" as used herein refers to T lymphocytes that remain in the body for a long period of time after an infection is removed. Examples of memory T cells include central memory T cells (CD45RA-CCR7+) and effector memory T cells (CD45RA-CCR7−). It is appreciated that memory T cells may not be fully restricted to these phenotypes.

"Regulatory T cells" or "Tregs" or "Treg" as used herein refers to T lymphocytes that regulate the activity of other T cell(s) and/or other immune cells, usually by suppressing their activity. An example of a Treg phenotype is $CD3^+CD4^+CD25^+CD127dim$. Tregs may further express Foxp3. It is appreciated that Tregs may not be fully restricted to this phenotype.

As used herein, the term "complement activation" refers to the activation of the classical complement pathway, which is initiated by a large macromolecular complex called C1 binding to antibody-antigen complexes on a surface. C1 is a complex, which consists of 6 recognition proteins C1q and a hetero-tetramer of serine proteases, C1r2C1s2. C1 is the first protein complex in the early events of the classical complement cascade that involves a series of cleavage reactions that starts with the cleavage of C4 into C4a and C4b and C2 into C2a and C2b. C4b is deposited and forms together with C2a an enzymatic active convertase called C3 convertase, which cleaves complement component C3 into C3b and C3a, which forms a C5 convertase This C5 convertase splits C5 in C5a and C5b and the last component is deposited on the membrane and that in turn triggers the late events of complement activation in which terminal complement components C5b, C6, C7, C8 and C9 assemble into the membrane attack complex (MAC). The complement cascade results in the creation of pores in the cell membrane which causes lysis of the cell, also known as complement-dependent cytotoxicity (CDC). In certain embodiments herein where the antibody has an inert Fc region the antibody does not induce complement activation.

Complement activation can be evaluated by using C1q binding efficacy, CDC kinetics CDC assays (as described in WO2013/004842, WO2014/108198) or by the method Cellular deposition of C3b and C4b described in Beurskens et al., J Immunol Apr. 1, 2012 vol. 188 no. 7, 3532-3541.

The term "C1q binding" as used herein, is intended to refer to the binding of C1q in the context of the binding of C1q to an antibody bound to its antigen. The antibody bound to its antigen is to be understood as happening both in vivo and in vitro in the context described herein. C1q binding can be evaluated for example by using antibody immobilized on artificial surfaces or by using antibody bound to a predetermined antigen on a cellular or virion surface, as described in Example 8 herein. The binding of C1q to an antibody oligomer is to be understood herein as a multivalent interaction resulting in high avidity binding. A decrease in C1q binding, for example resulting from the introduction of a mutation in the antibody of the invention, may be measured by comparing the C1q binding of the mutated antibody to the C1q binding of its parent antibody (the antibody of the invention without the mutation within the same assay).

The term "treatment" refers to the administration of an effective amount of a therapeutically active antibody of the present invention with the purpose of easing, ameliorating, arresting, or eradicating (curing) symptoms or disease states.

The term "effective amount" or "therapeutically effective amount" refers to an amount effective, at dosages and for periods of time necessary, to achieve a desired therapeutic result. A therapeutically effective amount of an antibody may vary according to factors such as the disease state, age, sex, and weight of the individual, and the ability of the antibody to elicit a desired response in the individual. A therapeutically effective amount is also one in which any toxic or detrimental effects of the antibody variant are outweighed by the therapeutically beneficial effects.

Specific Embodiments of the Invention

In a first aspect the invention provides an antibody capable of binding to human OX40, said antibody comprises an antigen-binding region comprising a heavy chain variable (VH) region wherein the CDR1, CDR2, and CDR3 comprising the sequences as set forth in SEQ ID NOs: 12, 13, and 14, respectively, and a light chain variable (VL) region wherein the CDR1, CDR2, and CDR3 comprising the sequences as set forth in SEQ ID NO: 16, DAS and 17, respectively, and a human IgG1 Fc region comprising a P329R mutation and an E345R mutation, wherein the amino acid positions are numbered according to Eu numbering. Hereby anti-OX40 antibodies are provided which are able to bind to human. In an embodiment of the invention the antibody binds OX40 e.g. on T cells and is agonistic upon binding to its target. Hereby an antibody is provided which stimulates the activation and proliferation of T cells. The antibody may further stimulate memory formation and survival of T cells. Such an antibody is useful e.g. in the treatment of cancer. The antibody is further capable of binding to cynomolgus monkey OX40 which is useful for toxicological studies of the antibody. Thus, in one embodiment the antibody according to the invention the antibody is capable of binding to cynomolgus monkey OX40 having the sequence of SEQ ID NO: 51.

In another embodiment of the invention the antibody is capable of binding to human OX40 having the sequence of SEQ ID NO: 52. Human OX40 is comprises four extracellular domains designated CRD1, CRD2, CRD3 and CRD4, respectively. Without being bund by theory it is contemplated that antibodies binding to CRD1 domain has enhanced capability of activating T cells. In one embodiment of the invention the antibody binds to the CRD1 domain of human OX40. In one embodiment of the invention the antibody binds to an epitope of human OX40, which allows binding of said antibody to human OX40 in the presence of OX40L.

It is well known in the art that binding affinity can be important for antibody function. Thus, the affinity of an antibody to its cognate antigen can be either too high or too low for the antibody to activate the desired intracellular pathway. In one embodiment the antibody has a binding affinity $K_D$ for human OX40 of $1\times10^{-9}$ M to $6\times10^{-9}$ M. In one embodiment the antibody has a binding affinity $K_D$ for human OX40 of $2\times10^{-9}$ M to $5\times10^{-9}$ M. In one embodiment the antibody has a binding affinity $K_D$ for human OX40 of $3\times10^{-9}$ M to 4×10⁻⁹ M. In another embodiment the antibody has a binding affinity $K_D$ for human OX40 of 3,4×10⁻⁹ M.

In another aspect of the invention the antibody is a humanized or chimeric antibody.

The immunogenicity of an antibody may be reduced by humanization and thereby reduce the level of an anti-drug antibody (ADA) response. Thus, in one embodiment of the invention the antibody is a humanized antibody.

In one embodiment of the invention the antibody comprises a VH region having the sequence as set forth in SEQ ID NO: 20 and a VL region having the sequence set forth in SEQ ID NO: 21. Hereby an antibody is provided comprising a humanized VH region as set forth in SEQ ID NO: 20 and a humanized VL region as set forth in SEQ ID NO: 21. It is well known in the art that mutations may be introduced into proteins having a well characterized sequence and three dimensional structure such as an antibody without the loss of function. Accordingly, in some embodiments of the invention variant having mutations in the framework region of the VH and/or VL sequence is also contemplated, particular variant of the VH and/or VL region as set forth in SEQ ID NO: 20 and SEQ ID NO 21, respectively. Variant may differ in one or more amino acids as compared to the framework regions i.e. FR1, FR2, FR3 and FR4 of the parent VH and/or VL sequence, e.g., in one or more framework regions, but still allows the antigen-binding region to retain at least a substantial proportion (at least about 90 percent, 95 percent or more) or even retain all of the affinity and/or specificity of the parent antibody. Typically, such functional variants retain significant sequence identity to the parent sequence. Exemplary variants include those which differ from the respective parent VH or VL region by 5 or less, such as 5, 4, 3, 2 or 1 mutation(s) such as substitutions, of amino acid residues. Exemplary variants include those which differ from the VH and/or VL regions of the parent sequences mainly by conservative amino acid substitutions; for instance, 5, such as 5, 4, 3, 2 or 1 of the amino acid substitutions in the variant can be conservative. In a further aspect of the invention the antibody may comprise at most 1, 2 or 3 mutations in the VH framework regions and/or in the VL framework regions, respectively. Such mutations may be substitutions. It is preferred that such substitutions do not significantly change the binding affinity and/or binding specificity of the anti-OX40 antibody of the invention. Accordingly, the present invention encompasses variants of the anti-OX40 antibody of the invention which variants have the same functional features as the antibody comprising the VH region CDR sequences as set forth in as set forth in SEQ ID NOs: 12, 13, and 14 and the VL region CDR sequences as set forth in SEQ ID NO: 16, DAS and 17.

In another aspect of the invention the antibody comprises a VH region comprising a sequence which is at least 80% identical to the VH region as set forth in SEQ ID NO: 20. In another aspect of the invention the antibody comprises a VH region comprising a sequence which is at least 85% identical to the VH region as set forth in SEQ ID NO: 20. In another aspect of the invention the antibody comprises a VH region comprising a sequence which is at least 90% identical to the VH region as set forth in SEQ ID NO: 20. In another aspect of the invention the antibody comprises a VH region comprising a sequence which is at least 95% identical to the VH region as set forth in SEQ ID NO: 20. In another aspect of the invention the antibody comprises a VH region comprising a sequence which is at least 96% identical to the VH region as set forth in SEQ ID NO: 20. In another aspect of the invention the antibody comprises a VH region comprising a sequence which is at least 97% identical to the VH region as set forth in SEQ ID NO: 20. In another aspect of the invention the antibody comprises a VH region comprising a sequence which is at least 98% identical to the VH region as set forth in SEQ ID NO: 20. In another aspect of the invention the antibody comprises a VH region comprising a sequence which is at least 99% identical to the VH region as set forth in SEQ ID NO: 20. In another aspect of the invention the antibody comprises a VH region comprising a sequence as set forth in SEQ ID NO: 20.

In another aspect of the invention the antibody comprises a VL region comprising a sequence which is at least 80% identical to the VL region as set forth in SEQ ID NO: 21. In another aspect of the invention the antibody comprises a VL region comprising a sequence which is at least 85% identical to the VL region as set forth in SEQ ID NO: 21. In another aspect of the invention the antibody comprises a VL region comprising a sequence which is at least 90% identical to the VL region as set forth in SEQ ID NO: 21. In another aspect of the invention the antibody comprises a VL region comprising a sequence which is at least 95% identical to the VL region as set forth in SEQ ID NO: 21. In another aspect of the invention the antibody comprises a VL region comprising a sequence which is at least 96% identical to the VL region as set forth in SEQ ID NO: 21. In another aspect of the invention the antibody comprises a VL region comprising a sequence which is at least 97% identical to the VL region as set forth in SEQ ID NO: 21. In another aspect of the invention the antibody comprises a VL region comprising a sequence which is at least 98% identical to the VL region as set forth in SEQ ID NO: 21. In another aspect of the invention the antibody comprises a VL region comprising a sequence which is at least 99% identical to the VL region as set forth in SEQ ID NO: 21. In another aspect of the invention the antibody comprises a VL region comprising a sequence as set forth in SEQ ID NO: 21.

In another aspect of the invention the antibody comprises the VH and VL regions comprising the sequences as set forth in SEQ ID NO: 20 and SEQ ID NO: 21, respectively.

In one aspect the antibody of the invention is an isolated antibody.

The antibody of the invention is in a preferred embodiment a full-length antibody. Accordingly, the antibody of the invention may further comprise a light chain constant region (CL) and a heavy chain constant region (CH). The CH preferably comprises a CH1 region, a hinge region, a CH2 region and a CH3 region.

The antibody according to the invention may comprise a light chain constant region which is a human kappa light chain. In another aspect it may comprise a human lambda light chain constant region.

The antibody according to the invention may preferably further comprise a heavy chain constant region, which is of a human IgG1 isotype. Thus, in one embodiment the antibody comprises a human IgG1 Fc region. The human IgG1 isotype exist in various allotypes such as IgG1m(f), IgG1m(a), IgG1m(x) and IgG1m(z), the allotype may also be written as IgG1mf, IgG1ma, IgG1mx and IgG1mz, respectively.

In one embodiment of the invention the antibody comprises an Fc region selected from the human IgG1mf, human IgG1ma, human IgG1mx or human IgG1mz allotype. In one embodiment of the invention the Fc region is of the human IgG1mf allotype. In one embodiment of the invention the antibody comprises the Fc region having the sequence set forth in SEQ ID NO:1.

Optimization of the effector functions by modifications of the Fc region of the antibody may improve the effectivity of therapeutic antibodies for treating cancer or other diseases, e.g., to improve the ability of an antibody to elicit an immune response to antigen-expressing cells. Such efforts are described in, e.g., WO2013/004842 A2; WO2014/108198 A1; WO2018/146317; WO2018/083126; WO2018/031258 A1.

US2014/0377284A1 discloses human OX40-binding antibody clone 12H3 (also designated SF2), which does not block binding of OX40L to OX40. The SF2 antibody induced T-cell activation and was shown to dampen the inhibitory effect of Tregs in vitro. Zhang et al demonstrated that the agonistic effects and effector functions of antibody clone SF2 could be enhanced by different engineering approaches, including introduction of hexamerization-enhancing mutation E345R (Zhang et al. J Biol Chem. 2016 Dec. 30; 291 (53): 27134-27146).

WO2016/164480A1 discloses human OX40-binding antibody clones, including clone h3C8, molecularly engineered to impart enhanced agonistic effects. Engineering strategies included the introduction of hexamerization-enhancing mutations E345R, E430G, S440Y or different combinations thereof. In addition, Fc inertness mutations were introduced, such as L234A-L235A-P329G.

US20190276549A1 describes methods to engineer antibodies with enhanced Fc-Fc interactions, while further containing mutations that reduce the binding of complement factor C1q and Fcγ receptors, to generate non-depleting immune cell-targeting antibodies with agonistic properties independent of engagement with Fcγ receptors.

Further engineering approaches to develop human OX40 agonistic constructs have been described, including a Fc domain covalently linked to 6 single domain antibodies to create a hexavalent construct (WO2017/019805A1) and a fusion protein consisting of the extracellular domain (ECD) of PD1 linked to the ECD of OX40L trimers through an IgG4 Fc linked protein (U.S. Pat. No. 10,449,233).

The antibody according to the invention preferably comprises a modified human IgG1 constant region.

Such human IgG1 comprise the Fc region which comprise the CH2 and CH3 region. By modifying the IgG1 constant region in the Fc region, it is for example possible to regulate the Fc effector functions of the antibody or to increase the Fc-Fc interactions and thereby the antibodies tendency to form clusters such as hexamers. In one aspect of the invention the human IgG1 or modified human IgG1 is selected from IgG1mf, IgG1ma, IgG1mx or IgG1mz. In one embodiment it is a modified IgG1 having at least two mutations. In another aspect it is IgG1mf having at least two mutations. In yet another aspect it is IgG1ma having at least two mutations. In a further aspect it is IgG1mx having at least two mutations. In yet another aspect of the invention it is IgG1mz having at least two mutations. In one particular aspect the IgG is a modified human IgG comprising two or more amino acid substitutions in the Fc region. In one embodiment it may be a human IgG1 comprising two or more amino acid substitutions in the Fc region. In a further aspect of the invention the IgG1mf comprises two or more amino acid substitutions in the Fc region. In a further aspect of the invention the IgG1mf comprises three amino acid substitutions in the Fc region. In a further aspect of the invention the IgG1mf comprises four amino acid substitutions in the Fc region. In a further aspect of the invention the IgG1mf comprises five amino acid substitutions in the Fc region. In one embodiment the IgG1 Fc region has at most three amino acid substitutions. In one embodiment the IgG1mf Fc region has at most three amino acid substitutions. In one embodiment the IgG1mf Fc region has at most four amino acid substitutions. In one embodiment the IgG1mf Fc region has at most five amino acid substitutions.

In a further aspect of the invention, the modified human IgG1 heavy chain constant region comprises in the Fc region at most five amino acid substitutions. In another aspect it comprises at most four amino acid substitutions. In another aspect it comprises at most three amino acid substitutions. In another aspect it comprises at most two amino acid substitutions.

Mutations in amino acid residues at positions corresponding to E345 in a human IgG1 heavy chain, wherein the amino acid residues are numbered according to the Eu numbering, can improve the ability of an antibody to induce CDC and other effector functions. Without being bound by theory, it is believed that by introducing the E345R substitution, oligomerization of the antibody can be stimulated, thereby modulating Fc-mediated effector functions so as to, e.g., increase C1q binding, complement activation, CDC, ADCP, internalization or other relevant function(s) that may provide in vivo efficacy. In one embodiment the antibody according to the invention comprises an Fc region comprising the sequence set forth in SEQ ID NO: 2.

The present invention in one aspect relates to a variant antibody comprising an antigen-binding region and a variant Fc region, wherein the antigen-binding region is capable of binding OX40.

Hereby, antibodies are provided which have enhanced Fc-Fc interaction which may lead to antibody-dependent clustering of OX40 on the cell surface upon antibody binding, thereby increasing the agonism of the antibody of the invention.

In one aspect of the present invention the antibody comprises a variant human IgG1 Fc region or a variant human IgG1 CH region comprising an E345R mutation and a P329R mutation. In the following, reference to the mutations in the Fc region may similarly apply to the mutation(s) in the human IgG1 CH region and vice versa.

As described herein, the position of an amino acid to be mutated in the Fc region can be given in relation to (i.e., "corresponding to") its position in a naturally occurring (wildtype) human IgG1 heavy chain, when numbered according to the Eu numbering. So, if the parent Fc region already contains one or more mutations and/or if the parent Fc region is, for example, an IgG1, IgG1mf, IgG1ma, IgG1mz or IgG1mz Fc region, the position of the amino acid corresponding to an amino acid residue such as, e.g., E345 in a human IgG1 heavy chain numbered according to the Eu numbering can be determined by alignment. Specifically, the parent Fc region is aligned with a wild-type human IgG1 heavy chain sequence so as to identify the residue in the position corresponding to E345 in the human IgG1 heavy chain sequence. Any wildtype human IgG1 constant region amino acid sequence can be useful for this purpose, including any one of the different human IgG1 allotypes set forth in Table 3.

In one aspect of the invention the modification in the IgG1 Fc region induces increased OX40 agonism compared to the identical antibody but comprising a wild type of IgG Fc region of the same isotype or allotype, such as IgG1. This may for example be obtained by introducing an R amino acid at the amino acid position corresponding to position E345, thus introducing the E345R mutation in a human IgG1 heavy chain according to Eu numbering.

In a preferred embodiment the amino acid residue at the position corresponding to position E345 in a human IgG1 heavy chain according to Eu numbering is R. Accordingly, the antibody of the invention may comprise an E345R substitution in the Fc region.

Hereby, antibodies are provided which have enhanced Fc-Fc interaction which may lead to antibody-dependent clustering of OX40 on the cell surface upon antibody binding, thereby increasing the agonism of the antibody of the invention.

In another embodiment of the antibody of the invention the amino acid residue at the position corresponding to position P329 in a human IgG1 heavy chain according to Eu numbering is substituted with an R amino acid, thus introducing the P329R mutation in a human IgG1 heavy chain according to Eu numbering.

In a further aspect of the invention the antibody has the amino acid residue R at the position corresponding to position P329 in a human IgG1 heavy chain according to Eu numbering. Accordingly, the antibody of the invention comprises a P329R substitution in the Fc region. Without being bound by theory, it is believed that the antibody of the invention comprising an E345R mutation in the Fc region has increased serum clearance. The inventors found that further introducing a mutation at position 329, such as P329R restored the clearance of the antibody of the invention to the level of the antibody comprising a human IgG1 Fc region wild-type sequence (i.e. without any mutations in the human IgG1 Fc region). Further, the P329R mutations decreases the ability of the antibody to bind to FcγR receptors, such as FcγRIa, FcγRIIa, FcγRIIb and FcγRIIIa.

In preferred embodiment of the invention Fc region comprises a P329R and E345R mutation at the positions corresponding to positions P329 and E345 in a human IgG1 heavy chain according to Eu numbering. Hereby an antibody is provided which has increased OX40 receptor agonism and comparable pharmacokinetic properties, such as e.g. serum clearance, when compared to an antibody comprising the same VH and VL region and comprising an identical IgG1 heavy chain constant region with the exception of comprising the wildtype amino acid P at position 329 and the wildtype amino acid E at position 345.

Thus, an embodiment the invention provides a OX40 binding antibody which has increased receptor agonism upon binding to OX40 and which further has pharmacokinetic properties which are comparable, such as similar or even identical pharmacokinetic properties, when compared to the pharmacokinetic properties of an antibody comprising the same VH and VL region but comprising a wild-type IgG1 heavy chain constant region such as e.g. set out in SEQ ID NO: 1. In other words the invention provides a OX40 binding antibody which has pharmacokinetic properties which are not significantly different than the pharmacokinetic properties of an identical OX40 binding antibody except for comprising a wild-type IgG1 heavy chain constant region.

In one embodiment, the parent Fc region and/or human IgG1 CH region is a wild-type human IgG1 isotype.

In one embodiment of the invention the parent human IgG1 Fc region and/or human IgG1 CH region is a wild-type human IgG1mf allotype. In one embodiment of the invention the parent human IgG1 Fc region and/or human IgG1 CH region is a wild-type human IgG1ma allotype. In one embodiment of the invention the parent human IgG1 Fc region and/or human IgG1 CH region is a wild-type human IgG1mx allotype. In one embodiment of the invention the parent human IgG1 Fc region and/or human IgG1 CH region is a wild-type human IgG1mz allotype.

Thus, the variant Fc region may except for the recited mutations E345R and P329R be a human IgG1 Fc region.

In another aspect the invention provides an antibody which comprises a heavy chain constant region comprising an amino acid sequence selected from the group comprising: SEQ ID NOs 58, 59, 60 and 61. In one aspect the heavy chain constant region has the amino acid sequence of SEQ ID NO: 58. In one aspect the heavy chain constant region has the amino acid sequence of SEQ ID NO: 59. In one aspect the heavy chain constant region has the amino acid sequence of SEQ ID NO: 60. In one aspect the heavy chain constant region has the amino acid sequence of SEQ ID NO: 61.

In an embodiment the antibody according to the invention comprises:
a. The VH region comprising the amino acid sequence set forth in SEQ ID No: 20
b. The VL region comprising the amino acid sequence set forth in SEQ ID No: 21, and
c. The Fc region comprises the amino acid sequence set forth in SEQ ID No: 3.

In another embodiment the antibody according to the invention comprises:
a. The VH region comprising the amino acid sequence set forth in SEQ ID No: 20
b. The VL region comprising the amino acid sequence set forth in SEQ ID No: 21, and
c. The CH region comprising the amino acid sequence set forth in SEQ ID No: 58.

In another embodiment the antibody according to the invention comprises a heavy chain comprising the amino acid sequence set forth in SEQ ID NO: 18 and a light chain comprising the amino acid sequence set forth in SEQ ID NO: 19.

In yet another aspect the invention provides an antibody which comprises a heavy chain constant region that is modified so that the antibody induces an Fc-mediated effector function to a lesser extent relative to an identical antibody except for the modification. An example hereof is the OX40 binding antibody of the invention comprising a P329R and an E345R substitution. Such antibody induces one or more Fc-mediated effector function(s) to a lesser extent compared to the antibody comprising the same sequence except not comprising the P329R substitution and also compared to the same antibody comprising the same sequence except not comprising the P329R and E345R substitutions, such as a wildtype IgG1 heavy chain. In one embodiment the Fc-mediated effector function is decreased by at least 20%. In another aspect the Fc-mediated effector function is decreased by at least 30%. In another aspect the Fc-mediated effector function is decreased by at least 40%. In another aspect the Fc-mediated effector function is decreased by at least 50%. In another aspect the Fc-mediated effector function is decreased by at least 60%. In another aspect the Fc-mediated effector function is decreased by at least 70%. In another aspect the Fc-mediated effector function is decreased by at least 80%. In another aspect the Fc-mediated effector function is decreased by at least 90%. In another aspect the antibody does not induce one or more Fc-mediated effector functions. The one or more Fc-effector functions that are decreased or not at all induced may be selected from the following group: complement-dependent cytotoxicity (CDC), complement-dependent cell-mediated cytotoxicity (CDCC), complement activation, antibody-dependent cell-mediated cytotoxicity (ADCC), antibody-dependent cell-mediated phagocytosis (ADCP), C1q binding and FcγR binding. Accordingly, in one embodiment the antibody of the invention induces CDC to a degree which is decreased by at least 20%, such as at least 30%, or at least 40%, or at least 50%, or at least 60%, or at least 70%, or at least 80%, or decreased by at least 90% relative to the identical antibody but a wildtype IgG1 HC constant region. In another embodiment the antibody of the invention does not induce CDC.

In another aspect, the antibody of the invention induces CDCC to a degree which is decreased by at least 20%, such as at least 30%, or at least 40%, or at least 50%, or at least 60%, or at least 70%, or at least 80%, or decreased by at least 90% relative to the identical antibody but having a wildtype IgG1 HC constant region. In another embodiment the antibody of the invention does not induce CDCC.

In another aspect, the antibody of the invention induces ADCC to a degree which is decreased by at least 20%, such as at least 30%, or at least 40%, or at least 50%, or at least 60%, or at least 70%, or at least 80%, or decreased by at least 90% relative to the identical antibody but having a wildtype IgG1 HC constant region. In another embodiment the antibody of the invention does not induce ADCC.

In another aspect, the antibody of the invention induces ADCP to a degree which is decreased by at least 20%, such as at least 30%, or at least 40%, or at least 50%, or at least 60%, or at least 70%, or at least 80%, or decreased by at least 90% relative to the identical antibody but having a wildtype IgG1 HC constant region. In another embodiment the antibody of the invention does not induce ADCP.

In another aspect, the antibody of the invention induces C1q binding to a degree which is decreased by at least 20%, such as at least 30%, or at least 40%, or at least 50%, or at least 60%, or at least 70%, or at least 80%, or decreased by at least 90% relative to the identical antibody but having a wildtype IgG1 HC constant region. In another embodiment the antibody of the invention does not induce C1q binding.

In one embodiment the antibody of the invention does not bind C1q. Hereby an embodiment is described where the antibody when bound to the cell membrane is not able to bind C1q to the Fc region of said antibody. In one embodiment the antibody does not induce target-independent fluid-phase complement activation.

In another aspect, the antibody of the invention induces FcγR binding to a degree which is decreased by at least 20%, such as at least 30%, or at least 40%, or at least 50%, or at least 60%, or at least 70%, or at least 80%, or least decreased by at least 90%, or least decreased by at least 95% or decreased by at least 98% relative to the identical antibody but having a wildtype IgG1 HC constant region. In another embodiment the antibody of the invention does not induce FcγR binding. Preferably the FcγR binding is determined as in example 8.

In one embodiment the antibody of the invention has reduced C1q binding and reduced FcγR binding compared to the antibody comprising the same amino acid sequences except not comprising the P329R substitution. In one embodiment of the antibody of the invention has reduced binding to FcγRIa, FcγRIIa, FcγRIIb, and FcγRIIIa. In one embodiment the antibody of the invention has reduced binding to FcγRIa by at least 20%, such as at least 30%, or at least 40%, or at least 50%, or at least 60%, or at least 70%, or at least 80%. In one embodiment the antibody of the invention has reduced binding to FcγRIIa, FcγRIIb and FcγRIIa by at least 60%, such as at least 70%, or at least 80%, or at least 85%, or at least 90%, or at least 95%, or at least 99%. In one embodiment of the invention the antibody has no binding to FcγRIIa, FcγRIIb and FcγRIIa.

In one embodiment, the antibody according to any aspect or embodiment herein is, except for the recited mutations, a human antibody.

In an embodiment of the invention the antibody is a monovalent antibody.

In another embodiment the antibody is a bivalent antibody.

Further, the antibody of the invention may be a monospecific antibody.

In one embodiment, the antibody according to any aspect or embodiment herein is a monoclonal antibody, such as a human monoclonal antibody, such as a human bivalent monoclonal antibody, such as a human bivalent full-length monoclonal antibody.

In a preferred embodiment, the antibody according to any aspect or embodiment herein is a humanized bivalent full-length monoclonal antibody. In a preferred embodiment, the antibody according to the invention is a humanized antibody comprising heavy chain as set forth in SEQ ID NO 18 and light chain as set forth in SEQ ID NO 19. Hereby an embodiment is described of a humanized antibody with an SI mean score of 2.66, which corresponds to an antibody with low clinical immunogenicity.

In a preferred embodiment, the antibody according to any aspect or embodiment herein is, except for the optional recited mutations in the Fc region, an IgG1 antibody, such as a full-length IgG1 antibody, such as a human full-length IgG1 antibody, optionally a human monoclonal full-length bivalent IgG1,K antibody, e.g. a human monoclonal full-length bivalent IgG1m(f),k antibody.

An antibody according to the present invention is advantageously in a bivalent monospecific format, comprising two antigen-binding regions binding to the same epitope. However, bispecific formats where one of the antigen-binding regions binds to a different epitope are also contemplated. So, the antibody according to any aspect or embodiment herein can, unless contradicted by context, be either a monospecific antibody or a bispecific antibody.

Accordingly, in another embodiment, the antibody of the invention is a bispecific antibody comprising a first antigen binding region capable of binding human OX40 as described herein and comprising a second antigen binding region capable of binding to a different epitope on human OX40. In another embodiment, the antibody of the invention is a bispecific antibody comprising a first antigen binding region capable of binding human OX40 as described herein and comprising a second antigen binding region capable of binding a different target. Such target may be on a different cell or on the same cell as OX40.

In an aspect of the invention the antibody is capable of binding to human OX40 having the sequence as set forth in SEQ ID NO: 52. In another embodiment, the antibody of the invention if further capable of binding to cynomolgus OX40, such as set forth in SEQ ID NO: 51.

In a further embodiment of the invention the antibody is capable of binding OX40-expressing human T cells.

In another embodiment of the invention the antibody is capable of binding OX40-expressing cynomolgus T cells.

In another embodiment of the invention the antibody has increased agonistic activity compared to a wild-type parent antibody without the P329R and E345R mutations.

In another embodiment of the invention the antibody induces increased T-cell proliferation.

In another embodiment of the invention the antibody induces increased T-cell proliferation compared to a parent antibody without the P329R and E345R mutations.

In one embodiment of the invention the full-length IgG1 antibody has had the C-terminal lysine of the HC cleaved off. Such an antibody is also considered a "full-length antibody".

In another embodiment of the invention the antibody is capable of inducing proliferation of human T cells such as CD4+ and CD8+ T cells, such as T helper cells and cytotoxic T cells, as described in Example 7. In another embodiment of the invention the antibody is capable of inducing proliferation of human CD4+ T cells. In another embodiment of the invention the antibody is capable of inducing proliferation of human CD8+ T cells.

In another embodiment of the invention the antibody is capable of inducing activation of human OX40-expressing T cells.

In another embodiment of the invention the antibody is capable of inducing expression of OX40 on T cells, such as CD4+ T cells and CD8+ T cells. Thus, the antibody is capable of increasing the expression of OX40 on CD4+ T cells and CD8+ T cells.

In another embodiment of the invention the antibody is capable of inducing activation of human OX40-expressing T cells in the absence of Fcγ receptor IIb crosslinking.

In another embodiment of the invention the antibody is capable of inducing expression of 4-1BB, CD25, and HLA-DR on CD4+ T cells and CD8+ T cells.

In another embodiment of the invention the antibody is capable of inducing proliferation of CD4+ and CD8+ T cells with a central memory T cell phenotype.

In another embodiment of the invention the antibody is capable of inducing secretion of TNFα, IFNγ, IL-2 and IL-13. In another embodiment of the invention the antibody is capable of inducing secretion of TNFα, IFNγ, IL-2 and IL-13 from CD8+ T cells.

In another embodiment of the invention the antibody is capable of inducing granzyme B in T cells, such as CD4+ T cells. In another embodiment of the invention the antibody is capable of inducing increased level of granzyme B in T cells, such as CD4+ T cells. Granzyme B may be used as a marker for cytotoxic T cells. Hereby an embodiment is disclosed where the antibody is able to generate T cells with increased level of cytolytic capability. Antibodies are well known as therapeutics which may be used in treatment of various diseases. Another method for administration of an antibody to a subject in need thereof includes administration of a nucleic acid or a combination of nucleic acids encoding said antibody for in vivo expression of said antibody.

Hence, in one aspect, the present invention also relates to a nucleic acid sequence encoding the heavy chain of an antibody according to the present invention, wherein said heavy chain comprises a VH region comprising a VH CDR1 comprising the sequence as set forth in SEQ ID NO:12, a VH CDR2 comprising the sequence as set forth in SEQ ID NO:13, a VH CDR3 comprising the sequence as set forth in SEQ ID NO:17.

In another aspect, the present invention also relates to a nucleic acid sequence encoding the heavy chain of an antibody according to the present invention, wherein said heavy chain comprises a VH region comprising a VH CDR1 comprising the sequence as set forth in SEQ ID NO:12, a VH CDR2 comprising the sequence as set forth in SEQ ID NO:13, a VH CDR3 comprising the sequence as set forth in SEQ ID NO:17 and a human IgG1 CH region.

In another aspect, the present invention also relates to a nucleic acid sequence encoding the encoding a VH region comprising the amino acid sequence as set forth in SEQ ID NO: 20.

In another aspect, the present invention also relates to a nucleic acid sequence encoding a VL region comprising the amino acid sequence as set forth in SEQ ID NO: 21.

In another aspect, the present invention also relates to a nucleic acid sequence encoding a heavy chain (HC) as set forth in SEQ ID NO: 18.

In another aspect, the present invention also relates to a nucleic acid sequence encoding a light chain (LC) as set forth in SEQ ID NO: 19.

In another aspect, the present invention also relates to a nucleic acid sequence encoding a heavy chain (HC) as set forth in SEQ ID NO: 18 and a light chain (LC) as set forth in SEQ ID NO: 19.

In one embodiment, the antibody of the present invention is encoded by one nucleic acid. Thus, the nucleotide sequences encoding the antibody of the present invention are present in one nucleic acid sequence or the same nucleic acid molecule.

In another embodiment the antibody of the present invention is encoded by a combination of nucleic acid sequences, typically by two nucleic acid sequences. In one embodiment said combination of nucleic acid sequences comprise a nucleic acid sequence encoding the heavy chain of said antibody and a nucleic acid sequence encoding the light chain of said antibody.

In some embodiments the present invention relates to a nucleic acid sequence or a combination of nucleic acid sequences encoding an antibody comprising:

In one embodiment, the antibody of the present invention is encoded by one nucleic acid. Thus, the nucleotide sequences encoding the antibody of the present invention are present in one nucleic acid or the same nucleic acid molecule.

In another embodiment the antibody of the present invention is encoded by a combination of nucleic acid sequences, typically by two nucleic acid sequences. In one embodiment said combination of nucleic acid sequences comprise a nucleic acid sequence encoding the heavy chain of said antibody and a nucleic acid sequence encoding the light chain of said antibody.

As described above the nucleic acid sequences may be used as a mean for supplying therapeutic proteins, such as antibodies, to a subject in need thereof.

In some embodiments, said nucleic acid may be deoxyribonucleic acid (DNA). DNAs and methods of preparing DNA suitable for in vivo expression of therapeutic proteins, such as antibodies are well known to a person skilled in the art and include but is not limited to that described by Patel A et al., 2018, Cell Reports 25, 1982-1993.

In some embodiments, said nucleic acid may be ribonucleic acid (RNA), such as messenger RNA (mRNA). In some embodiments, the mRNA may comprise only naturally occurring nucleotides. In some embodiments the mRNA may comprise modified nucleotides, wherein modified refers to said nucleotides being chemically different from the naturally occurring nucleotides. In some embodiments the mRNA may comprise both naturally occurring and modified nucleotides.

Different nucleic acid sequences suitable for in vivo expression of therapeutic proteins, such as antibodies, in a subject are well known to a person skilled in the art. For example, a mRNA suitable for expression of a therapeutic antibody in a subject, often comprise an Open Reading Frame (ORF), flanked by Untranslated Regions (UTRs) comprising specific sequences, and 5'and 3'ends being formed by a cap structure and a poly (A) tail (see e.g. Schlake et al., 2019, Molecular Therapy Vol. 27 No 4 Apr.).

Examples of methods for optimization of RNA and RNA molecules suitable, e.g. mRNA, for in vivo expression include, but are not limited to those described in U.S. Pat. Nos. 9,254,311; 9,221,891; US20160185840 and EP3118224.

Naked nucleic acid sequence(s) which are administered to a subject for in vivo expression are prone to degradation and/or of causing an immunogenic response in the subject. Furthermore, for in vivo expression of the antibody encoded by the nucleic acid sequences said nucleic acid sequences typically is administered in a form suitable for the nucleic acid sequences to enter the cells of the subject. Different methods for delivering a nucleic acid sequence for in vivo expression exist and include both methods involving mechanical and chemical means. For example, such methods may involve electroporation or tattooing the nucleic acid onto the skin (Patel et al., 2018, Cell Reports 25, 1982-1993). Other methods suitable for administration of the nucleic acid sequences to a subject involve administration of the nucleic acid in a suitable formulation. Thus, the present invention also relates to a delivery vehicle comprising a nucleic acid of the present invention.

In some embodiments, said delivery vehicle may comprise a nucleic acid sequence encoding a heavy chain of an antibody according to the present invention. Thus in one embodiment said nucleic acid sequence may encode a heavy chain comprising a VH region comprising a VH CDR1 comprising the sequence as set forth in SEQ ID NO:12, a VH CDR2 comprising the sequence as set forth in SEQ ID NO:13, a VH CDR3 comprising the sequence as set forth in SEQ ID NO:14 and a human IgG1 HC region with a P329R and E345R mutation, the amino acid residues being numbered according to the Eu numbering.

In some embodiments, the present invention also relates to a delivery vehicle comprising a nucleic acid sequence encoding a light chain of an antibody according to the present invention. Thus, in one embodiment said nucleic acid sequence may encode a light chain comprising a VL region comprising a VL CDR1 comprising the sequence as set forth in SEQ ID NO:16, a VL CDR2 comprising the sequence as set forth in: DAS, and a VL CDR3 comprising the sequence as set forth in SEQ ID NO:17.

The present invention also relates to a mixture of delivery vehicles comprising a delivery vehicle comprising a nucleic acid sequence encoding a heavy chain of an antibody according to the present invention and delivery vehicle comprising a nucleic acid sequence encoding a light chain of an antibody according to the present invention. Thus in one embodiment said mixture of delivery vehicles comprise a delivery vehicle comprising a nucleic acid sequence encoding a heavy chain comprising a VH region comprising a VH CDR1 comprising the sequence as set forth in SEQ ID NO:12, a VH CDR2 comprising the sequence as set forth in SEQ ID NO:13, a VH CDR3 comprising the sequence as set forth in SEQ ID NO:14 and a human IgG1 CH region with a P329R and an E345R mutation, the amino acid residues being numbered according to the Eu numbering; and a delivery vehicle comprising a nucleic acid sequence encoding a light chain comprising a VL region comprising a VL CDR1 comprising the sequence as set forth in SEQ ID NO:16, a VL CDR2 comprising the sequence as set forth in: DAS, and a VL CDR3 comprising the sequence as set forth in SEQ ID NO:17.

In some embodiments, said delivery vehicle comprises a nucleic acid sequence or a combination of nucleic acid sequences encoding the heavy and a nucleic light chain of an antibody according to the present invention.

Thus, in one embodiment said delivery vehicle may comprise a nucleic acid sequence encoding a heavy chain comprising a VH region comprising a VH CDR1 comprising the sequence as set forth in SEQ ID NO:12, a VH CDR2 comprising the sequence as set forth in SEQ ID NO:13, a VH CDR3 comprising the sequence as set forth in SEQ ID NO:14 and a human IgG1 CH region with the mutations P329R and E345R the amino acid residues being numbered according to the Eu index; and a light chain comprising a VL region comprising a VL CDR1 comprising the sequence as set forth in SEQ ID NO:16, a VL CDR2 comprising the sequence as set forth in DAS, and a VL CDR3 comprising the sequence as set forth in SEQ ID NO:17.

Thus, the nucleic acid sequences encoding the heavy and light chain of the antibody according to the present invention are present in one (the same) nucleic acid molecule.

In another embodiment said delivery vehicle may comprise a nucleic acid sequence encoding a heavy chain comprising the sequence as set forth in SEQ ID NO:9; and a nucleic acid encoding a light chain comprising the sequence as set forth in SEQ ID NO:10.

Thus, the nucleic acid sequences encoding the heavy and light chain of the antibody variant according to the present invention are present on separate or different nucleic acid molecules.

In some embodiments said delivery vehicle may be a lipid formulation. The lipids of the formulation may particle(s), such as a lipid nanoparticle(s) (LNPs). The nucleic acid sequence or combination of nucleic acid sequences of the present may be encapsulated within said particle, e.g. within said LNP.

Different lipid formulations suitable for administration of a nucleic acid to a subject for in vivo expression are well known to a person skilled in the art. For example, said lipid formulation may typically comprise lipids, ionizable amino lipids, PEG-lipids, cholesterol or any combination thereof.

Various forms and methods for preparation of lipid formulations suitable for administration of a nucleic acid sequence to a subject for expression of a therapeutic antibody are well known in the art. Examples of such lipid formulations include but are not limited to those described in US20180170866 (Arcturus), EP 2391343 (Arbutus), WO 2018/006052 (Protiva), WO2014152774 (Shire Human Genetics), EP 2 972 360 (Translate Bio), U.S. Pat. No. 10,195,156 (Moderna), and US20190022247 (Acuitas).

The invention also provides isolated nucleic acid sequences and vectors encoding an antibody variant according to any one of the aspects and embodiments described herein, as well as vectors and expression systems encoding the variants. Suitable nucleic acid constructs, vectors and expression systems for antibodies and variants thereof are known in the art, and include, but are not limited to, those described in the Examples. In embodiments where the variant antibody comprises HC and LC that are separate polypeptides rather than contained in a single polypeptide (e.g., as in a scFv-Fc fusion protein), the nucleotide sequences encoding the heavy and light chains may be present in the same or different nucleic acids or vectors.

Accordingly, in one aspect the invention provides an isolated nucleic acid sequence or a combination of nucleic acid sequences encoding the antibody according to any aspect or embodiment herein. The invention also provides a nucleic acid sequence encoding a VH region comprising a VH CDR1 comprising the sequence as set forth in SEQ ID NO:12, a VH CDR2 comprising the sequence as set forth in SEQ ID NO: 13, a VH CDR3 comprising the sequence as set forth in SEQ ID NO:14.

Further, the invention provides a nucleic acid sequence encoding a VL region comprising a VL CDR1 comprising the sequence as set forth in SEQ ID NO:16, a VL CDR2 comprising the sequence as set forth in: DAS, a VL CDR3 comprising the sequence set as forth in SEQ ID NO:17. Further, the invention provides a nucleic acid sequence encoding a VH region comprising the amino acid sequence as set forth in SEQ ID NO: 20. The invention also relates to a nucleic acid sequence encoding a VL region comprising the amino acid sequence as set forth in SEQ ID NO: 21.

In an embodiment of the invention the nucleic acid sequence or combination of nucleic acid sequences are RNA or DNA. In an embodiment of the invention the nucleic acid sequence or combination of nucleic acid sequences is/are mRNA.

The invention further provides an expression vector comprising the nucleic acid sequence or combination thereof according to any aspect or embodiment described herein.

In another aspect the invention relates to a nucleic acid sequence or a combination of nucleic acid sequences as described herein for use in expression in mammalian cells.

In a further embodiment the invention relates to a recombinant host cell, which produces an antibody as defined herein, optionally wherein the host cell comprises the expression vector described above. In certain embodiments the recombinant host cell is a eukaryotic or prokaryotic cell.

In another aspect the invention relates to a method of producing an antibody according to any aspect or embodiment herein, comprising cultivating the recombinant host cell as described above in a culture medium and under conditions suitable for producing the antibody and, optionally, purifying or isolating the antibody from the culture medium.

In one aspect, the invention relates to a nucleic acid or an expression vector comprising
(i) a nucleotide sequence encoding a heavy chain sequence of an antibody according to any one of the embodiments disclosed herein;
(ii) a nucleotide sequence encoding a light chain sequence of an antibody according to any one of the embodiments disclosed herein; or
(iii) both (i) and (ii).

In one aspect, the invention relates to a nucleic acid or an expression vector comprising a nucleotide sequence encoding a heavy chain sequence of an antibody variant according to any one of the embodiments disclosed herein.

In one aspect, the invention relates to a nucleic acid sequence or an expression vector comprising a nucleotide sequence encoding a heavy chain sequence and a light chain sequence of an antibody according to any one of the embodiments disclosed herein.

In one aspect, the invention relates to a combination of a first and a second nucleic acid or a combination of a first and second expression vector, optionally in the same host cell, where the first comprises a nucleotide sequence according to (i), and the second comprises a nucleotide sequence according to (ii).

An expression vector in the context of the present invention may be any suitable vector, including chromosomal, non-chromosomal, and synthetic nucleic acid vectors (a nucleic acid sequence comprising a suitable set of expression control elements). Examples of such vectors include derivatives of SV40, bacterial plasmids, phage DNA, baculovirus, yeast plasmids, vectors derived from combinations of plasmids and phage DNA, and viral nucleic acid (RNA or DNA) vectors. In one embodiment, a nucleic acid is comprised in a naked DNA or RNA vector, including, for example, a linear expression element (as described in for instance Sykes and Johnston, Nat Biotech 17, 355 59 (1997)), a compacted nucleic acid vector (as described in for instance U.S. Pat. No. 6,077,835 and/or WO 00/70087), a plasmid vector such as pBR322, pUC 19/18, or pUC 118/119, a "midge" minimally-sized nucleic acid vector (as described in for instance Schakowski et al., Mol Ther 3, 793 800 (2001)), or as a precipitated nucleic acid vector construct, such as a CaP04-precipitated construct (as described in for instance WO200046147, Benvenisty and Reshef, PNAS USA 83, 9551 55 (1986), Wigler et al., Cell 14, 725 (1978), and Coraro and Pearson, Somatic Cell Genetics 7, 603 (1981)). Such nucleic acid vectors and the usage thereof are well known in the art (see for instance U.S. Pat. Nos. 5,589,466 and 5,973,972).

In one embodiment, the vector is suitable for expression of the antibody in a bacterial cell. Examples of such vectors include expression vectors such as BlueScript (Stratagene), pIN vectors (Van Heeke & Schuster, J Biol Chem 264, 5503 5509 (1989), pET vectors (Novagen, Madison WI) and the like). An expression vector may also or alternatively be a vector suitable for expression in a yeast system. Any vector suitable for expression in a yeast system may be employed. Suitable vectors include, for example, vectors comprising constitutive or inducible promoters such as alpha factor, alcohol oxidase and PGH (reviewed in: F. Ausubel et al., ed. Current Protocols in Molecular Biology, Greene Publishing and Wiley InterScience New York (1987), and Grant et al., Methods in Enzymol 153, 516 544 (1987)).

An expression vector may also or alternatively be a vector suitable for expression in mammalian cells, e.g. a vector comprising glutamine synthetase as a selectable marker, such as the vectors described in Bebbington (1992) Biotechnology (NY) 10:169-175.

A nucleic acid and/or vector may also comprise a nucleic acid sequence encoding a secretion/localization sequence, which can target a polypeptide, such as a nascent polypeptide chain, to the periplasmic space or into cell culture media. Such sequences are known in the art and include secretion leader or signal peptides.

The expression vector may comprise or be associated with any suitable promoter, enhancer, and other expression-facilitating elements. Examples of such elements include strong expression promoters (e. g., human CMV IE promoter/enhancer as well as RSV, SV40, SL3 3, MMTV, and HIV LTR promoters), effective poly (A) termination sequences, an origin of replication for plasmid product in *E. coli*, an antibiotic resistance gene as selectable marker, and/or a convenient cloning site (e.g., a polylinker). Nucleic acids may also comprise an inducible promoter as opposed to a constitutive promoter such as CMV IE.

In one embodiment, the antibody-encoding expression vector may be positioned in and/or delivered to the host cell or host animal via a viral vector.

The invention also provides a recombinant host cell which produces an antibody as disclosed herein, optionally wherein the host cell comprises the isolated nucleic acid(s) or vector(s) according to the present invention. Typically, the host cell has been transformed or transfected with the nucleic acid(s) or vector(s). The recombinant host cell of claim can be, for example, a eukaryotic cell, a prokaryotic cell, or a microbial cell, e.g., a transfectoma. In a particular embodiment the host cell is a eukaryotic cell. In a particular embodiment the host cell is a prokaryotic cell. In some embodiments, the antibody is a heavy-chain antibody. In most embodiments, however, the antibody will contain both a heavy and a light chain and thus said host cell expresses both heavy- and light-chain-encoding construct, either on the same or a different vector.

Examples of host cells include yeast, bacterial, plant and mammalian cells, such as CHO, CHO-S, HEK, HEK293, HEK-293F, Expi293F, PER.C6, NSO cells, Sp2/0 cells or lymphocytic cells. In one embodiment the host cell is a CHO (Chinese Hamster Ovary) cell. For example, in one embodiment, the host cell may comprise a first and second nucleic acid construct stably integrated into the cellular genome, wherein the first encodes the heavy chain and the second encodes the light chain of an antibody variant as disclosed herein. In another embodiment, the present invention provides a cell comprising a non-integrated nucleic acid, such as a plasmid, cosmid, phagemid, or linear expression element, which comprises a first and second nucleic acid construct as specified above.

In one embodiment, said host cell is a cell which is capable of Asn-linked glycosylation of proteins, e.g. a eukaryotic cell, such as a mammalian cell, e.g. a human cell.

In one embodiment, said host cell is a host cell which is not capable of efficiently removing C-terminal lysine K447 residues from antibody heavy chains. For example, Table 2 in Liu et al. (2008) J Pharm Sci 97:2426 (incorporated herein by reference) lists a number of such antibody production systems, e.g. Sp2/0, NS/0 or transgenic mammary gland (goat), wherein only partial removal of C-terminal lysines is obtained. In one embodiment, the host cell is a host cell with altered glycosylation machinery. Such cells have been described in the art and can be used as host cells in which to express variants of the invention to thereby produce an antibody with altered glycosylation. See, for example, Shields, R. L. et al. (2002) J. Biol. Chem. 277:26733-26740; Umana et al. (1999) Nat. Biotech. 17:176-1, as well as EP1176195; WO03/035835; and WO99/54342. Additional methods for generating engineered glycoforms are known in the art, and include but are not limited to those described in Davies et al., 2001, Biotechnol Bioeng 74:288-294; Shields et al, 2002, J Biol Chem 277:26733-26740; Shinkawa et al., 2003, J Biol Chem 278:3466-3473), U.S. Pat. No. 6,602,684, WO00/61739A1; WO01/292246A1; WO02/311140A1; WO 02/30954A1; Potelligent™ technology (Biowa, Inc. Princeton, N.J.); GlycoMAb™ glycosylation engineering technology (GLYCART biotechnology AG, Zurich, Switzerland); US20030115614; Okazaki et al., 2004, JMB, 336:1239-49, as well as those described in WO2018/114877 WO2018/114878 and WO2018/114879.

In an even further aspect, the invention relates to a transgenic non-human animal or plant comprising nucleic acids encoding one or two sets of a human heavy chain and a human light chain, wherein the animal or plant produces an antibody as disclosed herein.

In one embodiment, there is provided an antibody obtained or obtainable by the method described above.

In another aspect, the present invention also relates to a method of increasing or decreasing at least one effector function of an antibody of the invention comprising introducing a P329R and an E345R mutation into the antibody in amino acid residue(s) corresponding to E345, and P329 in the Fc region of a human IgG1 heavy chain, numbered according to the Eu-numbering.

So, in certain embodiments, there is provided a method of increasing an effector function of a parent antibody, such as an Fc-mediated effector function or such as increasing the biological activity of the antibody, such as OX40 agonism, said parent antibody comprising an Fc region and an antigen-binding region binding to OX40, which method comprises introducing into the Fc region a P329R and an E345R mutation in amino acid residues corresponding to P329 and E345 in the Fc region of a human IgG1 heavy chain, wherein the amino acid residues are numbered according to the Eu numbering; and wherein the antigen-binding region comprises a VH CDR1 comprising the sequence as set forth in SEQ ID NO:12, a VH CDR2 comprising the sequence as set forth in SEQ ID NO:13, a VH CDR3 comprising the sequence as set forth in SEQ ID NO:14, a VL CDR1 comprising the sequence as set forth in SEQ ID NO:16, a VL CDR2 comprising the sequence as set forth in: DAS, and a VL CDR3 comprising the sequence as set forth in SEQ ID NO: 17.

In other certain embodiments, there is provided a method of decreasing an effector function, such as C1q binding or FcγR binding, of a parent antibody comprising a VH CDR1 comprising the sequence as set forth in SEQ ID NO:12, a VH CDR2 comprising the sequence as set forth in SEQ ID NO:13, a VH CDR3 comprising the sequence as set forth in SEQ ID NO:14, a VL CDR1 comprising the sequence as set forth in SEQ ID NO: 16, a VL CDR2 comprising the sequence as set forth in: DAS, and a VL CDR3 comprising the sequence as set forth in SEQ ID NO:17 and further comprising an E345R amino acid substitution in the Fc region of a human IgG1 heavy chain, wherein the amino acid residues are numbered according to the Eu numbering, the method comprising introducing a further P329R amino acid substitution in the Fc region of a human IgG1 heavy chain, numbered according to the Eu-numbering. Hereby an effector function of the parent antibody, such as C1q binding or FcgR binding may be decreased or may be completely eliminated.

In one embodiment of any one of the aforementioned methods, the effector function which is increased comprises OX40 agonism.

In one embodiment of any one of the aforementioned methods, the effector function is C1q binding.

In one embodiment of any one of the aforementioned methods, the effector function is FcgR binding.

In one embodiment of any one of the aforementioned methods, the effector functions that are decreseased comprises both C1q- and FcγR binding.

In one embodiment the effector function is C1q binding. Hereby embodiments are described where an antibody according to the present invention having an E345R and a P329R mutation has decreased C1q binding when compared to an antibody having the E345R mutation and not the P329R mutation.

In one embodiment the effector function that is decreased is binding to FcγR binding. Thus, in one embodiment binding to FcγRs, such as FcγRIa, FcγRIIa, FcγRIIb, and/or FcγRIIIa. In one embodiment the binding to FcγRIa is decreased. In one embodiment the binding to FcγRIIa is decreased. In one embodiment the binding to FcγRIIb is decreased. In one embodiment the binding to FcγRIIIa is decreased.

Hereby embodiments are described where an antibody according to the present invention having an E345R and a P329R mutation has decreased FcγRs when compared to an antibody having the E345R mutation and not the P329R mutation.

In one embodiment of any of the aforementioned methods, the Fc region comprises a E345R and a P329R mutation.

In one embodiment of any of the aforementioned methods, the Fc region of the antibody is, apart from the recited mutation(s), a human IgG1, more specifically a human IgG1m(f), IgG1m(a), human IgG1m(x) or human IgG1m(z)

Fc region. Optionally comprising an Fc region of one of the sequences set forth as SEQ ID NO: 58, SEQ ID NO:59, SEQ ID NO:60 and SEQ ID NO:61. In a preferred embodiment, the Fc region of the antibody is a human IgG1m(z) Fc region. For example, the antibody can be a human full-length IgG1 antibody, optionally a human monoclonal full-length bivalent IgG1,k antibody. Additionally, the antibody can be a monospecific or bispecific antibody, such as a monospecific antibody.

While the Fc region of the antibody may is an human IgG1 isotype, it may be any naturally occurring human IgG1 allotype sequence, such as human IgG1m(f), human IgG1m(a), human IgG1m(x) or human IgG1m(z), which may also be written as human IgG1mf, IgG1ma, human IgG1mx or human IgG1mz, wherein in some embodiments, the Fc region of the antibody comprises one or more further mutations, as described elsewhere herein.

The present invention also relates to an antibody obtained or obtainable according to any of the above described methods.

The present invention also relates to a composition comprising an antibody according to the present invention, a nucleic acid according to the present invention, an expression vector according to the present invention or a host cell according to the present invention.

In a further embodiment the composition according to the present invention is a pharmaceutical composition, typically comprising a pharmaceutically acceptable carrier. In one embodiment the pharmaceutical composition contains an antibody as defined in any aspect or embodiment disclosed herein, or an expression vector as defined in any aspect or embodiment disclosed herein.

In yet a further embodiment, the invention relates to a pharmaceutical composition comprising:
an antibody as defined in any of the aspects and embodiments disclosed herein, and
a pharmaceutically acceptable carrier.

In one embodiment the pharmaceutical composition is administered by intravenous or subcutaneous injection or infusion.

The invention also relates to kit-of-parts, such as a kit for use as a companion diagnostic for identifying within a population of patients those patients which have a propensity to respond to treatment with an antibody as defined herein, comprising an antibody as defined in any aspect or embodiment disclosed herein; and instructions for use of said kit.

The invention also relates to kit-of-parts for use in therapy comprising an antibody according to the invention, or a composition comprising an antibody according to the invention, optionally wherein the kit-of-parts contains more than one dosage of the antibody.

In one embodiment, the kit-of-parts comprises such an antibody or composition in one or more containers such as vials.

In one embodiment, the kit-of-parts comprises such an antibody or composition for simultaneous, separate or sequential use in therapy.

The antibodies of the present invention have numerous therapeutic utilities involving the treatment of diseases and disorders that may be treated by activating immune cells expressing OX40. For example, the antibodies may be administered to cells in culture, e.g., in vitro or ex vivo, or to human subjects, e.g., in vivo, to treat or prevent a variety of disorders and diseases. As used herein, the term "subject" is intended to include human and non-human animals which may benefit or respond to the antibody. Subjects may for instance include human patients having diseases or disorders that may be corrected or ameliorated by modulating OX40 function so that e.g. $CD4^+$ and/or $CD8^+$ T-cell populations are expanded. Accordingly, the antibodies may be used to elicit in vivo or in vitro proliferation of T-cell populations such as T helper cells and cytotoxic T cells.

Thus, in one aspect, the present invention relates to the antibodies according to the present invention, the nucleic acid or combination of nucleic acids according to the present invention, the delivery vehicle according to the present invention, the expression vector according to the present invention, the host cell according to the present invention, the composition according to the present invention, or the pharmaceutical composition according to the present invention for use as a medicament.

In one aspect, the present invention relates to the use of the antibodies according to the present invention, the nucleic acid or combination of nucleic acids according to the present invention, the delivery vehicle according to the present invention, the expression vector according to the present invention, the host cell according to the present invention, the composition according to the present invention, or the pharmaceutical composition according to the present invention in the preparation of a medicament for treating or preventing a disease or disorder.

In one aspect, the present invention relates to a method of treatment of a disease or disorder comprising administering the antibody according to the present invention, the nucleic acid or combination of nucleic acids according to the present invention, the delivery vehicle according to the present invention, the expression vector according to the present invention, the host cell according to claim the present invention, the composition according to the present invention, or the pharmaceutical composition according to the present invention to a subject in need thereof.

In one aspect, the invention relates to the antibody according to any aspect or embodiment for use as a medicament.

In one aspect, the invention relates to the use of the antibody according to any aspect or embodiment in the preparation of a medicament for treating or preventing a disease or disorder.

In one aspect, the invention relates to the antibody according to any aspect or embodiment for use in the treatment or prevention of a disease or disorder.

In one aspect, the invention relates to the antibody according to any aspect or embodiment for use in diagnostic or for use in a diagnostic method.

In one aspect, the invention relates to a method of treating a disease or disorder, comprising administering the antibody according to any aspect or embodiment to a subject in need thereof, typically in a therapeutically effective amount and/or for a time sufficient to treat the disease or disorder.

In one aspect, the invention relates to a pharmaceutical composition comprising the antibody according to any aspect or embodiment, for use as a medicament.

In one aspect, the invention relates to a pharmaceutical composition comprising the antibody according to any aspect or embodiment for use in the treatment or prevention of a disease or disorder.

In one aspect, the invention relates to a method of treatment of a disease or disorder comprising administering a pharmaceutical composition comprising the antibody according to any aspect or embodiment to a subject in need thereof, typically in a therapeutically effective amount and/or for a time sufficient to treat the disease or disorder.

In one aspect, the present invention relates to a method of treating a disease or disorder, comprising the steps of:

selecting a subject suffering from the disease or disorder, and administering to the subject the antibody according to any aspect or embodiment, or a pharmaceutical composition comprising the antibody, typically in a therapeutically effective amount and/or for a time sufficient to treat the disease or disorder.

In one embodiment, the disease or disorder is cancer, i.e. a tumorigenic disorder, such as for example, a hematological cancer or a solid tumor malignancy. In another embodiment the disease or disorder is an inflammatory and/or autoimmune disease or disorder.

In one embodiment of the invention the antibody is administered at a dose of 1 to 20 mg/kg. In another embodiment of the invention the antibody is administered at a dose of 1 mg/kg. In another embodiment of the invention the antibody is administered at a dose of 2.5 mg/kg. In another embodiment of the invention the antibody is administered at a dose of 5 mg/kg. In another embodiment of the invention the antibody is administered at a dose of 10 mg/kg. In another embodiment of the invention the antibody is administered at a dose of 20 mg/kg. In a further aspect, the invention relates to an anti-idiotypic antibody which binds to an antibody comprising at least one antigen-binding region capable of binding to OX40, i.e. an antibody according to the invention as described herein. In particular embodiments, the anti-idiotypic antibody binds to the antigen-binding region capable of binding to OX40 as described herein. In a preferred embodiment, the anti-idiotypic antibody binds to the antibody specified by the heavy chain as set forth in SEQ ID NO:18 and the light chain as set forth in SEQ ID NO:19.

An anti-idiotypic (Id) antibody is an antibody which recognizes unique determinants generally associated with the antigen-binding site of an antibody. An antiId antibody may be prepared by immunizing an animal of the same species and genetic type as the source of an anti-OX40 monoclonal antibody with the monoclonal antibody against which an anti-Id is being prepared. The immunized animal typically can recognize and respond to the idiotypic determinants of the immunizing antibody by producing an antibody to these idiotypic determinants (the anti-Id antibody). A method for producing such antibodies is described in for instance U.S. Pat. No. 4,699,880. Such antibodies are further features of the present invention.

An anti-Id antibody may also be used as an "immunogen" to induce an immune response in yet another animal, producing a so-called anti-anti-Id antibody. An anti-anti-Id antibody may be epitopically identical to the original monoclonal antibody, which induced the anti-Id antibody. Thus, by using antibodies to the idiotypic determinants of a monoclonal antibody, it is possible to identify other clones expressing antibodies of identical specificity. Anti-Id antibodies may be varied (thereby producing anti-Id antibody variants) and/or derivatized by any suitable technique, such as those described elsewhere herein with respect to OX40specific antibodies of the present invention. For example, a monoclonal anti-Id antibody may be coupled to a carrier such as keyhole limpet hemocyanin (KLH) and used to immunize BALB/c mice. Sera from these mice typically will contain anti-anti-Id antibodies that have the binding properties similar, if not identical, to an original/parental anti-OX40 antibody.

Fc regions may have at their C-terminus a lysine. The origin of this lysine is a naturally occurring sequence found in humans from which these Fc regions are derived. During cell culture production of recombinant antibodies, this terminal lysine can be cleaved off by proteolysis by endogenous carboxypeptidase(s), resulting in a constant region having the same sequence but lacking the C-terminal lysine. For manufacturing purposes of antibodies, the DNA encoding this terminal lysine can be omitted from the sequence such that antibodies are produced without the lysine. Antibodies produced from nucleic acid sequences that either do, or do not encode a terminal lysine are substantially identical in sequence and in function since the degree of processing of the terminal lysine is typically high when e.g. using antibodies produced in CHO-based production systems (Dick, L. W. et al. Biotechnol. Bioeng. 2008; 100:1132-1143). Hence, it is understood that proteins in accordance with the invention, such as antibodies, can be generated with or without encoding or having a terminal lysine. It is also understood in accordance with the invention that, sequences with a terminal lysine, such as a constant region sequence having a terminal lysine, can be understood as the corresponding sequences without a terminal lysine, and that sequences without a terminal lysine can also be understood as the corresponding sequences with a terminal lysine.

TABLE 3

Sequence List

| SEQ ID NO: | Identifier | Domain | Amino acid sequence |
|---|---|---|---|
| 1 | IgG1m(f) | Constant region | ASTKGPSVFPLAPSSKSTSGGTAALGCLVKDYFPEPVTVSWNSGALTSGVHTFP AVLQSSGLYSLSSVVTVPSSSLGTQTYICNVNHKPSNTKVDKRVEPKSCDKTHT CPPCPAPELLGGPSVFLFPPKPKDTLMISRTPEVTCVVVDVSHEDPEVKFNWY VDGVEVHNAKTKPREEQYNSTYRVVSVLTVLHQDWLNGKEYKCKVSNKALPA PIEKTISKAKGQPREPQVYTLPPSREEMTKNQVSLTCLVKGFYPSDIAVEWESN GQPENNYKTTPPVLDSDGSFFLYSKLTVDKSRWQQGNVFSCSVMHEALHNH YTQKSLSLSPG |
| 2 | IgG1m(f)-E345R | Constant region | ASTKGPSVFPLAPSSKSTSGGTAALGCLVKDYFPEPVTVSWNSGALTSGVHTFP AVLQSSGLYSLSSVVTVPSSSLGTQTYICNVNHKPSNTKVDKRVEPKSCDKTHT CPPCPAPELLGGPSVFLFPPKPKDTLMISRTPEVTCVVVDVSHEDPEVKFNWY VDGVEVHNAKTKPREEQYNSTYRVVSVLTVLHQDWLNGKEYKCKVSNKALPAP IEKTISKAKGQPRRPQVYTLPPSREEMTKNQVSLTCLVKGFYPSDIAVEWESN GQPENNYKTTPPVLDSDGSFFLYSKLTVDKSRWQQGNVFSCSVMHEALHNH YTQKSLSLSPG |

TABLE 3-continued

Sequence List

| SEQ ID NO: | Identifier | Domain | Amino acid sequence |
|---|---|---|---|
| 3 | IgG1m(f)-P329R-E345R | Constant region | ASTKGPSVFPLAPSSKSTSGGTAALGCLVKDYFPEPVTVSWNSGALTSGVHTFP AVLQSSGLYSLSSVVTVPSSSLGTQTYICNVNHKPSNTKVDKRVEPKSCDKTHT CPPCPAPELLGGPSVFLFPPKPKDTLMISRTPEVTCVVVDVSHEDPEVKFNWY VDGVEVHNAKTKPREEQYNSTYRVVSVLTVLHQDWLNGKEYKCKVSNKALRAP IEKTISKAKGQPRRPQVYTLPPSREEMTKNQVSLTCLVKGFYPSDIAVEWESN GQPENNYKTTPPVLDSDGSFFLYSKLTVDKSRWQQGNVFSCSVMHEALHNH YTQKSLSLSPG |
| 4 | IgG1m(f)-K322A-E345R | Constant region | ASTKGPSVFPLAPSSKSTSGGTAALGCLVKDYFPEPVTVSWNSGALTSGVHTFP AVLQSSGLYSLSSVVTVPSSSLGTQTYICNVNHKPSNTKVDKRVEPKSCDKTHT CPPCPAPELLGGPSVFLFPPKPKDTLMISRTPEVTCVVVDVSHEDPEVKFNWY VDGVEVHNAKTKPREEQYNSTYRVVSVLTVLHQDWLNGKEYKCAVSNKALPAP IEKTISKAKGQPRRPQVYTLPPSREEMTKNQVSLTCLVKGFYPSDIAVEWESN GQPENNYKTTPPVLDSDGSFFLYSKLTVDKSRWQQGNVFSCSVMHEALHNH YTQKSLSLSPG |
| 5 | IgG1m(f)-L234A-AGR | Constant region | ASTKGPSVFPLAPSSKSTSGGTAALGCLVKDYFPEPVTVSWNSGALTSGVHTFP AVLQSSGLYSLSSVVTVPSSSLGTQTYICNVNHKPSNTKVDKRVEPKSCDKTHT CPPCPAPEAAGGPSVFLFPPKPKDTLMISRTPEVTCVVVDVSHEDPEVKFNWY VDGVEVHNAKTKPREEQYNSTYRVVSVLTVLHQDWLNGKEYKCKVSNKALGA PIEKTISKAKGQPRRPQVYTLPPSREEMTKNQVSLTCLVKGFYPSDIAVEWES NGQPENNYKTTPPVLDSDGSFFLYSKLTVDKSRWQQGNVFSCSVMHEALHN HYTQKSLSLSPG |
| 6 | IgG1m(f)-RRE | Constant region | ASTKGPSVFPLAPSSKSTSGGTAALGCLVKDYFPEPVTVSWNSGALTSGVHTFP AVLQSSGLYSLSSVVTVPSSSLGTQTYICNVNHKPSNTKVDKRVEPKSCDKTHT CPPCPAPELLRGPSVFLFPPKPKDTLMISRTPEVTCVVVDVSHEDPEVKFNWYV DGVEVHNAKTKPREEQYNSTYRVVSVLTVLHQDWLNGKEYKCKVSNKALPAPI EKTISKAKGQPRRPQVYTLPPSREEMTKNQVSLTCLVKGFYPSDIAVEWESNG QPENNYKTTPPVLDSDGSFFLYSKLTVDKSRWQQGNVFSCSVMHEALHNHYT QESLSLSPG |
| 7 | Kappa light chain constant region | Constant region | RTVAAPSVFIFPPSDEQLKSGTASVVCLLNNFYPREAKVQWKVDNALQSGNSQ ESVTEQDSKDSTYSLSSTLTLSKADYEKHKVYACEVTHQGLSSPVTKSFNRGE C |
| 8 | Lamba light chain constant region | Constant region | GQPKAAPSVTLFPPSSEELQANKATLVCLISDFYPGAVTVAWKADSSPVKAGV ETTTPSKQSNNKYAASSYLSLTPEQWKSHRSYSCQVTHEGSTVEKTVAPTECS |
| 9 | IgG1-CD134-003 | Full heavy chain | EQLKETGGGLVQPGGSLTLSCKASGFDFSSGYMSWVRQAPGKGLEWIGYIDP VFGSTYYASWVNGRFAISSHNAQNTLYLQLNSLTAADTATYFCARDLRAFYSG WGGINLWGPGTLVTVSSASTKGPSVFPLAPSSKSTSGGTAALGCLVKDYFPEP VTVSWNSGALTSGVHTFPAVLQSSGLYSLSSVVTVPSSSLGTQTYICNVNHKPS NTKVDKRVEPKSCDKTHTCPPCPAPELLGGPSVFLFPPKPKDTLMISRTPEVTC VVVDVSHEDPEVKFNWYVDGVEVHNAKTKPREEQYNSTYRVVSVLTVLHQD WLNGKEYKCKVSNKALPAPIEKTISKAKGQPREPQVYTLPPSREEMTKNQVSL TCLVKGFYPSDIAVEWESNGQPENNYKTTPPVLDSDGSFFLYSKLTVDKSRWQ QGNVFSCSVMHEALHNHYTQKSLSLSPG |
| 10 | IgG1-CD134-003 | Full light chain | AAVLTQTPSPVSAAVGGTVTIKCQSSQIVVNNNFLSWYQQKPGQPPKLLIYDA SNLASGVPDRFSGSGSGTQFTLTISGVQSDDAATYYCLGGYDDDAENAFGGG TEVVVQRTVAAPSVFIFPPSDEQLKSGTASVVCLLNNFYPREAKVQWKVDNAL QSGNSQESVTEQDSKDSTYSLSSTLTLSKADYEKHKVYACEVTHQGLSSPVTKS FNRGEC |
| 11 | IgG1-CD134-003 | VH | EQLKETGGGLVQPGGSLTLSCKASGFDFSSGYMSWVRQAPGKGLEWIGYIDP VFGSTYYASWVNGRFAISSHNAQNTLYLQLNSLTAADTATYFCARDLRAFYSG WGGINLWGPGTLVTVSS |
| 12 | IgG1-CD134-003 | VH_CDR1 | GFDFSSGY |
| 13 | IgG1-CD134-003 | VH_CDR2 | IDPVFGST |
| 14 | IgG1-CD134-003 | VH_CDR3 | ARDLRAFYSGWGGINL |

TABLE 3-continued

Sequence List

| SEQ ID NO: | Identifier | Domain | Amino acid sequence |
|---|---|---|---|
| 15 | IgG1-CD134-003 | VL | AAVLTQTPSPVSAAVGGTVTIKCQSSQIVVNNNFLSWYQQKPGQPPKLLIYDA SNLASGVPDRFSGSGSGTQFTLTISGVQSDDAATYYCLGGYDDDAENAFGGG TEVVVQ |
| 16 | IgG1-CD134-003 | VL_CDR1 | QIVVNNNF |
|  | IgG1-CD134-003 | VL_CDR2 | DAS |
| 17 | IgG1-CD134-003 | VL_CDR3 | LGGYDDDAENA |
| 18 | IgG1-CD134-003-HC6LC2 P329R-E345R | Full heavy chain | EVQLLESGGGLVQPGGSLRLSCKASGFDFSSGYMSWVRQAPGKGLEWIGYID PVFGSTYYASWVNGRFTISRDNSKNTLYLQMNSLRAEDTATYYCARDLRAFYS GWGGINLWGQGTLVTVSSASTKGPSVFPLAPSSKSTSGGTAALGCLVKDYFPE PVTVSWNSGALTSGVHTFPAVLQSSGLYSLSSVVTVPSSSLGTQTYICNVNHKP SNTKVDKRVEPKSCDKTHTCPPCPAPELLGGPSVFLFPPKPKDTLMISRTPEVT CVVVDVSHEDPEVKFNWYVDGVEVHNAKTKPREEQYNSTYRVVSVLTVLHQ DWLNGKEYKCKVSNKALRAPIEKTISKAKGQPRRPQVYTLPPSREEMTKNQVS LTCLVKGFYPSDIAVEWESNGQPENNYKTTPPVLDSDGSFFLYSKLTVDKSRW QQGNVFSCSVMHEALHNHYTQKSLSLSPG |
| 19 | IgG1-CD134-003-HC6LC2 | Full light chain | AAVLTQSPSSLSASVGDRVTITCQSSQIVVNNNFLSWYQQKPGKAPKLLIYDAS NLASGVPDRFSGSGSGTDFTFTISSLQPEDIATYYCLGGYDDDAENAFGGGTKV EIKRTVAAPSVFIFPPSDEQLKSGTASVVCLLNNFYPREAKVQWKVDNALQSG NSQESVTEQDSKDSTYSLSSTLTLSKADYEKHKVYACEVTHQGLSSPVTKSFNR GEC |
| 20 | IgG1-CD134-003-HC6LC2 | VH | EVQLLESGGGLVQPGGSLRLSCKASGFDFSSGYMSWVRQAPGKGLEWIGYID PVFGSTYYASWVNGRFTISRDNSKNTLYLQMNSLRAEDTATYYCARDLRAFYS GWGGINLWGQGTLVTVSS |
| 12 | IgG1-CD134-003-HC6LC2 | VH_CDR1 | GFDFSSGY |
| 13 | IgG1-CD134-003-HC6LC2 | VH_CDR2 | IDPVFGST |
| 14 | IgG1-CD134-003-HC6LC2 | VH_CDR3 | ARDLRAFYSGWGGINL |
| 21 | IgG1-CD134-003-HC6LC2 | VL | AAVLTQSPSSLSASVGDRVTITCQSSQIVVNNNFLSWYQQKPGKAPKLLIYDAS NLASGVPDRFSGSGSGTDFTFTISSLQPEDIATYYCLGGYDDDAENAFGGGTKV EIK |
| 16 | IgG1-CD134-003-HC6LC2 | VL_CDR1 | QIVVNNNF |
|  | IgG1-CD134-003-HC6LC2 | VL_CDR2 | DAS |
| 17 | IgG1-CD134-003-HC6LC2 | VL_CDR3 | LGGYDDDAENA |

TABLE 3-continued

Sequence List

| SEQ ID NO: | Identifier | Domain | Amino acid sequence |
|---|---|---|---|
| 22 | IgG1-CD134-007 | Full heavy chain | QSVEESGGRLVTPGTFLTLTCTVSGFSLSSYAMNWVRQSPGKGLEWIGIIYSDD IAYYASWAKGRFTISKTSTTVTLKMTSLTVADTATYFCARGDGDRSIWSFDLW GPGTLVTVSSASTKGPSVFPLAPSSKSTSGGTAALGCLVKDYFPEPVTVSWNSG ALTSGVHTFPAVLQSSGLYSLSSVVTVPSSSLGTQTYICNVNHKPSNTKVDKRV EPKSCDKTHTCPPCPAPELLGGPSVFLFPPKPKDTLMISRTPEVTCVVVDVSHE DPEVKFNWYVDGVEVHNAKTKPREEQYNSTYRVVSVLTVLHQDWLNGKEYKC KVSNKALPAPIEKTISKAKGQPREPQVYTLPPSREEMTKNQVSLTCLVKGFYP SDIAVEWESNGQPENNYKTTPPVLDSDGSFFLYSKLTVDKSRWQQGNVFSCS VMHEALHNHYTQKSLSLSPG |
| 23 | IgG1-CD134-007 | Full light chain | AQVLTQTPSPVSAAVGGTVTISCQSSESVWNNNWLAWYQQKPGQPPNLLIY EASTLASGVSSRFKGSGSGTQFTLTVSEVQSDDAATYYCQGGYYDSSPIWTFG GGTEVVVKRTVAAPSVFIFPPSDEQLKSGTASVVCLLNNFYPREAKVQWKVDN ALQSGNSQESVTEQDSKDSTYSLSSTLTLSKADYEKHKVYACEVTHQGLSSPVT KSFNRGEC |
| 24 | IgG1-CD134-007 | VH | QSVEESGGRLVTPGTFLTLTCTVSGFSLSSYAMNWVRQSPGKGLEWIGIIYSDD IAYYASWAKGRFTISKTSTTVTLKMTSLTVADTATYFCARGDGDRSIWSFDLW GPGTLVTVSS |
| 25 | IgG1-CD134-007 | VH_CDR1 | GFSLSSYA |
| 26 | IgG1-CD134-007 | VH_CDR2 | IYSDDIA |
| 27 | IgG1-CD134-007 | VH_CDR3 | ARGDGDRSIWSFDL |
| 28 | IgG1-CD134-007 | VL | AQVLTQTPSPVSAAVGGTVTISCQSSESVWNNNWLAWYQQKPGQPPNLLIYE ASTLASGVSSRFKGSGSGTQFTLTVSEVQSDDAATYYCQGGYYDSSPIWTFG GGTEVVVK |
| 29 | IgG1-CD134-007 | VL_CDR1 | ESVWNNNW |
|  | IgG1-CD134-007 | VL_CDR2 | EAS |
| 30 | IgG1-CD134-007 | VL_CDR3 | QGGYYDSSPIWT |
| 31 | IgG1-CD134-012 | Full heavy chain | QSLEESGGRLVTPGTPLTLICTVSGIDLSSGAMGWVRQAPGKGLEYIGYIYTGS GTTSYASWVNGRFTISMTSTTVDLKITSPTTEDTATYFCARDAASSYWGHFTL WGQGTLVTVSSASTKGPSVFPLAPSSKSTSGGTAALGCLVKDYFPEPVTVSWN SGALTSGVHTFPAVLQSSGLYSLSSVVTVPSSSLGTQTYICNVNHKPSNTKVDK RVEPKSCDKTHTCPPCPAPELLGGPSVFLFPPKPKDTLMISRTPEVTCVVVDVS HEDPEVKFNWYVDGVEVHNAKTKPREEQYNSTYRVVSVLTVLHQDWLNGKE YKCKVSNKALPAPIEKTISKAKGQPREPQVYTLPPSREEMTKNQVSLTCLVKGF YPSDIAVEWESNGQPENNYKTTPPVLDSDGSFFLYSKLTVDKSRWQQGNVFS CSVMHEALHNHYTQKSLSLSPG |
| 32 | IgG1-CD134-012 | Full light chain | DIVMTQTPASVEAAVGGTVTIKCQASENIYSSLAWYQQKPGQPPKLLIYRTSTL ASGVPSRFKGSGSGTQFTLTISDLESDDAATYYCQSYYHNSGGGYDYGFGGGT EVVAKRTVAAPSVFIFPPSDEQLKSGTASVVCLLNNFYPREAKVQWKVDNALQ SGNSQESVTEQDSKDSTYSLSSTLTLSKADYEKHKVYACEVTHQGLSSPVTKSF NRGEC |
| 33 | IgG1-CD134-012 | VH | QSLEESGGRLVTPGTPLTLICTVSGIDLSSGAMGWVRQAPGKGLEYIGYIYTGS GTTSYASWVNGRFTISMTSTTVDLKITSPTTEDTATYFCARDAASSYWGHFTL WGQGTLVTVSS |
| 34 | IgG1-CD134-012 | VH_CDR1 | GIDLSSGA |

TABLE 3-continued

Sequence List

| SEQ ID NO: | Identifier | Domain | Amino acid sequence |
|---|---|---|---|
| 35 | IgG1-CD134-012 | VH_CDR2 | YTGSGTT |
| 36 | IgG1-CD134-012 | VH_CDR3 | ARDAASSYWGHFTL |
| 37 | IgG1-CD134-012 | VL | DIVMTQTPASVEAAVGGTVTIKCQASENIYSSLAWYQQKPGQPPKLLIYRTSTLASGVPSRFKGSGSGTQFTLTISDLESDDAATYYCQSYYHNSGGGYDYGFGGGTEVVAK |
| 38 | IgG1-CD134-012 | VL_CDR1 | ENIYSS |
|  | IgG1-CD134-012 | VL_CDR2 | RTS |
| 39 | IgG1-CD134-012 | VL_CDR3 | QSYYHNSGGGYDYG |
| 40 | IgG1-CD134-11D4 | Full heavy chain | EVQLVESGGGLVQPGGSLRLSCAASGFTFSSYSMNWVRQAPGKGLEWVSYISSSSSTIDYADSVKGRFTISRDNAKNSLYLQMNSLRDEDTAVYYCARESGWYLFDYWGQGTLVTVSSASTKGPSVFPLAPSSKSTSGGTAALGCLVKDYFPEPVTVSWNSGALTSGVHTFPAVLQSSGLYSLSSVVTVPSSSLGTQTYICNVNHKPSNTKVDKRVEPKSCDKTHTCPPCPAPELLGGPSVFLFPPKPKDTLMISRTPEVTCVVVDVSHEDPEVKFNWYVDGVEVHNAKTKPREEQYNSTYRVVSVLTVLHQDWLNGKEYKCKVSNKALPAPIEKTISKAKGQPREPQVYTLPPSREEMTKNQVSLTCLVKGFYPSDIAVEWESNGQPENNYKTTPPVLDSDGSFFLYSKLTVDKSRWQQGNVFSCSVMHEALHNHYTQKSLSLSPG |
| 41 | IgG1-CD134-11D4 | Full light chain | DIQMTQSPSSLSASVGDRVTITCRASQGISSWLAWYQQKPEKAPKSLIYAASSLQSGVPSRFSGSGSGTDFTLTISSLQPEDFATYYCQQYNSYPPTFGGGTKVEIKRTVAAPSVFIFPPSDEQLKSGTASVVCLLNNFYPREAKVQWKVDNALQSGNSQESVTEQDSKDSTYSLSSTLTLSKADYEKHKVYACEVTHQGLSSPVTKSFNRGEC |
| 42 | IgG1-CD134-11D4 | VH | EVQLVESGGGLVQPGGSLRLSCAASGFTFSSYSMNWVRQAPGKGLEWVSYISSSSSTIDYADSVKGRFTISRDNAKNSLYLQMNSLRDEDTAVYYCARESGWYLFDYWGQGTLVTVSS |
| 43 | IgG1-CD134-11D4 | VH_CDR1 | GFTFSSYS |
| 44 | IgG1-CD134-11D4 | VH_CDR2 | ISSSSSTI |
| 45 | IgG1-CD134-11D4 | VH_CDR3 | ARESGWYLFDY |
| 46 | IgG1-CD134-11D4 | VL | DIQMTQSPSSLSASVGDRVTITCRASQGISSWLAWYQQKPEKAPKSLIYAASSLQSGVPSRFSGSGSGTDFTLTISSLQPEDFATYYCQQYNSYPPTFGGGTKVEIK |
| 47 | IgG1-CD134-11D4 | VL_CDR1 | QGISSW |
|  | IgG1-CD134-11D4 | VL_CDR2 | AAS |
| 48 | IgG1-CD134-11D4 | VL_CDR3 | QQYNSYPPT |

TABLE 3-continued

Sequence List

| SEQ ID NO: | Identifier | Domain | Amino acid sequence |
|---|---|---|---|
| 49 | IgG2 constant region | Constant region | ASTKGPSVFPLAPCSRSTSESTAALGCLVKDYFPEPVTVSWNSGALTSGVHTFP AVLQSSGLYSLSSVVTVPSSNFGTQTYTCNVDHKPSNTKVDKTVERKCCVECPP CPAPPVAGPSVFLFPPKPKDTLMISRTPEVTCVVVDVSHEDPEVQFNWYVDG VEVHNAKTKPREEQFNSTFRVVSVLTVVHQDWLNGKEYKCKVSNKGLPAPIEK TISKTKGQPREPQVYTLPPSREEMTKNQVSLTCLVKGFYPSDIAVEWESNGQP ENNYKTTPPMLDSDGSFFLYSKLTVDKSRWQQGNVFSCSVMHEALHNHYTQ KSLSLSPG |
| 50 | IgG2s-E345R constant region | Constant region | ASTKGPSVFPLAPCSRSTSESTAALGCLVKDYFPEPVTVSWNSGALTSGVHTFP AVLQSSGLYSLSSVVTVPSSNFGTQTYTCNVDHKPSNTKVDKTVERKCCVECPP CPAPPAAASSVFLFPPKPKDTLMISRTPEVTCVVVDVSAEDPEVQFNWYVDG VEVHNAKTKPREEQFNSTFRVVSVLTVVHQDWLNGKEYKCKVSNKGLPSSIEK TISKTKGQPRRPQVYTLPPSREEMTKNQVSLTCLVKGFYPSDIAVEWESNGQP ENNYKTTPPMLDSDGSFFLYSKLTVDKSRWQQGNVFSCSVMHEALHNHYTQ KSLSLSPG |
| 51 | Cynomolgus monkey OX40 | Full-length protein | MCVGARRLGRGPCAALLLLGLGLSTTAKLHCVGDTYPSNDRCCQECRPGNG MVSRCNRSQNTVCRPCGPGFYNDVVSAKPCKACTWCNLRSGSERKQPCTAT QDTVCRCRAGTQPLDSYKPGVDCAPCPPGHFSPGDNQACKPWTNCTLAGKH TLQPASNSSDAICEDRDPPPTQPQETQGPPARPTTVQPTEAWPRTSQRPSTR PVEVPRGPAVAAILGLGLALGLLGPLAMLLALLLLRRDQRLPPDAPKAPGGGSF RTPIQEEQADAHSALAKI |
| 52 | Human OX40 | Full-length protein | MCVGARRLGRGPCAALLLLGLGLSTVTGLHCVGDTYPSNDRCCHECRPGNG MVSRCSRSQNTVCRPCGPGFYNDVVSSKPCKPCTWCNLRSGSERKQLCTATQ DTVCRCRAGTQPLDSYKPGVDCAPCPPGHFSPGDNQACKPWTNCTLAGKHT LQPASNSSDAICEDRDPPATQPQETQGPPARPITVQPTEAWPRTSQGPSTRP VEVPGGRAVAAILGLGLVLGLLGPLAILLALYLLRRDQRLPPDAHKPPGGGSFRT PIQEEQADAHSTLAKI |
| 53 | Mouse OX40; Ox40mm | Full-length protein | MYVWVQQPTALLLLALTLGVTARRLNCVKHTYPSGHKCCRECQPGHGMVSR CDHTRDTLCHPCETGFYNEAVNYDTCKQCTQCNHRSGSELKQNCTPTQDTVC RCRPGTQPRQDSGYKLGVDCVPCPPGHFSPGNNQACKPWTNCTLSGKQTRH PASDSLDAVCEDRSLLATLLWETQRPTFRPTTVQSTTVWPRTSELPSPPTLVTP EGPAFAVLLGLGLGLLAPLTVLLALYLLRKAWRLPNTPKPCWGNSFRTPIQEEH TDAHFTLAKI |
| 54 | Human OX40 with Mouse CRD1; OX40-CRD1mm | | MCVGARRLGRGPCAALLLLGLGLSTVTGLNCVKHTYPSGHKCCRECQPGHG MVSRCDHTRDTLCHPCETGFYNDVVSSKPCKPCTWCNLRSGSERKQLCTATQ DTVCRCRAGTQPLDSYKPGVDCAPCPPGHFSPGDNQACKPWTNCTLAGKHT LQPASNSSDAICEDRDPPATQPQETQGPPARPITVQPTEAWPRTSQGPSTRP VEVPGGRAVAAILGLGLVLGLLGPLAILLALYLLRRDQRLPPDAHKPPGGGSFRT PIQEEQADAHSTLAKI |
| 55 | Human OX40 with Mouse CRD2; OX40-CRD2mm | | MCVGARRLGRGPCAALLLLGLGLSTVTGLHCVGDTYPSNDRCCHECRPGNG MVSRCSRSQNTVCRPCETGFYNEAVNYDTCKQCTQCNHRSGSELKQNCTPT QDTVCRCRAGTQPLDSYKPGVDCAPCPPGHFSPGDNQACKPWTNCTLAGKH TLQPASNSSDAICEDRDPPATQPQETQGPPARPITVQPTEAWPRTSQGPSTRP VEVPGGRAVAAILGLGLVLGLLGPLAILLALYLLRRDQRLPPDAHKPPGGGSFRT PIQEEQADAHSTLAKI |
| 56 | Human OX40 with Mouse CRD3; OX40-CRD3mm | | MCVGARRLGRGPCAALLLLGLGLSTVTGLHCVGDTYPSNDRCCHECRPGNG MVSRCSRSQNTVCRPCGPGFYNDVVSSKPCKPCTWCNLRSGSERKQLCTATQ DTVCRCRPGTQPRQDSGYKLGVDCVPCPPGHFSPGDNQACKPWTNCTLAGK HTLQPASNSSDAICEDRDPPATQPQETQGPPARPITVQPTEAWPRTSQGPST RPVEVPGGRAVAAILGLGLVLGLLGPLAILLALYLLRRDQRLPPDAHKPPGGGS FRTPIQEEQADAHSTLAKI |
| 57 | Human OX40 with Mouse CRD4; OX40-CRD4mm | | MCVGARRLGRGPCAALLLLGLGLSTVTGLHCVGDTYPSNDRCCHECRPGNG MVSRCSRSQNTVCRPCGPGFYNDVVSSKPCKPCTWCNLRSGSERKQLCTATQ DTVCRCRAGTQPLDSYKPGVDCAPCPPGHFSPGNNQACKPWTNCTLSGKQT RHPASDSLDAVCEDRDPPATQPQETQGPPARPITVQPTEAWPRTSQGPSTRP VEVPGGRAVAAILGLGLVLGLLGPLAILLALYLLRRDQRLPPDAHKPPGGGSFRT PIQEEQADAHSTLAKI |
| 58 | Hinge, CH2, CH3 region of human IgG1m(f)-P329R-E345R | Fc region (including hinge) | EPKSCDKTHTCPPCPAPELLGGPSVFLFPPKPKDTLMISRTPEVTCVVVDVSHE DPEVKFNWYVDGVEVHNAKTKPREEQYNSTYRVVSVLTVLHQDWLNGKEYK CKVSNKALRAPI EKTISKAKGQPRRPQVYTLPPSREEMTKNQVSLTCLVKGFYP SDIAVEWESNGQPENNYKTTPPVLDSDGSFFLYSKLTVDKSRWQQGNVFSCS VMHEALHNHYTQKSLSLSPG |

TABLE 3-continued

Sequence List

| SEQ ID NO: | Identifier | Domain | Amino acid sequence |
|---|---|---|---|
| 59 | Hinge, CH2, CH3 region of human IgG1m(a)-P329R-E345R | Fc region (including hinge) | EPKSCDKTHTCPPCPAPELLGGPSVFLFPPKPKDTLMISRTPEVTCVVVDVSHE DPEVKFNWYVDGVEVHNAKTKPREEQYNSTYRVVSVLTVLHQDWLNGKEYK CKVSNKALRAPI EKTISKAKGQPRRPQVYTLPPSRDELTKNQVSLTCLVKGFYPS DIAVEWESNGQPENNYKTTPPVLDSDGSFFLYSKLTVDKSRWQQGNVFSCSV MHEALHNHYTQKSLSLSPG |
| 60 | Hinge, CH2, CH3 region of human IgG1m(x)-P329R-E345R | Fc region (including hinge) | EPKSCDKTHTCPPCPAPELLGGPSVFLFPPKPKDTLMISRTPEVTCVVVDVSH EDPEVKFNWYVDGVEVHNAKTKPREEQYNSTYRVVSVLTVLHQDWLNGKEYK CKVSNKALRAPI EKTISKAKGQPRRPQVYTLPPSREEMTKNQVSLTCLVKGFYP SDIAVEWESNGQPENNYKTTPPVLDSDGSFFLYSKLTVDKSRWQQGNVFSCS VMHEGLHNHYTQKSLSLSPG |
| 61 | Hinge, CH2, CH3 region of human IgG1m(z)-P329R-E345R | Fc region (including hinge) | EPKSCDKTHTCPPCPAPELLGGPSVFLFPPKPKDTLMISRTPEVTCVVVDVSH EDPEVKFNWYVDGVEVHNAKTKPREEQYNSTYRVVSVLTVLHQDWLNGKEYK CKVSNKALRAPI EKTISKAKGQPRRPQVYTLPPSREEMTKNQVSLTCLVKGFYP SDIAVEWESNGQPENNYKTTPPVLDSDGSFFLYSKLTVDKSRWQQGNVFSCS VMHEALHNHYTQKSLSLSPG |
| 62 | IgG1m(f)-L234F-L235E-D265A-F405L | Constant region | ASTKGPSVFPLAPSSKSTSGGTAALGCLVKDYFPEPVTVSWNSGALTSGVHTFP AVLQSSGLYSLSSVVTVPSSSLGTQTYICNVNHKPSNTKVDKRVEPKSCDKTHT CPPCPAPEFEGGPSVFLFPPKPKDTLMISRTPEVTCVVVDVSHEDPEVKFNWY VDGVEVHNAKTKPREEQYNSTYRVVSVLTVLHQDWLNGKEYKCKVSNKALPA PIEKTISKAKGQPREPQVYTLPPSREEMTKNQVSLTCLVKGFYPSDIAVEWESN GQPENNYKTTPPVLDSDGSFLLYSKLTVDKSRWQQGNVFSCSVMHEALHNH YTQKSLSLSPG |
| 63 | IgG1-CD134-003-RR-K409R | Constant region | ASTKGPSVFPLAPSSKSTSGGTAALGCLVKDYFPEPVTVSWNSGALTSGVHTFP AVLQSSGLYSLSSVVTVPSSSLGTQTYICNVNHKPSNTKVDKRVEPKSCDKTHT CPPCPAPELLGGPSVFLFPPKPKDTLMISRTPEVTCVVVDVSHEDPEVKFNWY VDGVEVHNAKTKPREEQYNSTYRVVSVLTVLHQDWLNGKEYKCKVSNKALRA PIEKTISKAKGQPRRPQVYTLPPSREEMTKNQVSLTCLVKGFYPSDIAVEWESN GQPENNYKTTPPVLDSDGSFFLYSRLTVDKSRWQQGNVFSCSVMHEALHNH YTQKSLSLSPG |
| 64 | VH CD52-CAMPATH-1H | VH | QVQLQESGPGLVRPSQTLSLTCTVSGFTFTDFYMNWVRQPPGRGLEWIGFIR DKAKGYTTEYNPSVKGRVTMLVDTSKNQFSLRLSSVTAADTAVYYCAREGHTA APFDYWGQGSLVTVSS |
| 65 | VH CD52-CAMPATH-1H CDR1 | VH_CDR1 | GFTFTDFY |
| 66 | VH CD52-CAMPATH-1H CDR2 | VH_CDR2 | IRDKAKGYTT |
| 67 | VH CD52-CAMPATH-1H CDR3 | VH_CDR3 | AREGHTAAPFDY |
| 68 | VL CD52-CAMPATH-1H | VL | DIQMTQSPSSLSASVGDRVTITCKASQNIDKYLNWYQQKPGKAPKLLIYNTNN LQTGVPSRFSGSGSGTDFTFTISSLQPEDIATYYCLQHISRPRTFGQGTKVEIK |
| 69 | VL CD52-CAMPATH-1H CDR1 | VL_CDR1 | QNIDKY |
|  | VL CD52-CAMPATH-1H CDR2 | VL_CDR2 | NTN |
| 70 | VL CD52-CAMPATH-1H CDR3 | VL_CDR3 | LQHISRPRT |
| 71 | VH gp120-b12 | VH | QVQLVQSGAEVKKPGASVKVSCQASGYRFSNFVIHWVRQAPGQRFEWMG WINPYNGNKEFSAKFQDRVTFTADTSANTAYMELRSLRSADTAVYYCARVGP YSWDDSPQDNYYMDVWGKGTTVIVSS |

TABLE 3-continued

Sequence List

| SEQ ID NO: | Identifier | Domain | Amino acid sequence |
|---|---|---|---|
| 72 | VH gp120-b12 CDR1 | VH_CDR1 | GYRFSNFV |
| 73 | VH gp120-b12 CDR2 | VH_CDR2 | INPYNGNK |
| 74 | VH gp120-b12 CDR3 | VH_CDR3 | ARVGPYSWDDSPQDNYYMDV |
| 75 | VL gp120-b12 | VL | EIVLTQSPGTLSLSPGERATFSCRSSHSIRSRRVAWYQHKPGQAPRLVIHGVSN RASGISDRFSGSGSGTDFTLTITRVEPEDFALYYCQVYGASSYTFGQGTKLERK |
| 76 | VL gp120-b12 CDR1 | VL_CDR1 | HSIRSRR |
|  | VL gp120-b12 CDR2 | VL_CDR2 | GVS |
| 77 | VL gp120-b12-CDR3 | VL_CDR3 | QVYGASSYT |
| 78 | IgG1-P329R-E345R-F405L | Constant region | ASTKGPSVFPLAPSSKSTSGGTAALGCLVKDYFPEPVTVSWNSGALTSGVHTFP AVLQSSGLYSLSSVVTVPSSSLGTQTYICNVNHKPSNTKVDKRVEPKSCDKTHT CPPCPAPELLGGPSVFLFPPKPKDTLMISRTPEVTCVVVDVSHEDPEVKFNWY VDGVEVHNAKTKPREEQYNSTYRVVSVLTVLHQDWLNGKEYKCKVSNKALRAP IEKTISKAKGQPRRPQVYTLPPSREEMTKNQVSLTCLVKGFYPSDIAVEWESN GQPENNYKTTPPVLDSDGSFLLYSKLTVDKSRWQQGNVFSCSVMHEALHNH YTQKSLSLSPG |

EXAMPLES

Example 1: Generation of Anti-Human OX40 Antibodies and Fc Variants Thereof

As described in WO2016/110584A1, for the generation of anti-human OX40 antibodies, nine rabbits were immunized with recombinant human OX40 (CD134) fused to the Fc portion of human IgG1 (Adipogen, cat. no. AG-40B-0014; MAB Discovery GmbH). Blood samples were collected at four different time points after a series of immunizations and were enriched for B cells. Individual B cells were sorted by flow cytometry and single clones were cultured and expanded at 37° C. for seven days. After seven days, culture supernatants were collected to assess production of human OX40-specific antibodies and B cells were frozen and stored at −80° C. until further use.

Identified unique sequences of OX40-binding VH and Vi combinations were transiently co-expressed in HEK293 cells to generate rabbit-human chimeric antibodies. Based on the results of the screening assays to assess the antibodies' capacity to bind human OX40 and the agonistic activity, 30 chimeric antibodies were selected for further testing. To this end, the VH and Vi regions of these antibodies were gene synthesized and cloned upstream of human IgG1 constant regions, after which antibodies were produced in HEK293 cells and purified. The antibodies were first tested for binding to human and cynomolgus monkey OX40 by flow cytometry. A selection of these antibodies was produced in an IgG1-P329R-E345R-K409R (IgG1-RR-K409R) backbone to assess agonistic activity using an OX40 bioluminescent reporter assay (Promega) and PBMC proliferation assays. Based on the results of this second round of screening, three chimeric antibody clones (IgG1-CD134-003-P329R-E345R-K409R [IgG1-CD134-003-RR-K409R], IgG1-CD134-007-RR-K409R, and IgG1-CD134-012-RR-K409R) were selected as most promising candidates, two of which were subsequently humanized (IgG1-CD134-003-RR-K409R and IgG1-CD134-012-RR-K409R). For humanization, a combination of CDR grafting and amino acid point mutations was used (Abzena), and five humanized $V_L$ chains (LC1 to LC5) and six humanized $V_H$ chains (HC1 to HC6) were designed per clone. DNA plasmids encoding all combinations of $V_H$ and $V_L$ chains (a total of 30 pairings per clone) and encoding an IgG1 constant region with the RR mutations in the heavy chain were transfected into Expi293F cells for antibody production. Supernatants of Expi293F cell cultures containing individual humanized OX40 antibody variants were used to assess antibody binding affinity to human and cynomolgus monkey OX40 by biolayer interferometry, and to activated primary human T cells (derived from five healthy donors) by flow cytometry.

As binding characteristics of all humanized antibody variants derived from IgG1-CD134-003-RR and IgG1-CD134-012-RR were quite similar to that of the parental antibodies, a further selection of 24 antibodies was made based on highest sequence similarity to the closest human homologue and purified for comparison of their ability to bind activated primary human T cells, to induce OX40 signaling, and to enhance T-cell proliferation. One humanized OX40-binding antibody (IgG1-CD134-003-HC6LC2-RR) was selected and further characterized in experiments described in the following Examples, alongside chimeric antibodies IgG1-CD134-003, IgG1-CD134-007, and IgG1-CD134-012 with different mutations in the Fc domain.

Sequences of the anti-human OX40 antibodies used herein have been obtained as follows: IgG1-CD134-Hu106 (WO2020/030570A1, SEQ ID Nos 5 and 11), IgG1-CD134-A4453 (WO2019/223733, SEQ ID Nos 26 and 28), IgG1-CD134-MEDI0562 (INN 10420, tavolimab), IgG1-CD134-ABBV368 (INN 11242, revdofilimab), IgG1-CD134-IBI101 (INN 11200, cudarolimab), IgG1-CD134-GBR830 (INN 11273, telazorlimab), IgG1-CD134-INCAGN1949 (U.S. Pat. No. 10,259,882B2, SEQ ID Nos 61 and 20), IgG1-CD134-SF2 and IgG2-CD134-SF2 (US2014/0377284A1, VL1VH2, SEQ ID Nos 78 and 80), IgG1-CD134-h3C8 (WO2016/164480A1, SEQ ID Nos 118 and 119), IgG1-CD134-RG7888 (INN 10272, vonlerolizumab), and IgG1-CD134-49B4 (WO2019/086497A2, SEQ ID Nos 40 and 41). A human IgG1 antibody comprising the $V_H/V_L$ of b12, an HIV1 gp120-specific antibody, was used as a negative control (Barbas et al., J Mol Biol. 1993 Apr. 5; 230 (3): 812-2).

Example 2: Binding Affinities of Anti-Human OX40 Antibodies for Recombinant Human and Cynomolgus Monkey OX40

The binding affinity of anti-human OX40 antibodies IgG1-CD134-003, IgG1-CD134-003-HC6LC2-P329R-E345R (IgG1-CD134-003-HC6LC2-RR), IgG1-CD134-007, IgG1-CD134-012, and of 12 anti-human OX40 IgG1 antibodies for recombinant human and cynomolgus monkey OX40 protein was determined using label-free biolayer interferometry on an Octet HTX instrument (Sartorius).

Experiments were carried out while shaking at 1,000 RPM at 30° C. To determine the affinity of the OX40 antibodies for human and cynomolgus monkey OX40, Anti-Human IgG Fc Capture (AHC) biosensors (Sartorius, cat. no. 18-5060) were pre-conditioned by exposure to 10 mM glycine (Sigma-Aldrich, cat. no. 15527) buffer pH 1.7 for 5 s, followed by neutralization in sample diluent (Sartorius, cat. no. 18-1104) for 5 s; both steps were repeated five times. Next, AHC sensors were loaded with antibody (1 µg/mL in Sample Diluent) for 600 s. After a baseline measurement in sample diluent (100 s), the association (200 s) and dissociation (1,000 s) of human OX40 (Acro Biosystems, cat. no. OX0-H5224), and cynomolgus monkey OX40 (Acro Biosystems, cat. no. OX0-C5220) was determined using a concentration range of 0.78 to 800 nM with 2-fold dilution steps.

The theoretical molecular masses of the antigens based on the amino acid sequences were used for calculations. For each antibody, a reference sensor was used which was incubated with Sample Diluent instead of antigen. AHC sensors were regenerated by exposure to 10 mM glycine buffer pH 1.7 for 5 s, followed by neutralization in Sample Diluent for 5 s; both steps were repeated twice. Subsequently sensors were loaded again with antibody for the next cycle of kinetic measurements.

Data were acquired using Data Acquisition Software v12.0 (Sartorius) and analyzed with Data Analysis Software v12.0 (Sartorius). Data traces were corrected per antibody by subtraction of the reference sensor. The Y-axis was aligned to the last 10 s of the baseline and Interstep Correction alignment to dissociation as well as Savitzky-Golay filtering were applied. Data traces with a response <0.05 nm were excluded from analysis. Data traces with a concentration higher than 100 nM were excluded from analysis for antibodies with $K_D$ values lower than 50 nM. The data was fitted with the 1:1 model using a window of interest for the association of 200 s and dissociation times set at 50 s, 200 s and 1,000 s. The dissociation time was chosen based upon $R^2$ value, visual inspection of the curve and at least 5% signal decay during the dissociation step.

Affinities for human OX40 could be accurately determined for fourteen OX40 antibodies (Table 4; all antibodies tested except IgG1-CD134-SF2, and IgG1-CD134-49B4-G236R-E345R-K439E [RRE] due to suboptimal curve fitting) with $K_D$ values mostly in the nanomolar range.

Affinities for cynomolgus monkey OX40 could be accurately determined for eight OX40 antibodies (IgG1-CD134-RG7888, IgG1-CD134-11D4, IgG1-CD134-003, IgG1-CD134-003-HC6LC2-RR, IgG1-CD134-007, IgG1-CD134-A4453, IgG1-CD134-MEDI0562, and IgG1-CD134-ABBV368). The measured $K_D$ values for these antibodies were mostly in the nanomolar range (Table 4).

Antibody IgG1-CD134-RG7888 had the highest affinity for human and cynomolgus monkey OX40. Antibodies IgG1-CD134-007, IgG1-CD134-012 and IgG1-CD134-003-HC6LC2-RR had a higher affinity for human OX40 than antibody IgG1-CD134-h3C8. No reliable interpretation of the binding characteristics to human and cynomolgus monkey OX40 could be determined for antibody IgG1-CD134-SF2.

TABLE 4

Binding affinities of anti-human OX40 antibodies to human and cynomolgus monkey OX40.

| Loading sample | Sample | $K_D$ (M) | $k_{on}$ (1/Ms) | $k_{dis}$ (1/s) |
| --- | --- | --- | --- | --- |
| IgG1-CD134-003 | Human OX40 | 1.1E−09 | 3.3E+05 | 3.5E−04 |
|  | Cyno OX40 | 3.5E−09 | 2.8E+05 | 9.6E−04 |
| IgG1-CD134-003-HC6LC2-P329R-E345R | Human OX40 | 3.4E−09 | 2.5E+05 | 8.6E−04 |
|  | Cyno OX40 | 2.7E−08 | 1.1E+05 | 2.9E−03 |
| IgG1-CD134-007 | Human OX40 | 2.0E−09 | 3.8E+05 | 7.5E−04 |
|  | Cyno OX40 | 7.1E−09 | 2.6E+05 | 1.8E−03 |
| IgG1-CD134-012 | Human OX40 | 1.1E−08 | 1.4E+05 | 1.6E−03 |
|  | Cyno OX40 | 1.8E−07* | 9.8E+04* | 1.8E−02* |
| IgG1-CD134-11D4 | Human OX40 | 2.4E−09 | 1.7E+05 | 4.1E−04 |
|  | Cyno OX40 | 2.8E−07 | 1.0E+05 | 2.8E−02 |
| IgG1-CD134-49B4-RRE | Human OX40 | 2.2E−07* | 1.7E+05* | 3.6E−02* |
|  | Cyno OX40 | 1.6E−07* | 1.5E+05* | 2.4E−02* |
| IgG1-CD134-A4453 | Human OX40 | 1.4E−08 | 1.6E+05 | 2.2E−03 |
|  | Cyno OX40 | 1.2E−08 | 1.5E+05 | 1.7E−03 |
| IgG1-CD134-ABBV368 | Human OX40 | 3.2E−08 | 5.1E+05 | 1.7E−02 |
|  | Cyno OX40 | 8.2E−08 | 2.3E+05 | 1.9E−02 |

TABLE 4-continued

Binding affinities of anti-human OX40 antibodies
to human and cynomolgus monkey OX40.

| Loading sample | Sample | $K_D$ (M) | $k_{on}$ (1/Ms) | $k_{dis}$ (1/s) |
| --- | --- | --- | --- | --- |
| IgG1-CD134-GBR830 | Human OX40 | 6.7E−08 | 1.2E+05 | 7.7E−03 |
|  | Cyno OX40 | ND | ND | ND |
| IgG1-CD134-h3C8 | Human OX40 | 1.5E−08 | 3.7E+05 | 5.6E−03 |
|  | Cyno OX40 | ND | ND | ND |
| IgG1-CD134-Hu106 | Human OX40 | 9.3E−09 | 2.6E+05 | 2.4E−03 |
|  | Cyno OX40 | 2.4E−07* | 1.2E+05* | 2.9E−02* |
| IgG1-CD134-IBI101 | Human OX40 | 5.3E−08 | 2.2E+05 | 1.2E−02 |
|  | Cyno OX40 | 4.0E−07* | 7.4E+04* | 3.0E−02* |
| IgG1-CD134-INCAGN1949 | Human OX40 | 1.6E−07 | 1.9E+05 | 3.2E−02 |
|  | Cyno OX40 | 2.3E−07* | 1.0E+05* | 2.4E−02* |
| IgG1-CD134-MEDI0562 | Human OX40 | 1.5E−08 | 1.5E+05 | 2.2E−03 |
|  | Cyno OX40 | 1.7E−08 | 1.1E+05 | 1.8E−03 |
| IgG1-CD134-RG7888 | Human OX40 | 2.3E−10 | 3.6E+05 | 8.4E−05 |
|  | Cyno OX40 | 6.1E−10 | 2.4E+05 | 1.4E−04 |
| IgG1-CD134-SF2 | Human OX40 | ND | ND | ND |
|  | Cyno OX40 | ND | ND | ND |

*binding was observed but $K_D$, $k_{on}$ and $k_{dis}$ are less reliable values due to suboptimal curve fitting, resulting in unreliable interpretation using the 1:1 model.
ND: not detectable.

Example 3: Assessment of Cross-Blocking of
Anti-Human OX40 IgG1 Antibodies Using
Biolayer Interferometry Antibody cross-block analysis of IgG1-CD134-003-HC6LC2-P329R-E345R (IgG1-CD134-003-HC6LC2-RR), IgG1-CD134-007, IgG1-CD134-012, and of 12 anti-human OX40 IgG1 antibodies was performed using biolayer interferometry on an Octet HTX instrument (Sartorius). Experiments were carried out while shaking at 1,000 RPM and at 30° C.

Amine Reactive $2^{nd}$ Generation (AR2G) biosensors (Sartorius, cat. no. 18-5092) were activated for 300 s with a solution of 20 mM EDC (N-(3-Dimethylaminopropyl)-N-ethylcarbodiimide hydrochloride; Sartorius, cat. no. 18-1033) and 10 mM s-NHS (N-hydroxysulfosuccinimide sodium salt; Sartorius, cat. no. 18-1067). Activated AR2G sensors were loaded with 20 µg/ml of the first antibody diluted in 10 mM Acetate pH 5.0 (Sartorius, cat. no. 18-1069) or pH 6.0 (Sartorius, cat. no. 18-1070) for 600 s and quenched with 1 M ethanolamine pH 8.5 (ETA; Sartorius, cat. no. 18-1071) for 300 s. After a baseline measurement in Sample Diluent (Sartorius, cat. no. 18-1104) for 50 s, the AR2G biosensors containing immobilized antibody were loaded for 300 s with human OX40 fused to a His-tag (100 nM diluted in Sample Diluent; Acro Biosystems, cat. no. OX0-H5224). The association (300 s) of a second antibody (10 µg/mL in Sample Diluent) was determined. Sensors were regenerated by three cycles of exposure to 10 mM Glycine (Sigma-Aldrich, cat. no. 15527) buffer pH 2.5 for 5 s followed by neutralization in Sample Diluent for 5 s.

Data were acquired using Data Acquisition Software v12.0 (Sartorius) and analyzed with Data Analysis HT Software v12.0 (Sartorius). Data traces were corrected by subtraction of a reference curve (Sample Diluent instead of second antibody) in order to correct for the dissociation of antigen from the immobilized first antibody. The Y-axis was aligned to the start of the association step and Savitzky-Golay filtering was applied. The corrected association responses of the second antibodies were plotted in a matrix format (Table 5). Responses ≥0.1 nm were considered non-blocking antibody pairs, while responses <0.1 were considered blocking antibody pairs. For some antibody pairs, the second antibody showed a decrease in signal compared to the buffer control. This was considered to be antibody displacement, i.e., the second antibody displacing the interaction between the first antibody and the antigen (Abdiche et al., PLOS ONE 2017 Jan. 6; 12 (1): e0169535).

The results of the cross-block analysis are summarized in Table 5. The data show that IgG1-CD134-003-HC6LC2-RR blocks binding of IgG1-CD134-003, IgG1-CD134-012, and of antibody IgG1-CD134-11D4 to human OX40, while it does not block binding of antibodies IgG1-CD134-MEDI0562, IgG1-CD134-SF2, IgG1-CD134-RG7888, IgG1-CD134-ABBV368, IgG1-CD134-INCAGN1949, IgG1-CD134-49B4-RRE, IgG1-CD134-Hu106, IgG1-CD134-h3C8, IgG1-CD134-GBR830, IgG1-CD134-IBI101, and IgG1-CD134-A4453. Subtle displacing behaviour was observed between IgG1-CD134-003-HC6LC2-RR and IgG1-CD134-007. IgG1-CD134-007 did not block binding of IgG1-CD134-012 to human OX40, but blocked binding of antibodies IgG1-CD134-ABBV368, IgG1-CD134-49B4-RRE, IgG1-CD134-Hu106, IgG1-CD134-h3C8, IgG1-CD134-GBR830, and IgG1-CD134-IBI101. From the tested antibodies, only IgG1-CD134-11D4 was blocked by IgG1-CD134-012.

Antibodies IgG1-CD134-ABBV368, IgG1-CD134-INCAGN1949, IgG1-CD134-49B4-RRE, IgG1-CD134-Hu106, IgG1-CD134-h3C8, IgG1-CD134-GBR830, and IgG1-CD134-IBI101 all cross-blocked each other. Similarly, antibodies IgG1-CD134-MEDI0562, IgG1-CD134-SF2, IgG1-CD134-RG7888, IgG1-CD134-ABBV368, and IgG1-CD134-INCAGN1949 all cross-blocked each other. Antibody IgG1-CD134-A4453 did not cross-block any of the other tested antibodies.

TABLE 5

Determination of antibody cross-block was performed using biolayer interferometry. Immobilized, first antibodies are shown vertically, and second antibodies are shown horizontally. Shown are corrected association responses of the second antibody. Responses <0.1 were considered blocking antibody pairs (indicated by grey boxes), and responses ≥0.1 nm were considered non-blocking antibody pairs (unmarked). For some antibody pairs, the second antibody showed a subtle decrease in signal compared to buffer control, illustrating that antibody displacement occurred (indicated by bold numbers). In some cases, the interaction between antibodies was manually adapted to non-blocking after visual inspection of the sensorgrams (indicated by underlined numbers).

|  | IgG1-CD134-MEDI0562 | IgG1-CD134-SF2 | IgG1-CD134-RG7888 | IgG1-CD134-ABBV368 | IgG1-CD134-INCAGN1949 | IgG1-CD134-49B4-RRE | IgG1-CD134-Hu106 | IgG1-CD134-h3C8 |
|---|---|---|---|---|---|---|---|---|
| IgG1-CD134-MEDI0562 | 0.00 | 0.01 | 0.02 | −0.01 | 0.01 | 0.20 | 0.31 | 0.31 |
| IgG1-CD134-SF2 | 0.01 | 0.01 | 0.01 | 0.04 | 0.02 | 0.03 | 0.03 | 0.18 |
| IgG1-CD134-RG7888 | 0.00 | 0.01 | 0.02 | 0.02 | 0.01 | 0.03 | 0.02 | 0.43 |
| IgG1-CD134-ABBV368 | −0.02 | 0.00 | 0.01 | −0.04 | −0.03 | −0.01 | −0.01 | −0.03 |
| IgG1-CD134-INCAGN1949 | 0.00 | 0.01 | 0.02 | 0.01 | 0.00 | 0.00 | 0.00 | 0.00 |
| IgG1-CD134-49B4-RRE | 0.15 | 0.00 | 0.02 | 0.00 | 0.00 | −0.01 | −0.01 | −0.01 |
| IgG1-CD134-Hu106 | 0.69 | 0.01 | 0.10 | 0.00 | −0.01 | 0.09 | 0.05 | 0.00 |
| IgG1-CD134-h3C8 | 0.54 | 0.23 | 0.41 | −0.03 | −0.02 | 0.00 | 0.01 | −0.03 |
| IgG1-CD134-GBR830 | 0.32 | 0.16 | 0.26 | 0.01 | 0.01 | 0.01 | 0.01 | 0.00 |
| IgG1-CD134-IBI101 | 0.28 | 0.04 | 0.23 | 0.01 | 0.01 | 0.03 | 0.01 | −0.01 |
| IgG1-CD134-007 | 1.14 | 0.78 | 0.47 | 0.00 | 0.55 | 0.04 | 0.05 | −0.01 |
| IgG1-CD134-003 | 1.39 | 0.92 | 0.66 | 1.27 | 1.39 | 0.93 | 1.06 | 0.39 |
| IgG1-CD134-003-HC6LC2-RR | 1.73 | 1.22 | 1.38 | 1.68 | 1.74 | 1.69 | 1.39 | 0.88 |
| IgG1-CD134-012 | 0.82 | 0.60 | 0.54 | 0.87 | 0.73 | 0.69 | 0.80 | 0.75 |
| IgG1-CD134-11D4 | 0.14 | 0.11 | 0.11 | 0.13 | 0.11 | 0.10 | 0.13 | 0.12 |
| IgG1-CD134-A4453 | 0.41 | 0.42 | 0.47 | 0.29 | 0.25 | 0.27 | 0.29 | 0.29 |

|  | IgG1-CD134-GBR830 | IgG1-CD134-IBI101 | IgG1-CD134-007 | IgG1-CD134-003 | IgG1-CD134-003-HC6LC2-RR | IgG1-CD134-012 | IgG1-CD134-11D4 | IgG1-CD134-A4453 |
|---|---|---|---|---|---|---|---|---|
| IgG1-CD134-MEDI0562 | 0.33 | 0.26 | 0.32 | 0.30 | 0.34 | 0.23 | 0.29 | 0.45 |
| IgG1-CD134-SF2 | 0.19 | 0.07 | 0.22 | 0.21 | 0.22 | 0.14 | 0.17 | 0.36 |
| IgG1-CD134-RG7888 | 0.61 | 0.31 | 0.64 | 0.66 | 0.65 | 0.42 | 0.48 | 1.04 |
| IgG1-CD134-ABBV368 | −0.01 | −0.02 | −0.05 | 0.72 | 0.85 | 0.51 | 0.62 | 0.80 |

TABLE 5-continued

Determination of antibody cross-block was performed using biolayer interferometry. Immobilized, first antibodies are shown vertically, and second antibodies are shown horizontally. Shown are corrected association responses of the second antibody. Responses <0.1 were considered blocking antibody pairs (indicated by grey boxes), and responses ≥0.1 nm were considered non-blocking antibody pairs (unmarked). For some antibody pairs, the second antibody showed a subtle decrease in signal compared to buffer control, illustrating that antibody displacement occurred (indicated by bold numbers). In some cases, the interaction between antibodies was manually adapted to non-blocking after visual inspection of the sensorgrams (indicated by underlined numbers).

| | | | | | | | | |
|---|---|---|---|---|---|---|---|---|
| IgG1-CD134-INCAGN1949 | 0.01 | 0.02 | 0.06 | 0.15 | 0.19 | 0.07 | 0.10 | 0.29 |
| IgG1-CD134-49B4-RRE | 0.00 | 0.00 | 0.00 | 0.20 | 0.25 | 0.10 | 0.13 | 0.20 |
| IgG1-CD134-Hu106 | 0.02 | −0.02 | 0.00 | 0.64 | 0.74 | 0.51 | 0.59 | 0.74 |
| IgG1-CD134-h3C8 | −0.02 | −0.03 | −0.02 | 0.46 | 0.50 | 0.35 | 0.42 | 0.51 |
| IgG1-CD134-GBR830 | 0.01 | 0.01 | 0.00 | 0.20 | 0.19 | 0.16 | 0.23 | 0.30 |
| IgG1-CD134-IBI101 | 0.02 | 0.01 | 0.00 | 0.23 | 0.34 | 0.28 | 0.35 | 0.39 |
| IgG1-CD134-007 | 0.07 | 0.02 | 0.01 | −0.07 | −0.04 | 0.82 | 0.98 | 1.18 |
| IgG1-CD134-003 | 0.97 | 0.74 | −0.02 | 0.02 | 0.04 | 0.00 | 0.09 | 1.51 |
| IgG1-CD134-003-HC6LC2-RR | 1.08 | 1.23 | −0.07 | −0.03 | 0.00 | 0.03 | 0.02 | 1.89 |
| IgG1-CD134-012 | 0.84 | 0.82 | 0.80 | −0.01 | −0.02 | 0.00 | 0.05 | 0.87 |
| IgG1-CD134-11D4 | 0.13 | 0.15 | 0.15 | 0.01 | 0.00 | 0.00 | 0.02 | 0.18 |
| IgG1-CD134-A4453 | 0.28 | 0.24 | 0.28 | 0.26 | 0.31 | 0.22 | 0.26 | 0.01 |

Example 4: Binding of Anti-Human OX40 Antibodies to Cell Surface-Expressed Human and Cynomolgus Monkey OX40

Binding of anti-human OX40 antibodies IgG1-CD134-003-HC6LC2-P329R-E345R (IgG1-CD134-003-HC6LC2-RR), IgG1-CD134-007-RR, IgG1-CD134-012-RR-K409R, and of 12 anti-human OX40 antibodies (eleven IgG1 antibodies and one IgG2 antibody) to cell surface-expressed human and cynomolgus monkey OX40 was analyzed by flow cytometry using transiently transfected FreeStyle 293-F suspension (HEK293F) cells. Non-binding antibody IgG1-b12-RR was used as negative control antibody.

HEK293F cells (ThermoFisher, cat. no. R79007) were transiently transfected with mammalian expression vector pSB encoding full-length human or cynomolgus monkey OX40 (SEQ ID NO: 52 and SEQ ID NO: 51, respectively) using 293fectin Transfection Reagent (ThermoFisher, cat. no. 12347019) and Opti-MEM® I Reduced Serum Medium with Glutamax (ThermoFisher, cat. no. 51985034), supplemented with 50 units penicillin and 50 units streptomycin (pen/strep; Lonza, cat. no. 17-603E), according to the manufacturer's instructions.

Transfected cells were seeded in 96-well plates (30,000 cells/well; ThermoFisher, cat. no. 163320) for sequential incubations, with washing steps in between using fluorescence-activated cell sorting (FACS) buffer 1 (phosphate buffered saline [PBS; Lonza, cat. no. BE17-517Q] supplemented with 0.1% bovine serum albumin [BSA; Roche, cat. no. 10735086001] and 0.02% sodium azide [NaN$_3$; Bio-World, cat. no. 41920044-3]) supplemented with 2 mM ethylenediaminetetraacetic acid (EDTA; Sigma-Aldrich, cat. no. 03690). Cells were incubated sequentially with 50 µL serial dilutions of anti-human OX40 antibodies (final concentration range of 0.005 to 50 µg/mL in 10-fold dilution steps in EDTA-supplemented FACS buffer 1) for 30 min at 4° C., and with a 50 µL solution of R-phycoerythrin (R-PE)-conjugated goat-anti-human IgG F(ab')$_2$ (Jackson ImmunoResearch, cat. no. 109-116-098, diluted 1:200) in EDTA-supplemented FACS buffer 1 for 30 min at 4° C. Cells were then washed using EDTA-supplemented FACS buffer 1, resuspended in a 30 µL solution of viability marker ToPro-3 (Invitrogen, cat. no. T3605, diluted 1:10,000) in EDTA-supplemented FACS buffer 1, and subsequently analyzed on an iQue® 3 flow cytometer (Satorius). Data were analyzed using FlowJo software and were visualized using GraphPad Prism.

All tested antibodies showed dose-dependent binding to human and cynomolgus monkey OX40 (FIG. 1A, B). The half-maximal effective concentration (EC50) of IgG1-CD134-003-HC6LC2-RR, IgG1-CD134-007-RR, and IgG1-CD134-012-RR-K409R for human and cynomolgus monkey OX40 was comparable to that of most other antibodies tested (FIG. 2). Compared to IgG1-CD134-003-HC6LC2-RR, IgG1-CD134-007-RR, and IgG1-CD134-012-RR-K409R, antibodies IgG2s-CD134-SF2-E345R, IgG1-CD134-GBR830, IgG1-CD134-Hu106, and IgG1-CD134-MEDI0562 had a higher EC50 for binding to human OX40, and IgG2s-CD134-SF2-E345R, IgG1-CD134-GBR830, and IgG1-CD134-h3C8-E345R had a higher $EC_{50}$ for binding to cynomolgus monkey OX40. Only antibodies IgG1-CD134-49B4-E345R and IgG1-CD134-ABBV368 had a slightly lower EC50 than IgG1-CD134-003-HC6LC2-RR, IgG1-CD134-007-RR, and IgG1-CD134-012-RR-K409R, both for binding to human and cynomolgus monkey OX40.

For most antibodies, the $EC_{50}$ for binding to human OX40 did not differ largely from that for binding to cynomolgus monkey OX40, except for antibodies IgG1-CD134-h3C8-E345R and IgG1-CD134-GBR830, which both had higher $EC_{50}$ values for cynomolgus monkey OX40 than for human OX40.

Example 5: Determining Domains Important for Binding of Anti-Human OX40 Antibodies to Human OX40 Using Domain-Shuffled OX40 Molecules The OX40 protein contains three full cysteine-rich domains (CRDs; CRD1, CRD2, and CRD4) and a truncated CRD (CRD3; Willoughby et al. Mol Immunol. 2017 March; 83:13-22). OX40L binding covers CRD1-3. OX40L is trimeric and each trimer associates with three OX40 molecules on the T-cell surface. The formation of trimeric receptor:ligand complexes ensures clustering of the cytoplasmic domains of OX40, which contain a QEE motif characteristic of many TNFR family members, creating docking sites for TNFR-associated factor (TRAF) adaptor proteins. These interactions link receptor ligation to activation of various signaling pathways, e.g., via activation of NF-κB and PI3K/AKT (Willoughby et al. Mol Immunol. 2017 March; 83:13-22).

To determine which CRD(s) is/are important for binding of anti-human OX40 antibodies to human OX40, DNA shuffling was performed between human and mouse OX40. Four shuffle constructs were prepared from DNA encoding human OX40 (FIG. 3) by replacing individual CRDs with the mouse CRD analogues. In this way, the following constructs were generated: human OX40 (SEQ ID NO: 52), mouse OX40 (SEQ ID NO: 53), human OX40 with mouse CRD1 (SEQ ID NO: 54), human OX40 with mouse CRD2 (SEQ ID NO: 55), human OX40 with mouse CRD3 (SEQ ID NO: 56), and human OX40 with mouse CRD4 (SEQ ID NO: 57). Homology between human and mouse OX40 is limited (FIG. 4). Thus, if a CRD in human OX40 is crucial for binding of an anti-OX40 antibody, binding will be lost upon replacement of that domain with the mouse analogue. Vice versa, retention of binding of the OX40 antibodies to domain-shuffled OX40 molecules illustrates that the shuffled domain of human OX40 is not crucial for binding.

The four shuffle constructs, as well as wild-type human and mouse OX40 were transiently expressed on ExpiCHO-S cells using the ExpiFectamine™ CHO Transfection Kit (ThermoFisher, cat. no. A29131), according to the manufacturer's protocol. To determine binding of anti-human OX40 antibodies IgG1-CD134-003-HC6LC2-P329R-E345R (IgG1-CD134-003-HC6LC2-RR), IgG1-CD134-007-RR, IgG1-CD134-012-RR-K409R, and of 11 additional OX40 antibodies (ten IgG1 antibodies and one IgG2 antibody) to the cell surface-expressed shuffle constructs and to wild-type human and mouse OX40, the transfected cells (30,000 cells/well) were incubated in 96-well plates (ThermoFisher, cat. no. 163320) with 50 UL serial dilutions of the individual OX40 antibodies (final concentration range of 0.005 to 50 μg/mL in 10-fold dilution steps) in FACS buffer 1 for 30 min at 4° C. The cells were washed twice in FACS buffer 1 and were subsequently incubated with a 50 μl solution of secondary antibody R-PE-conjugated goat-anti-human IgG F(ab')$_2$ (Jackson ImmunoResearch, cat. no. 109-116-098; diluted 1:200) in FACS buffer 1 for 30 min at 4° C. in the dark. Next, cells were washed twice in FACS buffer 1, were resuspended in a 30 μL solution of viability marker ToPro-3 (Invitrogen, cat. no. T3605, diluted 1:10,000) in FACS buffer 1 supplemented with 2 mM EDTA, and were analyzed on an iQue Screener Plus (Intellicyt Corporation, USA). Data were analyzed using FlowJo software and visualized using GraphPad Prism. Non-target binding antibody IgG1-b12-RR was included as a negative control antibody.

All tested anti-human OX40 antibodies showed binding to wild-type human OX40 (FIG. 5-9), while none of the tested antibodies showed binding to wild-type mouse OX40, except for antibody IgG1-CD134-RG7888 at the highest concentrations (FIG. 6A).

Antibody IgG1-CD134-A4453 was the only antibody that showed loss of binding to human OX40 with mouse CRD4 (FIG. 7B, F), and hence was used to normalize binding data of other antibodies in order to combine the results of two individual experiments (FIG. 10). The combined, normalized data show that IgG1-CD134-003-HC6LC2-RR lost binding to human OX40 with mouse CRD1 (FIG. 10B), similarly to IgG1-CD134-012-RR-K409R and antibody IgG1-CD134-11D4, while binding to all other shuffle constructs was retained (FIG. 10C-E). IgG1-CD134-007-RR and antibodies IgG1-CD134-h3C8-E345R, IgG1-CD134-ABBV368, IgG1-CD134-GBR830, IgG1-CD134-Hu106, IgG1-CD134-IBI101, and IgG1-CD134-INCAGN1949 showed loss of binding to human OX40 with mouse CRD2 (FIG. 10C). Antibodies IgG1-CD134-RG7888, IgG2s-CD134-SF2-E345R, IgG1-CD134-INCAGN1949, and IgG1-CD134-MEDI0562 showed loss of binding to human OX40 with mouse CRD3 (FIG. 10D).

Together, these data illustrate that CRD1 is crucial for binding of IgG1-CD134-003-HC6LC2-RR and IgG1-CD134-012-RR-K409R to human OX40, while for all tested antibodies other than IgG1-CD134-11D4, other CRDs are crucial for human OX40 binding (Table 6). For IgG1-CD134-007-RR and IgG1-CD134-h3C8-E345R, CRD2 seems to be crucial for binding to human OX40, while for IgG2s-CD134-SF2-E345R and IgG1-CD134-RG7888, CRD3 seems to be crucial.

TABLE 6

Binding regions crucial for binding of anti-human OX40 antibodies to human OX40

| Antibodies | CRD1 | CRD2 | CRD3 | CRD4 |
|---|---|---|---|---|
| IgG1-CD134-003-HC6LC2-RR | X | | | |
| IgG1-CD134-012-RR-K409R | X | | | |
| IgG1-CD134-11D4 | X | | | |
| IgG1-CD134-007-RR | | X | | |
| IgG1-CD134-h3C8-E345R | | X | | |
| IgG1-CD134-ABBV368 | | X | | |
| IgG1-CD134-GBR830 | | X | | |

TABLE 6-continued

Binding regions crucial for binding of anti-human OX40 antibodies to human OX40

| Antibodies | Binding region | | | |
|---|---|---|---|---|
| | CRD1 | CRD2 | CRD3 | CRD4 |
| IgG1-CD134-Hu106 | | X | | |
| IgG1-CD134-IBI101 | | X | | |
| IgG1-CD134-INCAGN1949 | | X | X | |
| IgG1-CD134-RG7888 | | | X | |
| IgG2s-CD134-SF2-E345R | | | X | |
| IgG1-CD134-MEDI0562 | | | X | |
| IgG1-CD134-A4453 | | | | X |

Example 6: Agonistic Activity of Anti-Human OX40 Antibodies in a Cell-Based OX40 Reporter Assay The OX40 agonist activity of different anti-human OX40 antibodies with a hexamerization-enhancing mutation (E345R), and further consisting of an active or inactive Fc backbone was measured using Jurkat cells transfected with human OX40 (OX40 Bioassay; Promega, cat. no. JA2191). These cells express the firefly luciferase gene under the control of NF-κB response elements and constitutively express human OX40, resulting in luciferase production in response to OX40 agonism. OX40+Jurkat cells were thawed and left to rest overnight at 37° C./5% $CO_2$ in white opaque 96-well flat bottom culture plates (30,000 cells/well; PerkinElmer, cat. no. 6005680) in assay buffer (RPMI1640 medium [Promega, cat. no. G708A] supplemented with 5% heat-inactivated Fetal Bovine Serum [FBS; cat. no. J121A]). The next day, antibody dilution series (final concentration range of 0.000026 to 10 μg/mL [FIG. 11A-D] or 0.00064 to 50 g/mL FIG. 11E in 5-fold dilution steps in assay buffer) were added to the wells and incubated for 5 h at 37° C./5% $CO_2$. Test antibodies were IgG1-CD134-003-HC6LC2-P329R-E345R (IgG1-CD134-003-HC6LC2-RR), IgG1-CD134-007-RR, IgG1-CD134-012-RR, and antibodies IgG1-h3C8-K322A-E345R, IgG1-CD134-h3C8-E345R-L234A-L235A-P329G (IgG1-CD134-h3C8-E345R-LA-LAPG), IgG1-CD134-RG7888-K322A-E345R, IgG1-CD134-RG7888-E345R-LALAPG, and IgG2s-CD134-SF2-E345R. Non-binding antibody IgG1-b12-RR was used as a negative control. After incubation, Bio-Glo Luciferase Assay Reagent, prepared by mixing Bio-Glo Luciferase Assay Buffer (Promega, cat. no. G719A) and Bio-Glo Luciferase Assay Substrate (Promega, cat. no. G720A) according to the manufacturer's instructions, was added in a 1:1 ratio to each well containing OX40+ Jurkat cells and antibody dilution series and incubated for 5-10 min at RT in the dark. Luminescence was measured using an EnVision Multilabel Reader (PerkinElmer) and presented as relative luminescence units (RLU) in bar diagrams generated using GraphPad Prism software. EC50 values were calculated using GraphPad Prism.

IgG1-CD134-003-HC6LC2-RR induced stronger activation of the human OX40-expressing reporter cells than two hexamerization-enhanced (E345R) variants of the IgG1-h3C8 antibody with either an inert Fc backbone (LALAPG) or an Fc backbone that shows no C1q binding and reduced FcγR binding (K322A; FIG. 11A). This was illustrated by a higher maximal level of cellular activation induced by IgG1-CD134-003-HC6LC2-RR compared with the IgG1-h3C8 variants, as reflected by the higher maximal RLU signals observed for the former antibody (FIG. 11A), and by the slightly lower ECso values for IgG1-CD134-003-HC6LC2-RR (FIG. 12). Similarly, IgG1-CD134-003-HC6LC2-RR outperformed two hexamerization-enhanced variants of the IgG1-RG7888 antibody (IgG1-CD134-RG7888-E345R-LALAPG and IgG1-CD134-RG7888-K322A-E345R) in the induction of reporter cell activation (FIG. 11B, 12). IgG1-CD134-003-HC6LC2-RR also induced a higher maximal level of activation than the IgG1-RG7888 variants (FIG. 12). Furthermore, IgG1-CD134-003-HC6LC2-RR induced stronger activation of the reporter cells than an Fc-inert variant of IgG2-CD134-SF2 carrying a hexamerization-enhancing mutation reflected by the higher maximal RLU signal and lower EC50 values (IgG2s-CD134-SF2-E345R; FIG. 11C, 12). Both IgG1-CD134-007-RR and IgG1-CD134-012-RR induced reporter cell activation, with IgG1-CD134-012-RR inducing a higher maximal activation, which was comparable to IgG1-CD134-003-HC6LC2-RR (FIG. 11D, 12). No reporter cell activation was observed for antibody IgG1-CD134-11D4 (FIG. 11E).

In conclusion, IgG1-CD134-003-HC6LC2-RR showed a higher potency to induce activation of reporter cells overexpressing human OX40 than antibodies IgG1-CD134-h3C8, IgG1-CD134-RG7888, and IgG2-CD134-SF2 that carried the E345R hexamerization-enhancing mutation and consisted of either an inert Fc backbone or an Fc backbone that shows no C1q binding and reduced FcγR binding. Also, IgG1-CD134-007-RR and IgG1-CD134-012-RR induced activation of the reporter cells, while no activity could be detected for antibody IgG1-CD134-11D4 in this assay. The non-humanized variants of 007 and 012 were tested here, alongside the humanized 003 clone. In initial PBMC proliferation experiments, the 007 clone was less functionally active than 003 and 012. The 012 clone lost functional activity in T-cell proliferation assays after humanization.

Example 7: The Capacity of Anti-Human OX40 Antibodies to Enhance T-Cell Proliferation To investigate the capacity of IgG1-CD134-003-HC6LC2-P329R-E345R (IgG1-CD134-003-HC6LC2-RR) to induce T-cell proliferation, and to compare this capacity with that of antibodies with a hexamerization-enhancing mutation (E345R), and further consisting of either an active Fc backbone, an inactive Fc backbone (L234A-L235A-P329G; LALAPG), or an Fc backbone which shows no C1q binding and reduced FcγR binding (K322A), a polyclonal T-cell proliferation assay was conducted using healthy donor human peripheral blood mononuclear cells (PBMCs).

PBMCs were obtained from buffy coats of healthy donors (Transfusionszentrale, University Hospital, Mainz, Germany) by Ficoll-Paque density gradient separation (GE Healthcare, cat. no. 17-1440-03). Where applicable, CD4+ or CD8+ T cells were depleted from PBMCs using CD4 or CD8 microbeads (Miltenyi Biotec GmbH, cat. nos. 130-097-48 and 130-045-201) respectively. The separation procedure was generally carried out according to the manufacturer's instructions with a minor modification (volume of microbeads was reduced) and was in principle the same for the isolation of CD4; and CD8" PBMCs. In short, after determining the cell numbers, cell suspensions were centrifuged, and the supernatants discarded. The cells were resuspended in MACS buffer (DPBS [Thermo Fisher Scientific, cat. no. 14190250], 5 mM ethylenediaminetetraacetic acid [EDTA; Sigma-Aldrich, cat. no. 03690], 1% human albumin [CSL Behring, cat. no. PZN-00504775]) at $1 \times 10^7$ live cells per 80 µl buffer. Per 10⁷ cells, 12 µL CD4 or CD8 microbeads were added. Cells and beads were mixed well prior to and two times during the 15 min incubation at 2 to 8° C. to ensure homogeneous labeling. The cell suspensions were then washed with MACS buffer (8 min, 300×g, RT) and filtered through 30 µm cell strainer (BD Biosciences, cat. no. 340626). LS columns (Miltenyi Biotec GmbH, cat. no. 130-042-401) were placed in a QuadroMACS separator on a MACS MultiStand (Miltenyi Biotec GmbH) and equilibrated with MACS buffer. Columns were loaded with the bead-labeled cells, and the suspension allowed to flow through by gravity flow, retaining the bead-labeled cells in the column. The columns were then washed three times with MACS buffer. Columns containing bead-labeled CD4⁺ and CD8⁺ cells were discarded. Unlabeled CD4⁻ and CD8⁻ PBMC in the flow through were centrifuged (8 min, 300×g, RT), resuspended in DPBS, and counted.

PBMC samples were labelled with CellTrace™ Violet (Thermo Fisher Scientific, cat. no. C34557), each according to the manufacturer's instructions.

CellTrace™ Violet-labelled PBMCs were incubated in the presence of 0.3 µg/mL soluble anti-human CD3 antibody (STEMCELL technologies, cat. no. 60011) and serial dilutions of IgG1-CD134-003-HC6LC2-RR, IgG1-CD134-h3C8-K322A-E345R, IgG1-CD134-h3C8-E345R-L234A-L235A-P329G (E345R-LALAPG), IgG1-CD134-RG7888-K322A-E345R, IgG1-CD134-RG7888-E345R-LALAPG, IgG2s-CD134-SF2-E345R or non-binding negative control antibody IgG1-b12-RR (final antibody concentration range of 0.00098 to 10 µg/mL in 2-fold or 10-fold dilution steps) in Iscove's Modified Dulbecco's Medium GlutaMAX (Thermo Fisher Scientific, cat. no. 31980030) containing 5% pooled human serum(One Lambda Inc., cat. no. A25761) in a 96-well round-bottom plate. After four days of culture, the cells were stained with a viability dye (Thermo Fisher Scientific, cat. no 65-0865-14, diluted 1:1,500) and fluorescently labelled antibodies against human CD4 (eBioscience, cat. no. 17-0048-42, diluted 1:100), CD8 (BD Biosciences, cat. no. 564116, diluted 1:400), CCR7 (BioLegend, cat. no. 353206, diluted 1:50) and CD45RA (BD Biosciences, cat. no. 560675, diluted 1:100). T-cell proliferation was evaluated by flow cytometric analysis of CellTrace™ Violet dilution in CD4⁺ and CD8⁺ T cells using a BD FACSCelesta™ flow cytometer (BD Biosciences). Expansion indices were calculated using the integrated formula in the proliferation modeling tool in FlowJo software. In addition, the percentage of central memory cells (CCR7⁺CD45RA⁻) among CD4+ and CD8⁺ T cells was assessed.

IgG1-CD134-003-HC6LC2-RR dose-dependently enhanced CD4⁺ and CD8⁺ T-cell proliferation with high potency (FIG. 13). IgG1-CD134-h3C8-E345R-LALAPG also enhanced CD4⁺ and CD8⁺ T-cell proliferation but showed a reduced potency compared with IgG1-CD134-003-HC6LC2-RR (FIG. 13A, B). In contrast, IgG1-CD134-h3C8-K322A-E345R, IgG1-CD134-RG7888-K322A-E345R, IgG1-CD134-RG7888-E345R-LALAPG, IgG2s-SF2-E345R or IgG1-b12-RR did not enhance CD4⁺ or CD8⁺ T-cell proliferation (FIG. 13A, B). When testing the capacity of IgG1-CD134-003-HC6LC2-RR to enhance CD4⁺ and CD8⁺ T-cell proliferation in a larger cohort of healthy donor PBMCs, a consistent dose-dependent enhancement of CD4⁺ and CD8⁺ T-cell proliferation was observed, for which the EC₅₀ could be calculated (n=17; Table 7).

TABLE 7

$EC_{50}$ values for IgG1-CD134-003-HC6LC2-RR-enhanced CD4⁺ and CD8⁺ T-cell proliferation in a polyclonal T-cell proliferation assay, based on results from 17 healthy human donors.

| Donor | $EC_{50}$ CD4⁺ T-cell proliferation | | $EC_{50}$ CD8⁺ T-cell proliferation | |
|---|---|---|---|---|
| | µg/mL | nM | µg/mL | nM |
| 1 | 0.009 | 0.057 | 0.028 | 0.190 |
| 2 | 0.024 | 0.159 | 0.029 | 0.195 |
| 3 | 0.012 | 0.084 | 0.013 | 0.087 |
| 4 | 0.007 | 0.048 | 0.007 | 0.048 |
| 5 | 0.008 | 0.053 | 0.009 | 0.058 |
| 6 | 0.006 | 0.038 | 0.008 | 0.051 |
| 7 | 0.019 | 0.129 | 0.041 | 0.273 |
| 8 | 0.016 | 0.107 | 0.005 | 0.033 |
| 9 | 0.007 | 0.048 | 0.008 | 0.052 |
| 10 | 0.017 | 0.111 | 0.016 | 0.109 |
| 11 | 0.010 | 0.067 | 0.014 | 0.095 |
| 12 | 0.009 | 0.060 | 0.009 | 0.058 |
| 13 | 0.019 | 0.125 | 0.052 | 0.346 |
| 14 | 0.008 | 0.052 | 0.008 | 0.054 |
| 15 | 0.020 | 0.132 | 0.018 | 0.117 |
| 16 | 0.008 | 0.053 | 0.011 | 0.074 |
| 17 | 0.018 | 0.119 | 0.017 | 0.116 |
| Average $EC_{50}$ | 0.013 | 0.085 | 0.017 | 0.115 |
| Average SD | 0.006 | 0.038 | 0.013 | 0.088 |

To assess whether the IgG1-CD134-003-HC6LC2-RR-increased proliferation of CD4⁺ T cells was dependent on the presence of CD8⁺ T cells, and vice versa, the polyclonal T-cell proliferation assay was performed using CD8⁺ or CD4⁺ T-cell depleted PBMC samples. The IgG1-CD134-003-HC6LC2-RR-induced increase in T-cell proliferation was retained for CD4⁺ T cells in absence of CD8⁺ T cells, but not for CD8⁺ T cells in absence of CD4⁺ T cells (FIG. 13C, D). This suggests that the presence of CD4⁺ T cells is essential for IgG1-CD134-003-HC6LC2-RR-induced CD8⁺ T-cell proliferation in a polyclonal T-cell proliferation assay.

Furthermore, IgG1-CD134-003-HC6LC2-RR treatment dose-dependently increased the percentage of CCR7⁺ CD45RA⁻ central memory CD4⁺ and CD8⁺ T cells (FIG. 14). IgG1-CD134-h3C8-E345R-LALAPG also dose-dependently increased the percentage of central memory CD4⁺

T cells, but with reduced potency compared with IgG1-CD134-003-HC6LC2-RR. In contrast, no clear difference in the percentage of central memory CD4+ T cells was observed upon treatment with IgG1-CD134-h3C8-K322A-E345R, IgG1-CD134-RG7888-K322A-E345R, or IgG1-CD134-RG7888-E345R-LALAPG (FIG. 14).

Example 8: Binding of Anti-Human OX40 Antibodies to Human and Cynomolgus Monkey Fc Gamma Receptors Binding to human Fcγ receptors (FcγRs) by different anti-human OX40 antibodies with a hexamerization-enhancing mutation (E345R), and further consisting of either an active Fc backbone, an inactive Fc backbone (L234A-L235A-P329G; LALAPG, or P329R), or an Fc backbone which shows no C1q binding and reduced FcγR binding (K322A), was analyzed using two methods, i.e., by surface plasmon resonance (SPR), and by flow cytometric analysis of anti-human OX40 antibodies binding to FcγRIa-transfected ExpiCHO-S cells.

For the former method, binding of OX40-specific antibody variants IgG1-CD134-003-HC6LC2, IgG1-CD134-003-HC6LC2-E345R, IgG1-CD134-003-HC6LC2-P329R-E345R (IgG1-CD134-003-HC6LC2-RR), and a selection of other OX40-specific antibodies (see FIG. 15-16) to human FcγR variants was analyzed using a Biacore SPR system and compared to an anti-HIV gp120 antibody with a wild-type Fc domain (IgG1-b12) as the reference sample. Biacore Series S Sensor Chips CM5 (Cytiva, cat. no. 29104988) were covalently coated with anti-His antibody using amine-coupling and His capture kits (Cytiva, cat. no. BR100050 and cat. no. 29234602) according to the manufacturer's instructions. Next, His-tagged FcγRIa, FcγRIIa (167-His [H] and 167-Arg [R]), FcγRIIb, or FcγRIIIa (176-Phe [F] and 176-Val [V]) (Sino Biological, cat. no. 10256-H08S-B, cat. no. 10374-H08H1, cat. no. 10374-H27H, cat. no. 10259-H27H-B, cat. no. 10389-H27H, and cat. no. 10389-H27H1-B, respectively) were reversibly captured in HBS-EP+ buffer (Cytiva, cat. no. BR100669) onto the anti-His chip surface until 400 RU of capture response was reached. After three start-up cycles of HBS-EP+ buffer, antibody samples were injected for 12 cycles per sample to generate binding curves using antibody concentration ranges of 0 to 3,000 nM for FcγRIa and 0 to 10,000 nM for the other FcγRs. Each sample that was analyzed on an FcγR-coated surface (Active Surface) was also analyzed on a parallel flow cell without FcγR (Reference Surface), which was used for background correction. Dissociation from the anti-His-coated surface was performed by regeneration of the surface using 10 mM Glycine-HCl pH 1.5 (Cytiva, cat. no. BR100354). Sensorgrams were generated using Biacore Insight Evaluation software (Cytiva) and a four-parameter logistic (4PL) fit was applied to calculate binding of the individual human OX40-specific antibodies relative to the reference sample (IgG1-b12).

For the latter method, ExpiCHO-S cells (ThermoFisher, cat. no. A29127) were transiently transfected with human FcγRIa as follows. ExpiCHO-S cells (approximately 3.0×10$^6$ cells/ml; ThermoFisher Scientific, cat. no. A29133) were cultured in ExpiCHO™ Expression Medium (Thermo Fisher Scientific, cat. no. A2910001). For each transfection, 10 μg DNA encoding FcγRIa was mixed in 0.39 mL cold OptiPro™ Serum-Free Medium (OptiPro™ SFM, ThermoFisher Scientific, cat. no. A29131), and in parallel, 0.03 ml ExpiFectamineCHO™ reagent (ThermoFisher Scientific, cat. no. A29131) was added to 0.37 mL cold OptiPro™ SFM. Then, 0.4 mL of the latter mixture was added to the DNA/OptiPro mixture and incubated for 1-5 min at RT. Next, this mixture was added drop-wise to the cultured ExpiCHO-S cells. After 18 to 22 h of incubation, 0.06 mL ExpiCHO™ Enhancer (ThermoFisher Scientific, cat. no. A29131) and 2.4 ml ExpiCHO Feed (ThermoFisher Scientific, cat. no. A29131) were added per culture flask. After transfection, cells were incubated 24 h at 37° C., 70% humidity, 8% $CO_2$ while shaking, and then frozen in ExpiCHO™ Expression Medium supplemented with 10% DMSO (Sigma-Aldrich, cat. no. D2438).

Transfected cells were plated in 96-well U-bottom plates (20,000 cells/well; ThermoFisher, cat. no. 163320) in culture medium (RPMI1640 with L-glutamine and 25 mM HEPES [Capricorn Scientific, cat. no. RPMI-HA] supplemented with 50 units penicillin and 50 units streptomycin [pen/strep; Lonza, cat. no. 17-603E] and 10% Donor Bovine Serum with Iron [DBSI; Gibco, cat. no. 20371-030]). Next, cells were incubated with 25 μl serial dilutions of OX40-specific antibodies IgG1-CD134-003-HC6LC2-RR, IgG1-CD134-003-HC6LC2, IgG1-CD134-003, or (variants) of other OX40-specific antibodies (see FIG. 17; final concentration range of 0.00051 to 10 μg/mL in 3-fold dilution steps) in FACS buffer 1 for 30 min at 4° C. After incubation, the cells were washed twice using FACS buffer 1 and were subsequently incubated with a 50 μL solution of R-PE-labeled F(ab')$_2$ fragment goat anti-human IgG, F(ab')$_2$ fragment specific (Jackson ImmunoResearch, cat. no. 109-116-097, diluted 1:200) in FACS buffer 1 for 30 min at 4° C. Next, cells were washed twice using FACS buffer 1 and were incubated with a 30 μl solution of viability marker ToPro-3 (Invitrogen, cat. No. T3605, diluted 1:10,000) in FACS buffer 1 supplemented with 2 mM EDTA for 20 min at RT in the dark. All samples were measured on an iQue® 3 flow cytometer (Satorius). Data were analyzed using FlowJo software and were visualized using GraphPad Prism.

In the SPR measurements, IgG1-CD134-003-HC6LC2-RR showed low residual binding to high-affinity receptor FcγRIa, while no binding by this antibody was observed to FcγRIIa (H and R variants), FcγRII2b, or FcγRIIIa (F and V variants; FIG. 15-16). IgG1-CD134-h3C8-K322A-E345R and IgG1-CD134-RG7888-K322A-E345R showed binding to all FcγRs tested, albeit slightly less than positive control IgG1-b12 (FIG. 15-16). In contrast, variants of the latter antibodies harboring the E345R-LALAPG Fc backbone did not show binding to any of the tested FcγRs. Using similar methods, low residual binding by IgG1-CD134-003-HC6LC2-RR to cynomolgus monkey FcγRIa was observed at high antibody concentrations (above 100 nM [14.9 μg/mL]).

Using FcγRIa-transfected ExpiCHO-S cells and flow cytometric analysis, IgG1-CD134-003-HC6LC2-RR did not show binding to FcγRIa (FIG. 17A). Binding to FcγRIa was observed for antibody variants carrying a wild-type Fc domain, including IgG1-CD134-003-HC6LC2, IgG1-CD134-003, IgG1-CD134-11D4, IgG1-CD134-INCAGN1949, IgG1-CD134-IBI101, IgG1-CD134-h3C8, IgG1-CD134-h3C8-E345R, IgG1-CD134-RG7888, IgG1-CD134-RG7888-E345R and for the variants of IgG1-CD134-h3C8 and IgG1-CD134-RG7888 harboring the E345R-K322A mutations (FIG. 17A, C-E). No binding to FcγRIa was observed for IgG2 antibodies IgG2-SF2 and IgG2s-SF2-E345R, and for variants of IgG1-h3C8 and IgG1-RG7888 harboring the E345R-LALAPG mutations (FIG. 17B, D-E).

In conclusion, IgG1-CD134-003-HC6LC2-RR shows minimal (FcγRIa) or no (FcγRIIa, FcγRIIb, and FcγRIIIa) binding to human IgG Fc gamma receptors.

Example 9: Antibody Binding Capacity of IgG1-CD134-003-HC6LC2-RR on Activated Primary CD4+ and CD8+ T cells The number of binding sites on the cell surface of activated primary human CD4+ and CD8+ T cells was quantitatively determined after 24 h, 48 h, and 72 h of activation. First, total human T cells were enriched by negative selection directly from buffy coats using the RosetteSep® Human T Cell Enrichment Cocktail (StemCell Technologies, cat. no. 15021) followed by density centrifugation over a Ficoll gradient (PromoCell, cat. no. C-44010 or Corning, cat. no. 25-072-CI), both according to the manufacturer's instructions. The enriched T cells were washed once in PBS (GE Healthcare, cat. no. SH3A3830.03 or Capricorn Scientific, cat. no. SP-2121-500 mL), centrifuged for 3 min at 300×g and resuspended in activation medium (RPMI-1640 medium [Lonza, cat. no. BE12-115F/Capricorn, cat. no. RPMI-HA], supplemented with 10% heat inactivated FBS [ATCC, cat. no. 30-2020], 1% penicillin/ streptomycin, and 1% L-glutamine [Gibco, cat. no. 25030-081]). The enriched T cells were counted on a Cellometer Auto 2000 Cell Viability Counter (Nexcelom Biosciences) using Cellometer ViaStain® AOPI solution (Nexcelom Bioscience, cat. no. CS2-0106) in PBS to discriminate live from dead cells. Cells were pelleted and resuspended in activation medium.

To induce T-cell activation, anti-CD3/CD28 beads (Dynabeads™ Human T-Activator CD3/CD28; ThermoFisher Scientific, cat. no. 11131D) were washed with PBS, and T cells and beads were resuspended in activation medium at a 1:2 bead-to-cell ratio. Next, 300,000 T cells with beads (150 μL) were plated per well in a round-bottom 96-well plate (ThermoFisher Scientific, cat. no. 163320), and incubated at 37° C., 5% CO$_2$ for one, two, and three days. Next, the beads were removed using a Dynal® bead separator (Invitrogen, cat. no. 3019669), after which the T cells were washed in activation medium. This bead removal step was repeated twice. Cells were counted using AOPI solution to discriminate live from dead cells.

The number of IgG1-CD134-003-HC6LC2-RR binding sites was analyzed using the Human IgG Calibrator Kit (Biocytex, cat. no. CP010) and flow cytometry, according to the manufacturer's instructions. The bead-activated T cells were plated in a round-bottom 96-well plate (50,000 cells/well; ThermoFisher Scientific, cat. no. 163320). Cells were washed once with PBS and once with FACS buffer 1 and were incubated for 30 min at 4° C. with 1 μg/mL, ie, saturating antibody concentration levels, of IgG1-CD134-003-HC6LC2-RR diluted in FACS buffer 1. Next, calibration beads containing a well-defined number of human IgG monoclonal antibodies per bead (included in the kit) were plated, separately from the cells, in FACS buffer 1 (15 μl beads per well). After washing in FACS buffer 1, cells and calibration beads were incubated with the antibody panel described in Table 8 in FACS buffer 1 at 4° C. for 30 min, protected from light. Both cell and bead suspensions were washed twice and resuspended in 80 μL ToPro-3 viability marker diluted in FACS buffer 1 (1:10,000; Invitrogen, cat. no. T3605) and measured on a BD FACSCelesta Cell Analyzer. Data was analyzed using FlowJo software. Compensation was performed using UltraComp eBEADS (Thermo Fisher Scientific, cat. no. 01-2222-42). The antibody binding capacity (sABC) of IgG1-CD134-003-HC6LC2-RR representing the number of IgG1-CD134-003-HC6LC2-RR-binding sites per cell was determined by interpolation from the standard curve using GraphPad Prism software.

TABLE 8

Antibody panel to analyze IgG1-CD134-003-HC6LC2-RR binding sites on activated CD4+ and CD8+ T-cell subsets

| Target | Clone | Label | Cat. no. | Supplier | Dilution |
|---|---|---|---|---|---|
| CD4 | RPA-T4 | Pacific Blue | 300521 | BioLegend | 1:200 |
| CD8 | SK1 | APC-Cy7 | 557834 | BD Biosciences | 1:100 |
| goat-anti-human IgG F(ab')$_2$ | n.a. | R-PE | 109-116-098 | Jackson ImmunoResearch | 1:200 |

The number of IgG1-CD134-003-HC6LC2-RR-binding sites was higher after two and three days of stimulation compared with one day of stimulation for both CD4+ and CD8+ T cells (FIG. 18). Furthermore, the number of IgG1-CD134-003-HC6LC2-RR-binding sites (i.e., sABC) was approximately 4.5 to 8.5-fold higher on CD4+ T cells than on CD8+ T cells across all time points (CD4: 11,285 and 21,682 mean sABC; CD8: 1,322 and 4,816 mean sABC for one and three days of stimulation, respectively).Example 10: Binding of anti-human OX40 antibodies to activated T cells expressing OX40.

As described in Example 9, the expression of OX40 on T cells can be induced upon activation of T cells, with a maximal expression observed after two to three days of activation. Here, the binding of anti-human OX40 antibodies to anti-CD3/CD28 antibody-activated T cells was assessed using flow cytometry.

Healthy human donor PBMCs were purified essentially as described in Example 7. The cell concentration was adjusted to 2×10$^6$ cells per ml (final concentration) in assay medium and plated in 6-well plates (Greiner, cat. no. 657160). PBMCs were stimulated with 0.3 μg/mL anti-CD3 (STEMCELL Technologies, cat. no. 60011) and 0.5 μg/mL anti-CD28 antibodies (BioLegend, cat. no. 302934) and cultured for two days at 37° C., 5% CO$_2$. Next, the PBMCs were harvested, counted and brought to a concentration of 2×10$^6$ cells per ml in FACS buffer 1 (DPBS with 2% heat-inactivated FBS and 2 mM ethylenediaminetetraacetic acid [EDTA]). OX40 expression on the stimulated T cells was confirmed by staining with a commercial anti-OX40 antibody (data not shown). The activated PBMCs were transferred at 1×10$^5$ cells per well in a 96-well round-bottom plate and incubated either with IgG1-CD134-003-HC6LC2-RR, IgG1-CD134-IBI101, IgG1-CD134-11D4, IgG1-CD134-RG7888, or non-binding control antibody IgG1-b12-RR (final concentration: 0.00061 to 10 g/mL in 4-fold dilution steps). After 60 min at RT, the cells were prepared for flow cytometric analyses. To this end, the cells were washed twice with 150 μL FACS buffer 1 and 30 μL/well cell-surface antibody mix (Table 9) in FACS buffer 1 containing antibody against human Fcγ antibody (Table 9) and fixable viability dye eFluor780 (1:1,500) was added. The staining procedures were carried out at 4° C. for 15-20 min protected from light. Stained cells were washed twice with 120-150 μL FACS buffer 1 (5 min, 460×g, RT) and resuspended in 60-100 μL FACS buffer 1 for direct flow cytometric analyses. Flow cytometric data were acquired on a FACSymphony A3 and analyzed with FlowJo software.

TABLE 9

Antibody panel used to assess binding of anti-human OX40 antibodies to activated human T cells

| Target | Clone | Label | Cat. no. | Supplier | Dilution |
|---|---|---|---|---|---|
| CD4 | SK3 | PerCP-eFluor710 | 46-0047-42 | Thermo Fisher Scientific | 1:100 |
| CD8α | SK1 | APC | 345775 | BD Biosciences | 1:100 |
| CD19 | HIB19 | BV421 | 562440 | BD Biosciences | 1:150 |
| CD56 | B159 | PE-Cy7 | 557747 | BD Biosciences | 1:100 |
| Human Fcγ | Polyclonal | AF488 | 109-546-098 | Jackson | 1:500 |

All tested anti-human OX40 antibodies dose-dependently bound to stimulated CD4$^+$ and CD8$^+$ T cells from all donors tested (representative donor shown in FIG. 19). EC$_{50}$ values of IgG1-CD134-003-HC6LC2-RR binding to stimulated T cells were in the high picomolar range, with mean EC$_{50}$ values of 0.140 nM/0.021 μg/mL (CD4$^+$ T cells; Table 10) and 0.159 nM/0.024 μg/mL (CD8$^+$ T cells; Table 10). EC$_{50}$ values of the other anti-human OX40 antibodies were in a similar range (IgG1-CD134-11D4), slightly higher (IgG1-CD134-RG7888) or markedly higher (IgG1-CD134-IBI101), while IgG1-CD134-RG7888 reached a higher maximal binding plateau.

bioactive nature of these soluble forms is supported by reports that sOX40 can compete for OX40L interactions with membrane-expressed OX40. This can inhibit the inflammatory response and thus mimic the Treg function (Laustsen et al. Arthritis Res Ther. 2014 Oct. 30; 16 (5): 474).

Most agonistic OX40 antibodies currently in clinical development bind to the same region as OX40L, the natural ligand for OX40, and antibody binding to this region has been associated with strong OX40 agonist and antitumor activity (Zhang et al. 2019. Ligand-Blocking and Membrane-Proximal Domain Targeting Anti-OX40 Antibodies Mediate Potent T Cell-Stimulatory and Anti-Tumor Activity. Cell Rep 27:3117-3123 e3115). The binding of IgG1-CD134-003-HC6LC2-RR to human OX40 expressed on activated T cells was tested in the presence of soluble OX40L (sOX40L) and vice versa.

To define the saturating concentration of sOX40L for binding to activated human CD4+ and CD8+ T cells, and to evaluate the binding of IgG1-CD134-003-HC6LC2-RR in the presence of this saturating concentration of sOX40L, human PBMCs were stimulated with anti-CD3/CD28 beads for two days (essentially as described in Example 9, with the

TABLE 10

EC$_{50}$ values for binding of anti-human OX40 antibodies to activated human CD4$^+$ and CD8$^+$ T cells.

| | Binding to CD4$^+$ T cells - EC$_{50}$ [μg/mL] | | | | Binding to CD8$^+$ T cells - EC$_{50}$ [μg/mL] | | | |
|---|---|---|---|---|---|---|---|---|
| | IgG1-CD134-003-HC6LC2-RR | IgG1-CD134-11D4 | IgG1-CD134-RG7888 | IgG1-CD134-IBI101 | IgG1-CD134-003-HC6LC2-RR | IgG1-CD134-11D4 | IgG1-CD134-RG7888 | IgG1-CD134-IBI101 |
| Donor 1 | 0.0273 | 0.0300 | 0.0453 | 0.101 | 0.0329 | 0.0394 | 0.0627 | 0.128 |
| Donor 2 | 0.0167 | 0.0178 | 0.0292 | 0.100 | 0.0163 | 0.0146 | 0.0332 | 1.860 |
| Donor 3 | 0.0187 | 0.0224 | 0.0316 | 0.111 | 0.0217 | 0.0295 | 0.0393 | 0.192 |
| Mean | 0.0209 | 0.0234 | 0.0354 | 0.104 | 0.0236 | 0.0278 | 0.0451 | 0.727 |
| SD | 0.0056 | 0.0062 | 0.0087 | 0.0056 | 0.0085 | 0.0125 | 0.0156 | 0.982 |

SD: standard deviation.

These results indicate that IgG1-CD134-003-HC6LC2-RR bound to OX40-expressing activated human T cells with a similar (IgG1-CD134-11D4) or higher apparent affinity (IgG1-CD134-RG7888, IgG1-CD134-IBI101) than benchmark OX40 agonistic antibodies.

Example 11: Binding of IgG1-CD134-003-HC6LC2-RR to Human OX40 in the Presence of Soluble OX40L Besides their membrane-bound forms, OX40 and OX40L are both present in soluble forms (sOX40 and sOX40L) that have previously been linked to autoimmune diseases. The exception that here, 6-well plates [Greiner, cat. no. and IMDM medium containing 5% pooled human serum [PHS, One Lambda Inc., cat. no. A25761] were used). Stimulated PBMCs were pelleted, resuspended in FACS buffer 2 (DPBS with 2% heat-inactivated FBS [Sigma-Aldrich, cat. no. F7524] and 2 mM EDTA [Sigma-Aldrich, cat. no. 03690]), and seeded (100,000 cells/well) in round-bottom 96-well plates (VWR International GmbH, cat. no. 734-197). Next, cells were incubated at RT for 30 min with either murine Fc-tagged human sOX40L (Sino Biological, cat. no. 13127-H04H) at final concentrations ranging from 0.00017 to 30 μg/ml (threefold dilution steps in FACS buffer 2 for stimulated cells, or 30 μg/mL for unstimulated cells) to determine saturating binding concentration of sOX40L, or with IgG1-CD134-003-HC6LC2-RR and IgG1-b12-RR antibody at final concentrations ranging from 0.00046 to 10 μg/mL (10-fold dilution in the first step, subsequently threefold dilution steps in FACS buffer 2) in the presence or absence of 2 μg/mL sOX40L to determine binding competition. Next, the cells were washed twice with 150 μL FACS buffer 2 and incubated in 30 μl APC-conjugated goat-anti-mouse IgG F(ab')2 secondary antibody (diluted 1:1,000 in FACS buffer 2; Jackson ImmunoResearch, cat. no. 115-135-164) alone or together with AF488-conjugated goat-anti-human IgG F(ab')2 secondary antibody (diluted 1:500 in FACS buffer 2; Jackson ImmunoResearch, cat. no. 109-546-098) at 4° C. for 20 min, protected from light. Next, cells were washed twice in FACS buffer, and incubated with 30 μl of the antibody panel described in Table 11 diluted in FACS buffer 2 containing 1:1,500 Fixable Viability Stain eFluor 780 at 4° C. for 20 min, protected from light. The cells were subsequently washed twice with 120-150 μL FACS buffer 2 and measured on a BD FACSCelesta flow cytometer using a BD High Throughput sampler and subsequent analysis was done using FlowJo software.

TABLE 11

Antibody panel used to stain $CD4^+$ and $CD8^+$ T cells

| Target | Clone | Label | Cat. no. | Supplier | Dilution |
|---|---|---|---|---|---|
| CD4 | SK3 | BV421 | 565997 | BD Biosciences | 1:100 |
|  |  | BV605 | 564116 | BD Biosciences | 1:400 |

The saturating concentration of sOX40L was determined to be 2 μg/mL. Maximal binding of IgG1-CD134-003-HC6LC2-RR to OX40 was not hampered in the presence of 2 μg/mL sOX40L (FIG. 20A), although the $EC_{50}$ values for binding to $CD4^+$ and $CD8^+$ T cells were approximately threefold higher in the presence of sOX40L (Table 12). Conversely, sOX40L binding was dose-dependently lost in the presence of IgG1-CD134-003-HC6LC2-RR (FIG. 20B), indicating that IgG1-CD134-003-HC6LC2-RR could block the binding of sOX40L. This suggests that OX40L and IgG1-CD134-003-HC6LC2-RR bind overlapping domains on OX40, but that the presence of OX40L has a minimal impact of binding of IgG1-CD134-003-HC6LC2-RR (but not vice versa).

Example 12: Agonist Activity of Anti-Human OX40 Antibodies in the Absence and Presence of Fcγ Receptor-Expressing Cells In Example 6, an assay was described that was performed using Jurkat cells transfected with human OX40 to investigate the potency of different anti-human OX40 antibodies. Here, using the same assay, the potency to induce OX40 agonist activity was investigated, both in the absence and presence of FcγR-expressing cells, for IgG1-CD134-003-HC6LC2-RR and variants thereof with an Fc-active backbone (IgG1-CD134-003; SEQ ID No 9 and 10), or with an Fc backbone harboring a hexamerization enhancing mutation E345R as shown for the constant region illustrated by SEQ ID NO: 2., or with an Fc backbone harboring the Fc-inertness mutations L234F, L235E, and D265A, in addition to the F405L mutation which promotes heterodimerization of a half-molecule with another half-molecule harboring the K409R mutation (Labrijn et al. Efficient generation of stable bispecific IgG1 by controlled Fab-arm exchange. PNAS 2013; 110 (13): 5145-50) as shown for the constant region illustrated by SEQ ID NO: 62. In a separate set of experiments, the potency to induce OX40 agonist activity was assessed for IgG1-CD134-003-HC6LC2-RR, IgG1-CD134-11D4, IgG1-RG7888, and IgG1-CD134-IBI101. In all experiments described herein, nonbinding control antibody IgG1-b12-RR was used as a negative control.

The assay was performed essentially as described in Example 6 with a few exceptions: here, OX40-expressing Jurkat cells were stimulated with anti-human OX40 antibodies either in the absence or presence of CHO-K1 cells transfected to express human Fcγ receptor 2B (Promega, cat. no. JA2255; FcγRIIb-CHO K1 cells). Vials of FcγRIIb-CHO K1 cells were thawed and cells were suspended in 14.5 to 29 mL RPMI 1640 medium(provided with Promega kit, cat. no. JA2191) supplemented with 5% fetal bovine serum(FBS, provided with Promega kit, cat. no. JA2191). The cells were plated in a 96-well white flat-bottom assay plate (Fisher Scientific, cat. no. 10072151) at 100 μl per well. After 5 to 6 h of incubation (37° C., 5% $CO_2$), the medium was discarded from the wells and OX40-expressing Jurkat effector cells were added at 60 μL per well (with or without FcγRIIb-CHO K1 cells), and incubated for 16-20 h (37° C., 5% $CO_2$). In addition, here, luminescence was measured using a CLARIOstar® Plus microplate reader (BMG Labtech). Data were fitted with the sigmoidal, 4PL, X is log

TABLE 12

Binding of IgG1-CD134-003-HC6LC2-RR to activated human T cells in the presence of soluble OX40L and vice versa.

| | | IgG1-CD134-003-HC6LC2-RR binding | | | |
|---|---|---|---|---|---|
| | | Average $EC_{50}$ ± SD (μg/mL) | | Average $EC_{50}$ ± SD (nM) | |
| | n | $CD4^+$ | $CD8^+$ | $CD4^+$ | $CD8^+$ |
| IgG1-CD134-003-HC6LC2-RR | 3 | 0.019 ± 0.009 | 0.017 ± 0.004 | 0.130 ± 0.058 | 0.114 ± 0.029 |
| IgG1-CD134-003-HC6LC2-RR + 2 μg/mL sOX40L | 3 | 0.054 ± 0.022 | 0.038 ± 0.009 | 0.359 ± 0.150 | 0.254 ± 0.061 |

| | | sOX40L binding | | | |
|---|---|---|---|---|---|
| | | Average $IC_{50}$ ± SD (μg/mL) | | | |
| | | $CD4^+$ | $CD8^+$ | $CD4^+$ | $CD8^+$ |
| IgG1-CD134-003-HC6LC2-RR + 2 μg/mL sOX40L | 3 | 0.086 ± 0.014 | 0.084 ± 0.005 | 0.579 ± 0.094 | 0.561 ± 0.037 |

(concentration) equation and presented as RLU in line graphs generated using GraphPad Prism software. $EC_{50}$ values were derived from the fitted curves.

IgG1-CD134-003-HC6LC2-RR induced potent dose-dependent OX40 agonist activity, independent of Fc engagement via FcγRIIb-expressing cells (FIG. 21A). In the absence of FcγRIIb-expressing cells, strong OX40 agonist activity was only observed for anti-human OX40 antibodies containing a hexamerization-enhancing mutation (IgG1-CD134-003-HC6LC2-RR and IgG1-CD134-003-E345R), whereas anti-human OX40 antibodies without a hexamerization-enhancing mutation (IgG1-CD134-003 and IgG1-CD134-003-FEAL) induced only very weak OX40 signaling. The presence of FcγRIIb-expressing cells clearly enhanced OX40 signaling activity for the FcγR-binding anti-human OX40 antibodies (IgG1-CD134-003 and IgG1-CD134-003-E345R), whereas addition of FcγRIIb-expressing cells did not or only minimally increase activity for the anti-human OX40 antibodies with an inert Fc backbone (IgG1-CD134-003-HC6LC2-RR and IgG1-CD134-003-FEAL).

In contrast to IgG1-CD134-003-HC6LC2-RR, the anti-human OX40 antibodies IgG1-CD134-11D4, IgG1-RG7888, and IgG1-CD134-IBI101 only induced OX40 agonist activity in the presence, and not in the absence, of FcγR-expressing cells in the described assay (FIG. 21B).

In conclusion, IgG1-CD134-003-HC6LC2-RR induced potent dose-dependent OX40 agonist activity independently of FcγR-expressing cells, in contrast to other anti-human OX40 antibodies lacking a hexamerization-enhancing mutation.

Example 13: Expression of T-Cell Activation Markers Upon Incubation with IgG1-CD134-003-HC6LC2-RR Using the T-cell proliferation assay described in Example 7, the expression of T-cell activation-associated cell surface-expressed markers after incubation of healthy human donor PBMCs with IgG1-CD134-003-HC6LC2-RR was studied. Also, the potency to enhance expression of T-cell activation-associated cell surface-expressed markers was assessed for OX40 agonistic reference antibody analogs IgG1-CD134-BMS986178, IgG1-CD134-RG7888, and IgG1-CD134-IBI101. To measure the expression levels of 4-1BB, CD25, HLA-DR, and PD-1 on CD4$^+$ and CD8$^+$ T cells, the cells were washed and stained for CD4, CD8, 4-1BB, CD25, HLA-DR, PD-1, as well as viability, in 30 μL FACS buffer with a titrated amount of antibody (Table 13), Viability Dye eFluor 780 (1:1,500; ThermoFisher Scientific, cat. no. 65-0865-14) and brilliant stain buffer plus (1:10; BD Biosciences, cat. no. 566385) in 96-well round-bottom plates (VWR International, cat. no. 734-1797). The staining procedure was carried out at 4° C. for 15 min protected from light. Cells were then washed twice with 150 μL FACS buffer and resuspended in 60-100 μL FACS buffer for flow cytometry analysis. Flow cytometry data were acquired on a BD FACSymphony A3 flow cytometer using a BD High Throughput sampler. The percentages of cells expressing the activation markers 4-1BB, CD25, HLA-DR, and PD-1 within the CD4$^+$ and CD8$^+$ T-cell populations were determined using FlowJo and presented in line curves using GraphPad Prism.

TABLE 13

Antibody panel used to assess expression levels of T-cell activation associated markers.

| Target | Clone | Label | Cat. no. | Supplier | Dilution |
|---|---|---|---|---|---|
| CD4 | OKT4 | APC | 17-0048-42 | ThermoFisher Scientific | 1:100 |
| CD8α | SK1 | BV605 | 564116 | BD Biosciences | 1:400 |
| 4-1BB | 4B4-1 | BV711 | 740798 | BD Biosciences | 1:80 |
| CD25 | 2A3 | BUV395 | 564034 | BD Biosciences | 1:80 |
| HLA-DR | L243 | PE-Cy7 | 307616 | BioLegend | 1:50 |
| PD-1 | EH12.2H7 | AF488 | 329936 | BioLegend | 1:50 |

Expression of activation markers was analyzed after two and five days of IgG1-CD134-003-HC6LC2-RR incubation. In all donors, IgG1-CD134-003-HC6LC2-RR increased CD4$^+$ and CD8$^+$ T-cell proliferation dose-dependently, as assessed on day five (data not shown). IgG1-CD134-003-HC6LC2-RR induced a dose-dependent increase in the percentages of CD4$^+$ and CD8$^+$ T cells expressing 4-1BB, CD25, and HLA-DR either on day two or five, or both days, but not PD-1 on most donors analyzed (FIG. 22A-H).

In contrast to IgG1-CD134-003-HC6LC2-RR, the tested OX40 agonistic reference antibody analogs IgG1-CD134-RG7888, IgG1-CD134-BMS986178 and IgG1-CD134-IBI101 did not increase the percentage of CD4$^+$ and CD8$^+$ T cells expressing 4-1BB, CD25 or HLA-DR (FIG. 22I-P).

Example 14: IgG1-CD134-003-HC6LC2-RR Enhances Cytokine Secretion in a Polyclonally Activated T-Cell Proliferation Assay Using Healthy Human Donor PBMCs Cytokine concentrations in supernatants that were collected from a polyclonal T-cell proliferation assay (general assay set-up described in Example 7; cells were either stained with CellTrace Violet [using the CellTrace™ Violet Kit, Thermo Fisher Scientific, cat. no. C34557] or CFSE [using the Vybrant CFDA SE Cell Tracer Kit, Life Technologies, cat. No. V12883]) after 1, 2, 3, 4, and/or 6 days of culture were determined by multiplexed ECLIA using the V-Plex Proinflammatory Panel 1 Human Kit (as 10-plex: IFN-γ, IL-1β, IL-2, IL-4, IL-6, IL-8, IL 10, IL 12p70, IL-13 and TNF-α; MSD, cat. no. K15049D-2) or the V-PLEX Human Proinflammatory Panel I Kit (4-plex: IFN-γ, IL-1β, IL-6 and TNF-α, MSD, cat. no. K15052D-2) following the manufacturer's protocol. Briefly, after MSD plates had been washed with 150 μL PBST (DPBS with 0.05% Tween® 20 [Sigma-Aldrich, cat. no. P7949]), standards or samples (1:2-1:200 diluted) were added to the wells (50 μL/well) and the plates incubated for 2 h at RT with constant shaking. The plates were washed 3 times with PBST and detection antibodies (25 μl/well) were added. Following incubation for 2 h at RT with constant shaking, the plates were washed 3 times with PBST. Subsequently, the read buffer was added (150 μL/well) and the plates were immediately analyzed on a MESO QuickPlex SQ 120 reader. In addition, cytokine concentrations were determined in supernatants collected from the mentioned polyclonal T-cell proliferation assay, after four days of culture, from which either CD4⁺ or CD8⁺ T cells were depleted, following the procedures as described in Example 7. Also, the capacity of IgG1-CD134-003-HC6LC2-RR to induce cytokine secretion was compared to anti-human OX40 antibodies IgG1-h3C8-K322A-E345R, IgG1-CD134-h3C8-E345R-LALAPG, IgG1-CD134-RG7888-K322A-E345R, IgG1-CD134-RG7888-E345R-LALAPG, and IgG2s-CD134-SF2-E345R after four 4 days of culture. Non-binding antibody IgG1-b12-RR was used as a negative control. Results were presented in line graphs using GraphPad Prism.

In all donors, IgG1-CD134-003-HC6LC2-RR increased CD4⁺ and CD8⁺ T-cell proliferation dose-dependently (data not shown). In a kinetic experiment, IgG1-CD134-003-HC6LC2-RR enhanced cytokine secretion at the highest tested concentrations of IgG1-CD134-003-HC6LC2-RR (0.2 and 2 μg/mL), after three to four days for TNFα (FIG. 23A), after two days for IL-2, followed by a relatively rapid decrease on day three to six (FIG. 23B), and after two days for IFNγ (FIG. 23C) and IL-13 (FIG. 23D).

IgG1-CD134-003-HC6LC2-RR induced an increase in TNFα, IFNγ, and IL-13 secretion in CD8⁺ T-cell depleted PBMCs on day four, whereas these cytokines were not or only minimally secreted in CD4⁺ T-cell depleted PBMCs (FIG. 24).

IgG1-CD134-003-HC6LC2-RR induced higher cytokine levels of TNFα, IL-2, and IL-13, while a similar trend was observed for IFNγ, despite relatively large variations between duplicate measurements in the latter case, as compared with variants of IgG1-CD134-h3C8 and IgG1-CD134-RG7888 (harboring the K322A-E345 or E345R-LALAPG mutations), and IgG2s-CD134-SF2-E345R (FIG. 25, 26, 27).

In summary, the results described here indicate that IgG1-CD134-003-HC6LC2-RR enhanced proinflammatory cytokine release in a polyclonal T-cell proliferation assay using healthy human donor PBMCs, which was dependent on the presence of CD4⁺ T cells. Moreover, IgG1-CD134-003-HC6LC2-RR more potently enhanced cytokine secretion in this assay than the other tested hexamerization-enhanced anti-human OX40 antibodies, namely variants of IgG1-CD134-h3C8, IgG1-CD134-RG7888, and IgG2s-SF2.

Example 15: Capacity of IgG1-CD134-003-HC6LC2-RR to Enhance CD8⁺ T-Cell Proliferation in an Antigen-Specific T-Cell Proliferation Assay The capacity of IgG1-CD134-003-HC6LC2-RR to increase CD8⁺ T-cell proliferation was studied by flow cytometry using T cells that were stimulated by their cognate antigen. Human CD8⁺ T cells electroporated with OX40 and a TCR that recognizes a CLDN6-derived peptide presented by major histocompatibility type I (MHC-I) molecules were cocultured with autologous immature moDCs (iDCs) electroporated with human full-length CLDN6.

PBMCs were isolated from buffy coats obtained from healthy human donors by Ficoll-Paque density gradient separation, essentially as described in Example 7 and used for cell separation. Before cell separation, PBMCs were confirmed to be HLA-A*02-positive by flow cytometry. MACS columns or an AutoMACS Pro Separator (both Miltenyi Biotec GmbH) were used for cell separation, depending on availability. CD14 magnetic microbeads (Miltenyi Biotec GmbH, cat. no. 130-050-201) were used to positively select CD14+ monocytes and negatively select CD14 peripheral blood lymphocytes (PBL) from freshly isolated PBMCs. CD8 magnetic microbeads were used to isolate CD8+ T cells from previously frozen PBLs. The separation procedure was generally carried out according to the manufacturer's instructions with a minor modification (volume of microbeads was reduced; 12 μl beads per $10^7$ cells) and was in principle the same for the separation of CD14⁺/CD14⁻ cells and the isolation of CD8⁺ T cells.

The isolated CD14⁺ monocytes were differentiated into iDCs. To this end, up to 40×10⁶ CD14⁺ monocytes per T175 suspension culture flask (Greiner Bio-One GmbH, cat. no. 661195) were cultured in DC medium (RPMI 1640, 5% PHS, 1×minimum essential medium nonessential amino acids [MEM-NEAA; Life Technologies GmbH, cat. no. 11140-035], 1 mM sodium pyruvate [Life Technologies GmbH, cat. no. 11360-039]) containing 200 ng/ml GM-CSF (Miltenyi Biotec GmbH, cat. no. 130-093-868) and 200 ng/ml IL-4 (Miltenyi Biotec, cat. no. 130-093-924) for five days in the incubator (37° C., 5% $CO_2$). After three days in culture, half of the medium per flask was changed. Since the medium taken from the flask contained nonadherent monocytes, it was centrifuged (8 min, 300×g, RT), the supernatant discarded, the cell pellet resuspended in fresh DC medium and then returned into the originator flask together with 200 ng/ml GM-CSF and 200 ng/ml IL-4 (final concentration). After five days, adherent cells were detached from the cell culture flasks by incubation with 10 mL DPBS containing 2 mM EDTA for 10 min at 37° C. and harvested together with nonadherent cells prior to further use. The iDCs were washed (8 min, 300×g, RT) with DPBS, counted and cryo-preserved in FBS (Sigma-Aldrich, cat. no. F7524) containing 10% DMSO (AppliChem GmbH, cat. no. A3672,0100) or resuspended in X-VIVO 15 medium for direct electroporation.

CD8⁺ T cells, isolated from PBLs, and iDCs were electroporated using an ECM 830 Electroporation System. CD8⁺ T cells were electroporated with RNAs encoding the alpha- and beta-chain of a CLDN6 specific TCR (10 μg each, TCR #12a, TCR #12B), and 10 μg OX40-encoding RNA. IDCs were electroporated with 2 μg RNA encoding CLDN6 or without RNA as mock control (Table 14).

TABLE 14

| RNA used for electroporation | |
|---|---|
| RNA | Description |
| CLDN6 | RNA encoding human CLDN6 (GRCh37 code uc002csu.5) |
| OX40 | RNA encoding human OX40 (UniProt P43489) |
| TCR#12α | RNA encoding CLDN6-specific TCR alpha chain (WO_2015_150327) |
| TCR#12β | RNA encoding CLDN6-specific TCR beta chain (WO_2015_150327) |

Electroporation of iDCs was generally carried out with $5 \times 10^6$ cells in 250 UL X-VIVO 15 medium. T cells were electroporated at a higher cell density of 10 to $15 \times 10^6$ cells in 250 µL X-VIVO 15 medium. The cells were pipetted into the cuvettes (4.0 mm gap size; VWR International, cat. no. 732-0023) at RT. The RNA was added to the cells and mixed by pipetting. Immediately after mixing the electroporation was performed at 500 V, 3 ms, and 1 pulse for T cells and at 300 V, 12 ms, 1 pulse for iDCs. Immediately after electroporation, 750 µL prewarmed assay medium (IMDM, 5% PHS) was added to the cells. To evaluate electroporation efficiency, $2.5 \times 10^5$ iDCs per well and 2 to $3 \times 10^5$ CD8$^+$ T cells per well (nonelectroporated cells and electroporated post-CFSE staining, see below) were cultured in 96-well round-bottom plates in 150 µL assay medium. The remaining iDCs were transferred to 6-well plates (Greiner, cat. no. 657160) and cultured O/N in 3 mL assay medium per 6-well and electroporation (37° C., 5% $CO_2$). Electroporated T cells were transferred to a 15 ml tube and incubated for at least 2 h (37° C., 5% $CO_2$) prior to labeling with CFSE.

Electroporated CD8$^+$ T cells were labeled with CFSE using the Vybrant CFDA SE Cell Tracer Kit (Life Technologies GmbH, cat. no. V12883). CFSE was dissolved in DMSO at a stock concentration of 9 mM and stored in aliquots at −20° C. PBMCs were washed with DPBS (8 min, 300×g, RT). The pellets were resuspended in DPBS at a concentration of $20 \times 10^6$ cells/mL. An equal volume of 1.6 M CFSE solution (diluted in DPBS from stock) was added. The cells were incubated for 10 min in the incubator (37° C., 5% $CO_2$). The labeling reaction was stopped by adding a twofold excess volume of FBS (Sigma-Aldrich, cat. no. F7524) followed by resting for 2 min at RT. To wash the cells, the volume of the cell suspension was topped with assay medium, followed by centrifugation (8 min, 300×g, RT). After CFSE-labeling, the cells were resuspended in 3 mL assay medium per electroporation, transferred to a 6-well plate and cultured O/N (37° C., 5% $CO_2$).

Electroporated iDCs and CFSE-labeled CD8+ T cells were harvested after O/N incubation and counted using C-Chip cell counting chambers and erythrosine B solution. The concentration was adjusted to $1.5 \times 10^6$ T cells/mL and $1.5 \times 10^5$ iDCs/mL in assay medium. CD8$^+$ T cells and iDCs were seeded at a 10:1 ratio ($7.5 \times 10^4$ T cells and $7.5 \times 10^3$ iDCs per well) in a 96-well round-bottom plate. For IgG1-CD134-003-HC6LC2-RR dose-response analysis, serial dilutions were prepared of IgG1-CD134-003-HC6LC2-RR (0.0003 to 10 µg/ml, final concentration). IgG1-b12-RR was used as nonbinding control antibody at the same concentrations as IgG1-CD134-003-HC6LC2-RR. Diluted antibodies were added to the seeded cells. Assay medium was added as appropriate to reach a total volume of 150 UL in each well. The plates were rocked gently on a vibrating platform (150 RPM, 1 min) and cultured for four days (37° C., 5% $CO_2$). Proliferation of cells was analyzed by flow cytometry as described below.

For proliferation analysis, cultured cells were stained with CD8 antibody (BD Biosciences, cat. no. 564116; dilution 1:400) and Fixable Viability Dye eFluor780 (ThermoFisher Scientific, cat. no. 65-0865-14; 1:1,500) in 30 µL FACS buffer in 96-well round-bottom plates. The staining and washing procedures were carried out as described in Example 10. Flow cytometry data were acquired on a BD FACSCelesta flow cytometer using a BD™ High Throughput sampler. Flow cytometry data were analyzed with FlowJo software.

The expansion index values were plotted against the respective antibody concentrations using GraphPad Prism software and the data fit with the 'sigmoidal, 4PL, X is log (concentration)' equation. $EC_{50}$ values were derived from the fitted curves.

IgG1-CD134-003-HC6LC2-RR induced a dose-dependent increase in the proliferation of purified CFSE-labeled OX40- and CDLN6-TCR-electroporated CD8$^+$ T cells that were cocultured with autologous CLDN6-electroporated iDCs for four days (FIG. 28A). IgG1-CD134-003-HC6LC2-RR only increased CD8$^+$ T-cell proliferation in presence of antigen stimulation, confirming that TCR activation is a prerequisite for OX40 costimulation and that IgG1-CD134-003-HC6LC2-RR did not induce proliferation of resting T cells (FIG. 28B).

Example 16: Binding of IgG1-CD134-003-HC6LC2-RR to FcγRIa-Expressing Human Monocyte-Derived M2c-Like Macrophages To evaluate whether the minimal binding of IgG1-CD134-003-HC6LC2-RR to FcγRIa described in Example 8, as detected by SPR, could be of biological relevance, binding of IgG1-CD134-003-HC6LC2-RR to physiologically expressed FcγRIa by human monocyte-derived M2c-like macrophages was assessed by flow cytometry.

To this end, human peripheral blood mononuclear cells (PBMCs) were purified from buffy coats of healthy human donors (Sanquin blood supply foundation, the Netherlands) in LeucoSep™ tubes (Greiner, cat. no. 227290) by density gradient centrifugation (20 min at 800×g, with low brake) over Lymphocyte Separation Medium (Promocell, cat. no. C-44010), according to the manufacturer's instructions. The PBMC layer was carefully transferred to 50 ml tubes and washed with excess volume of PBS (HyClone, cat. no. SH3A3830.03). Purified PBMCs were pelleted by centrifugation (10 min at 300×g), washed and resuspended in PBS, and counted on a Cellometer Auto 2000 Cell Viability Counter (Nexcelom Bioscience) using Cellometer ViaStain™ AOPI Staining Solution (Nexcelom Bioscience, cat. no. CS2-0106) in PBS to discriminate live from dead cells.

Human monocytes were purified from PBMCs by positive selection using CD14 MicroBeads (Miltenyi Biotec, cat. no. 130-050-201), according to the manufacturer's instruction. The CD14+ cells were counted and resuspended at a density of $1.0 \times 10^6$ cells/mL in CellGenix® GMP DC medium (CellGenix, cat. no. 20801-0500) supplemented with 50 ng/ml macrophage colony-stimulating factor (M-CSF; Gibco, cat. no. PHC9501).

For the polarization of monocytes toward M2c-like macrophages, purified monocytes were plated in 100 mm2 Nunc™ dishes with UpCell™ Surface ($8 \times 10^6$ cells/dish at a density of $1.0 \times 10^6$ cells/ml; Thermo Fisher Scientific, cat. no. 174902) in M-CSF-supplemented CellGenix GMP DC medium (CellGenix, cat. no. 20801-0500). Cells were cultured (37° C./5% $CO_2$) in above-mentioned medium for 7 days, followed by 3 days of culture in CellGenix GMP DC medium supplemented with 50 ng/ml M-CSF, 50 ng/ml interleukin (IL)-4 (R&D Systems, cat. no. 204-IL), and 50 ng/ml IL-10 (R&D Systems, cat. no. 1064-IL/CF). After ten days of culture, macrophages were detached from the culture dish surface by leaving the dish at RT for 40 to 60 min. Detached macrophages were pelleted by centrifugation (5 min at 300×g), counted and resuspended at a density of $1.5 \times 10^6$ cells/mL in CellGenix GMP DC medium.

The M2c-like phenotype of the monocyte-derived macrophages, and their concomitant expression of FcγRIa, was confirmed by flow cytometry. Cells were plated in 96-well round bottom plates (75,000 cells/well; Thermo Fisher Scientific, cat. no. 163320), centrifuged, and washed twice in FACS buffer. Next, cells were incubated with 50 μL of FITC-labeled anti-human CD64 (FcγRIa) antibody (BioLegend, cat. no. 305006; diluted 1:25) or with 50 μl of a mixture of antibodies for human M2c macrophage characterization (Table 15) in FACS buffer at 4° C. for 30 min, protected from light, and were subsequently washed twice in FACS buffer.

TABLE 15

Antibody panel used for confirmation of M2c phenotype

| Target | Label | Clone | Isotype | Supplier | Cat. no. | Dilution |
|---|---|---|---|---|---|---|
| Human CD163 | BV421 | GHI/61 | Mouse IgG1, κ | BioLegend | 333612 | 1:200 |
| Human CD206 | BV711 | 15-2 | Mouse IgG1, κ | BioLegend | 321136 | 1:200 |

Next, cells that were incubated with antibodies for M2c characterization were resuspended in 100 μL FACS buffer supplemented with viability marker 7-AAD (7 aminoactinomycin D; BD Pharmingen, cat. no. 68981E; diluted 1:240) and were measured on a BD FACSymphony™ Cell Analyzer (BD Biosciences). Cells that were incubated with FcγRIa antibody were resuspended in 100 μL FACS buffer supplemented with viability marker DAPI (4',6-diamidino-2-phenylindol; BD Pharmingen, cat. no. 564907; diluted 1:5,000) and measured on a BD LSRFortessa™ Cell Analyzer.

To assess binding of IgG1-CD134-003-HC6LC2-RR, monocyte-derived macrophages were plated in 96-well round-bottom plates (75,000 cell/well), washed twice using FACS buffer, and incubated with 50 μl of IgG1-CD134-003-HC6LC2-RR, IgG1-b12, or IgG1-b12-RR in CellGenix GMP DC medium(final antibody concentration of 10 μg/mL) at 37° C./5% $CO_2$ for either 15 min or 24 h. Next, cells were washed twice using FACS buffer and incubated with 50 μl of R-PE-conjugated goat anti-human IgG F(ab')2 (Jackson ImmunoResearch, cat. no. 109 116 097; diluted 1:200) in FACS buffer at 4° C. for 30 min. After washing twice in FACS buffer, cells were resuspended in 100 μL FACS buffer supplemented with viability marker DAPI (BD Pharmingen, cat. no. 564907; diluted 1:5,000) and were subsequently measured on a BD LSRFortessa Cell Analyzer.

IgG1-b12, which has a wild-type Fc domain, was included as a positive control for binding to M2c-like macrophages, and Fc-inert IgG1-b12-RR was included as a negative control. Whereas IgG1-b12 showed efficient binding to the FcγRIa-expressing M2c-like macrophages after 15 min and 24 h of incubation, no binding was observed for IgG1-CD134-003-HC6LC2-RR and IgG1-b12-RR at either of the time points for any of the three donors tested (FIG. 29). In addition, no binding was observed by IgG1-CD134-003-HC6LC2-RR to cynomolgus monkey FcγRIa expressed by cynomolgus monkey monocytes (data not shown). Therefore, IgG1-CD134-003-HC6LC2-RR is considered unable to bind FcγRIa in a physiological setting.

Example 17: Binding of IgG1-CD134-003-HC6LC2-RR to the Neonatal Fc Receptor

The binding of IgG1-CD134-003-HC6LC2-RR to immobilized neonatal Fc receptor (FcRn) was assessed in vitro at pH 6.0 and pH 7.4 by SPR. Aliquots of recombinant His-tagged FcRn protein (SinoBiological, cat. no. CT009-H08H-B) were diluted in PBS-P+ buffer pH 7.4 (Cytiva, cat. no. 28995084) or in PBS-P+ buffer with the pH adjusted to 6.0 (by addition of hydrochloric acid [Sigma-Aldrich, cat. no. 30721-M]) and were used for capturing of FcRn protein onto the surface of anti-His antibody-coated sensor chips using a flow rate of 10 μL/min and a contact time of 60 s. This resulted in captured levels ranging from 35 to 60 RU.

After three start-up cycles of pH 6.0 or pH 7.4 PBS-P+ buffer, concentration series of antibodies (6.25 to 100 nM in twofold dilution steps in pH 6.0 or pH 7.4 PBS-P+ buffer) were injected to generate binding curves. Each sample that was analyzed on a surface with captured FcRn (active surface) was also analyzed on a parallel flow cell without captured FcRn (reference surface), which was used for background correction. The signal of the third start-up cycle containing HBS-EP+ as a (mock) analyte was subtracted from other sensorgrams to yield double-referenced data. At the end of each cycle, the surface was regenerated using 10 mM Glycine HCl pH 1.5 (Cytiva, cat. no. BR100354). The data were analyzed using the predefined "Multi-cycle kinetics using capture" evaluation method in the Biacore Insight Evaluation software (Cytiva).

At pH 6.0, dose-dependent binding of IgG1-CD134-003-HC6LC2-RR to FcRn was observed (FIG. 30A-E), whereas no FcRn binding was observed at pH 7.4 (FIG. 30F). These results show that IgG1-CD134-003-HC6LC2-RR binds FcRn at pH 6.0 but not at pH 7.4, as expected for an IgG1 molecule.

Example 18: Assessment of C1q Binding to Membrane-Bound IgG1-CD134-003-HC6LC2-RR To confirm lack of complement binding to the Fc domain of IgG1-CD134-003-HC6LC2-RR, binding of C1q to IgG1-CD134-003-HC6LC2-RR bound to OX40 expressed on the membrane of activated human T cells was determined by flow cytometry. As a positive control for C1q binding, IgG1-CD52-E345R (VH SEQ ID No: 64, VL SEQ ID No: 68; Constant region SEQ ID No: 2), which bears the same hexamerization-enhancing mutation as IgG1-CD134-003-HC6LC2-RR but lacks the Fc inertness mutation, was included. Fc-inert non-binding control antibody IgG1-b12-RR was included as a negative control.

Human T cells were purified from buffy coats obtained from healthy volunteers (Sanquin blood supply foundation, the Netherlands) by negative selection using the RosetteSep™ Human T Cell Enrichment Cocktail (Example 9) followed by density centrifugation (800×g, 20 min, with low brake) over Lymphocyte Separation Medium(Corning, cat. no. 25-072-CI), all according to the manufacturer's instructions.

Purified T cells were washed in PBS (HyClone), pelleted, and resuspended in activation medium(RPMI 1640 with 25 mM HEPES and L-glutamine [Lonza, cat. no. BE12-115F] supplemented with 10% FBS [Sanquin, cat. no. K1146], 50 units penicillin and 50 μg/ml streptomycin [Lonza, cat. no. DE17-603E], and 1% L-glutamine [Lonza, cat. no. BE17-

605E]). Next, T cells were counted on a Cellometer Auto 2000 Cell Viability Counter (Nexcelom Bioscience), using Cellometer ViaStain™ AOPI Staining Solution (Nexcelom Bioscience, cat. no. CS2-0106) to discriminate live from dead cells. Cells were subsequently plated in round-bottom 96-well plates (Thermo Fisher Scientific, cat. no. 170189; $3 \times 10^5$ cells/well in 150 µL). To induce OX40 expression, T cells were activated by incubation with anti-CD3/CD28 beads (Dynabeads™ Human T-Activator CD3/CD28; Thermo Fisher Scientific, cat. no. 11132D) at a 1:2 bead to cell ratio at 37° C. for 72 h. After incubation, the beads were removed using a magnet and the cells were pooled, washed once in PBS, and counted.

To assess binding of C1q to cell-bound IgG1-CD134-003-HC6LC2-RR, the CD3/CD28-activated human T cells were plated in round-bottom 96-well plates (50,000 cells/well) and incubated with serial dilutions of IgG1-CD134-003-HC6LC2-RR, IgG1-CD52-E435R, or IgG1-b12-RR (final concentration of 0.00051 to 30 µg/ml in 3-fold dilution steps) in activation medium in a total volume of 80 µl at 37° C. for 15 min to allow the antibodies to bind to the cells. Next, 20 µl of normal human serum (NHS; Sanquin; final concentration of 20%) was added as a source of C1q and the mixture was incubated on ice for 45 min. Cells were washed twice with cold FACS buffer and subsequently incubated with 50 µl of a mixture of fluorescein isothiocyanate (FITC)-conjugated rabbit anti-human C1q antibody (DAKO, cat. no. F0254; diluted 1:100; final concentration of 20 µg/mL) and antibodies for human T-cell characterization (Table 16) in FACS buffer at 4° C. for 30 min, protected from light.

TABLE 16

Antibody panel used for T-cell characterization.

| Target | Label | Clone | Isotype | Supplier | Cat. no. | Dilution |
|---|---|---|---|---|---|---|
| Human CD4 | Pacific Blue | RPA-T4 | Mouse IgG1, κ | BioLegend | 300521 | 1:200 |
| Human CD8 | APC-Cy7 | RPA-T8 | Mouse IgG1, κ | BD Biosciences | 557834 | 1:100 |

Next, cells were washed twice with cold FACS buffer, pelleted, and resuspended in 80 µL FACS buffer supplemented with viability marker TO-PRO™-3 Iodide (Invitrogen, cat. no. T3605; diluted 1:10,000). C1q binding was analyzed by flow cytometry on a BD FACSCelesta™ Cell Analyzer (BD Biosciences). Binding curves were analyzed using nonlinear regression analysis (sigmoidal dose-response with variable slope) using GraphPad Prism software. Binding of OX40 antibodies to the activated T cells was assessed after the incubation step with serial dilutions of antibodies. Cells were washed twice with cold FACS buffer and incubated with 50 µl of a mixture of R-phycoerythrin (R-PE)-conjugated goat anti-human IgG F(ab')2 (Jackson ImmunoResearch, cat. no. 109-116-098; diluted 1:200) and antibodies for human T-cell characterization (Table 16) in FACS buffer at 4° C. for 30 min, protected from light. Next, cells were washed twice with cold FACS buffer, pelleted, and resuspended in 80 µL FACS buffer supplemented with viability marker TO-PRO-3 Iodide (diluted 1:10,000). Antibody binding was analyzed by flow cytometry on a BD FACSCelesta Cell Analyzer. Binding curves were analyzed using nonlinear regression analysis (sigmoidal dose-response with variable slope) using GraphPad Prism software.

Binding of IgG1-CD134-003-HC6LC2-RR and IgG1-CD52-E345R to the activated CD4+ and CD8+ T cells was confirmed by flow cytometry (FIG. 31A-C). While C1q efficiently bound to membrane-bound IgG1-CD52-E345R, no binding of C1q to membrane-bound IgG1-CD134-003-HC6LC2-RR was observed at any of the tested antibody concentrations (FIG. 31D, E). No binding of C1q was observed to cells incubated with IgG1-b12-RR. These results indicate that C1q cannot bind membrane-bound IgG1-CD134-003-HC6LC2-RR.

To confirm that IgG1-CD134-003-HC6LC2-RR does not induce target-independent fluid-phase complement activation, IgG1-CD134-003-HC6LC2-RR was incubated in normal human serum(NHS) and production of C4d, as a measure for complement activation, was determined by ELISA. It was shown that IgG1-CD134-003-HC6LC2-RR did not induce fluid-phase complement activation in vitro (data not shown).

Example 19: Assessment of Monovalent Versus Bivalent Binding of IgG1-CD134-003-HC6LC2-RR and Variants Thereof To determine if IgG1-CD134-003-HC6LC2-RR binds monovalently or can also bind bivalently to OX40, binding of IgG1-CD134-003-HC6LC2-RR to activated T cells was compared with binding of a functionally monovalent OX40-specific antibody (BsIgG1-b12-RR-F405LxCD134-003-RR-K409R; generated through controlled Fab-arm exchange of parental antibodies IgG1-b12-RR-F405L [comprised of SEQ ID No 78, 75 and 71] and IgG1-CD134-003-RR-K409R [comprised of SEQ ID No 63, 21 and 20]). Healthy donor T cells were stimulated in vitro with anti-CD3/CD28 beads for three days to induce OX40 expression. Subsequently, binding of IgG1-CD134-003-HC6LC2-RR, monovalent-binding antibody BsIgG1-b12-RR-F405LxCD134-003-RR-K409R, chimeric control antibody IgG1-CD134-003, or negative control antibody IgG1-b12-RR, to the activated CD4+ and CD8+ T cells was analyzed by flow cytometry.

Total human T cells were enriched by negative selection directly from buffy coats as described in Example 18. The enriched T cells were washed once or twice in PBS (Capricorn Scientific, cat. no. SP-2121-500 mL) or in PBS supplemented with 2% DBSi (Gibco, cat. no. 20371-030) and 2 mM EDTA (Sigma-Aldrich, cat. no. 03690). Purified cells were counted on a Cellometer Auto 2000 Cell Viability Counter (Nexcelom Biosciences) using Cellometer ViaStain® AOPI solution (Nexcelom Bioscience, cat. no. CS2-0106) in PBS to discriminate live from dead cells. T cells were pelleted and resuspended in activation medium.

T cells were activated by CD3 and CD28 stimulation for 72 h using anti-CD3/CD28 beads (Dynabeads™ Human T-Activator CD3/CD28) as described in Example 9; ThermoFisher Scientific, cat. no. 11131D). Activated T cells were either used directly or cryopreserved in a 1:1 mixture of IMDM medium with L-Glutamine and HEPES (Lonza, cat. no. 12-115F) and cryoprotective freezing medium(Lonza; cat. no. 12-132A) for further use.

Activated T cells were seeded (50,000 cells/well) in round-bottom 96-well plates (Thermo Scientific, cat. no.

163320) washed once with PBS (GE Healthcare, cat. no. SH3A3830.03) and once with FACS buffer. after which the cells were resuspended in 50 µl of primary antibodies (IgG1-CD134-003-HC6LC2-RR, BsIgG1-b12-RR-F405LxCD134-003-RR-K409R, or control antibodies IgG1-CD134003-RR-K409R, IgG1-b12-RR, and IgG1-CD134-003) diluted in FACS buffer at concentrations ranging from 0.0005 to 10 µg/ml, in threefold dilution steps and incubated at 4° C. for 30 min measured by flow cytometry on a BD FACSymphony A1 Cell Analyzer (BD Biosciences) and analyzed using FlowJo software.

The monovalent OX40-specific antibody BsIgG1-b12-RR-F405LxCD134-003-RR-K409R showed dose-dependent binding to activated $CD4^+$ and $CD8^+$ T cells, with higher maximal binding to both CD4+ and CD8+ T cells compared with IgG1-CD134-003-HC6LC2-RR, as defined by the gMFI Y-span (FIG. 32). The chimeric control antibody IgG1-CD134-003 showed similar binding to $OX40^+$ $CD4^+$ and $CD8^+$ T cells as IgG1-CD134-003-HC6LC2-RR, indicating that higher maximal binding was driven by monovalency of BsIgG1-b12-RR-F405LxCD134-003-RR-K409R rather than CDR chimerism or the functionally irrelevant mutations in the different Fc backbone. These data suggest that IgG1-CD134-003-HC6LC2-RR does not exclusively bind in a monovalent manner but may also bind bivalently.

Example 20: Functional Comparison of IgG1-CD134-003-HC6LC2-RR and a Monovalently Binding Variant Thereof As described in Example 19, IgG1-CD134-003-HC6LC2-RR does not exclusively bind in a monovalent manner but may also bind bivalently. Here, the functional activity of IgG1-CD134-003-HC6LC2-RR and monovalently binding variant BsIgG1-b12-RR-F405LxCD134-003-RR-K409R was compared in two separate assays, namely a cell-based OX40 reporter assay and a polyclonal T-cell proliferation assay using healthy human donor PBMCs.

To measure OX40 agonist activity in a cellular reporter assay, the OX40 Bioassay kit (Thaw and Use Kit; Promega, cat. no. JA2191) was used, essentially as described in Example 6. Briefly, after thawing, OX40+Jurkat cells were plated in a fresh 96-well white flat-bottom assay plate (PerkinElmer, cat. no. 6005680) at 60 µl per well and incubated for 16-20 h (37° C., 5% $CO_2$). The next day, dilutions of IgG1-CD134-003-HC6LC2-RR, BsIgG1-b12-RR-F405LxCD134-003-RR-K409R, and control antibodies IgG1-CD134-003-RR-K409R, IgG1-CD134-003, IgG1-CD134-003-FEAL, and IgG1-b12-RR were prepared in RPMI 1640 medium with 5% FBS (final concentration 0.000457-1 µg/mL, in threefold dilution steps). 20 µL of the prepared antibody dilution series or medium only were added to the wells and the assay plate was incubated for 5 h (37° C., 5% $CO_2$). After the incubation, assay plates were equilibrated to RT. Subsequently, 80 µL of Bio-Glo™ Luciferase Assay substrate was added to each well, and the plate was incubated for 10 min with constant shaking and protected from light. Luminescence was measured using an EnVision Multiplate Reader (PerkinElmer). Data are presented as relative luminescence units (RLU) in line graphs generated using GraphPad Prism software. Data were fitted with the sigmoidal, 4PL, X is log (concentration) equation.

To assess the capacity of IgG1-CD134-003-HC6LC2-RR, BsIgG1-b12-RR-F405LxCD134-003-RR-K409R, and negative control antibody IgG1-b12-RR (concentration ranges between 0.0015 µg/mL to 30 µg/mL) in a polyclonal T-cell proliferation assay, the procedures as described in Example 7 were followed.

In the cell-based OX40 reporter assay, BsIgG1-b12-RR-F405LxCD134-003-RR-K409R induced OX40 agonist activity at an approximately fivefold lower potency than IgG1-CD134-003-HC6LC2-RR, indicating that optimal agonist activity of IgG1-CD134-003-HC6LC2-RR is reached via its capacity to bind with both Fab arms (FIG. 33A). In the polyclonal T-cell proliferation assay, BsIgG1-b12-RR-F405LxCD134-003-RR-K409R enhanced $CD4^+$ T-cell proliferation (FIG. 33B), however, a higher concentration was required to reach maximal effect compared with IgG1-CD134-003-HC6LC2-RR.

Together, these results indicate that optimal biological activity of IgG1-CD134-003-HC6LC2-RR is reached via its capacity to bind OX40 with two Fab arms.

Example 21: T-Cell OX40 Expression and OX40 Shedding in Response to Incubation with IgG1-CD134-003-HC6LC2-RR In Vitro Changes in the expression level of OX40 on $CD4^+$ and $CD8^+$ T cells in response to IgG1-CD134-003-HC6LC2-RR treatment were analyzed in polyclonal T-cell proliferation assays, using PBMCs obtained from ten healthy human donors, (general assay set-up described in Example 7; PBMCs were either stained with cell trace violet using the CellTrace™ Violet Kit [Thermo Fisher Scientific, cat. no. C34557; staining description see Example 7] or CFSE using the Vybrant CFDA SE Cell Tracer Kit [Life Technologies, cat. No. V12883; staining description see Example 15]). For seven of the tested donors, membrane-expressed OX40 was determined by flow cytometry after two and five days of incubation with IgG1-CD134-003-HC6LC2-RR as described in Example 13 (antibody staining: APC-labeled CD4 antibody [ThermoFisher Scientific, cat. no. 17-0048-42; dilution 1:100], BV605-labeled CD8α antibody [BD Biosciences, cat. no. 564116; dilution 1:400], PE-labeled OX40 antibody [BD Biosciences, cat. no. 340420; dilution 1:80]), whereas for the remaining three donors expression was assessed after one to four days and six days of incubation (antibody staining: PerCP-eFluor710-labeled CD4 antibody [ThermoFisher Scientific, cat. no. 46-0047-42; dilution 1:100], PE-Cy7-labeled CD8a antibody [TONBO, cat. no. 60-0088-T100; dilution 1:100], BV421-labeled OX40 antibody (BD Biosciences, cat. no. 744881; dilution 1:80). OX40 expression on $CD4^+$ and $CD8^+$ T cells was assessed in a one-dimensional histogram analyzing geometric mean fluorescence intensity (gFMI) values.

Soluble OX40 (sOX40) has been detected in serum of both healthy donors and patients with autoimmune disease and cancer (Taylor and Schwarz. Identification of a soluble OX40 isoform: development of a specific and quantitative immunoassay. J Immunol Methods 255:67-72) and is thought to act as a decoy receptor by blocking OX40 ligand (OX40L) binding to membrane-bound OX40. Shedding of OX40 in response to IgG1-CD134-003-HC6LC2-RR in vitro treatment was assessed by ECLIA, on the day OX40 expression was determined. sOX40 concentrations in supernatants that had been collected from the polyclonal T-cell proliferation assay were determined by multiplexed ECLIA using the U-PLEX Human OX40/TNFRSF4 Assay (MSD, cat. no. K151T7K-2) following the manufacturer's protocol. Briefly, 25 µl biotinylated antibody diluted in diluent 100 were added per well to MSD Gold Small Spot Streptavidin plates and incubated for 1 h at RT. Plates were washed three times with PBST and standards or samples (samples diluted 1:8 in diluent 58) were added to the wells (total 50 µl/well), and the plates incubated for 2 h at RT with constant shaking. The plates were washed three times with PBST, and detection antibodies diluted in diluent 3 were added (50 µl/well). The plates were incubated for 1 h at RT with constant shaking, and the plates were washed three times with PBST. Subsequently, the Gold Read Buffer B was added (150 µl/well), and the plate was immediately analyzed on a MESO QuickPlex SQ 120 imager (MSD).

IgG1-CD134-003-HC6LC2-RR (at a concentration of 0.01 µg/mL or higher) enhanced the CD3-induced expression of OX40 on CD4$^+$ in three out of ten donors after two days of incubation, and on CD4$^+$ and CD8$^+$ T cells in six out of ten donors after three to six days, or after five days, of incubation and CD8$^+$ T cells after two and three days of incubation, respectively (as exemplified in FIG. 34A for one responding donor out of three donors in total; donor variability was observed in additionally tested donors). In parallel, for all three donors tested for sOX40 release, IgG1-CD134-003-HC6LC2-RR treatment dose-dependently enhanced the concentrations of sOX40 in the supernatants over time, indicating that IgG1-CD134-003-HC6LC2-RR induced a continuous release of sOX40, which started at day three and continued to increase up until day six (FIG. 34B). Although a partial interference of IgG1-CD134-003-HC6LC2-RR with the sOX40 detection ECLIA kit has been observed, an increase of sOX40 levels upon treatment with 0.2 and 2 µg/ml IgG1-CD134-003-HC6LC2-RR was clearly detected.

These data suggest that IgG1-CD134-003-HC6LC2-RR may enhance OX40 expression on the membrane of CD4$^+$ and CD8$^+$ T cells, although with high donor variability, and in parallel enhances OX40 shedding from the plasma membrane.

Example 22: Assessment of Interference of Soluble OX40 in IgG1-CD134-003-HC6LC2-RR Agonist Activity In Example 21, it was Described that IgG1-CD134-003-HC6LC2-RR May Enhance OX40 Membrane expression on CD4$^+$ and CD8$^+$ T cells and, in parallel, enhance OX40 shedding from the plasma membrane. Here, the impact of sOX40 on the observed capacity of IgG1-CD134-003-HC6LC2-RR to induce OX40 agonism in the cell-based OX40 reporter assay (see Example 6) and to increase T-cell proliferation in the polyclonal T-cell proliferation assay (see Example 7) was studied.

To study whether the presence of sOX40 interferes with IgG1-CD134-003-HC6LC2-RR-mediated OX40 agonist activity, the assay was performed as described in Example 13 without FcγRIIb-CHO K1 cells. IgG1-CD134-003-HC6LC2-RR or IgG1-b12-RR to final concentrations ranging between 0.0024 to 40 g/mL (1:4 serial dilution) was added without or together with sOX40 (human OX40, AcroBiosystems, cat. no. OX0-H5224) to a final concentration ranging between 1 and 1,000 ng/ml (1:10 serial dilution) and luminescence was measured using a CLARIOstar Plus microplate reader. To study whether the presence of sOX40 interferes with IgG1-CD134-003-HC6LC2-RR-increased T-cell proliferation, 0.002 to 40 µg/ml IgG1-CD134-003-HC6LC2-RR or IgG1-b12-RR (1:4 serial dilution) was added without or together with sOX40 (0.1 ng/ml to 1,000 ng/ml; 1:10 serial dilution), further following the methods described in Example 7 with the omission of CD45RA and CCR7 staining.

Whereas IgG1-CD134-003-HC6LC2-RR-induced dose-dependent OX40 agonist activity was retained in presence of low concentrations of sOX40, a decrease was observed at 1,000 ng/ml sOX40, and to a lesser extent at 100 ng/ml sOX40 (FIG. 35). Similarly, IgG1-CD134-003-HC6LC2-RR-induced dose-dependent increases in CD4$^+$ and CD8$^+$ T-cell proliferation were retained in presence of concentrations of sOX40 up to 10 ng/ml, whereas a reduced increase was observed in both CD4$^+$ and CD8$^+$ T-cell proliferation at 100 ng/ml sOX40 and 1,000 ng/ml sOX40 for IgG1-CD134-003-HC6LC2-RR concentrations up to 0.625 µg/ml (FIG. 36). No interference by sOX40 was observed in PBMC samples incubated with the higher tested IgG1-CD134-003-HC6LC2-RR concentrations (≥2.5 µg/mL).

In summary, interference of sOX40 with IgG1-CD134-003-HC6LC2-RR-induced OX40 agonism in reporter cells and polyclonally activated T cells was only observed at concentrations considerably higher than those expected to be clinically relevant.

Example 23: Preclinical Immunogenicity Assessment of IgG1-CD134-003-HC6LC2-RR

Immunogenicity assessments for the heavy chain (HC) and light chain (LC) of IgG1-CD134-003-HC6LC2-RR were performed in silico using augmented intelligence (AI) platform iTope-AI and TCED (Abzena). The immunogenic potential of IgG1-CD134-003-HC6LC2-RR was further analyzed in vitro using the EpiScreen DC: T-cell proliferation assay (Abzena) by measuring the proliferation of human CD4$^+$ T cells cocultured with MoDCs that had previously been incubated with IgG1-CD134-003-HC6LC2-RR.

9-mer peptides that overlap by eight amino acids spanning the protein sequence of the IgG1-CD134-003-HC6LC2-RR HC and LC were generated in silico. Using iTope-AI technology, favorable interactions between the amino acid side chains of each 9-mer and the 46 most common human leukocyte antigen (HLA) alleles found worldwide (HLA-DR, DP and -DQ allotypes) were predicted. For peptides showing favorable interactions, P1 anchor position indicates the first amino acid of their sequence. Individual peptides were given a binding score from 0 (no binding) to 3 (strong binding) for each of the 46 allotypes, and those scores were added together for all allotypes to provide an overall risk score per 9-mer, referred to as the Position Risk Score. Promiscuous peptides (Position Risk Score >0) were considered weak, medium, or strong MHC class II binders when their Position Risk Scores reached 1-2, 3-5, or 6+, respectively. The total score for the whole test protein sequence was calculated by adding the Position Risk Scores obtained for all individual peptides. 9-mer peptides fully homologous to sequences from the human proteome were excluded from the analysis since germline sequences are unlikely to have immunogenic potential due to T-cell tolerance. The Total Score for IgG1-CD134-003-HC6LC2-RR could then be compared to the Total Scores observed for benchmark mAbs, e.g., murine, chimeric, humanized, and human mAbs.

To assess the immunogenicity risk of the IgG1-CD134-003-HC6LC2-RR HC and LC sequences, the identified promiscuous peptides were interrogated against peptide sequences in TCED by a basic local alignment search tool (BLAST) search to identify any high sequence homology with >10,000 peptides from unrelated proteins and antibodies that stimulated T-cell responses in previous ex vivo EpiScreen studies (i.e., T-cell epitopes) at Abzena.

An EpiScreen DC: T cell assay was used to assess the potential immunogenicity of IgG1-CD134-003-HC6LC2-

RR in vitro by measuring CD4+ T-cell responses, the primary drivers of memory-based immunogenicity. First, PBMC were isolated from healthy donor leukocyte cones (within 24 h after the blood was drawn) obtained under consent from the UK National Health Service blood transfusion service. The donors were characterized by HLA-DR haplotypes using the sequence-specific oligonucleotide (SSO) HLA typing method (VHBio). A cohort of 50 healthy PBMC donors was used, selected to represent all known HLA alleles except HLA-DP, which is not considered in the selection due to its low prevalence and likely low levels of expression.

IgG1-CD134-003-HC6LC2-RR was diluted to 0.75 µM (112.5 µg/mL) in MoDC culture medium(RPMI 1640 [ThermoFisher, cat. no. 21875-034] supplemented with human serum [HS; VWR, cat. no. 21001PM]), 2-mercaptoethanol (2 ME; Sigma, cat. no. M3148], L glutamine [ThermoFisher, cat. no. 25030-024], penicillin/streptomycin [ThermoFisher, cat. no. 15140-122], interleukin (IL)-4 [Peprotech, cat. no. 200-04], and granulocyte macrophage colony-stimulating factor [GM-CSF; Peprotech, cat. no. 300-03]) prior to use. As a positive control, T-cell responses to the neoantigen keyhole limpet hemocyanin (KLH) were also determined. KLH (Pierce Life Technologies, cat. no. 77600) was stored at −20° C. as a 10 mg/ml stock solution in distilled water. An aliquot of KLH was thawed immediately before diluting to 1 mg/ml in MoDC culture media. Herceptin® (Roche, cat. no. HERC/150/1/BG) was used as benchmark antibody known for its low clinical immunogenicity and was stored at −80° C. as a 20 mg/mL stock solution and thawed and diluted to 125 µg/mL in MoDC culture media immediately before use.

For the preparation of MoDCs, CD14+ monocytes were purified from donor PBMCs with negative human monocyte purification kits (StemCell Technologies, cat. no. 19058RF) and an automated cell purification instrument (RoboSep™ StemCell Technologies), according to the manufacturer's instructions. Monocytes were resuspended in MoDC culture medium and plated in low-bind 24-well plates at $1.5 \times 10^6$ per well in 2 mL culture medium(final volume) and incubated at 37° C. On day two, the cells were fed by exchanging 1 mL MoDC culture medium with fresh medium. On day four, the cells were fed again with 1 mL MoDC culture medium, which also contained the following reagents (final concentrations): 0.3 µM (45 µg/mL) IgG1-CD134-003-HC6LC2-RR, 0.3 µM (45 µg/mL) Herceptin (benchmark antibody) or 100 µg/mL KLH (positive control). Except for the addition of the reagents, the untreated control wells were treated the same as the reagent-containing wells. Cells were incubated for 1 h (37° C./5% $CO_2$). After incubation, 0.01 µg/ml lipopolysaccharide (LPS; Sigma, cat. no. L4391) was added to induce maturation of the MoDC. On day five, matured MoDC were harvested, counted and viability was assessed using trypan blue (Sigma, cat. no. T8154) dye exclusion. Viability was expressed as a percentage of cells unstained with trypan blue out of the total number of cells. Cell viability assessment confirmed that IgG1-CD134-003-HC6LC2-RR and the KLH and Herceptin controls did not affect the viability of the MoDC used in the EpiScreen analyses. Matured MoDC were then γ-irradiated (40 Gy) prior to use in the proliferation assays. Lastly, autologous CD4+ T cells were purified by negative selection from PBMC of the same donor using human CD4+ T-cell enrichment kits (StemCell Technologies, cat. no. 19052) and an automated cell purification instrument.

After counting and assessing cell viability, $1 \times 10^6$ CD4+ T cells were cocultured at a T: DC ratio of 10:1 with $1 \times 10^5$ γ-irradiated MoDC in 24-well plates for 12 days in culture medium(RPMI 1640 supplemented with human serum, 2-mercaptoethanol, L-glutamine). At day 9, 10, 11, and 12, the cultures were gently resuspended and 3×100 µL aliquots were each transferred to a round-bottom 96-well for pulse labeling. The cells were pulsed by adding 100 µl culture medium containing 1.0 µCi [$^3$H]-thymidine (Perkin Elmer) and incubated for 6 h at 37° C. before harvesting onto filter mats using a TomTec Mach Ill cell harvester. For each sample, counts per minute (CPM) were determined by MeltiLex™ (Perkin Elmer) scintillation counting on a MicroBeta Microplate Beta Counter in ParaLux™ low background count mode. Immunogenicity was expressed as stimulation index (SI), defined for each sample as mean CPM of wells containing T cells treated with compounds/CPM mean of baseline (untreated control wells).

$$\text{Stimulation Index(SI)}=(\text{mean CPM(treated wells)})/(\text{mean CPM(untreated control wells)})$$

Based on previous analyses carried out by Abzena, an empirical threshold of SI ≥1.90 was established as the minimum signal-to-noise threshold allowing maximum sensitivity without detecting large numbers of false-positive responses or omitting subtle immunogenic events. Samples inducing responses above this threshold are scored positive for inducing a T-cell immune response in the test donor. For each sample at a given time point, positive proliferation responses were considered statistically significant ($P<0.05$) by comparing triplicate CPM of CD4+ T cells incubated with reagent-loaded matured DC samples to triplicate CPM of CD4+ T cells incubated with matured MoDC cultured with medium only, using unpaired two sample Student's t-test. Donors that were positive (SI ≥1.90, $p<0.05$) at least at one time point during the time course assay were scored as positive donors and the mean magnitude SI was calculated from the average of positive donor responses.

iTope-A1 analysis of the IgG1-CD134-003-HC6LC2-RR HC sequence, harboring the P329R and E345R Fc mutations, predicted a total of 12 non-germline promiscuous binding peptides in the HC constant region, which were classified as strong (2), intermediate (2) or weak (8) MHC class II binders (Table 17). The P329R mutation was located in two of the identified weak binders (P1 anchor positions C317 and K318; Table 17), but these did not match any known T-cell epitope in TCED. The E345R mutation was not present in either of these peptides. In addition, 10 out of 12 non-germline promiscuous binding peptides were predicted in the HC variable domain (VH), of which two were predicted to be medium binders, and two were predicted to be strong binders (Table 17). A peptide identified in framework (Fw)3 (Position Risk Score: 1) was found to be homologous to a peptide in TCED. In total, the iTope Total Score for the IgG1-CD134-003-HC6LC2-RR HC was 45.

TABLE 17

Non-germline promiscuos IgG1-CD134-003-HC6LC2-RR
HC peptides identified by iTope-AI and
TCED analyses. Each 9-mer peptide is represented by its P1
anchor position. The variable region was numbered according to Kabat
numbering, followed by linear numbering for the constant region.
Position Risk Scores of promiscuous binding peptides were divided
into weak (1-2), medium (3-5) and strong (6+) affinity binders.
Homologous peptides identified from TCED are listed.

| P1 anchor position [a] | P1 location [b] | Peptide sequence [c, d] | Risk Score | Position Homologous sequence | TCED homology [f] TCED Key Anchor Positions |
|---|---|---|---|---|---|
| 27 | CDR-H1 | FDFSSGYMS | 1 | None | N.A. |
| 45 | Fw2 | LEWIGYIDP | 1 | None | N.A. |
| 47 | Fw2 | WIGYIDPVF | 15 | None | N.A. |
| 54 | CDR-H2 | FGSTYYASW | 2 | None | N.A. |
| 58 | Fw3 | YYASWVNGR | 4 | None | N.A. |
| 59 | Fw3 | YASWVNGRF | 2 | None | N.A. |
| 82C | Fw3 | LRAEDTATY | 1 | L-A-D-ATY | 1, 7, 9 |
| 90 | Fw3 | YYCARDLRA | 13 | None | N.A. |
| 92 | Fw3 | CARDLRAFY | 3 | None | N.A. |
| 99 | CDR-H3 | FYSGWGGIN | 1 | None | N.A. |
| 317 | Constant | CKVSNKALR | 1 | None | N.A. |
| 318 | Constant | KVSNKALRA | 1 | None | N.A. |
| iTope-IA total score [e] | | | 45 | | |

[a] First amino acid of the 9-mer peptide.
[b] P1 location according to Kabat numbering for variable region; linear numbering for constant region.
[c] Underlined residues indicate positions in the IgG1-CD134-003-HC6LC2-RR VH CDRs that were defined according to IMGT definition.
[d] R = P329R mutation in the IgG1-CD134-003-HC6LC2-RR Fc region; position according to Eu numbering.
[e] Total Score for the test sequence is calculated by adding the Position Risk Scores obtained for all individual peptides.
[f] Summary of HC TCED interrogation of nongermline binding peptides. Homologous peptides identified from TCED and matching P1>P9>P7 anchor positions are listed. There is a hierarchy in the contribution of specific 'anchor' positions to MHC class II binding with the greatest effect observed for P1>P9>P7≥P6≥P4.

[a]"First amino acid of the 9-mer peptide.
[b]P1 location according to Kabat numbering for variable region; linear numbering for constant region." Underlined residues indicate positions in the IgG1-CD134-003-HC6LC2-RR VH CDRs that were defined according to IMGT definition.
[d]R=P329R mutation in the IgG1-CD134-003-HC6LC2-RR Fc region; position according to Eu numbering.
[e]Total Score for the test sequence is calculated by adding the Position Risk Scores obtained for all individual peptides.
[f]Summary of HC TCED interrogation of nongermline binding peptides. Homologous peptides identified from TCED and matching P1>P9>P7 anchor positions are listed. There is a hierarchy in the contribution of specific 'anchor' positions to MHC class II binding with the greatest effect observed for P1>P9>P7≥P6≥P4.

iTope-AI analysis predicted the presence of three strong-binding, two medium-binding, and 10 weak-binding non-germline promiscuous MHC class II-binding peptides in the LC of IgG1-CD134-003-HC6LC2-RR, all present in the variable domain of the LC (VL) sequence (Table 18). For three of the predicted peptides (two weak-binding and one medium-binding peptide), a homologous peptide in TCED was identified. The iTope Total Score for the IgG1-CD134-003-HC6LC2-RR LC sequence was 74. The Total Score for IgG1-CD134-003-HC6LC2-RR, which is the sum of the HC and LC Total Scores, was 119, which is in line with benchmark humanized mAbs.

TABLE 18

Non-germline promiscuous IgG1-CD134-003-HC6LC2-RR LC peptides
identified by iTope-AI and TCED analyses. Each 9-mer peptide is
represented by its P1 anchor position. The variable region was
numbered according to Kabat numbering, followed by linear
numbering for the constant region. Position Risk Scores
of promiscuous binding peptides were divided into
weak (1-2), medium (3-5) and strong (6+) affinity binders.
Homologous peptides identified from TCED are listed.

| P1 anchor position [a] | P1 location [b] | Peptide sequence [c] | Risk Score | Position Homologous sequence | TCED homology [e] TCED Key Anchor Positions |
|---|---|---|---|---|---|
| 21 | Fw1 | ITCQSSQIV | 2 | None | N.A. |
| 27A | CDR-L1 | IVVNNNFLS | 17 | None | N.A. |
| 31 | CDR-L1 | NFLSWYQQK | 5 | N-L-WYQQK | 1, 6, 7, 9 |

TABLE 18-continued

Non-germline promiscuous IgG1-CD134-003-HC6LC2-RR LC peptides
identified by iTope-AI and TCED analyses. Each 9-mer peptide is
represented by its P1 anchor position. The variable region was
numbered according to Kabat numbering, followed by linear
numbering for the constant region. Position Risk Scores
of promiscuous binding peptides were divided into
weak (1-2), medium (3-5) and strong (6+) affinity binders.
Homologous peptides identified from TCED are listed.

| P1 anchor position [a] | P1 location [b] | Peptide sequence [c] | Position Risk Score | TCED homology [e] Homologous TCED sequence | Key Anchor Positions |
|---|---|---|---|---|---|
| 32 | CDR-L1 | FLSWYQQKP | 2 | --SWYQQKP | 4, 6, 7, 9 |
| 47 | Fw2 | LIYDASNLA | 29 | None | N.A. |
| 49 | Fw2 | YDASNLASG | 3 | None | N.A. |
| 50 | CDR-L2 | DASNLASGV | 7 | None | N.A. |
| 51 | CDR-L2 | ASNLASGVP | 1 | None | N.A. |
| 52 | CDR-L2 | SNLASGVPD | 2 | None | N.A. |
| 53 | CDR-L2 | NLASGVPDR | 1 | None | N.A. |
| 54 | CDR-L2 | LASGVPDRF | 1 | L--GVP-RF | 1, 4, 6, 9 |
| 88 | Fw3 | CLGGYDDDA | 1 | None | N.A. |
| 89 | CDR-L3 | LGGYDDDAE | 1 | None | N.A. |
| 98 | CDR-L3 | NAFGGGTKV | 1 | None | N.A. |
| 99 | CDR-L3 | AFGGGTKVE | 1 | None | N.A. |
| iTope-IA total score [d] | | | 74 | | |

[a] First amino acid of the 9-mer peptide.
[b] P1 location according to Kabat numbering for variable region; linear numbering for constant region.
[c] Underlined residues indicate positions in the IgG1-CD134-003-HC6LC2-RR VL CDRs, that were defined according to IMGT definition.
[d] Total Score for the test sequence is calculated by adding the Position Risk Scores obtained for all individual peptides.
[e] Summary of LC TCED interrogation of nongermline binding peptides. Homologous peptides identified from TCED and matching P1 > P9 > P7 > P6 > P4 anchor positions are listed.

Mature MoDCs loaded with IgG1-CD134-003-HC6LC2-RR induced a low frequency of positive T-cell proliferation responses (SI ≥1.90), ie, in 8% (4/50) of the donor cohort (Table 19). This is in the same range as Herceptin (proliferation induction in 8% [4/50] of the donor cohort), which is known to show low clinical immunogenicity, and below the threshold of 10% that is set by Abzena based on historical EpiScreen data for proteins considered to have an increased immunogenicity risk in the clinic. The neoantigen KLH, included as a positive control for immunogenicity, showed an 88% positive response rate. The mean magnitude SI (the average SI of positive donor responses) for IgG1-CD134-003-HC6LC2-RR and Herceptin was comparable (SI=2.66±0.6, SI=2.64±0.7, respectively), and lower compared to KLH (SI=4.6±2.54).

TABLE 19

Summary of the extent of CD4+ T-cell proliferative
responses elicited by mature MoDC loaded with
IgG1-CD134-003-HC6LC2-RR, Herceptin, or KLH

| Sample | Mean SI | SD | % Response[1] |
|---|---|---|---|
| IgG1-CD134-003-HC6LC2-RR | 2.66 | 0.60 | 8 |
| Herceptin | 2.64 | 0.70 | 8 |
| KLH | 4.60 | 2.54 | 88 |

[1]Percentage of donors with a T-cell proliferative response on at least one of the time points (SI ≥ 1.90, p < 0.05 where the mean magnitude SI was calculated from the average of positive donor responses).

Together, these data indicate a low risk of clinical immunogenicity for IgG1-CD134-003-HC6LC2-RR, i.e., in the

Example 24: Pharmacokinetic Analysis of IgG1-CD134-003-HC6LC2-RR in Absence of Target Binding, Studied in Mice The pharmacokinetic (PK) characteristics of anti-human OX40 antibody IgG1-CD134-003-HC6LC2-RR in absence of target binding was analyzed in mice and compared to two chimeric control antibodies, either containing the inertness mutations L234F-L235E-D265A and DuoBody mutation F405L, or containing the same RR Fc-mutations as IgG1-CD134-003-HC6LC2-RR, in addition to DuoBody mutation K409R (IgG1-CD134-003-FEAL and IgG1-CD134-003-RR-K409R, respectively). IgG1-CD134-003-HC6LC2-RR does not bind to mouse OX40 as shown in Example 5 and FIG. 5A, and thus the experiment was designed to test pharmacokinetic behavior of the mentioned anti-human OX40 antibodies in vivo, in absence of target binding. Also, IgG1-CD134-003-FEAL and IgG1-CD134-003-RR-K409R do not bind mouse OX40 (data not shown). Female severe combined immunodeficient mice (SCID mice, Envigo; C.B-17/IcrHan®Hsd Prkdcscid) were housed at the Central Laboratory Animal Research Facility (Gemeenschappelijk Dierenlaboratorium, GDL) of Utrecht University in sterile individually ventilated cages (IVC), five mice per cage, with sterile food and water provided ad libitum. Mice received tail tattoos for identification purposes upon arrival at the GDL. Animal experiments were performed in compliance with the Dutch animal protection law (WoD) translated from the directives (2010/63/EU) and the Code of Practice "animal experiments for cancer research" (Inspection V&W, Zutphen, The Netherlands, 1999) and are approved by the Ethical Committee of Utrecht. The animals were housed and handled in accordance with good animal practice as defined by the Federation of European Laboratory Animal Science Associations (FELASA), in an animal facility (GDL) accredited by the Association for Assessment and Accreditation of Laboratory Animal Care (AAALAC) and ISO 9001:2018.

At 10 weeks old, female SCID mice (3 mice per group) were injected intravenously in the tail vein with a 60 µL solution containing either of the mentioned test and control antibodies, corresponding to approximately 0.125, 1.25 and 12.5 mg antibody per kg body weight. 40 µl blood samples were collected at 10 minutes, 4 h, 1 day, 2 days, 8 days, 14 days and 21 days after antibody administration, plasma was collected from blood samples and stored at −65° C. until determination of total human IgG concentrations by ELISA. To obtain plasma, blood was collected into Microvette® CB 300 K2 EDTA vials (Sarstedt, cat. no. 16.444.100) and centrifuged for 10 min at 14,000×g without heat-inactivation. 96-well MULTI-ARRAY Standard plates (MSD, cat. no. L15XA-3) were coated with 2 µg/ml mouse anti-huIgG capture antibody (IgG2amm-1015-6A05; Genmab, batch no. 3093-008-EP) in PBS for 16-24 h at 2-8° C. After washing the plate with PBS-T (PBS-Lonza, cat. no. BE17-156Q-supplemented with 0.05% Tween 20-Sigma, cat. no. P1379) to remove unbound antibody, the unoccupied surfaces were blocked with 3% (w/v) BSA for 60±5 min at RT using MSD Blocker A in PBS-T, followed by washing with PBS-T. Calibration samples for generating reference curves were prepared by spiking 2% Pooled Mouse Plasma K2EDTA (BIOIVT, cat. no. MSE00PLK2PNN) in assay buffer with dilution series of IgG1-CD134-003-HC6LC2-RR, IgG1-CD134-003-FEAL or IgG1-CD134-003-RR-K409R (final antibody concentration ranges from 0.156 to 20 µg/mL). Quality control samples, used to confirm the validity of individual assay runs, were prepared by spiking undiluted Pooled Mouse Plasma K2EDTA with three antibody concentrations covering the range of the reference curve: 0.5 µg/ml (quality control for low concentrations; LQC), 1.75 µg/ml (quality control for medium concentrations; MQC) and 15 µg/ml (quality control for high concentrations; HQC).

Next, the coated plates were incubated with 50 µl mouse plasma samples diluted in assay buffer (1% [w/v] MSD Blocker A [Meso Scale Discovery—MSD—, cat. no. R93AA-1] in PBS-T [PBS—Lonza, cat. no. BE17-156Q—supplemented with 0.05% Tween 20—Sigma, cat. no. P1379]), calibration samples and quality control samples (all singlicate samples) for 90±5 min at RT. After washing with PBS-T, the plates were incubated with SULFO-TAG-conjugated anti-huIgG detection antibody (IgG2amm-1015-4A01-ST; Genmab, batch no. 210329_PSM_0053 #001; IgG2amm-1015-4A01 antibody labeled using MSD GOLD SULFO-TAG NHS-Ester [MSD, cat. no. R91AO-1]) for 90±5 min at RT. After washing with PBS-T, electrochemiluminescence (ECL) signal was generated by adding tripropylamine (TPA)-containing Read Buffer (MSD GOLD Read Buffer, cat. no. R92TG-2) that electrochemically stimulates the SULFO-TAG on the immobilized antibodies at the electrode surfaces of the plate. ECL signal was measured at 620 nm on a MESO Sector S 600 plate reader (MSD) and processed using SoftMax® Pro GxP Software (Molecular Devices).

The predicted IgG concentration-time curves for WT huIgG in mice in absence of target binding were defined based on a two-compartment PK model of a WT huIgG antibody with linear clearance described in literature (Bleeker W. K., et al. 2001. Accelerated autoantibody clearance by intravenous immunoglobulin therapy: studies in experimental models to determine the magnitude and time course of the effect. Blood 98:3136-3142). This model appropriately described the PK profiles observed in previous in-house studies with other (non-binding) huIgG molecules in mice.

PK parameters were derived by non-compartmental methods for IV (or extravascular where relevant) drug administration using Phoenix WinNonlin software (Certara). The following parameters were calculated:

$C_{max}$—maximum observed antibody concentration (µg/ml), defined as the highest antibody concentration observed in blood samples post antibody injection.

$t_{max}$—sampling time point at which $C_{max}$ was observed (h).

$t_{1/2}$—terminal elimination half-life (h), determined by linear regression of at least three data points on the terminal phase of the log (concentration) vs time plot (d).

$AUC_{inf}$—the area under the plasma concentration-time curve from time point zero (t=0) to infinity (h*µg/mL). The area between t=0 and the last measured time point ($t_{last}$=21 d) was calculated by the linear up-log-linear down trapezoidal method. The area from $t_{last}$ to infinity was calculated using the elimination rate ($\lambda z$) estimated between 3 days and 21 days post antibody injection.

CL—total body plasma clearance (ml/h/kg), calculated as Dose/$AUC_{inf}$. For mice with an extravascular PK profile, the CL calculated is CL implicitly normalized by apparent bioavailability (F).

PK parameters were summarized by mean±standard deviation (SD) per treatment group, except for $t_{max}$, which was summarized by median and range. Results were visualized using GraphPad Prism.

IgG1-CD134-003-HC6LC2-RR showed PK properties consistent with and typical for IV administered non-target-binding human IgG antibody in mice, with maximum exposure at the earliest tested post-injection time point, followed by a two-phase decline (FIG. 37). IgG1-CD134-003-HC6LC2-RR showed a slightly lower total CL and a slightly longer ty than the two chimeric OX40-targeting control antibodies. The $C_{max}$ was similar for all three antibodies across the dose-range tested (FIG. 38, Table 20).

TABLE 20

Antibody PK parameters per treatment group. Shown are the mean ± SD for the antibody CL, $t_{1/2}$, $AUC_{inf}$ and $C_{max}$, and the median with range for the antibody $t_{max}$ of three mice per treatment group, unless otherwise specified.

| Antibody treatment | Antibody dose (mg/kg) | Median $t_{max}$ with range (h) | Mean $C_{max}$ ± SD (µg/mL) | Mean $t_{1/2}$ ± SD (h) | Mean $AUC_{inf}$ ± SD (h*µg/mL) | Mean CL ± SD (mL/h/kg) |
|---|---|---|---|---|---|---|
| IgG1-CD134-003-HC6LC2-RR | 0.125 | 0.16 (0.16-0.16) | 1.64 ± 0.259 | 277 ± 63.6 | 284 ± 60.6 | 0.454 ± 0.0903 |
| | 1.25 | 0.16 (0.16-0.16) | 25.8 ± 4.39 | 211 ± 7.95 | 4,180 ± 748 | 0.305 ± 0.0505 |
| | 12.5 | 0.16 (0.16-0.16) | 226 ± 9.87 | 292 ± 41.8[a] | 57,800 ± 6,030[a] | 0.217 ± 0.0227[a] |
| IgG1-CD134-003-FEAL | 0.125 | 24 (0.16-24) | 0.938 ± 0.363 | 166 ± 3.92[a] | 174 ± 44.7[a] | 0.741 ± 0.190[a] |
| | 1.25 | 0.16 (0.16-0.16) | 17.2 ± 4.01 | 139 ± 7.7 | 2,150 ± 169 | 0.583 ± 0.0445 |
| | 12.5 | 0.16 (0.16-0.16) | 182 ± 50.6 | 205 ± 19.6 | 28,400 ± 2,090 | 0.441 ± 0.0315 |
| IgG1- CD134-003-K409R-RR | 0.125 | 0.16 (0.16-24) | 1.01 ± 0.493 | 126 ± 17.6[a] | 129 ± 17[a] | 0.975 ± 0.128[a] |
| | 1.25 | 0.16 (0.16-24) | 16.7 ± 8.82 | 152 ± 10.7 | 2,150 ± 374 | 0.594 ± 0.111 |
| | 12.5 | 0.16 (0.16-0.16) | 226 ± 45.1 | 185 ± 14.8 | 25,300 ± 1,620 | 0.496 ± 0.031 |

[a]Mean and SD were based on samples from two mice.

Together, these data indicate that the PK properties of IgG1-CD134-003-HC6LC2-RR are comparable to those of a WT huIgG in absence of target binding.

Example 25: In Vivo Antitumor Efficacy of IgG1-CD134-003-HC6LC2-RR

Due to lack of binding to mouse OX40 (mOX40) as demonstrated in Example 5, the antitumor activity of IgG1-CD134-003-HC6LC2-RR was assessed in immunocompetent C57BL/6 mice genetically engineered to express the extracellular domain of human OX40 (hOX40 knock-in [KI] mice) with a mOX40 intracellular domain. In vivo antitumor activity of IgG1-CD134-003-HC6LC2-RR was assessed in hOX40 KI mice inoculated with syngeneic MC38 mouse colon cancer cells. In addition, pharmacodynamic changes in response to treatment with IgG1-CD134-003-HC6LC2-RR were studied in peripheral blood of MC38-bearing hOX40 KI mice.

hOX40 KI mice on a C57BL/6 background (strain C57BL/6-Tnfrsf4$^{tm1(TNFRSF4)}$/Bcgen, cat no. 110014) were obtained from Beijing Biocytogen Co., Ltd., featuring a humanized drug target (ie, OX40) in immunocompetent mice. Mice were bred at Biocytogen Co., Ltd. and transferred to CrownBioscience, Inc. All animal experiments were performed at Crown Bioscience, Inc. and approved by their Institutional Animal Care and Use Committee (IACUC) prior to execution. Animals were housed and handled according to good animal practice as defined by the Association for Assessment and Accreditation of Laboratory Animal Care (AAALAC) regulations. All experimental data management and reporting procedures were in strict accordance with applicable Crown Bioscience, Inc. Guidelines and Standard Operating Procedures. 8 to 9 weeks-old female hOX40 KI mice were injected subcutaneously (SC) in the lower flank region with 1×10$^6$ MC38 cells (FuDan IBS cell center, cat. no. 1101MOU-PUMC000523, 100 µL in PBS).

Tumor growth was evaluated three times per week using a caliper. Tumor volumes (mm$^3$) were calculated from caliper measurements as ([length]×[width]×[width])/2, where the length is the longest tumor dimension, and the width is the longest tumor dimension perpendicular to the length.

The study consisted of an antitumor activity study and a pharmacodynamics (PD) study. Randomization of mice was done based on tumor volume using the Matched Distribution method (StudyDirector™ software). From all 84 animals inoculated with MC38 cells, first, 40 mice with an average tumor volume of 58.2 mm3 were enrolled into four groups with 10 mice/group to assess antitumor activity (Table 21). In addition, the remaining 44 animals were randomized, and 16 of them, with an average tumor volume of 63.6 mm3, were enrolled into four groups with four mice/group for PD analysis (referred to as PD part 1), (Table 22). Due to blood clot formation in some tubes during blood collection of these 16 animals (PD part 1), it was decided to include 16 additional mice as a part 2 of the study (PD part 2). For this, a third randomization on the remaining 28 mice was performed seven days later, leading to four groups of four mice each with an average tumor volume of 146.81 mm$^3$.

TABLE 21

Treatment groups and dose levels for hOX40 KI mice (antitumor activity part)

| Group | Group size | Mean Tumor Volume on Day 0 (+/− SEM; mm$^3$) | Antibody | Antibody dose | Dosage regimen |
|---|---|---|---|---|---|
| 1 | 10 | 58.2 +/− 1.88 | IgG1-b12-FEAL | 20 mg/kg | 2QW × 3 |
| 2 | 10 | 58.2 +/− 1.90 | IgG1-CD134-003-HC6LC2-RR | 20 mg/kg | IP administration on Day 0, 3, 7, 10, 14, 17 |
| 3 | 10 | 58.2 +/− 1.88 | IgG1-CD134-003-HC6LC2-RR | 5 mg/kg | |
| 4 | 10 | 58.2 +/− 1.88 | IgG1-CD134-003-HC6LC2-RR | 1 mg/kg | |

TABLE 22

Treatment groups and dose levels for hOX40 KI mice (PD part 1 and 2)

| Study | Group | Group size | Mean Tumor Volume on Day 0 (+/− SEM; mm$^3$) | Antibody | Antibody dose | Dosage regimen |
|---|---|---|---|---|---|---|
| PD part 1 | 1 | 4 | 63.9 +/− 3.64 | IgG1-b12-FEAL | 20 mg/kg | IP administration on Day 0, 3 |
| | 2 | 4 | 63.8 +/− 3.08 | IgG1-CD134-003-HC6LC2-RR | 20 mg/kg | |
| | 3 | 4 | 63.8 +/− 3.08 | IgG1-CD134-003-HC6LC2-RR | 5 mg/kg | |
| | 4 | 4 | 62.9 +/− 3.79 | IgG1-CD134-003-HC6LC2-RR | 1 mg/kg | |
| PD part 2 | 5 | 4 | 158.3 +/− 22.76 | IgG1-b12-FEAL | 20 mg/kg | |
| | 6 | 4 | 143.2 +/− 18.26 | IgG1-CD134-003-HC6LC2-RR | 20 mg/kg | |
| | 7 | 4 | 143.6 +/− 18.70 | IgG1-CD134-003-HC6LC2-RR | 5 mg/kg | |
| | 8 | 4 | 142.2 +/− 14.09 | IgG1-CD134-003-HC6LC2-RR | 1 mg/kg | |

Treatment was started on the day of randomization (Day 0). Mice were injected IP with IgG1-CD134-003-HC6LC2-RR (1, 5, or 20 mg/kg) or IgG1-b12-FEAL control antibody (20 mg/kg). For each mouse, the dosing volume was adjusted for body weight (10 µl/g in PBS). After the start of dosing, tumor growth was evaluated three times per week. To evaluate antitumor activity over time, animals were dosed twice per week for three weeks (2QW×3). To evaluate pharmacodynamics in PD parts 1 and 2, animals were dosed twice on Days 0 and 3.

Determination of tumor growth inhibition (TGI) was based on the difference between mean tumor volumes on Day 0 (start of dosing) and the last day where all groups were complete, and was calculated for each treatment group using the following formula:

$$TGI = \left(1 - \left(\frac{Tt - T0}{Ct - C0}\right)\right) \times 100\%$$

with Tt=mean tumor volume of the treatment group on the last day where all groups were complete, Ct =mean tumor volume of the control group on the last day where all groups were complete, T0=mean tumor volume of the treatment group on Day 0, and C0=mean tumor volume of the control group on Day 0. The TGI response classifications for this study were categorized as detailed in Table X.

TABLE 23

Tumor growth inhibition classification

| TGI response classification | TGI (%) |
|---|---|
| non-responder | TGI < 30% |
| intermediate | 30% ≤ TGI ≤ 90% |
| responder | TGI > 90% |

The experiment ended for individual mice when the tumor volume exceeded 1,500 mm$^3$ or when the animal reached other humane endpoints (e.g., body weight loss >20% relative to the first day of dosing [i.e., Day 0], tumor ulceration with an ulceration diameter greater than 5 mm, or upon observation of serious clinical signs). Any animal exhibiting an ulcerated or necrotic tumor was separated immediately and housed individually.

For progression-free survival analysis, a tumor volume cut-off of 500 mm$^3$ was applied. The time point of tumor progression >500 mm$^3$ was calculated in GraphPad Prism using nonlinear regression curve fitting of individual tumor growth curves, assuming an exponential growth equation, and plotted as Kaplan-Meier curves. Progression-free survival was compared between the treatment groups and the control group by nonparametric log-rank Mantel-Cox analysis, followed by pairwise comparisons using SPSS software.

To evaluate the pharmacodynamic effects of IgG1-CD134-003-HC6LC2-RR treatment, mice were euthanized after two dosings and changes in peripheral blood immune-cell populations, including CD4$^+$ and CD8$^+$ T-cell proliferation and activation were analyzed at Day 5. Approximately 50 to 100 μL of whole blood was collected via cardiac puncture on Day 5 of the experiment under isoflurane anesthesia and transferred into K2-EDTA tubes (BD, cat. no. 36597499). For cell surface staining, the whole blood samples (both PD part 1 [9 animals] and PD part 2 [14 animals]; whole blood samples with blood clots were excluded from analysis; 50-100 μL) were incubated with 1 μg/mL Mouse BD Fc Block™ (cat. no. 553141; diluted in PBS+0.09% sodium azide) for 10 min in the dark at 4 C. Then, the cells were stained either with an antibody panel for general immunophenotyping (Table 24), or with an antibody panel for T-cell characterization (Table 25).

For general immunophenotyping, the antibody mixture detailed in Table 24, except anti-FOXP3 antibody, diluted in Fc-blocking buffer was added to each sample and stained for 30 min at 4° C. Cells were lysed by adding 2 ml of room-temperate red blood cell lysing buffer (1×; BioGems, cat. no. 64010-00100) to each tube, incubated at RT in the dark for 10 min, and vortexed gently. The samples were washed twice using PBS by centrifuging at 300×g for 5 min and discarding the supernatant. After resuspending the cell pellets, 200 μl of Fixation/Permeabilization buffer (eBioscience, cat. no. 00-5523) was added, pulse vortexed to mix, and incubated for 30 min at RT in the dark. The cells were washed twice using 1X Permeabilization buffer (eBioscience, cat. no. 00-5523; diluted in distilled H2O), followed by centrifugation and decanting of the supernatant. The FOXP3 antibody was added in 100 μL Permeabilization Buffer to each sample and incubated for 30 min at RT in the dark. After washing the cells twice with 2 mL PBS, the cells were resuspended in 250 μL PBS and analyzed on a BD LSRFortessa™ X-20 cell analyzer (BD Biosciences). Data were analyzed using Kaluza Analysis Software. Absolute numbers were calculated using 123count eBeads (ThermoFisher Scientific, cat. no. 01-1234-42). 100 μL beads were added to each sample to be counted. The following equation was used to calculate the absolute counts:

$$\text{Absolute count (cells/}\mu\text{L)} = \frac{(\text{Cell Count} \times eBead \text{ Volume})}{(eBead \text{ Count} \times \text{Cell Volume})} \times eBead \text{ Concentration}$$

For T-cell characterization, the ADPGK tetramer was added to each sample after blocking the cells, gently vortexed, and incubated for 30 min at 4° C. in the dark. Then, the antibody mixture detailed in Table 25, except Ki67, diluted in Fc-blocking buffer was added to each sample and stained for 30 min at 4° C. Cells were lysed and washed as described above. After resuspending the cell pellets, the cells were intracellularly stained for Ki67 following the methods as described above. After washing the cells twice with 2 mL PBS, the cells were resuspended in 250 μL PBS and analyzed on a BD LSRFortessa X-20 cell analyzer (BD Biosciences). Data were analyzed using Kaluza Analysis Software. Absolute numbers were calculated using 123count eBeads as described above.

TABLE 24

Flow cytometry panel for immunophenotyping

| Markers | Fluorochrome | Clone | Cat. no. | Isotype | Vendor | Dilution |
|---|---|---|---|---|---|---|
| Cell surface staining | | | | | | |
| CD3 | BUV395 | 17A2 | 740268 | Rat IgG2b, κ | BD | 1:100 |
| CD4 | BV421 | GK1.5 | 100438 | Rat IgG2b, κ | BioLegend | 1:50 |
| CD8 | PE-eFluor ™ 610 | 53-6.7 | 61-0081-82 | Rat IgG2a, κ | eBioscience | 1:50 |
| CD11b | PE-Cy7 | M1/70 | 101216 | Rat IgG2b, κ | BioLegend | 1:100 |
| CD19 | BV711 | 6D5 | 115555 | Rat IgG2a, κ | BioLegend | 1:100 |
| CD45 | FITC | 30-F11 | 103108 | Rat IgG2b, κ | BioLegend | 1:100 |
| CD206 | PerCP/Cyanine5.5 | C068C2 | 141708 | Rat IgG2a, κ | BioLegend | 1:100 |
| CD335 | BV605 | 29A1.4 | 137619 | Rat IgG2a, κ | BioLegend | 1:50 |
| F4/80 | BV510 | BM8 | 123135 | Rat IgG2a, κ | BioLegend | 1:50 |
| I-A/I-E | AF700 | M5/114.15.2 | 107622 | Rat IgG2b, κ | BioLegend | 1:50 |
| Ly-6G | BV785 | 1A8 | 127645 | Rat IgG2a, κ | BioLegend | 1:100 |
| Ly-6C | APC | HK1.4 | 128016 | Rat IgG2c, κ | BioLegend | 1:50 |
| Viability | eFluor 780 | NA | 65-0865-18 | NA | eBioscience | 1:100 |
| Intracellular staining | | | | | | |
| FOXP3 | PE | FJK-16s | 12-5773-82 | Rat IgG2a, κ | eBioscience | 1:20 |

TABLE 25

Flow cytometry panel for T-cell characterization

| Markers | Fluorochrome | Clone | Cat. | Isotype | Vendor | Dilution |
|---|---|---|---|---|---|---|
| Cell surface staining | | | | | | |
| CD3 | BUV395 | 17A2 | 740268 | Rat IgG2b, κ | BD | 1:100 |
| CD4 | BV421 | GK1.5 | 100438 | Rat IgG2b, κ | BioLegend | 1:100 |
| CD8 | FITC | KT15 | D271-4 | Rat IgG2a, κ | MBL | 1:20 |
| CD25 | BV510 | PC61 | 102042 | Rat IgG1, λ | BioLegend | 1:20 |
| CD45 | BV785 | 30-F11 | 103149 | Rat IgG2b, κ | BioLegend | 1:100 |

TABLE 25-continued

Flow cytometry panel for T-cell characterization

| Markers | Fluorochrome | Clone | Cat. | Isotype | Vendor | Dilution |
|---|---|---|---|---|---|---|
| CD137 | PE-Cyanine7 | 17B5 | 25-1371-82 | Syrian Hamster | eBioscience | 1:20 |
| H-2D$^b$-ADPGK tetramer | APC | NA | TB-5113-2 | NA | MBL | 1:10 |
| hOX40(ACL-134106) | PE | L106 | 340420 | Mouse IgG1, κ | BD | 1:20 |
| I-A/I-E | AF700 | M5/114.15.2 | 107622 | Rat IgG2b, κ | BioLegend | 1:100 |
| PD-1 | BV605 | 29F.1A12 | 135219 | Rat IgG2a, κ | BioLegend | 1:20 |
| Viability | eFluor 780 | NA | 65-0865-18 | NA | eBioscience | 1:100 |
| Intracellular staining | | | | | | |
| Ki67 | PerCP-eFluor 710 | SolA15 | 46-5698-82 | Mouse IgG1, κ | eBioscience | 1:100 |

Plasma samples were obtained from mice in PD parts 1 and 2 on Days 0, 2, and 5. Per mouse, 50 μL blood was drawn via the mandibular vein (Day 0 and 2), or via cardiac puncture on Day 5, and collected in EDTA anticoagulation tubes (BD, cat. no. 365974). The tubes were mixed well to ensure the blood samples were in full contact with the anticoagulant, before centrifuging (8000 RPM, 5 min at 4° C.). After centrifugation, the supernatant was transferred to a 1.5 mL Eppendorf tube.

The levels of mouse cytokines (IFNγ, IL-2, IL-4, IL-10, TNFα, IP-10, MCP-1, IL-27p28) in plasma samples were determined in a multiplexed ECLIA using the V-PLEX Proinflammatory Panel 1 Mouse kit (MSD LLC, cat. no. K15048D-2) on a MESO QuickPlex SQ 120 instrument (MSD, LLC., cat. no. AI0AA-0), according to the manufacturer's instructions. Cytokine concentrations were calculated using standard curve data fitted to a four-parameter logistic (4PL) fit by the MSD workbench software and plotted using GraphPad Prism software.

Treatments were well-tolerated, with no reported clinical signs of illness or observed body weight loss in response to antibody treatment in any of the mice in these studies. Treatment with 5 mg/kg IgG1-CD134-003-HC6LC2-RR significantly delayed tumor outgrowth (Mann Whitney, P=0.0011) compared with IgG1-b12-FEAL treatment as measured 14 days after start of treatment, the last day all treatment groups were still complete, resulting in an intermediate response based on TGI (50.0%; FIG. 39A, B; Table 26). Treatment with the low (1 mg/kg) and high (20 mg/kg) IgG1-CD134-003-HC6LC2-RR doses did not result in significantly smaller tumor volumes on Day 14 compared with the control group (Mann-Whitney, P=0.3527 and P=0.0753, respectively). Progression-free survival was significantly longer for IgG1-CD134-003-HC6LC2-RR-treated mice (5 mg/kg or 20 mg/kg) compared with the IgG1-b12-FEAL treated control group (Mantel-Cox, P<0.001 and P=0.031, respectively; FIG. 39C and Table 27).

TABLE 26

Mann-Whitney analysis of tumor volumes in hOx40 KI mice upon treatment. Tumor volumes of the IgG1-CD134-003-HC6LC2-RR treatment groups were compared with those of the IgG1-b12-FEAL control group using Mann-Whitney analysis on the last day that all groups were complete (Day 14). TGI values per treatment group were calculated based on the tumor volumes on Day 14.

| Treatment | Dose (mg/kg) | P value | P value summary | TGI (%) |
|---|---|---|---|---|
| IgG1-b12-FEAL | 20 | NA | NA | NA |
| IgG1-CD134-003-HC6LC2-RR | 20 | 0.0753 | ns | 27.9 |
| IgG1-CD134-003-HC6LC2-RR | 5 | 0.0011 | ** | 50.0 |
| IgG1-CD134-003-HC6LC2-RR | 1 | 0.3527 | ns | 18.5 |

** = P < 0.01.

TABLE 27

Mantel-Cox analysis of progression-free survival in hOX40 KI mice upon treatment. Progression-free survival (based on a tumor volume cut-off of 500 mm³) was analyzed by means of Mantel-Cox analysis to identify overall difference in survival between groups, followed by pairwise comparisons between groups (SPSS).

| Treatment group | IgG1-b12-FEAL 20 mg/kg | IgG1-CD134-003-HC6LC2-RR 20 mg/kg | IgG1-CD134-003-HC6LC2-RR 5 mg/kg | IgG1-CD134-003-HC6LC2-RR 1 mg/kg | Median survival (days) |
|---|---|---|---|---|---|
| IgG1-b12-FEAL 20 mg/kg | NA | 0.031 | <0.001 | 0.086 | 11.6 |
| IgG1-CD134-003-HC6LC2-RR 20 mg/kg | * | NA | 0.266 | 0.427 | 12.5 |

TABLE 27-continued

Mantel-Cox analysis of progression-free survival in hOX40 KI mice upon treatment. Progression-free survival (based on a tumor volume cut-off of 500 mm³) was analyzed by means of Mantel-Cox analysis to identify overall difference in survival between groups, followed by pairwise comparisons between groups (SPSS).

| Treatment group | IgG1-b12-FEAL 20 mg/kg | IgG1-CD134-003-HC6LC2-RR 20 mg/kg | IgG1-CD134-003-HC6LC2-RR 5 mg/kg | IgG1-CD134-003-HC6LC2-RR 1 mg/kg | Median survival (days) |
|---|---|---|---|---|---|
| IgG1-CD134-003-HC6LC2-RR 5 mg/kg | *** | ns | NA | 0.968 | 14.6 |
| IgG1-CD134-003-HC6LC2-RR 1 mg/kg | ns | ns | ns | NA | 12.9 |

* = P < 0.05, and *** = P < 0.001.

The percentage of tumor-specific CD8$^+$ T cells after treatment was determined using an MHC class I ADPGK tetramer.

Upon treatment with 1, 5, and 20 mg/kg IgG1-CD134-003-HC6LC2-RR, a significant increase in the percentage of CD4$^+$ T cells was observed in peripheral blood of MC38 tumor-bearing hOX40 KI mice (FIG. 40A), as compared with mice treated with 20 mg/kg IgG1-b12-FEAL. The absolute number of CD4$^+$ T cells did not change, possibly indicating the increased frequency of CD4+ cells could be attributed to a decrease in CD8+ T cells (FIG. 40B, D). Treatment of hOX40 KI mice with IgG1-CD134-003-HC6LC2-RR induced proliferation and activation of peripheral blood CD4$^+$ T cells, as shown by a significant increase in the percentage of CD4$^+$ T cells expressing proliferation marker Ki67 and activation markers CD25, IA/IE, PD-1, and 4-1BB (FIG. 41A-E). Moreover, IgG1-CD134-003-HC6LC2-RR treatment resulted in significantly lower percentages of OX40-expressing CD4$^+$ T cells compared with IgG1-b12-FEAL treatment, possibly due to OX40 shedding (data not shown). All observed effects on CD4$^+$ T cells were dose-independent except for the upregulation of 4-1BB, which showed dose-dependency (FIG. 41E).

Upon treatment with 1, 5 and 20 mg/kg IgG1-CD134-003-HC6LC2-RR, a reduction in the percentage and absolute numbers of CD8$^+$ T cells was observed in peripheral blood, along with an increase in the percentage of proliferating CD8$^+$Ki67$^+$ T cells (1, 5, and 20 mg/kg) and percentage and absolute numbers of tumor-specific (ADPGK$^+$) CD8$^+$ T cells (1 and 5 mg/kg; FIG. 40C, D, FIG. 42).

IgG1-CD134-003-HC6LC2-RR treatment induced activation of CD8$^+$ T cells in peripheral blood, as detected by a significant increase in the percentages of CD8$^+$ T cells expressing CD25 (all IgG1-CD134-003-HC6LC2-RR doses), IA/IE (1 and 5 mg/kg), PD-1 (all IgG1-CD134-003-HC6LC2-RR doses), and 4-1BB (5 and 20 mg/kg; FIG. 43). Mice treated with 1 or 20 mg/kg IgG1-CD134-003-HC6LC2-RR showed a significant reduction of CD8$^+$OX40$^+$ T cells in peripheral blood compared with IgG1-b12-FEAL control-treated mice, potentially due to OX40 shedding (data not shown).

The concentrations of IFNγ, IP-10, IL-2, IL-4, IL-10, MCP-1, IL-27p28, and TNFα were determined in plasma samples collected from mice on Day 0 (pretreatment), and on Days 2 and 5 (two days after first and second treatment with IgG1-CD134-003-HC6LC2-RR or IgG1-b12-FEAL), by ECLIA. An increase in plasma concentrations of IFNγ, IP-10, IL-2, IL-4, IL-10, MCP-1, IL-27p28, and TNFα was observed on Day 5 after treatment with IgG1-CD134-003-HC6LC2-RR as compared to treatment with IgG1-B12-FEAL (FIG. 44). No clear dose-response relationship could be observed in these cytokine secretion profiles.

In conclusion, 5 mg/kg IgG1-CD134-003-HC6LC2-RR exhibited significant antitumor activity in MC38 tumor bearing hOX40 KI mice compared with nonbinding control antibodies. In addition, IgG1-CD134-003-HC6LC2-RR treatment resulted in CD8$^+$ T-cell and CD4$^+$ T-cell activation in peripheral blood, as demonstrated by the relative increase in expression of several activation markers and tumor-specific CD8$^+$ T cells. Lastly, increased concentrations of IFNγ, IP-10, IL-2, IL-4, IL-10, MCP-1, IL-27p28, and TNFα were measured in mouse plasma samples upon treatment with IgG1-CD134-003-HC6LC2-RR.

Example 26: Quantitative Immunohistochemistry Analysis on Tumor Tissues Derived from Mice Treated with IgG1-CD134-003-HC6LC2-RR As described in Example 25, IgG1-CD134-003-HC6LC2-RR exhibited antitumor activity in MC38 tumor bearing hOX40 KI mice compared with nonbinding control antibodies. Here, quantitative immunohistochemistry (IHC) was performed to analyze the presence of T-cell populations, T-cell phenotypes, and the tumor proliferation index within tumor tissues derived from MC38-tumor bearing hOX40 KI mice treated with 1, 5, and 20 mg/kg IgG1-CD134-003-HC6LC2-RR or 20 mg/kg IgG1-b12-FEAL as control.

Tumors derived from hOX40 KI mice treated as described in Example 25 were harvested after five days of treatment, dissected, fixed in formalin, paraffin embedded and sectioned (4 μm). For histologic assessment, tumor sections were deparaffinized and stained with the Tissue-Tek Prisma H&E Stain Kit (Sakura, cat. no. 6190) using the Tissue-Tek Prisma Plus Automated Slide Stainer (Sakura). For evaluation of marker-positive cells within the tumor, sections were deparaffinized and antigens were retrieved using CC1 buffer (Roche, cat. no. 950-124), followed by quenching of endogenous peroxidase (Dako Agilent, cat. no. S2003) and blocking of nonspecific binding sites with blocking buffer (Roche, cat. no. 05268869001) using the Roche Ventana Discovery (DISC) autostainer platform. Sections were incubated with primary antibodies (Table 28), which were detected using anti-rabbit immunohistochemistry detection kits: for CD4 and Granzyme B with only anti-rabbit DISC Omnimap (Roche, cat. no. 05269679001), for CD8 and OX40 sequentially with DISC anti-rabbit HQ (Roche, cat. no. 07017812001) and amplification with anti-HQ HRP Multimer (Roche, cat. no. 06442544001). HRP was visualized using 3,3'-diaminobenzidine (ChromoMap DAB; Roche, cat. no. 05266645001) according to manufacturer instructions.

TABLE 28

Primary antibodies used for quantitative immunohistochemistry analysis.

| Target | Host | Cat. no. | Supplier | Clone | Stock conc (mg/mL) | Final conc/ Dilution (mg/mL) |
|---|---|---|---|---|---|---|
| CD4 | Rabbit | ab183685 | Abcam | EPR19514 | 0.623 | 0.005 |
| CD8 | Rabbit | 98941 | Cell Signaling | D4W2Z | Unknown | 1:200 |
| Granzyme B | Rabbit | ab255598 | Abcam | EPR22645-206 | 0.543 | 0.005 |
| hOX40 | Rabbit | ab264465 | Abcam | EPR23001-88 | 0.513 | 0.010 |
| Isotype | Rabbit | 3900S | Cell Signaling | DA1E | 2.5 | 0.006 |
| Neg ctrl | N.A. | 5266319001 | Roche | N/A | N/A | N/A |

N/A: not applicable; conc: concentration; hOX40: human OX40; RTU: ready-to-use (prediluted by vendor).

In all assays, nuclei were counterstained by incubation with Mayer's hematoxylin. Staining specificity was controlled by incorporating isotype, positive and negative control staining on consecutive tissue sections. Stained slides were subjected to whole slide imaging on AxioScan Z1 (Zeiss).

A multiplex immunofluorescent assay was performed to co-stain CD3 (RTU assay, clone 2GV6, cat. no. 790-4341, Roche), Ki-67 (RTU assay, clone 30-9, Roche, cat. no. 790-4286) and pan-cytokeratin (polyclonal, 50× dilution, ThermoFisher, cat. no. PA1-27114). IHC tissue sections of standard thickness (4 µm) were subjected to standard protocols for deparaffinization and antigen retrieval (Tris-EDTA buffer pH 7.8). For multiplex immunofluorescence fluorophore-conjugated secondary antibodies were used (FAM-labeled for CD3 [Discovery-FAM kit, Roche, cat. no. 7988150001], Rhodamine6G-labeled for Ki-67 [Discovery-Rhodamine6G kit, Roche, cat. no. 7988168001], Cy5-labeled for pan-cytokeratin [Discovery-Cy5 kit, Roche, cat. no. 7551215001]). Staining specificity was controlled by incorporating isotype control stainings on consecutive tissue sections. Tissues were counterstained with DAPI. Sections were mounted with ProLong Gold Antifade Mountant (ThermoFisher, cat. no. P10144). Whole tissue slides were scanned with standardized scanning profiles on AxioScan Z1 (Zeiss).

Digital images were analyzed for cellular quantitation within viable intratumoral regions in HALO software (Indica Labs) using preprogrammed software analysis algorithms (CytoNuclear v2.0.9 for brightfield images, HighPlex FL v4.2.14 for fluorescent images). Cellular quantitation readouts have been generated by calculating (1) the percentage of marker-positive cells within the total number of nucleated cells and (2) the number of marker-positive cells per surface area (mm$^2$).

A significant increase in the number of CD4$^+$ T cells per mm$^2$ tissue was observed after treatment with any of the IgG1-CD134-003-HC6LC2-RR treatment doses (FIG. 45A-D). In addition, the number of Granzyme B$^+$ cells per mm$^2$ tissue was significantly increased after treatment with 1 mg/kg or 5 mg/kg IgG1-CD134-003-HC6LC2-RR, with the strongest increase observed in tumor tissue derived from mice treated with 5 mg/kg IgG1-CD134-003-HC6LC2-RR (FIG. 45E). No effects of treatment were observed in the number of OX40$^+$ cells per mm$^2$ tissue (FIG. 45F).

In summary, IgG1-CD134-003-HC6LC2-RR treatment led to increased numbers of CD4$^+$ T cells and Granzyme-B$^+$ cells in murine MC38 tumors in hOX40 KI mice after five days of treatment, as assessed using quantitative IHC.

Example 27: In Vivo Antitumor Efficacy of IgG1-CD134-003-HC6LC2-RR

In Example 25, it was described that anti-human OX40 antibody IgG1-CD134-003-HC6LC2-RR exhibited significant antitumor activity in MC38 tumor bearing hOX40 KI mice compared with nonbinding control antibodies. Using the same murine tumor model and methods described in Example 25, here, an in vivo dose-range finding study was performed. The only deviation from the methods described in Example 25 is that here, hOX40 KI mice were injected IP with IgG1-CD134-003-HC6LC2-RR (1, 2.5, 5, 10, or 20 mg/kg) or IgG1-b12-FEAL control antibody (20 mg/kg) twice a week, for three weeks. Randomization was performed with an average tumor volume of 61.77 mm$^3$. 60 animals were allocated to 6 groups with 10 animals per group (1 group per dose level).

Treatment with 1, 5, or 20 mg/kg IgG1-CD134-003-HC6LC2-RR significantly delayed tumor outgrowth (Mann Whitney, P=0.0433, P=0.0052, P=0.0133, respectively) compared with IgG1-b12-FEAL treatment as measured 15 days after start of treatment, resulting in an intermediate response based on TGI (41.7%, 52.2%, or 43.2%, respectively; FIG. 46A, B). Treatment with the 2.5 mg/kg and 10 mg/kg IgG1-CD134-003-HC6LC2-RR doses did not result in significantly smaller tumor volumes on Day 15 compared with the control group (Mann-Whitney, P=0.5787 and P=0.0753, respectively). Progression-free survival was significantly longer for IgG1-CD134-003-HC6LC2-RR-treated mice (1 mg/kg, or 5 mg/kg) compared with the IgG1-b12-FEAL treated control group (Mantel-Cox, P=0.015 and P=0.01, respectively; FIG. 46C). In summary, significant antitumor activity was observed after treating mice with 1, 5, or 20 mg/kg IgG1-CD134-003-HC6LC2-RR, shown by analysis of tumor outgrowth on day 15 and progression-free survival, in an in vivo dose-range finding study in hOX40 KI mice bearing MC38 tumors. These results confirmed the conclusions drawn in Example 25.

Example 28: In Vivo Effects on MC38 Tumors after Treatment with IgG1-CD134-003-HC6LC2-RR In Example 25, the MC38 in vivo tumor model in hOX40 KI mice was described to study the efficacy of IgG1-CD134-003-HC6LC2-RR treatment. Following essentially the procedures described in Example 25, here, the effects of IgG1-CD134-003-HC6LC2-RR treatment on T-cell numbers and T-cell activation were studied in murine tumor samples. In contrast to the procedures described in Example 25, randomization of mice into treatment groups (n=7 per treatment group; i.p. treatment with 20 mg/kg, 5 mg/kg, or 1 mg/kg IgG1-CD134-003-HC6LC2-RR, or 20 mg/kg IgG1-b12-RR) was performed when an average tumor volume of 200 mm$^3$ was reached, and pharmacodynamic effects were measured in tumor samples collected on day 5 after starting treatment (i.e., after 2 treatments were given). Immunophenotyping and T-cell activation were analyzed using flow cytometry, as described in Example 25, using the fluorescently labeled antibodies in Table 29.

The following gating strategy was employed to phenotype and analyze the activation of the immune cell subsets. After gating the singlets, live cells were discriminated from dead cells by gating on the L/D$^-$ cells. Within the live cell gate, CD45$^+$ cells were gated, after which CD19$^+$ were gated out. CD3$^+$ cells within the CD45$^+$CD19$^-$ population were further divided into CD4$^+$ and CD8$^+$ T cells. Conventional CD4+ T cells were defined by the expression of CD4 and absence of FOXP3 expression. Tregs were defined by the expression of CD4, CD25, and FOXP3. The expression of CD25, Granzyme B (GZMB), human OX40, and PD-1 was analyzed for conventional CD4 and CD8 T-cell subsets.

TABLE 29

Flow cytometry panel for immunophenotyping and T-cell activation

| Marker | Fluorophore | Clone | CAT# | Isotype | Vendor |
|---|---|---|---|---|---|
| CD45 | BV785 | 30-F11 | 103149 | Rat IgG2b, κ | BioLegend |
| CD3 | BUV395 | 17A2 | 740268 | Rat IgG2b, κ | BD |
| CD19 | APC | 6D5 | 115512 | Rat IgG2a, κ | BioLegend |
| CD4 | FITC | GK1.5 | 100406 | Rat IgG2b, κ | BioLegend |
| CD8 | PE-ef610 | 53-6.7 | 61-0081-82 | Rat IgG2a, κ | eBioscience |
| CD25 | BV605 | PC61 | 102036 | Rat IgG1, λ | BioLegend |
| PD-1 | BV711 | 29F.1.A12 | 135231 | Rat IgG2a, κ | BioLegend |
| FoxP3 | PE | FJK-16s | 12-5773-82 | Rat IgG2a, κ | eBioscience |
| GZMB | PE-Cy7 | QA16A02 | 372214 | Mouse IgG1, κ | BioLegend |
| hOX40 | BV421 | L106 | 744881 | Mouse IgG1, κ | BD |
| L/D | eFluor780 | N/A | 65-0865-14 | N/A | eBioscience |

Upon treatment with 1, 5, and 20 mg/kg IgG1-CD134-003-HC6LC2-RR, a significant change was only observed in the percentage of Tregs in the collected tumor samples after treatment with 20 mg/kg IgG1-CD134-003-HC6LC2-RR, while no significant changes were observed in the percentages of CD45$^+$ cells, CD3$^+$ cells, conventional CD4$^+$ T cells, or CD8$^+$ T cells, as compared with tumor samples derived from mice treated with 20 mg/kg IgG1-b12-RR (FIG. 47). Despite a trend toward an increase in the absolute numbers of CD45$^+$ cells, CD3$^+$ cells, CD4$^+$ T cells, and CD8$^+$ T cells, a significant increase was only observed for Tregs at the 5 mg/kg dose of IgG1-CD134-003-HC6LC2-RR (FIG. 47).

A significant increase in the percentage of conventional CD4$^+$ T cells expressing human OX40 was observed after treatment with each of the doses of IgG1-CD134-003-HC6LC2-RR (FIG. 48). Significant increases in conventional CD4$^+$ T cells expressing PD-1 or Granzyme B (GZMB) were observed in tumor samples after treatment with 1 or 20 mg/kg IgG1-CD134-003-HC6LC2-RR (Table 30; FIG. 48). An increasing trend, despite not being statistically significant, was observed in conventional CD4$^+$ T cells expressing CD25 after treatment with IgG1-CD134-003-HC6LC2-RR.

A significant increase in the percentage of CD8$^+$ T cells expressing human OX40 was also observed after treatment with each of the doses of IgG1-CD134-003-HC6LC2-RR (Table 31; FIG. 49). Although slight increases in the percentages of CD8$^+$ T cells expressing GZMB or PD-1 were observed, these effects were not statistically significant. No consistent increase was observed in CD8$^+$ T cells expressing CD25 after treatment with IgG1-CD134-003-HC6LC2-RR (Table 31; FIG. 49).

TABLE 30

Mann-Whitney analysis of percentages of conventional CD4$^+$ T cells expressing CD25, human OX40, GZMB, or PD-1 in tumors collected from hOX40 KI mice after treatment with IgG1-CD134-003-HC6LC2-RR. Percentages of the IgG1-CD134-003-HC6LC2-RR treatment groups were compared with those of the IgG1-b12-RR control group using Mann-Whitney analysis.

| IgG1-CD134-003-HC6LC2-RR treatment group | CD4$^+$CD25$^+$ T cells | CD4$^+$GZMB$^+$ T cells | CD4$^+$OX40$^+$ T cells | CD4$^+$PD-1$^+$ T cells |
|---|---|---|---|---|
| 20 mg/kg | 0.0793 | 0.0012 | 0.0006 | 0.0163 |
| 5 mg/kg | 0.2593 | 0.0973 | 0.0111 | 0.2086 |
| 1 mg/kg | 0.2593 | 0.0041 | 0.0262 | 0.0262 |

\* = P < 0.05; \*\* = P < 0.01, \*\*\* = P < 0.001.

TABLE 31

Mann-Whitney analysis of percentages of CD8+ T cells expressing CD25, human OX40, GZMB, or PD-1 in tumors collected from hOx40 KI mice after treatment with IgG1-CD134-003-HC6LC2-RR. Percentages of the IgG1-CD134-003-HC6LC2-RR treatment groups were compared with those of the IgG1-b12-RR control group using Mann-Whitney analysis.

| IgG1-CD134-003-HC6LC2-RR treatment group | CD8+CD25+ T cells | CD8+GZMB+ T cells | CD8+OX40+ T cells | CD8+PD-1+ T cells |
| --- | --- | --- | --- | --- |
| 20 mg/kg | 0.3992 | 0.0728 | 0.0023 | 0.2593 |
| 5 mg/kg | 0.6043 | 0.0973 | 0.0006 | 0.1649 |
| 1 mg/kg | 0.1550 | 0.6200 | 0.0006 | 0.3176 |

* = P < 0.05;  = P < 0.01; * = P < 0.001.

---

The invention claimed is:

1. An antibody capable of binding to human OX40, wherein the antibody comprises a VH having the sequence as set forth in SEQ ID NO: 20 and a VL having the sequence as set forth in SEQ ID NO: 21.

2. The antibody of claim 1, wherein the antibody comprises a human IgG1 Fc region is of the human IgG1mf, human IgG1ma, human IgG1mx or human IgG1mz allotype.

3. The antibody of claim 1, wherein the antibody comprises a human IgG1 Fc region comprising the sequence set forth in SEQ ID NO: 3.

4. The antibody of claim 1, wherein the antibody is bivalent.

5. The antibody of claim 1, wherein the antibody is a monospecific, bispecific or multi-specific antibody.

6. The antibody of claim 1, wherein the antibody is a full-length antibody.

7. The antibody of claim 1, wherein the antibody has a heavy chain constant region (CH) comprising a sequence selected from the group consisting of SEQ ID NOs: 58, 59, 60, and 61.

8. The antibody of claim 7, wherein the antibody has a CH comprising the sequence as set forth in SEQ ID NO: 58.

9. An antibody capable of binding to human OX40, wherein the antibody comprises a heavy chain (HC) as set forth in SEQ ID NO: 18 and a light chain (LC) as set forth in SEQ ID NO: 19.

10. A pharmaceutical composition comprising the antibody of claim 1 and a pharmaceutically acceptable carrier.

11. A kit-of-parts comprising the antibody of claim 1 and instructions for use of said kit.

12. The antibody of claim 9, wherein the antibody is bivalent.

13. The antibody of claim 9, wherein the antibody is a monospecific, bispecific or multi-specific antibody.

14. The antibody of claim 9, wherein the antibody is a full-length antibody.

15. A pharmaceutical composition comprising the antibody of claim 9 and a pharmaceutically acceptable carrier.

16. A kit-of-parts comprising the antibody of claim 9 and instructions for use of said kit.

17. An antibody capable of binding to human OX40, wherein said antibody comprises:
a) a VH having the sequence as set forth in SEQ ID NO: 20 and a VL having the sequence as set forth in SEQ ID NO: 21
b) a human IgG1 Fc region comprising a P329R mutation and an E345R mutation, wherein the amino acid positions are numbered according to Eu numbering.

18. The antibody of claim 17, wherein the Fc region is of the human IgG1mf, human IgG1ma, human IgG1mx or human IgG1mz allotype.

19. The antibody of claim 17, wherein the antibody is bivalent.

20. The antibody of claim 17, wherein the antibody is a monospecific, bispecific or multi-specific antibody.

21. The antibody of claim 17, wherein the antibody is a full-length antibody.

22. A pharmaceutical composition comprising the antibody of claim 17 and a pharmaceutically acceptable carrier.

23. A kit-of-parts comprising the antibody of claim 17 and instructions for use of said kit.

* * * * *

UNITED STATES PATENT AND TRADEMARK OFFICE
CERTIFICATE OF CORRECTION

| | | |
|---|---|---|
| PATENT NO. | : 12,410,258 B2 | Page 1 of 1 |
| APPLICATION NO. | : 18/660672 | |
| DATED | : September 9, 2025 | |
| INVENTOR(S) | : Kemper et al. | |

It is certified that error appears in the above-identified patent and that said Letters Patent is hereby corrected as shown below:

On the Title Page

Item (73), delete "Ganmab A/S" and insert --Genmab A/S--.

Signed and Sealed this
Twenty-third Day of December, 2025

John A. Squires
*Director of the United States Patent and Trademark Office*